United States Patent
Vrba et al.

(10) Patent No.: US 10,524,859 B2
(45) Date of Patent: Jan. 7, 2020

(54) THERAPEUTIC TISSUE MODULATION DEVICES AND METHODS

(71) Applicant: Metavention, Inc., Eden Prairie, MN (US)

(72) Inventors: Anthony Ciro Vrba, Maple Grove, MN (US); Scott Raymond Smith, Chaka, MN (US); Bobak Robert Azamian, Newport Coast, CA (US); James G. Hansen, Coon Rapids, MN (US)

(73) Assignee: Metavention, Inc., Maple Grove, MN (US)

( * ) Notice: Subject to any disclaimer, the term of this patent is extended or adjusted under 35 U.S.C. 154(b) by 191 days.

(21) Appl. No.: 15/614,460

(22) Filed: Jun. 5, 2017

(65) Prior Publication Data

US 2017/0348049 A1 Dec. 7, 2017

Related U.S. Application Data

(60) Provisional application No. 62/458,990, filed on Feb. 14, 2017, provisional application No. 62/346,990, filed on Jun. 7, 2016.

(51) Int. Cl.
*A61B 18/14* (2006.01)
*A61B 18/00* (2006.01)
(Continued)

(52) U.S. Cl.
CPC .. *A61B 18/1492* (2013.01); *A61B 2018/0022* (2013.01); *A61B 2018/00023* (2013.01);
(Continued)

(58) Field of Classification Search
CPC ...... A61B 18/1492; A61B 2018/00434; A61B 2018/00577; A61B 2018/00404;
(Continued)

(56) References Cited

U.S. PATENT DOCUMENTS

| 4,033,331 A | 7/1977 | Guss et al. |
| 5,561,165 A | 10/1996 | Lautt et al. |

(Continued)

FOREIGN PATENT DOCUMENTS

| CN | 1817382 A | 8/2006 |
| EP | 0643601 B1 | 8/2001 |

(Continued)

OTHER PUBLICATIONS

Adkins-Marshall, B. et al, "Role of hepatic nerves in response of liver to intraportal glucose deliver in dogs," American Journal of Physiology—Endocrinology and Metabolism, vol. 262, pp. E679-E686 (1992).

(Continued)

*Primary Examiner* — Linda C Dvorak
*Assistant Examiner* — Annabeth E Rodriguez
(74) *Attorney, Agent, or Firm* — Knobbe Martens Olson & Bear LLP

(57) ABSTRACT

According to various embodiments, systems, devices and methods for modulating targeted nerve fibers (e.g., hepatic neuromodulation) or other tissue are provided. Systems, devices and methods for cooling energy delivery members are also provided. The systems may be configured to access tortuous anatomy of or adjacent hepatic vasculature. The systems may be configured to target nerves surrounding (e.g., within adventitia of or within perivascular space of) an artery or other blood vessel, such as the common hepatic artery.

20 Claims, 50 Drawing Sheets

(51) Int. Cl.
  *A61N 1/05* (2006.01)
  *A61N 1/36* (2006.01)
  *A61N 7/02* (2006.01)
  *A61N 7/00* (2006.01)

(52) U.S. Cl.
  CPC ............... *A61B 2018/00029* (2013.01); *A61B 2018/00166* (2013.01); *A61B 2018/00255* (2013.01); *A61B 2018/00285* (2013.01); *A61B 2018/00404* (2013.01); *A61B 2018/00434* (2013.01); *A61B 2018/00511* (2013.01); *A61B 2018/00529* (2013.01); *A61B 2018/00577* (2013.01); *A61B 2018/00642* (2013.01); *A61B 2018/00702* (2013.01); *A61B 2018/00791* (2013.01); *A61B 2018/00875* (2013.01); *A61B 2018/00994* (2013.01); *A61B 2018/1467* (2013.01); *A61B 2018/1475* (2013.01); *A61B 2218/003* (2013.01); *A61N 1/0558* (2013.01); *A61N 1/36057* (2013.01); *A61N 7/022* (2013.01); *A61N 2007/0021* (2013.01); *A61N 2007/0026* (2013.01)

(58) Field of Classification Search
  CPC ........... A61B 2018/00511; A61B 2018/00267; A61B 2018/0022; A61B 2018/00255; A61B 2018/0016; A61B 2018/00214; A61B 2018/1465; A61B 2018/1475
  See application file for complete search history.

(56) References Cited

U.S. PATENT DOCUMENTS

| | | | |
|---|---|---|---|
| 5,707,400 A | 1/1998 | Baker | |
| 5,893,885 A | 4/1999 | Webster | |
| 6,113,593 A | 9/2000 | Tu et al. | |
| 6,142,994 A | 11/2000 | Swanson et al. | |
| 6,161,049 A | 12/2000 | Rudie et al. | |
| 6,178,354 B1 | 1/2001 | Gibson | |
| 6,183,468 B1 | 2/2001 | Swanson et al. | |
| 6,283,959 B1 | 9/2001 | Lalonde et al. | |
| 6,290,697 B1 | 9/2001 | Tu et al. | |
| 6,292,695 B1 | 9/2001 | Webster | |
| 6,425,877 B1 | 7/2002 | Edwards | |
| 6,428,537 B1 | 8/2002 | Swanson et al. | |
| 6,451,011 B2 | 9/2002 | Tu et al. | |
| 6,491,710 B2 | 12/2002 | Satake | |
| 6,494,880 B1 | 12/2002 | Swason et al. | |
| 6,496,737 B2 | 12/2002 | Rudie et al. | |
| 6,511,478 B1 | 1/2003 | Burnside et al. | |
| 6,514,249 B1 * | 2/2003 | Maguire | A61B 18/00 606/37 |
| 6,542,781 B1 | 4/2003 | Koblish et al. | |
| 6,551,274 B2 * | 4/2003 | Heiner | A61B 18/02 604/102.02 |
| 6,575,932 B1 | 6/2003 | O'Brien et al. | |
| 6,582,423 B1 * | 6/2003 | Thapliyal | A61B 18/1206 128/898 |
| 6,589,238 B2 | 7/2003 | Edwards et al. | |
| 6,638,278 B2 | 10/2003 | Falwell et al. | |
| 6,648,879 B2 | 11/2003 | Joye et al. | |
| 6,666,858 B2 | 12/2003 | Lafontaine | |
| 6,666,862 B2 | 12/2003 | Jain et al. | |
| 6,699,242 B2 | 3/2004 | Heggeness | |
| 6,728,563 B2 | 4/2004 | Rashidi | |
| 6,730,078 B2 | 5/2004 | Simpson et al. | |
| 6,745,080 B2 | 6/2004 | Koblish | |
| 6,796,979 B2 | 9/2004 | Lentz | |
| 6,832,114 B1 | 12/2004 | Whitehurst | |
| 6,845,267 B2 | 1/2005 | Harrison | |
| 6,885,888 B2 | 4/2005 | Rezai | |
| 6,887,236 B2 | 5/2005 | Gilboa | |
| 6,893,433 B2 | 5/2005 | Lentz | |
| 6,926,669 B1 | 8/2005 | Stewart et al. | |
| 6,936,047 B2 | 8/2005 | Nasab et al. | |
| 6,952,615 B2 | 10/2005 | Satake | |
| 6,955,675 B2 | 10/2005 | Jain | |
| 6,972,015 B2 | 12/2005 | Joye et al. | |
| 6,972,016 B2 | 12/2005 | Hill, III et al. | |
| 6,978,174 B2 | 12/2005 | Gelfand et al. | |
| 7,004,961 B2 | 2/2006 | Wong et al. | |
| 7,013,170 B2 | 3/2006 | Bowe | |
| 7,037,269 B2 | 5/2006 | Nix et al. | |
| 7,048,716 B1 | 5/2006 | Kucharczyk et al. | |
| 7,089,063 B2 | 8/2006 | Lesh et al. | |
| 7,101,368 B2 | 9/2006 | Lafontaine | |
| 7,112,198 B2 | 9/2006 | Satake | |
| 7,144,407 B1 | 12/2006 | Lasersohn | |
| 7,149,574 B2 | 12/2006 | Yun et al. | |
| 7,150,745 B2 | 12/2006 | Stern et al. | |
| 7,155,284 B1 | 12/2006 | Whitehurst | |
| 7,162,303 B2 | 1/2007 | Levin et al. | |
| 7,195,625 B2 | 3/2007 | Lentz | |
| 7,195,629 B2 | 3/2007 | Behl et al. | |
| 7,220,257 B1 | 5/2007 | Lafontaine | |
| 7,288,089 B2 | 10/2007 | Yon et al. | |
| 7,363,076 B2 | 4/2008 | Yun et al. | |
| 7,371,231 B2 | 5/2008 | Rioux et al. | |
| 7,387,628 B1 | 6/2008 | Behl et al. | |
| 7,416,549 B2 | 8/2008 | Young et al. | |
| 7,477,945 B2 | 1/2009 | Rezai et al. | |
| 7,510,536 B2 | 3/2009 | Foley et al. | |
| 7,517,349 B2 | 4/2009 | Truckai et al. | |
| 7,524,318 B2 | 4/2009 | Young et al. | |
| 7,529,582 B1 | 5/2009 | DiLorenzo | |
| 7,556,628 B2 | 7/2009 | Utley et al. | |
| 7,591,816 B2 | 9/2009 | Wang et al. | |
| 7,599,736 B2 | 10/2009 | DiLorenzo | |
| 7,599,737 B2 | 10/2009 | Yomtov et al. | |
| 7,617,005 B2 | 11/2009 | Demarais et al. | |
| 7,620,451 B2 | 11/2009 | Demarais et al. | |
| 7,647,115 B2 | 1/2010 | Levin et al. | |
| 7,653,438 B2 | 1/2010 | Deem et al. | |
| 7,655,006 B2 | 2/2010 | Sauvageau et al. | |
| 7,670,337 B2 | 3/2010 | Young | |
| 7,689,276 B2 | 3/2010 | Dobak | |
| 7,689,277 B2 | 3/2010 | Dobak, III | |
| 7,702,386 B2 | 4/2010 | Dobak et al. | |
| 7,717,948 B2 | 5/2010 | Demarais et al. | |
| 7,727,228 B2 | 6/2010 | Abboud et al. | |
| 7,738,952 B2 | 6/2010 | Yun et al. | |
| 7,756,583 B2 | 7/2010 | Demarais et al. | |
| 7,758,623 B2 | 7/2010 | Dzeng et al. | |
| 7,769,470 B1 | 8/2010 | Rezai et al. | |
| 7,778,704 B2 | 8/2010 | Rezai | |
| 7,819,826 B2 | 10/2010 | Diederich | |
| 7,819,870 B2 | 10/2010 | Thao et al. | |
| 7,831,308 B2 | 11/2010 | Rezai et al. | |
| 7,850,685 B2 | 12/2010 | Kunis et al. | |
| 7,853,333 B2 | 12/2010 | Demarais | |
| 7,865,237 B2 | 1/2011 | Machado et al. | |
| 7,873,417 B2 | 1/2011 | Demarais et al. | |
| 7,877,146 B2 | 1/2011 | Rezai | |
| 7,881,784 B2 | 2/2011 | Pasricha et al. | |
| 7,917,230 B2 | 3/2011 | Bly | |
| 7,937,143 B2 | 5/2011 | Demarais et al. | |
| 7,937,144 B2 | 5/2011 | Dobak | |
| 7,937,145 B2 | 5/2011 | Dobak | |
| 7,938,828 B2 | 5/2011 | Koblish | |
| 7,963,287 B2 | 6/2011 | Lanphere et al. | |
| 8,000,764 B2 | 8/2011 | Rashidi | |
| 8,021,361 B2 | 9/2011 | Paul et al. | |
| 8,042,251 B2 | 10/2011 | Asmus et al. | |
| 8,043,289 B2 | 10/2011 | Behl et al. | |
| 8,043,351 B2 | 10/2011 | Yon et al. | |
| RE42,961 E | 11/2011 | Rahme | |
| 8,075,498 B2 | 12/2011 | Leo et al. | |
| 8,123,741 B2 | 2/2012 | Marrouche et al. | |
| 8,123,742 B2 | 2/2012 | Berger | |
| 8,123,789 B2 | 2/2012 | Khanna | |
| 8,128,617 B2 | 3/2012 | Bencini et al. | |
| 8,131,371 B2 | 3/2012 | Demarais et al. | |
| 8,131,372 B2 | 3/2012 | Levin et al. | |

(56) References Cited

U.S. PATENT DOCUMENTS

| | | |
|---|---|---|
| 8,137,342 B2 | 3/2012 | Crossman |
| 8,140,170 B2 | 3/2012 | Rezai et al. |
| 8,145,299 B2 | 3/2012 | Dobak, III |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,160,690 B2 | 4/2012 | Wilfley et al. |
| 8,162,935 B2 | 4/2012 | Paul et al. |
| 8,172,693 B1 | 5/2012 | Guerzini et al. |
| 8,175,711 B2 | 5/2012 | Demarais et al. |
| 8,182,433 B2 | 5/2012 | Leo et al. |
| 8,197,409 B2 | 6/2012 | Foley et al. |
| 8,211,017 B2 | 7/2012 | Foley et al. |
| 8,211,102 B2 | 7/2012 | Paul et al. |
| 8,216,231 B2 | 7/2012 | Behl et al. |
| 8,224,416 B2 | 7/2012 | De la Rama et al. |
| 8,226,602 B2 | 7/2012 | Quijana et al. |
| 8,226,648 B2 | 7/2012 | Paul et al. |
| 8,257,413 B2 | 9/2012 | Danek et al. |
| 8,265,745 B2 | 9/2012 | Hauck et al. |
| 8,267,926 B2 | 9/2012 | Paul et al. |
| 8,277,398 B2 | 10/2012 | Weng et al. |
| 8,295,902 B2 | 10/2012 | Salahieh et al. |
| 8,295,912 B2 | 10/2012 | Gertner |
| 8,313,482 B2 | 11/2012 | McIntyre et al. |
| 8,317,783 B2 | 11/2012 | Cao et al. |
| 8,323,274 B2 | 12/2012 | Jakus |
| 8,337,492 B2 | 12/2012 | Kunis et al. |
| 8,343,031 B2 | 1/2013 | Gertner |
| 8,364,237 B2 | 1/2013 | Stone et al. |
| 8,364,285 B2 | 1/2013 | Rezai |
| 8,372,009 B2 | 2/2013 | Emery et al. |
| 8,374,674 B2 | 2/2013 | Gertner |
| 8,396,548 B2 | 3/2013 | Perry et al. |
| 8,401,667 B2 | 3/2013 | Gustus et al. |
| 8,403,925 B2 | 3/2013 | Miller et al. |
| 8,406,866 B2 | 3/2013 | Deno et al. |
| 8,409,195 B2 | 4/2013 | Young |
| 8,414,508 B2 | 4/2013 | Thapliyal et al. |
| 8,417,331 B2 | 4/2013 | Pasricha et al. |
| 8,435,232 B2 | 5/2013 | Aeby et al. |
| 8,439,909 B2 | 5/2013 | Wang et al. |
| 8,444,640 B2 | 5/2013 | Demarais et al. |
| 8,449,535 B2 | 5/2013 | Deno et al. |
| 8,454,594 B2 | 6/2013 | Demarais et al. |
| 8,465,486 B2 | 6/2013 | Danek et al. |
| 8,469,904 B2 | 6/2013 | Gertner |
| 8,475,449 B2 | 7/2013 | Werneth et al. |
| 8,483,830 B2 | 7/2013 | Tweden et al. |
| 8,489,184 B2 | 7/2013 | Wilfley et al. |
| 8,504,132 B2 | 8/2013 | Friedman et al. |
| 8,504,147 B2 | 8/2013 | Deem et al. |
| 8,512,262 B2 | 8/2013 | Gertner |
| 8,517,962 B2 | 8/2013 | Gertner et al. |
| 8,536,667 B2 | 9/2013 | De Graff et al. |
| 8,568,399 B2 | 10/2013 | Azamian et al. |
| 8,577,447 B2 | 11/2013 | Tegg et al. |
| 8,579,891 B2 | 11/2013 | Coe et al. |
| 8,583,229 B2 | 11/2013 | Rezai et al. |
| 8,585,696 B2 | 11/2013 | Young |
| 8,588,886 B2 | 11/2013 | De la Rama et al. |
| 8,612,022 B1 | 12/2013 | Morero et al. |
| 8,617,156 B2 | 12/2013 | Werneth et al. |
| 8,641,704 B2 | 2/2014 | Werneth et al. |
| 8,641,705 B2 | 2/2014 | Leo et al. |
| 8,641,711 B2 | 2/2014 | Kelly et al. |
| 8,652,129 B2 | 2/2014 | Wu et al. |
| 8,672,936 B2 | 3/2014 | Thao et al. |
| 8,676,309 B2 | 3/2014 | Deem et al. |
| 8,679,109 B2 | 3/2014 | Paul |
| 8,700,161 B2 | 4/2014 | Harel et al. |
| 8,712,550 B2 | 4/2014 | Grunewald |
| 8,715,209 B2 | 5/2014 | Gertner |
| 8,721,637 B2 | 5/2014 | Zarins et al. |
| 8,728,068 B2 | 5/2014 | Nye et al. |
| 8,728,069 B2 | 5/2014 | Azamian et al. |
| 8,728,070 B2 | 5/2014 | Azamian et al. |
| 8,728,075 B2 | 5/2014 | Wu et al. |
| 8,728,077 B2 | 5/2014 | Kunis et al. |
| 8,738,127 B1 | 5/2014 | Lebovitz et al. |
| 8,740,896 B2 | 6/2014 | Zarins et al. |
| 8,758,334 B2 | 6/2014 | Coe et al. |
| 8,764,742 B2 | 7/2014 | Pappone et al. |
| 8,771,267 B2 | 7/2014 | Kunis et al. |
| 8,774,942 B2 | 7/2014 | Lund et al. |
| 8,777,943 B2 | 7/2014 | Mayse et al. |
| 8,790,281 B2 | 7/2014 | Diederich et al. |
| 8,805,466 B2 | 8/2014 | Salahieh et al. |
| 8,808,345 B2 | 8/2014 | Clark et al. |
| 8,818,514 B2 | 8/2014 | Zarins et al. |
| 8,819,928 B2 | 9/2014 | Nix et al. |
| 8,834,464 B2 | 9/2014 | Stewart et al. |
| 8,845,629 B2 | 9/2014 | Demarais et al. |
| 8,845,707 B2 | 9/2014 | Lafontaine |
| 8,876,815 B2 | 11/2014 | Coe et al. |
| 8,888,773 B2 | 11/2014 | Chang et al. |
| 8,894,589 B2 | 11/2014 | Leo et al. |
| 8,894,639 B2 | 11/2014 | Azamian et al. |
| 8,894,642 B2 | 11/2014 | Gibson et al. |
| 8,911,485 B2 | 12/2014 | Brian, III et al. |
| 8,920,414 B2 | 12/2014 | Stone et al. |
| 8,934,978 B2 | 1/2015 | Deem et al. |
| 8,939,970 B2 | 1/2015 | Stone et al. |
| 8,940,010 B2 | 1/2015 | Lee et al. |
| 8,945,110 B2 | 2/2015 | Fish et al. |
| 8,956,352 B2 | 2/2015 | Mauch et al. |
| 8,961,436 B2 | 2/2015 | Leo et al. |
| 8,979,839 B2 | 3/2015 | De la Rama et al. |
| 8,979,841 B2 | 3/2015 | Kunis et al. |
| 8,983,609 B2 | 3/2015 | Rezai et al. |
| 8,986,294 B2 | 3/2015 | Demarais et al. |
| 8,996,091 B2 | 3/2015 | De la Rama et al. |
| 9,005,190 B2 | 4/2015 | Azamian et al. |
| 9,005,191 B2 | 4/2015 | Azamian et al. |
| 9,011,422 B2 | 4/2015 | Azamian et al. |
| 9,014,821 B2 | 4/2015 | Wang |
| 9,023,010 B2 | 5/2015 | Chiu et al. |
| 9,023,037 B2 | 5/2015 | Zarins et al. |
| 9,028,472 B2 | 5/2015 | Mathur et al. |
| 9,033,969 B2 | 5/2015 | Azamian et al. |
| 9,037,244 B2 | 5/2015 | Sharma |
| 9,037,259 B2 | 5/2015 | Mathur |
| 9,039,700 B2 | 5/2015 | Kirschenman |
| 9,044,245 B2 | 6/2015 | Condie et al. |
| 9,055,950 B2 | 6/2015 | Beani et al. |
| 9,060,755 B2 | 6/2015 | Buckley et al. |
| 9,060,756 B2 | 6/2015 | Bencini et al. |
| 9,060,784 B2 | 6/2015 | Coe et al. |
| 9,061,153 B1 | 6/2015 | Lebovitz |
| 9,066,713 B2 | 6/2015 | Turovskiy |
| 9,066,725 B2 | 6/2015 | Christian |
| 9,066,726 B2 | 6/2015 | Srivastava |
| 9,072,902 B2 | 7/2015 | Mathur et al. |
| 9,084,609 B2 | 7/2015 | Smith |
| 9,084,610 B2 | 7/2015 | Goshgarian et al. |
| 9,084,611 B2 | 7/2015 | Amirana et al. |
| 9,089,341 B2 | 7/2015 | Chomas et al. |
| 9,089,541 B2 | 7/2015 | Azamian et al. |
| 9,089,542 B2 | 7/2015 | Azamian et al. |
| 9,101,365 B2 | 8/2015 | Highsmith |
| 9,114,123 B2 | 8/2015 | Azamian et al. |
| 9,114,124 B2 | 8/2015 | Azamian et al. |
| 9,119,600 B2 | 9/2015 | Richardson et al. |
| 9,125,666 B2 | 9/2015 | Steinke et al. |
| 9,131,982 B2 | 9/2015 | VanScoy et al. |
| 9,138,292 B2 | 9/2015 | Chang et al. |
| 9,138,575 B2 | 9/2015 | Osypka |
| 9,149,328 B2 | 10/2015 | Dimmer et al. |
| 9,149,329 B2 | 10/2015 | Azamian et al. |
| 9,155,589 B2 | 10/2015 | Jenson |
| 9,162,046 B2 | 10/2015 | Hill et al. |
| 9,168,093 B2 | 10/2015 | Mihalik et al. |

(56) References Cited

U.S. PATENT DOCUMENTS

| | | |
|---|---|---|
| 9,168,094 B2 | 10/2015 | Lee et al. |
| 9,173,586 B2 | 11/2015 | Deno et al. |
| 9,174,050 B2 | 11/2015 | Mathur et al. |
| 9,179,974 B2 | 11/2015 | Ku et al. |
| 9,186,060 B2 | 11/2015 | De Graff et al. |
| 9,186,211 B2 | 11/2015 | Mathur et al. |
| 9,192,435 B2 | 11/2015 | Jenson |
| 9,204,929 B2 | 12/2015 | Solis |
| 9,220,433 B2 | 12/2015 | Ditter et al. |
| 9,220,558 B2 | 12/2015 | Willard |
| 9,237,920 B2 | 1/2016 | Leo et al. |
| 9,254,163 B2 | 2/2016 | Paul et al. |
| 9,265,575 B2 | 2/2016 | Coe |
| 9,271,782 B2 | 3/2016 | Paul et al. |
| 9,272,132 B2 | 3/2016 | Laufer et al. |
| 9,283,026 B2 | 3/2016 | Paul et al. |
| 9,283,374 B2 | 3/2016 | Hollett et al. |
| 9,289,255 B2 | 3/2016 | Deem et al. |
| 9,314,208 B1 | 4/2016 | Altmann et al. |
| 9,320,565 B2 | 4/2016 | Schneider et al. |
| 9,326,816 B2 | 5/2016 | Srivastava |
| 9,333,031 B2 | 5/2016 | Salahieh et al. |
| 9,333,033 B2 | 5/2016 | Gliner |
| 9,333,113 B2 | 5/2016 | Abunassar et al. |
| 9,339,325 B2 | 5/2016 | Miller et al. |
| 9,339,331 B2 | 5/2016 | Tegg et al. |
| 9,345,538 B2 | 5/2016 | Deem et al. |
| 9,345,540 B2 | 5/2016 | Maillin et al. |
| 9,375,154 B2 | 6/2016 | Wang |
| 9,393,068 B1 | 7/2016 | Leo et al. |
| 9,402,684 B2 | 8/2016 | Mathur et al. |
| 9,408,661 B2 | 8/2016 | Haverkost |
| 9,408,663 B2 | 8/2016 | Hall et al. |
| 9,414,885 B2 | 8/2016 | Willard |
| 9,433,428 B2 | 9/2016 | Hakala et al. |
| 9,452,017 B2 | 9/2016 | Chang et al. |
| 9,463,062 B2 | 10/2016 | Smith et al. |
| 9,463,066 B2 | 10/2016 | Deem et al. |
| 9,504,518 B2 | 11/2016 | Condie et al. |
| 9,510,777 B2 | 12/2016 | Hezi-Yamit et al. |
| 9,510,901 B2 | 12/2016 | Steinke et al. |
| 9,522,036 B2 | 12/2016 | Panescu et al. |
| 9,545,216 B2 | 1/2017 | D'Angelo et al. |
| 9,554,848 B2 | 1/2017 | Stewart et al. |
| 9,554,850 B2 | 1/2017 | Lee et al. |
| 9,566,114 B2 | 2/2017 | Mathur |
| 9,579,149 B2 | 2/2017 | Kelly et al. |
| 9,585,587 B2 | 3/2017 | Roy et al. |
| 9,592,386 B2 | 3/2017 | Mathur et al. |
| 9,597,148 B2 | 3/2017 | Olson |
| 9,655,677 B2 | 5/2017 | Salahieh et al. |
| 9,662,171 B2 | 5/2017 | Dimmer et al. |
| 9,687,166 B2 | 6/2017 | Subramaniam et al. |
| 9,700,372 B2 | 7/2017 | Schaer |
| 9,713,730 B2 | 7/2017 | Mathur et al. |
| 9,717,557 B2 | 8/2017 | Salahieh et al. |
| 9,717,559 B2 | 8/2017 | Ditter et al. |
| 9,723,998 B2 | 8/2017 | Wang |
| 9,743,984 B1 | 8/2017 | Curley et al. |
| 9,750,560 B2 | 9/2017 | Ballakur et al. |
| 9,757,193 B2 | 9/2017 | Zarins et al. |
| 9,795,442 B2 | 10/2017 | Salahieh et al. |
| 9,795,780 B2 | 10/2017 | Serna et al. |
| 9,820,799 B2 | 11/2017 | Schwagten et al. |
| 9,827,041 B2 | 11/2017 | Zarins et al. |
| 9,848,795 B2 | 12/2017 | Mareckim et al. |
| 9,848,948 B2 | 12/2017 | Fuimaono et al. |
| 9,855,096 B2 | 1/2018 | Chang et al. |
| 9,872,717 B2 | 1/2018 | Bencini et al. |
| 9,999,461 B2 | 6/2018 | Azamian et al. |
| 10,064,674 B2 | 9/2018 | Azamian et al. |
| 10,070,911 B2 | 9/2018 | Azamian et al. |
| 2001/0029393 A1 | 10/2001 | Tierney et al. |
| 2001/0037081 A1 | 11/2001 | Heiner |
| 2002/0016565 A1 | 2/2002 | Zadno-Azizi et al. |
| 2002/0087208 A1 | 7/2002 | Koblish et al. |
| 2002/0147480 A1 | 10/2002 | Mamayek |
| 2002/0183735 A1 | 12/2002 | Edwards et al. |
| 2003/0060813 A1 | 3/2003 | Loeb et al. |
| 2003/0065371 A1 | 4/2003 | Satake |
| 2003/0088240 A1 | 5/2003 | Saadat |
| 2003/0120271 A1 | 6/2003 | Burnside et al. |
| 2003/0149368 A1 | 8/2003 | Hennemann et al. |
| 2003/0195501 A1 | 10/2003 | Sherman et al. |
| 2004/0019364 A1 | 1/2004 | Kieval et al. |
| 2004/0082859 A1 | 4/2004 | Schaer |
| 2004/0082947 A1 | 4/2004 | Oral et al. |
| 2004/0254572 A1 | 12/2004 | McIntyre et al. |
| 2004/0260328 A1 | 12/2004 | Zvuloni et al. |
| 2004/0267191 A1 | 12/2004 | Gifford, III et al. |
| 2004/0267250 A1 | 12/2004 | Yon et al. |
| 2005/0015084 A1 | 1/2005 | Hill, III et al. |
| 2005/0033136 A1 | 2/2005 | Govari et al. |
| 2005/0033137 A1 | 2/2005 | Oral et al. |
| 2005/0049293 A1 | 3/2005 | Lautt |
| 2005/0215990 A1 | 9/2005 | Govari |
| 2005/0288661 A1 | 12/2005 | Sauvageau et al. |
| 2005/0288730 A1 | 12/2005 | Deem et al. |
| 2006/0025821 A1 | 2/2006 | Gelfand et al. |
| 2006/0089637 A1 | 4/2006 | Wernet et al. |
| 2006/0111704 A1 | 5/2006 | Brenneman et al. |
| 2006/0122508 A1 | 6/2006 | Slayton et al. |
| 2006/0167498 A1 | 7/2006 | Di Lorenzo |
| 2006/0212076 A1 | 9/2006 | Demaris et al. |
| 2006/0235286 A1 | 10/2006 | Stone et al. |
| 2006/0258978 A1 | 11/2006 | Vanney |
| 2006/0265014 A1 | 11/2006 | Demaris et al. |
| 2006/0271111 A1 | 11/2006 | Demaris et al. |
| 2007/0060971 A1 | 3/2007 | Glasberg et al. |
| 2007/0083239 A1 | 4/2007 | Demaris et al. |
| 2007/0106293 A1 | 5/2007 | Oral et al. |
| 2007/0129720 A1 | 6/2007 | Demaris et al. |
| 2007/0129760 A1 | 6/2007 | Demaris et al. |
| 2007/0142879 A1 | 6/2007 | Greenberg |
| 2007/0265563 A1 | 11/2007 | Heuser |
| 2007/0265687 A1 | 11/2007 | Deem et al. |
| 2007/0287994 A1 | 12/2007 | Patel |
| 2008/0009925 A1 | 1/2008 | Abboud et al. |
| 2008/0027358 A1 | 1/2008 | Gregersen et al. |
| 2008/0140074 A1 | 6/2008 | Horne et al. |
| 2008/0161803 A1 | 7/2008 | Oral et al. |
| 2008/0183237 A1 | 7/2008 | Errico et al. |
| 2008/0188912 A1 | 8/2008 | Stone et al. |
| 2008/0195171 A1 | 8/2008 | Sharma |
| 2008/0213331 A1 | 9/2008 | Gelfand et al. |
| 2008/0243071 A1 | 10/2008 | Quijano et al. |
| 2008/0255642 A1 | 10/2008 | Zarins et al. |
| 2008/0294096 A1* | 11/2008 | Uber, III ............... A61M 5/142 604/66 |
| 2008/0300587 A1 | 12/2008 | Anderson |
| 2008/0312642 A1 | 12/2008 | Kania et al. |
| 2008/0312643 A1 | 12/2008 | Kania et al. |
| 2008/0312714 A1 | 12/2008 | Pasricha et al. |
| 2009/0036948 A1 | 2/2009 | Levin et al. |
| 2009/0062873 A1 | 3/2009 | Wu et al. |
| 2009/0062874 A1 | 3/2009 | Tracey et al. |
| 2009/0076409 A1 | 3/2009 | Wu et al. |
| 2009/0093801 A1 | 4/2009 | Crossman |
| 2009/0118777 A1 | 5/2009 | Iki et al. |
| 2009/0118780 A1 | 5/2009 | DiLorenzo |
| 2009/0131993 A1 | 5/2009 | Rousso et al. |
| 2009/0247933 A1 | 10/2009 | Maor et al. |
| 2009/0254143 A1 | 10/2009 | Tweden et al. |
| 2009/0275827 A1 | 11/2009 | Aiken et al. |
| 2009/0275996 A1 | 11/2009 | Burnes et al. |
| 2009/0275997 A1 | 11/2009 | Faltys et al. |
| 2009/0324701 A1 | 12/2009 | Williams |
| 2010/0010567 A1 | 1/2010 | Deem et al. |
| 2010/0030210 A1 | 2/2010 | Paulus |
| 2010/0057161 A1 | 3/2010 | Machado et al. |
| 2010/0076425 A1 | 3/2010 | Carroux |
| 2010/0106207 A1 | 4/2010 | Dobak, III |
| 2010/0137860 A1 | 6/2010 | Demaris et al. |
| 2010/0137952 A1 | 6/2010 | Demaris et al. |

(56) References Cited

U.S. PATENT DOCUMENTS

| | | |
|---|---|---|
| 2010/0168731 A1 | 7/2010 | Wu et al. |
| 2010/0168739 A1 | 7/2010 | Wu et al. |
| 2010/0174282 A1 | 7/2010 | Demaris et al. |
| 2010/0191112 A1 | 7/2010 | Demaris et al. |
| 2010/0222851 A1 | 9/2010 | Deem et al. |
| 2010/0249773 A1 | 9/2010 | Clark et al. |
| 2010/0249859 A1 | 9/2010 | DiLorenzo |
| 2010/0256629 A1* | 10/2010 | Wylie ............... A61B 18/1492 606/41 |
| 2010/0268307 A1 | 10/2010 | Demaris et al. |
| 2010/0286684 A1 | 11/2010 | Hata et al. |
| 2011/0029037 A1 | 2/2011 | Rezai |
| 2011/0060324 A1 | 3/2011 | Wu et al. |
| 2011/0092781 A1 | 4/2011 | Gertner |
| 2011/0092880 A1 | 4/2011 | Gertner |
| 2011/0098762 A1 | 4/2011 | Rezai |
| 2011/0112400 A1 | 5/2011 | Emery et al. |
| 2011/0118726 A1 | 5/2011 | De La Rama et al. |
| 2011/0118747 A1 | 5/2011 | Pasricha et al. |
| 2011/0118812 A1 | 5/2011 | Pasricha et al. |
| 2011/0137298 A1 | 6/2011 | Nguyen et al. |
| 2011/0144637 A1 | 6/2011 | Pageard et al. |
| 2011/0152857 A1 | 6/2011 | Ingle |
| 2011/0152974 A1 | 6/2011 | Rezai et al. |
| 2011/0160514 A1 | 6/2011 | Long et al. |
| 2011/0166499 A1 | 7/2011 | Demaris et al. |
| 2011/0168739 A1 | 7/2011 | Brouwer |
| 2011/0172527 A1 | 7/2011 | Gertner |
| 2011/0178570 A1 | 7/2011 | Demaris |
| 2011/0200171 A1 | 8/2011 | Beetel et al. |
| 2011/0202098 A1 | 8/2011 | Demaris et al. |
| 2011/0207758 A1 | 8/2011 | Sobotka et al. |
| 2011/0208096 A1 | 8/2011 | Demaris et al. |
| 2011/0208173 A1 | 8/2011 | Sobotka et al. |
| 2011/0208175 A1 | 8/2011 | Sobotka et al. |
| 2011/0230939 A1 | 9/2011 | Weinstock |
| 2011/0257523 A1 | 10/2011 | Hastings et al. |
| 2011/0257561 A1 | 10/2011 | Gertner et al. |
| 2011/0257562 A1 | 10/2011 | Schaer |
| 2011/0257564 A1 | 10/2011 | Demaris et al. |
| 2011/0257641 A1 | 10/2011 | Hastings et al. |
| 2011/0257647 A1 | 10/2011 | Mayse et al. |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270046 A1 | 11/2011 | Paul et al. |
| 2011/0270238 A1 | 11/2011 | Rizq et al. |
| 2011/0276047 A1 | 11/2011 | Sklar et al. |
| 2011/0301664 A1 | 12/2011 | Rezai |
| 2011/0306851 A1 | 12/2011 | Wang |
| 2011/0307034 A1 | 12/2011 | Hastings et al. |
| 2011/0313417 A1 | 12/2011 | De La Rama et al. |
| 2012/0016256 A1 | 1/2012 | Mabary et al. |
| 2012/0022409 A1 | 1/2012 | Gertner et al. |
| 2012/0029496 A1 | 2/2012 | Smith |
| 2012/0029505 A1 | 2/2012 | Jenson |
| 2012/0029511 A1 | 2/2012 | Smith et al. |
| 2012/0029512 A1 | 2/2012 | Willard et al. |
| 2012/0065494 A1 | 3/2012 | Gertner et al. |
| 2012/0065554 A1 | 3/2012 | Pikus |
| 2012/0089047 A1 | 4/2012 | Ryba et al. |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0116383 A1 | 5/2012 | Mauch et al. |
| 2012/0116486 A1 | 5/2012 | Naga et al. |
| 2012/0123276 A1 | 5/2012 | Govari et al. |
| 2012/0130289 A1 | 5/2012 | Demaris et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136346 A1 | 5/2012 | Condie et al. |
| 2012/0136348 A1 | 5/2012 | Condie et al. |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143177 A1 | 6/2012 | Avitall |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157992 A1 | 6/2012 | Smith et al. |
| 2012/0158101 A1 | 6/2012 | Stone et al. |
| 2012/0158104 A1 | 6/2012 | Huynh et al. |
| 2012/0157988 A1 | 7/2012 | Stone et al. |
| 2012/0172723 A1 | 7/2012 | Gertner |
| 2012/0191083 A1 | 7/2012 | Moll et al. |
| 2012/0197246 A1 | 8/2012 | Mauch |
| 2012/0221082 A1 | 8/2012 | Khanna |
| 2012/0253239 A1 | 10/2012 | Gertner et al. |
| 2012/0271302 A1 | 10/2012 | Behl et al. |
| 2012/0303098 A1 | 11/2012 | Perryman |
| 2012/0310239 A1 | 12/2012 | Stewart et al. |
| 2013/0006232 A1 | 1/2013 | Pellegrino et al. |
| 2013/0012866 A1 | 1/2013 | Deem et al. |
| 2013/0012867 A1 | 1/2013 | Demarais et al. |
| 2013/0023802 A1 | 1/2013 | McIntosh et al. |
| 2013/0035681 A1 | 2/2013 | Subramaniam et al. |
| 2013/0053792 A1 | 2/2013 | Fischell et al. |
| 2013/0053821 A1 | 2/2013 | Fischell et al. |
| 2013/0066308 A1 | 3/2013 | Landman |
| 2013/0066316 A1 | 3/2013 | Steinke et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1* | 4/2013 | Smith ............... A61B 18/1492 606/41 |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0110106 A1 | 5/2013 | Richardson |
| 2013/0116505 A1 | 5/2013 | Seidel |
| 2013/0116685 A1 | 5/2013 | Deem et al. |
| 2013/0123770 A1 | 5/2013 | Smith |
| 2013/0165923 A1 | 6/2013 | Mathur et al. |
| 2013/0165924 A1 | 6/2013 | Mathur et al. |
| 2013/0172875 A1 | 7/2013 | Govari et al. |
| 2013/0172877 A1 | 7/2013 | Subramaniam et al. |
| 2013/0197555 A1 | 8/2013 | Schaer |
| 2013/0197614 A1 | 8/2013 | Gustus et al. |
| 2013/0211396 A1 | 8/2013 | Sverdlik et al. |
| 2013/0231658 A1 | 9/2013 | Wang et al. |
| 2013/0231659 A1 | 9/2013 | Hill et al. |
| 2013/0274658 A1 | 10/2013 | Steinke et al. |
| 2013/0289678 A1 | 10/2013 | Clark et al. |
| 2013/0289686 A1 | 10/2013 | Masson et al. |
| 2013/0304052 A1 | 11/2013 | Rizq et al. |
| 2013/0304054 A1 | 11/2013 | Zarins et al. |
| 2013/0345670 A1 | 12/2013 | Rajagopalan et al. |
| 2014/0005591 A1 | 1/2014 | Melder et al. |
| 2014/0012251 A1 | 1/2014 | Himmelstein et al. |
| 2014/0012253 A1 | 1/2014 | Mathur |
| 2014/0025069 A1 | 1/2014 | Willard et al. |
| 2014/0031727 A1 | 1/2014 | Warnking |
| 2014/0039358 A1 | 2/2014 | Zhou et al. |
| 2014/0046313 A1 | 2/2014 | Pederson et al. |
| 2014/0058377 A1 | 2/2014 | Deem et al. |
| 2014/0067029 A1 | 3/2014 | Schauer et al. |
| 2014/0074076 A1 | 3/2014 | Gertner |
| 2014/0081254 A1 | 3/2014 | Rudie |
| 2014/0088575 A1 | 3/2014 | Loeb |
| 2014/0088585 A1 | 3/2014 | Hill et al. |
| 2014/0110296 A1 | 3/2014 | Terzibashian |
| 2014/0094688 A1 | 4/2014 | Tegg et al. |

(56) References Cited

U.S. PATENT DOCUMENTS

| | | |
|---|---|---|
| 2014/0094789 A1 | 4/2014 | Brannan |
| 2014/0094797 A1 | 4/2014 | Brannan |
| 2014/0121537 A1 | 5/2014 | Aeby et al. |
| 2014/0121568 A1 | 5/2014 | Weng et al. |
| 2014/0128859 A1 | 5/2014 | Lee |
| 2014/0135715 A1 | 5/2014 | Lambert et al. |
| 2014/0163652 A1 | 6/2014 | Witzel et al. |
| 2014/0171936 A1 | 6/2014 | Govari et al. |
| 2014/0180196 A1 | 6/2014 | Stone et al. |
| 2014/0187619 A1 | 7/2014 | Pasricha et al. |
| 2014/0188103 A1 | 7/2014 | Millett |
| 2014/0194784 A1 | 7/2014 | Gertner |
| 2014/0200478 A1 | 7/2014 | Phan et al. |
| 2014/0200489 A1 | 7/2014 | Behar et al. |
| 2014/0200578 A1 | 7/2014 | Groff et al. |
| 2014/0207136 A1 | 7/2014 | De La Rama et al. |
| 2014/0214018 A1 | 7/2014 | Behar et al. |
| 2014/0228713 A1 | 8/2014 | Thao et al. |
| 2014/0243807 A1 | 8/2014 | Mergolis |
| 2014/0243809 A1 | 8/2014 | Gelfand et al. |
| 2014/0249524 A1 | 9/2014 | Kocur |
| 2014/0257266 A1 | 9/2014 | Kasprzyk et al. |
| 2014/0276707 A1 | 9/2014 | Jaxx |
| 2014/0276752 A1 | 9/2014 | Wang et al. |
| 2014/0276764 A1 | 9/2014 | Shuman et al. |
| 2014/0276787 A1 | 9/2014 | Wang et al. |
| 2014/0276811 A1 | 9/2014 | Koblish et al. |
| 2014/0296846 A1 | 10/2014 | Huszar et al. |
| 2014/0296902 A1 | 10/2014 | Huszar et al. |
| 2014/0303617 A1 | 10/2014 | Shimada |
| 2014/0309579 A1 | 10/2014 | Rubinsky et al. |
| 2014/0316254 A1 | 10/2014 | Eversull et al. |
| 2014/0336639 A1 | 11/2014 | Young et al. |
| 2014/0350551 A1 | 11/2014 | Raatikka et al. |
| 2014/0350553 A1 | 11/2014 | Okuyama |
| 2014/0358136 A1 | 12/2014 | Kelly et al. |
| 2014/0364715 A1 | 12/2014 | Hauck |
| 2014/0364848 A1 | 12/2014 | Heimbecher et al. |
| 2014/0378962 A1 | 12/2014 | Anderson et al. |
| 2014/0378966 A1 | 12/2014 | Haverkost et al. |
| 2014/0378967 A1 | 12/2014 | Willard et al. |
| 2014/0378968 A1 | 12/2014 | Sutermeister et al. |
| 2015/0005764 A1 | 1/2015 | Hanson et al. |
| 2015/0005766 A1 | 1/2015 | Rioux et al. |
| 2015/0018818 A1 | 1/2015 | Willard et al. |
| 2015/0018819 A1 | 1/2015 | Sutermeister |
| 2015/0018820 A1 | 1/2015 | Cao et al. |
| 2015/0018821 A1 | 1/2015 | Zarins et al. |
| 2015/0018904 A1 | 1/2015 | Lafontaine |
| 2015/0025525 A1 | 1/2015 | Willard et al. |
| 2015/0025533 A1 | 1/2015 | Groff et al. |
| 2015/0025605 A1 | 1/2015 | Kaplan et al. |
| 2015/0045728 A1 | 2/2015 | Heuser |
| 2015/0045787 A1 | 2/2015 | Bloom |
| 2015/0051595 A1 | 2/2015 | Margolis |
| 2015/0057654 A1 | 2/2015 | Leung et al. |
| 2015/0057655 A1 | 2/2015 | Osypka |
| 2015/0057656 A1 | 2/2015 | Gupta et al. |
| 2015/0066017 A1 | 3/2015 | Desai |
| 2015/0066023 A1 | 3/2015 | Anderson et al. |
| 2015/0073409 A1 | 3/2015 | Watson et al. |
| 2015/0080875 A1 | 3/2015 | Kasprzyk et al. |
| 2015/0080882 A1 | 3/2015 | Skinner et al. |
| 2015/0080883 A1 | 3/2015 | Haverkost et al. |
| 2015/0105770 A1 | 4/2015 | Amit |
| 2015/0105772 A1 | 4/2015 | Hill et al. |
| 2015/0105773 A1 | 4/2015 | Weber et al. |
| 2015/0105774 A1 | 4/2015 | Lindquist et al. |
| 2015/0112328 A1 | 4/2015 | Willard et al. |
| 2015/0112329 A1 | 4/2015 | Ng |
| 2015/0112331 A1 | 4/2015 | Olson et al. |
| 2015/0119870 A1 | 4/2015 | Rudie |
| 2015/0119875 A1 | 4/2015 | Fischell |
| 2015/0119876 A1 | 4/2015 | Willard |
| 2015/0119877 A1 | 4/2015 | Jameson |
| 2015/0119878 A1 | 4/2015 | Heisel et al. |
| 2015/0119882 A1 | 4/2015 | Cao et al. |
| 2015/0126996 A1 | 5/2015 | Tegg |
| 2015/0141785 A1 | 5/2015 | Hayam et al. |
| 2015/0141978 A1 | 5/2015 | Subramaniam et al. |
| 2015/0141982 A1 | 5/2015 | Lee |
| 2015/0150624 A1 | 6/2015 | Petersohn |
| 2015/0157382 A1 | 6/2015 | Avitall et al. |
| 2015/0157400 A1 | 6/2015 | Gelbart et al. |
| 2015/0157401 A1 | 6/2015 | Falwell et al. |
| 2015/0157402 A1 | 6/2015 | Kunis et al. |
| 2015/0190194 A1 | 7/2015 | Weber et al. |
| 2015/0190195 A1 | 7/2015 | Hanson et al. |
| 2015/0196354 A1 | 7/2015 | Haverkost et al. |
| 2015/0196356 A1 | 7/2015 | Kauphusman et al. |
| 2015/0209107 A1 | 7/2015 | Rudie et al. |
| 2015/0216591 A1 | 8/2015 | Cao et al. |
| 2015/0223866 A1 | 8/2015 | Buelna et al. |
| 2015/0230859 A1 | 8/2015 | Mauch |
| 2015/0238247 A1 | 8/2015 | Shikhman et al. |
| 2015/0238249 A1 | 8/2015 | Edmunds et al. |
| 2015/0238251 A1 | 8/2015 | Shikhman et al. |
| 2015/0257825 A1 | 9/2015 | Kelly et al. |
| 2015/0257929 A1 | 9/2015 | Brian, III et al. |
| 2015/0265334 A1 | 9/2015 | Franke et al. |
| 2015/0265339 A1 | 9/2015 | Lindquist et al. |
| 2015/0290427 A1 | 10/2015 | Warnking |
| 2015/0297281 A1 | 10/2015 | Sutermeister et al. |
| 2015/0297292 A1 | 10/2015 | Sutermeister et al. |
| 2015/0327923 A1 | 11/2015 | Just et al. |
| 2015/0342491 A1 | 12/2015 | Marecki et al. |
| 2015/0342673 A1 | 12/2015 | Squire et al. |
| 2015/0342675 A1 | 12/2015 | Highsmith |
| 2015/0351652 A1 | 12/2015 | Marecki et al. |
| 2015/0359589 A1 | 12/2015 | Mauch et al. |
| 2015/0366508 A1 | 12/2015 | Chou et al. |
| 2015/0366608 A1 | 12/2015 | Weber et al. |
| 2015/0374427 A1 | 12/2015 | Goertzen et al. |
| 2016/0000498 A1 | 1/2016 | Zarins et al. |
| 2016/0008066 A1 | 1/2016 | Kaplan et al. |
| 2016/0016016 A1 | 1/2016 | Taylor et al. |
| 2016/0022353 A1 | 1/2016 | Forsyth et al. |
| 2016/0030773 A1 | 2/2016 | Burdette |
| 2016/0051321 A1 | 2/2016 | Salaheih et al. |
| 2016/0051465 A1 | 2/2016 | Azamian et al. |
| 2016/0058502 A1 | 3/2016 | Clark et al. |
| 2016/0058503 A1 | 3/2016 | Tunev et al. |
| 2016/0058505 A1 | 3/2016 | Condie et al. |
| 2016/0066988 A1 | 3/2016 | Chang et al. |
| 2016/0066992 A1 | 3/2016 | Mathur |
| 2016/0081746 A1 | 3/2016 | Solis |
| 2016/0095642 A1 | 4/2016 | Deno et al. |
| 2016/0095656 A1 | 4/2016 | Peled et al. |
| 2016/0106984 A1 | 4/2016 | Mathur et al. |
| 2016/0113713 A1 | 4/2016 | Ku et al. |
| 2016/0120597 A1 | 5/2016 | Azamian et al. |
| 2016/0128767 A1 | 5/2016 | Azamian et al. |
| 2016/0129223 A1 | 5/2016 | Kirschenman |
| 2016/0135879 A1 | 5/2016 | Beasley et al. |
| 2016/0143696 A1 | 5/2016 | Govari et al. |
| 2016/0175041 A1 | 6/2016 | Govari et al. |
| 2016/0175044 A1 | 6/2016 | Abunassar et al. |
| 2016/0184011 A1 | 6/2016 | Krishnan |
| 2016/0199116 A1 | 7/2016 | Jameson et al. |
| 2016/0199127 A1 | 7/2016 | Prutchi |
| 2016/0213262 A1 | 7/2016 | Ghaffari et al. |
| 2016/0223704 A1 | 8/2016 | Haverkost et al. |
| 2016/0249978 A1 | 9/2016 | Lee et al. |
| 2016/0256683 A1 | 9/2016 | Butera et al. |
| 2016/0262821 A1 | 9/2016 | Azamian et al. |
| 2016/0262833 A1 | 9/2016 | Rudie |
| 2016/0278853 A1 | 9/2016 | Ogle et al. |
| 2016/0287114 A1 | 10/2016 | Srivastava |
| 2016/0296747 A1 | 10/2016 | Glenn et al. |
| 2016/0331294 A1 | 11/2016 | Imran et al. |
| 2016/0331459 A1 | 11/2016 | Townley et al. |
| 2016/0335263 A1 | 11/2016 | Yin et al. |
| 2016/0367316 A1 | 12/2016 | Smith et al. |
| 2016/0374754 A1 | 12/2016 | Asirvatham et al. |

(56) References Cited

U.S. PATENT DOCUMENTS

| | | |
|---|---|---|
| 2016/0375235 A1 | 12/2016 | Schoenle et al. |
| 2017/0000560 A1 | 1/2017 | Mathur et al. |
| 2017/0007810 A1 | 1/2017 | Parsons et al. |
| 2017/0014639 A1 | 1/2017 | Preston et al. |
| 2017/0035341 A1 | 2/2017 | Nagale et al. |
| 2017/0035497 A1 | 2/2017 | Nagale et al. |
| 2017/0042613 A1 | 2/2017 | Schultheis et al. |
| 2017/0049513 A1 | 2/2017 | Cosman, Jr. et al. |
| 2017/0056087 A1 | 3/2017 | Buckley et al. |
| 2017/0056105 A1 | 3/2017 | Steinke et al. |
| 2017/0086907 A1 | 3/2017 | Satake |
| 2017/0105871 A1 | 4/2017 | Nierich |
| 2017/0128129 A1 | 5/2017 | Kelly et al. |
| 2017/0135758 A1 | 5/2017 | Danek et al. |
| 2017/0143405 A1 | 5/2017 | Rooks et al. |
| 2017/0143412 A1 | 5/2017 | O'Fallon |
| 2017/0143421 A1 | 5/2017 | Mayse et al. |
| 2017/0157366 A1 | 6/2017 | Assif et al. |
| 2017/0164999 A1 | 6/2017 | Hettel |
| 2017/0231694 A1 | 8/2017 | Mathur et al. |
| 2017/0252560 A1 | 9/2017 | Imran |
| 2017/0259057 A1 | 9/2017 | Muessig et al. |
| 2017/0296254 A1 | 10/2017 | Mitsumune et al. |
| 2017/0296264 A1 | 10/2017 | Wang |
| 2017/0311829 A1 | 11/2017 | Beeckler et al. |
| 2017/0311893 A1 | 11/2017 | Beeckler et al. |
| 2017/0312022 A1 | 11/2017 | Beeckler et al. |
| 2017/0312026 A1 | 11/2017 | Harlev et al. |
| 2017/0312029 A1 | 11/2017 | Schaer |
| 2017/0333123 A1 | 11/2017 | Liu |
| 2017/0340383 A1 | 11/2017 | Bloom et al. |
| 2017/0348049 A1 | 12/2017 | Vrba et al. |
| 2017/0354449 A1 | 12/2017 | Avitall et al. |
| 2017/0354462 A1 | 12/2017 | Dong et al. |
| 2017/0354463 A1 | 12/2017 | Mori |
| 2018/0036072 A1 | 2/2018 | Mathur et al. |
| 2018/0036073 A1 | 2/2018 | Kaplan et al. |
| 2018/0036075 A1 | 2/2018 | Gelbart et al. |
| 2018/0036076 A1 | 2/2018 | Gelbart et al. |
| 2018/0036077 A1 | 2/2018 | Gelbart et al. |

FOREIGN PATENT DOCUMENTS

| | | |
|---|---|---|
| EP | 1233718 B1 | 8/2002 |
| EP | 1485034 B1 | 12/2004 |
| EP | 3023052 | 5/2016 |
| EP | 3023069 | 5/2016 |
| EP | 3040042 | 7/2016 |
| JP | 60-76937 | 5/1985 |
| JP | 2001/37868 | 2/2001 |
| JP | 2009/534123 | 9/2009 |
| RU | 2277381 | 6/2006 |
| RU | 2421163 | 6/2011 |
| WO | WO 93/02743 | 2/1993 |
| WO | WO 00/10475 | 3/2000 |
| WO | WO 00/019992 | 4/2000 |
| WO | WO 02/007601 | 1/2002 |
| WO | WO 02/70039 | 9/2002 |
| WO | WO 2005/023081 | 3/2005 |
| WO | WO 2007/015139 | 2/2007 |
| WO | WO 2007/018788 | 2/2007 |
| WO | WO 2006/029257 | 4/2008 |
| WO | WO 2007/018788 | 9/2008 |
| WO | WO 2009/082569 | 7/2009 |
| WO | WO 2009/090440 | 7/2009 |
| WO | WO 2009/137819 | 11/2009 |
| WO | WO 2009/149390 | 12/2009 |
| WO | WO 2010/111400 | 9/2010 |
| WO | WO 2011/046880 | 4/2011 |
| WO | WO 2011/057157 | 5/2011 |
| WO | WO 2011/060200 | 5/2011 |
| WO | WO 2011/130531 | 10/2011 |
| WO | WO 2011/139589 | 11/2011 |
| WO | WO 2011/139589 A2 | 11/2011 |
| WO | WO 2012/019156 | 2/2012 |
| WO | WO 2012/025245 | 3/2012 |
| WO | WO 2012/025246 | 3/2012 |
| WO | WO 2012/061159 | 5/2012 |
| WO | WO 2012/099974 | 7/2012 |
| WO | WO 2012/149205 | 11/2012 |
| WO | WO 2013/086461 | 6/2013 |
| WO | WO 2013/111136 | 8/2013 |
| WO | WO 2012/068471 | 9/2013 |
| WO | WO 2013/130655 | 9/2013 |
| WO | WO 2013/134133 | 9/2013 |
| WO | WO 2013/134479 | 9/2013 |
| WO | WO 2013/134541 | 9/2013 |
| WO | WO 2013/134543 | 9/2013 |
| WO | WO 2013/159066 | 10/2013 |
| WO | WO 2013/162722 | 10/2013 |
| WO | WO 2014/022436 | 2/2014 |
| WO | WO 2014/026055 | 2/2014 |
| WO | WO 2014/055997 | 4/2014 |
| WO | WO 2014/091401 | 6/2014 |
| WO | WO 2014/102756 | 7/2014 |
| WO | WO 2014/102760 | 7/2014 |
| WO | WO 2014/197625 | 12/2014 |
| WO | WO 2015/069446 | 5/2015 |
| WO | WO 2015/069887 | 5/2015 |
| WO | WO 2015/170281 | 11/2015 |
| WO | WO 2015/183952 | 12/2015 |
| WO | WO 2015/191938 | 12/2015 |
| WO | WO 2016/007851 | 1/2016 |
| WO | WO 2016/054379 | 4/2016 |
| WO | WO 2016/075536 | 5/2016 |
| WO | WO 2016/084081 | 6/2016 |
| WO | WO 2016/090175 | 6/2016 |
| WO | WO 2016/118934 | 7/2016 |
| WO | WO 2016/123390 | 8/2016 |
| WO | WO 2016/151595 | 9/2016 |
| WO | WO 2016/179527 | 11/2016 |
| WO | WO 2016/183468 | 11/2016 |
| WO | WO 2016/205431 | 12/2016 |
| WO | WO 2017/062753 | 4/2017 |
| WO | WO 2017/085102 | 5/2017 |
| WO | WO 2017/095689 | 6/2017 |
| WO | WO 2017/103105 | 6/2017 |
| WO | WO 2017/118986 | 7/2017 |
| WO | WO 2017/194557 | 11/2017 |
| WO | WO 2017/203380 | 11/2017 |
| WO | WO 2018/202877 | 11/2018 |

OTHER PUBLICATIONS

Agah, Ramtin et al., "Rate Process Model for Arterial Tissue Thermal Damage: Implications on Vessel Photocoagulation," Lasers in Surgery and Medicine, vol. 15, pp. 176-184 (1994).

Anderson, Erling A. et al, "Hyperinsulinemia Produces both Sympathetic Neural Activation and Vasodilation in Normal Humans," Journal of Clinical Investigation, vol. 87, pp. 2246-2252 (1991).

Atherton, Daniel S. et al., « Micro-anatomy of the Renal Sympathetic Nervous System: A Human Postmortem Histologic Study, » Clinical Anatomy, vol. 25, pp. 628-633 (2012).

Aytac, Suat K. et al., «Correlation Between the Diameter of the Main Renal Artery and the Presence of an Accessory Renal Artery, » Journal of Ultrasound in Medicine, vol. 22, pp. 433-439 (2003).

Bergman, Richard N. et al., « Direct enhancement of insulin secretion by vagal stimulation of the isolated pancreas, » American Journal of Physiology, vol. 225, No. 2, pp. 481-486 (1973).

Bernal-Mizrachi, Afferent Vagal Nerve Pathway Links Hepatic Ppar Activation to Glucocorticoid-Induced Insulin Resistance and Hypertension; Cell Metabolism 5, Feb. 2007; pp. 91-102.

Berthoud, H. R. et al., « Evidence for a role of the gastric, coeliac and hepatic branches in vagally stimulated insulin secretion in the rat, Journal of the Autonomic Nervous System, vol. 7, pp. 97-110 (1983).

Berthoud, Hans-Rudolf, "Anatomy and Function of Sensory Hepatic Nerves," The Anatomical Record Part A, vol. 280A, pp. 827-835 (2004).

Borrelli, M.J. et al., « Time-Temperature Analysis of Cell Killing of BHK Cells Heated at Temperatures in the Range of 43.5° C. to 57.0°

(56) References Cited

OTHER PUBLICATIONS

C., International Journal of Radiation Oncology, Biology and Physics, vol. 19, No. 2, pp. 389-399 (Aug. 1990).
Brace, Christopher L. "Temperature-dependent dielectric properties of liver tissue measured during thermal ablation: Toward an improved numerical model," 30th Annual International IEEE EMBS Conference pp. 230-233 (2008).
Brandt, Mathias C. et al., « Renal Sympathetic Denervation Reduces Left Ventricular Hypertrophy and Improves Cardiac Function in Patients With Resistant Hypertension, » Journal of the American College of Cardiology, vol. 59, No. 10, pp. 901-909 (2012).
Brashers-Krug, G. "Understanding Oral Diabetes Medications," Retrieved Feb. 10, 2015 from https://nfb.org/images/nfb/publications/vod/vod_22_4/vodfal0712.htm (Mar. 2, 2008).
Bruce, D.G. et al., « The effects of sympathetic nervous system activation and psychological stress on glucose metabolism and blood pressure in subjects with Type 2 (non-insulin-dependent) diabetes mellitus, Diabetologia, vol. 35, pp. 835-843 (1992).
Bruinstroop, Eveline et al., "Hypothalamic neuropeptide Y (NPY) controls hepatic VLDL-triglyceride secretion in rats via the sympathetic nervous system," Diabetes, vol. 61 (5), pp. 1043-1050 (May 2012).
Buch, Eric et al., "A Novel Method to Prevent Phrenic Nerve Injury During Catheter Ablation," Heart Rhythm, vol. 4, No. 1, pp. 95-98 (Jan. 2007).
Buijs, Ruud M. et al., « The Suprachiasmatic Nucleus Balances Sympathetic and Parasympathetic Output to Peripheral Organs through Separate Preautonomic Neurons, Journal of Comparative Neurology, vol. 464, pp. 36-48 (2003).
Bunch, T. Jared et al., "Mechanisms of Phrenic Nerve Injury During Radiofrequency Ablation at the Pulmonary Vein Orifice," Journal of Cardiovascular Electrophysiology, vol. 16, No. 12, pp. 1318-1325 (Dec. 2005).
Burdio, Fernando et al., "Research and development of a new RF-assisted device for bloodless rapid transection of the liver: Computational modeling and in vivo experiments," BioMedical Engineering Online, vol. 8, No. 6 (2009), available at http://www.biomeidcal-engineering-on line. com/content/8/1/6.
Cailotto, Cathy et al., "The suprachiasmatic nucleus controls the daily variation of plasma glucose via the autonomic output to the liver: are the clock genes involved?" European Journal of Neuroscience, vol. 22, pp. 2531-2540 (2005).
Cardin, Sylvain et al., "Effect of hepatic vagotomy on hormonal response to exercise in gluconeogenesis-inhibited rats," American Journal of Physiology—Regulatory Integrative Comparative Physiology, vol. 260, pp. R67-R72 (1991).
Cardin, Sylvain et al., "Involvement of the vagus nerves in the regulation of basal hepatic glucose production in conscious dogs," American Journal of Physiology—Endocrinology and Metabolism, vol. 283, op. E958-E964 (2002).
Carnethon, Mercedes R. et al., « Prospective Investigation of Autonomic Nervous System Function and the Development of Type 2 Diabetes, » Circulation, vol. 107, pp. 2190-2195 (2003).
Chang, Isaac A. et al., « Thermal modeling of lesion growth with radiofrequency ablation, BioMedical Engineering Online, vol. 3, No. 27 (2004), available at http://www.biomeidcal-enqineering-online.com/content/3/1/27.
Chen et al., Development and application of rodent models for type 2 diabetes, Diabetes, Obesity and Metabolism, vol. 7, 2005, pp. 307-317 (2004).
Chen, J. et al., "Hepatic electrical stimulation reduces blood glucose in diabetic rats," Neurogastroenterology & Motility vol. 22, pp. 1109-e286 (2010).
Cherrington, Alan D, "Banting Lecture 1997: Control of Glucose Uptake and Release by the Liver In Vivo," Diabetes, vol. 48, DD. 1198-1214 (May 1999).
Chinushi, Masaomi et al., "Blood Pressure and Autonomic Responses to Electrical Stimulation of the Renal Arterial Nerves Before and After Ablation of the Renal Artery," Hypertension, vol. 61, pp. 450-456 (Jan. 2, 2013).
Coad, James E., "Thermal Tissue Injury and Host Response: A Pathologist Perspective," Slide Presentation (Mar. 2008).
Coate, KC et al., "Chronic Consumption of a High-Fat/High Fructose Diet Renders the Liver Incapable of Net Hepatic Glucose Uptake," Am. J. Physiolo. Endocrinol. Metab. vol. 299, pp. E887-E898 (Sep. 2010).
Coker, Robert H. et al., « Glucoregulation During Exercise: The Role of the Neuroendocrine System, » Sports Medicine, vol. 35, No. 7, pp. 575-583 (2005).
Consiglieri, Luisa et al., "Theoretical analysis of the heat convection coefficient in large vessels and the significance for thermal ablative therapies," Physics in Medicine and Biology, vol. 487, pp. 4125-4134 (2003).
Dancygier, H. "Clinical hepatology: Principles and practice of hepatobiliary diseases"; Berlin: Springer (2009).
Davies, Justin E. et al., « First-in-man safety evaluation of renal denervation for chronic systolic heart failure: Primary outcome from REACH-Pilot study, » International Journal of Cardiology (2012).
Defronzo, Ralph A., "From the Triumvirate to the Ominous Octet: A New Paradigm for the Treatment of Type 2 Diabetes Mellitus," Diabetes, vol. 58 (Apr. 2009), pp. 773-795.
Despa, F. et al., "The relative thermal stability of tissue macromolecules and cellular structure in burn injury," Burns, vol. 31, pp. 568-577 (2005).
Dicostanzo, Catherine A. et al., Aug. 16, 2005, Role of the Hepatic Sympathetic Nerves in the Regulation of Net Hepatic Glucose Uptake and the Mediation of the Portal Glucose Signal, Am J Physiol Endocrinol Metab 290:E9-E16.
Dodge, Jr., JT et al., "'Lumen diameter of normal human coronary arteries. Influence of age, sex, anatomic variation, and left ventricular hypertrophy or dilation," Circulation, vol. 86, pp. 232-246 (1992).
Doumas, Michael et al., "Renal sympathetic denervation in hypertension," Current Opinion in Nephrology and Hypertension, vol. 20, pp. 647-653 (2011).
Esler, Murray D et al., « Renal sympathetic denervation in patients with treatment-resistant hypertension (The Symplicity HTN-2 Trial): a randomised controlled trial, » Lancet, vol. 376, pp. 1903-1909 (2010).
Flaa Arnljot et al ., "Increased sympathetic reactivity may predict insulin resistance: an 18-year follow-up study," Metabolism Clinical and Experimental, vol. 57, pp. 1422-1427 (2008).
Grassi, G. et al., "Neuroadrenergic and reflex abnormalities in patients with metabolic syndrome," Diabetologia, vol. 48, pp. 1359-1365 (2005).
Guiot, Aurelie et al., "Collateral Nervous Damages After Cryoballoon Pulmonary Vein Isolation," Journal of Cardiovascular Electrophysiology, vol. 23, No. 4, pp. 346-351 (Apr. 2012).
Haines, David E. et al., Tissue Heating During Radiofrequency Catheter Ablation—A Thermodynamic Model, PACE, vol. 12, pp. 963-976 (Jun. 1989).
Haque, Mohammad Shahidul et al, "Role of the Sympathetic Nervous System and Insulin in Enhancing Glucose Uptake in Peripheral Tissues After Intrahypothalamic Injection of Leptin in Rats," Diabetes, vol. 48, pp. 1706-1712 (1999).
Hiatt, Jonathan R. et al., "Surgical Anatomy of the Hepatic Arteries in 1000 Cases," Annals of Surgery, vol. 220, No. 1, pp. 50-52 (1994).
Huang, W.C., et al. "Renal denervation prevents and reverses hyperinsulinemia-induced hypertension in rats." Hypertension, 32:249-254 (1998).
Huggett et al., "Impact of Type 2 Diabetes Mellitus on Sympathetic Neural Mechanisms in Hypertension," Circulation, vol. 108 (Dec. 15, 2003), pp. 3097-3101.
Imai, Junta et al., "Regulation of Pancreatic β Cell Mass by Neuronal Signals from the Liver," Science, vol. 322, pp. 1250-1254 (2008).
Inomoto, Takuya et al., "Experiences of 120 microsurgical reconstructions of hepatic artery in living related liver transplantation," Surgery, vol. 119, No. 1, pp. 20-26 (Jan. 1996).
Jackson, Patricia A, "Effect of hepatic denervation on the counterregulatory response to insulin-induced hypoglycemia in the dog,"

(56) References Cited

OTHER PUBLICATIONS

American Journal of Physiology—Endocrinology and Metabolism, vol. 279, pp. E1249-E1257 (2000).
Jones, R. M. et al., « The hepatic artery: a reminder of surgical anatomy, » Journal of the Royal College of Surgeons of Edinburgh, vol. 46, pp. 168-170 (Jun. 2001).
Kalsbeek, A et al., "Hypothalamic control of energy metabolism via the autonomic nervous system," Annals of the New York Academy of Sciences, vol. 1212, pp. 114-129 (2010).
Kalsbeek, Andries et al., "Suprachiasmatic GABAergic Inputs to the Paraventricular Nucleus Control Plasma Glucose Concentrations in the Rat via Sympathetic Innervation of the Liver," Journal of Neuroscience, vol. 24(35) pp. 7604-7613 (2004).
Kandzari, David E., SYMPLICITY HTN Program Expanding Therapeutic Options for HTN and New Indications, Slides from Lecture presented at EuroPCR (May 2013).
Katholi, Richard K., "Renal nerves in the pathogenesis of hypertension in experimental animals and humans," Am. Physiol. Society (1983) F1-F14.
Katona, Peter G., "Biomedical engineering in heart-brain medicine: a review," Cleveland Clinic Journal of Medicine, vol. 77, Supplement 3, pp. S46-S50 (Jul. 2010).
Kimani, SM et al., "Comparative intimal-media morphology of the human splenic and common hepatic arteries," Journal of Morphological Science, vol. 28, No. 1, pp. 52-56 (2011).
King, Andrew J., "Splanchnic Circulation Is a Critical Neural Target in Angiotensin II Salt Hypertension in Rats," Journal of Hypertension, vol. 50, pp. 547-556 (2007).
Klieverik, Lars P. et al., "Effects of thyrotoxicosis and selective hepatic autonomic denervation on hepatic glucose metabolism in rats," American Journal of Physiology—Endocrinology and Metabolism, vol. 294, pp. E513-E520 (2008).
Klieverik, Lars P. et al., "Thyroid hormone modulates glucose production via a sympathetic pathway from the hypothalamic paraventricular nucleus to the liver," PNAS, vol. 106 (14), pp. 5966-5971 (2009).
Kolios, M. C. et al., « Large blood vessel cooling in heated tissues: a numerical study, Physics in Medicine and Biology, vol. 40, pp. 477-494 (1995).
Krum, Henry et al., "Catheter-based renal sympathetic denervation for resistant hypertension: a multicentre safety and proof-of-principle cohort study," Lancet, vol. 373, pp. 1275-1281 (2009).
Lambert, Gavin W. et al., "Sympathetic Nervous Activation in Obesity and the Metabolic Syndrome—Causes, consequences and therapeutic implications," Pharmacology & Therapeutics, vol. 126, pp. 159-172 (2010).
Lautt, W. Wayne et al., "Hepatic glucose balance in response to direct stimulation of sympathetic nerves in the intact liver of cats," Canadian Journal of Physiology and Pharmacology, vol. 56, pp. 1022-1028 (1978).
Lautt, W. Wayne et al., "Hepatic parasympathetic neural effect on glucose balance in the intact liver," Canadian Journal of Physiology and Pharmacology, vol. 56, pp. 679-682 (1978).
Lee, Aram J. et al., « The Road Less Traveled: Importance of the Lesser Branches of the Celiac Axis in Liver Embolotherapy, » RadioGraphics, vol. 32, pp. 1121-1132 (2012).
Lee, Bong-Ki et al, « Right Phrenic Nerve Injury Following Electrical Disconnection of the Right Superior Pulmonary Vein, » PACE, vol. 27, pp. 1444-1446 (2004).
Lee, King C. et al., "The Hepatic Vagus Nerve and the Neural Regulation of Insulin Secretion," Endocrinology, vol. 117, No. 1, pp. 307-315 (1985).
Lehmann, K. S. et al., "Ex situ quantification of the cooling effect of liver vessels on radiofrequency ablation," Langenbecks Archives of Surgery, vol. 394, pp. 475-481 (2009).
Licht, Carmilla M. M. et al., « Increased Sympathetic and Decreased Parasympathetic Activity Rather Than Changes in Hypothalamic-Pituitary-Adrenal Axis Activity Is Associated with Metabolic Abnormalities, Journal of Clinical Endocrinology and Metabolism, vol. 95, No. 5, pp. 2458-2466 (2010).

Lindfeldt, J. et al., "Hepatic sympathetic denervation potentiates glucagon-stimulated glycogenolysis and hyperinsulinaemia in the rat," Journal of the Autonomic Nervous System, vol. 19, pp. 211-217 (1987).
Liu, David M. et al., « Angiographic Considerations in Patients Undergoing Liver-directed Therapy, » Journal of Vascular Interventional Radiology, vol. 16, pp. 911-935 (2005).
Liu, Z. et al., "Computer modeling of the effect of perfusion on heating patterns in radiofrequency tumor ablation," International Journal of Hyperthermia, vol. 23, No. 1, pp. 49-58 (Feb. 2007).
Loukas, Marios et al., 2010, "A Review of the Thoracic Splanchnic Nerves and Celiac Ganglia," Clinical Anatomy, vol. 23, pp. 512-522.
Mahfoud, Felix et al., "Effect of Renal Sympathetic Denervation on Glucose Metabolism in Patients With Resistant Hypertension: A Pilot Study," Circulation, vol. 123, pp. 1940-1946 (Apr. 25, 2011 ).
Mancia, Giuseppe et al., "The sympathetic nervous system and the metabolic syndrome," Journal of Hypertension, vol. 25, No. 5, pp. 909-920 (2007).
McCuskey, Robert S., "Anatomy of Efferent Hepatic Nerves," The Anatomical Record Part A, vol. 280A, pp. 821-826 (2004).
Medtronic ATAKR® II 4802 Ablation System Technical Manual (2001).
Moore, Mary Courtney et al., "Chronic hepatic artery ligation does not prevent liver from differentiating portal vs. peripheral glucose delivery," American Journal of Physiology—Endocrinology and Metabolism, vol. 285, pp. E845-E853 (2003).
Moore, Mary Courtney et al., "Effect of hepatic denervation on peripheral insulin sensitivity in conscious dogs," American Journal of Physiology—Endocrinology and Metabolism, vol. 282, pp. E286-E296 (2002).
Nathan, David M. "Finding New Treatments for Diabetes—How Many, How Fast . . . How Good?," New England Journal of Medicine, vol. 356(5) (Feb. 1, 2007), pp. 437-440.
Niijima, Akira, "Glucose-Sensitive Afferent Nerve Fibres in the Hepatic Branch of the Vagus Nerve in the Guinea-Pig," Journal of Physiology, vol. 322, pp. 315-323 (1982).
Nobin, A. et al., "Organization and Function of the Sympathetic Innervation of Human Liver," Acta Physiological Scandinavia suppl., vol. 452, pp. 103-106 (1977).
Nonogaki, K., "New insights into sympathetic regulation of glucose and fat metabolism," Diabetologia, vol. 43, pp. 533-549 (2000).
Okazaki, Hiroshi et al., "Modulation of Insulin Secretion by Hepatic Vagotomy in Cirrhotic Rats," Physiology & Behavior, vol. 53, pp. 521-525 (1993).
Panescu, Dorin et al., "Three-Dimensional Finite Element Analysis of Current Density and Temperature Distributions During Radio-Frequency Ablation," IEEE Transactions on Biomedical Engineering, vol. 42, No. 9, pp. 879-890 (Sep. 1995).
Pearce, John A. et al., "Blood vessel architectural features and their effect on thermal phenomena," Critical Reviews, vol. CR75, pp. 231-277, SPIE Optical Engineering Press (2000).
Perseghin, Gianluca et al., "Regulation of Glucose Homeostasis in Humans with Denervated Livers," The Journal of Clinical Investigation, vol. 100 No. 4, pp. 931-941 (Aug. 1997).
Pocai, Alessasndro et al., "Hypothalamic KATP channels control hepatic glucose production," Nature, vol. 434, pp. 1026-1031 (2005).
Prochnau, Dirk et al., "Catheter-based renal denervation for drug-resistant hypertension by using a standard electrophysiology catheter," EuroIntervention, vol. 7, pp. 1077-1080 (Sep. 2011).
Puschel, Gerhard P., "Control of Hepatocyte Metabolism by Sympathetic and 13 Parasympathetic Hepatic Nerves," The Anatomical Record Part A, vol. 280A (2004), pp. 854-867.
Rippy, Marian K. et al., « Catheter-based renal sympathetic denervation: chronic preclinical evidence for renal artery safety, » Clinical Research in Cardiology, vol. 100, pp. 1095-1101 (2011).
Rizza, Robert, "Pathogenesis of Fasting and Postprandial Hyperglycemia in Type 2 Diabetes: Implications for Therapy," Diabetes, vol. 59 (Nov. 2010), pp. 2697-2707.
Roemer, R. B., « Optimal power deposition in hyperthermia, » International Journal of Hyperthermia, vol. 7, No. 2, pp. 317-341 (1991).

(56) References Cited

OTHER PUBLICATIONS

Roth, Steven M, "Endovenous Radiofrequency Ablation of Superficial and Perforator Veins," Surgical Clinics of North America, vol. 87, pp. 1267-1284 (2007).
Sacher, Frederic et al, "Phrenic Nerve Injury After Atrial Fibrillation Catheter Ablation," Journal of the American College of Cardiology, vol. 47, No. 12, pp. 2498-2503 (2006).
Schenk, Jr., Worthington G. et al., "Direct Measurement of Hepatic Blood Flow in Surgical Patients," Annals of Surgery, vol. 156, No. 3, pp. 463-469 (Sep. 1962).
Schlaich, Markus P. et al., "Renal Denervation in Human Hypertension: Mechanisms, Current Findings, and Future Prospects," Current Hypertension Reports, vol. 14, pp. 247-253 (2012).
Schlaich, Markus P. et al., "Renal denervation: a potential new treatment modality for polycystic ovary syndrome?" Journal of Hypertension, vol. 29, pp. 991-996 (2011).
Schlaich, Markus P. et al., "Renal Sympathetic Nerve Ablation: The New Frontier in the Treatment of Hypertension," Current Hypertension Reports, vol. 12, pp. 39-46 (2010).
Schlaich, Markus P. et al., "Renal Sympathetic-Nerve Ablation for Uncontrolled Hypertension," New England Journal of Medicine, vol. 361, No. 9, pp. 932-934 (Aug. 27, 2009).
Sherif, R.Z. et al., "Liver Anatomy," Surgical Clinics of North America, vol. 90, pp. 643-653 (2010).
Singh, Sheldon M. et al., "Esophageal Injury and Temperature Monitoring During Atrial Fibrillation Ablation," Circulation: Arrythmia and Electrophysiology, vol. 1, pp. 162-168 (Jun. 9, 2008).
Smith, Harold P. et al., "Radiofrequency neurolysis in a clinical model," Journal of Neurosurgery, vol. 55, pp. 246-253 (1981).
Steigerwald, Kristin et al. "Morphological assessment of renal arteries after radiofrequency catheter-based sympathetic denervation in a porcine model," Journal of Hypertension, vol. 30, No. 1, pp. 1-10 (2012).
Stiimpel, F., "Loss of regulation by sympathetic hepatic nerves of liver metabolism and haemodynamics in chronically streptozotocin-diabetic rats," Diabetologia, vol. 39, pp. 161-165 (1996).
Stovichek, GV et al., "Morphological Regularities of Adventitial Nerve Plexus Variability in Visceral Arteries on Different Stages of Human Postnatal Ontogenesis," Morphology, vol. 112, No. 5, pp. 43-48 (1997).
Stovichek, GV, "Comparative evaluation of age-related and organic characteristics of the structure of the adventitial nerve plexuses in human arteries," Archives of Anatomy, Histology and Embryology, vol. 93, No. 9, pp. 77-82 (1987).
Stovichek, GV, "Myeloarchitectonics of visceral nerves during human ontogeny," Archives of Anatomy, Histology and Embryology, vol. 80, No. 1, pp. 30-38 (1981).
Stovichek, GV, "Regularities of the Morphogenesis of Visceral Organ Nervous Connections at Different Stages of Human Postnatal Development," Morphology, vol. 125, No. 3, pp. 14-18 (2004).
Straznicky, Nora E. et al., « Neuroadrenergic Dysfunction Along the Diabetes Continuum: A Comparative Study in Obese Metabolic Syndrome Subjects, » Diabetes, vol. 61, pp. 2506-2516 (2012).
Taborsky, Jr., Gerald J. et al., "Minireview: The Role of the Autonomic Nervous System in Mediating the Glucagon Response to Hypoglycemia," Endocrinology, vol. 153, pp. 1055-1062 (2012).
Takahashi, Akira, "Effects of hepatic nerve stimulation on blood glucose and glycogenolysis in rat liver: Studies with in vivo microdialysis," Journal of the Autonomic Nervous System, vol. 61, pp. 181-185 (1996).
Takahashi, Kanji A. et al., « Fasting Induces a Large, Leptin-Dependent Increase in the Intrinsic Action Potential Frequency of Orexigenic Arcuate Nucleus Neuropeptide Y/Agouti-Related Protein Neurons, » Endocrinology, vol. 146, No. 3, pp. 1043-1047 (2005).
Tangwongsan, Chanchana, "Fluid Velocity Measurement Using Convective Heat Transfer Coefficient Measuring System," 2007 IEEE/NIH Life Science Systems and Applications Workshop, pp. 81-87 (2007).

Tavares, Fabio Luis et al., « Hepatic denervation impairs the assembly and secretion of VLDL-TAG, » Cell Biochemistry and Function, vol. 26, pp. 557-565 (2008).
Tentolouris, N. et al., "Sympathetic System Activity in Obesity and Metabolic Syndrome," Annals New York Academy of Sciences, vol. 1083, pp. 129-152 (2006).
Tentolouris, Nicholas et al., Perturbed Autonomic Nervous System Function in Metabolic Syndrome, Neuromolecular Medicine, vol. 10, pp. 169-178 (2008).
Thompson, Mary et al., "Renal Denervation Sparks Device Market Gold Rush," Elsevier Business Intelligence, Medtech Insight, vol. 24, No. 5 (May 2012).
Tungjitkusolmun, Supan et al., "Three-Dimensional Finite-Element Analyses for Radio-Frequency Hepatic Tumor Ablation," IEEE Transactions on Biomedical Engineering, vol. 49, No. 1, pp. 3-9 (Jan. 2002).
Tziafalia, Christina et al., "Echo-Doppler Measurements of Portal Vein and Hepatic Artery in Asymptomatic Patients with Hepatitis B Virus and Healthy Adults," Journal of Gastrointestinal and Liver Diseases, vol. 15, No. 4, pp. 343-346 (Dec. 2006).
Uchida, F., et al. "Effect of radio frequency catheter ablation on parasympathetic denervation: A comparison of three different ablation sites," PACE, 21:2517-2521 (1998).
Uchida, Masfumi et al., "CT Image Fusion for 3D Depiction of Anatomic Abnormalities of the Hepatic Hilum," American Journal of Roentgenology, vol. 189, pp. W184-W191 (Oct. 2007).
Ulucakli, M. Erol, "Simulation of Radiofrequency Ablation and Thermal Damage to Tissue," IEEE Annual Northeast Bioengineering Conference, pp. 93-94 (2006).
Unger, Roger H. et al., "Glucagonocentric restructuring of diabetes: a pathophysiologic and therapeutic makeover," The Journal of Clinical Investigation, vol. 122, No. 1 (2012).
Uno, Kenji et al., « Neuronal Pathway from the Liver Modulates Energy Expenditure and Systemic Insulin Sensitivity, Science, vol. 312, pp. 1656-1659 (Jun. 16, 2006).
Valvano, J.W. et al., « Thermal Conductivity and Diffusivity of Biomaterials Measured with Self-Heated Thermistors, » International Journal of Thermophysics, vol. 6, No. 3, pp. 301-311 (1985).
Van Den Hoek, Anita M. et al., Sep. 2008, Intracerebroventricular Administration of Neuropeptide Y Induces Hepatic Insulin Resistance via Sympathetic Innervation, Diabetes, vol. 57, pp. 2304-2310.
Vaz, Mario et al., "Regional Sympathetic Nervous Activity and Oxygen Consumption in Obese Normotensive Human Subjects," Circulation, vol. 96, pp. 3423-3429 (1997).
Wada, Masahiko et al., "Hepatic denervation does not significantly change the response of the liver to glucagon in conscious dogs," American Journal of Physiology—Endocrinology and Metabolism, vol. 268, pp. E194-E203 (1995).
Watton, Paul N. et al., "Modelling the mechanical response of elastin for arterial tissue," Journal of Biomechanics, vol. 42, pp. 1320-1325 (2009).
Wiersma, Mariska M.L. et al., Effect of liver denervation on glucose production during running in guinea pigs, »American Journal of Physiology—Regulatory Integrative Comparative Physiology, vol. 268, pp. R72-R77 (1995).
Witkowski, Adam et al., "Effects of Renal Sympathetic Denervation on Blood Pressure, Sleep Apnea Course, and Glycemic Control in Patients With Resistant Hypertension and Sleep Apnea," Journal of Hypertension, vol. 58, pp. 559-565 (2011).
Wood, Thomas H., "Lethal Effects of High and Low Temperatures on Unicellular Organisms," Advanced Biology of Medicine and Physics, vol. 4, pp. 119-165 (1956).
Wright, Neil T., "On a Relationship Between the Arrhenius Parameters from Thermal Damage Studies," Transactions of the ASME, vol. 125, pp. 300-304 (Apr. 2003).
Xie, Hongheng et al., "Insulin resistance of skeletal muscle produced by hepatic parasympathetic interruption," American Journal of Physiology—Endocrinology and Metabolism, vol. 270, pp. E858-E863 (1996).
Xie, Hongsheng et al., "Insulin resistance of glucose response produced by hepatic denervations," Canadian Journal of Physiology and Pharmacology, vol. 71, pp. 175-178 (Feb. 1993).

(56) References Cited

OTHER PUBLICATIONS

Yi, Chun-Xia et al., « Pituitary Adenylate Cyclase-Activating Polypeptide Stimulates Glucose Production via the Hepatic Sympathetic Innervation in Rats, » Diabetes, vol. 59, pp. 1591-1600 (Jul. 2010).
Yi, Chun-Xia et al., «A Major Role for Perifornical Orexin Neurons in the Control of Glucose Metabolismin Rats, » Diabetes, vol. 58, Sep. 2009, pp. 1998-2005.
Yi, Chun-Xia et al., 2010, "The Role of the Autonomic Nervous Liver Innervation in the Control of Energy Metabolism," Biochimica et Biophysica Acta vol. 1802, pp. 416-431.
Yu, Nam C. et al., "Microwave Liver Ablation: Influence of Hepatic Vein Size on Heat-sink Effect in a Porcine Model," Journal of Vascular Interventional Radiology, vol. 19, pp. 1087-1092 (2008).
Zile, Michael R. et al., Effects of Autonomic Modulation, » Journal of the American College of Cardiology, vol. 59, No. 10, pp. 910-912 (2012).

\* cited by examiner

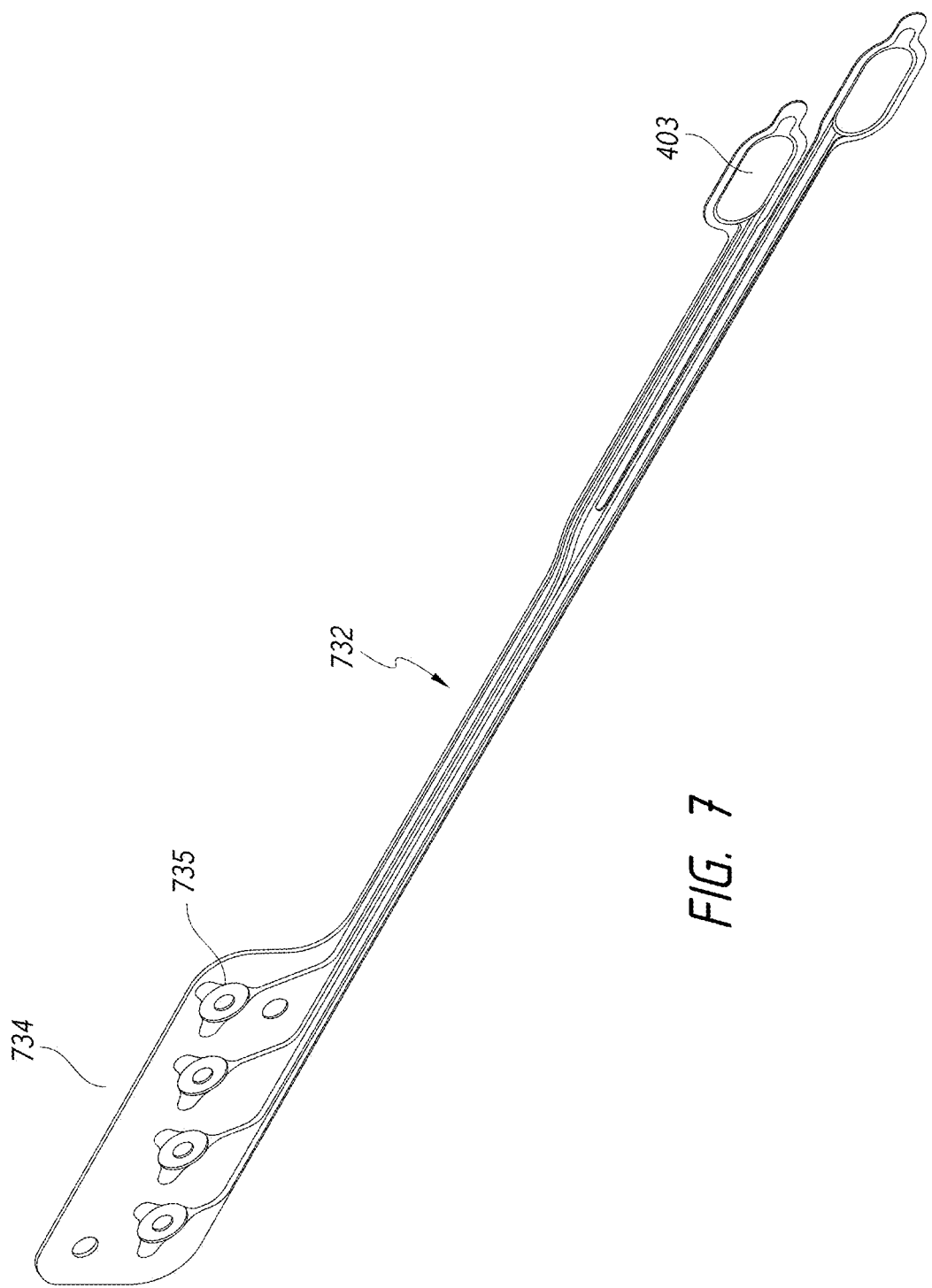

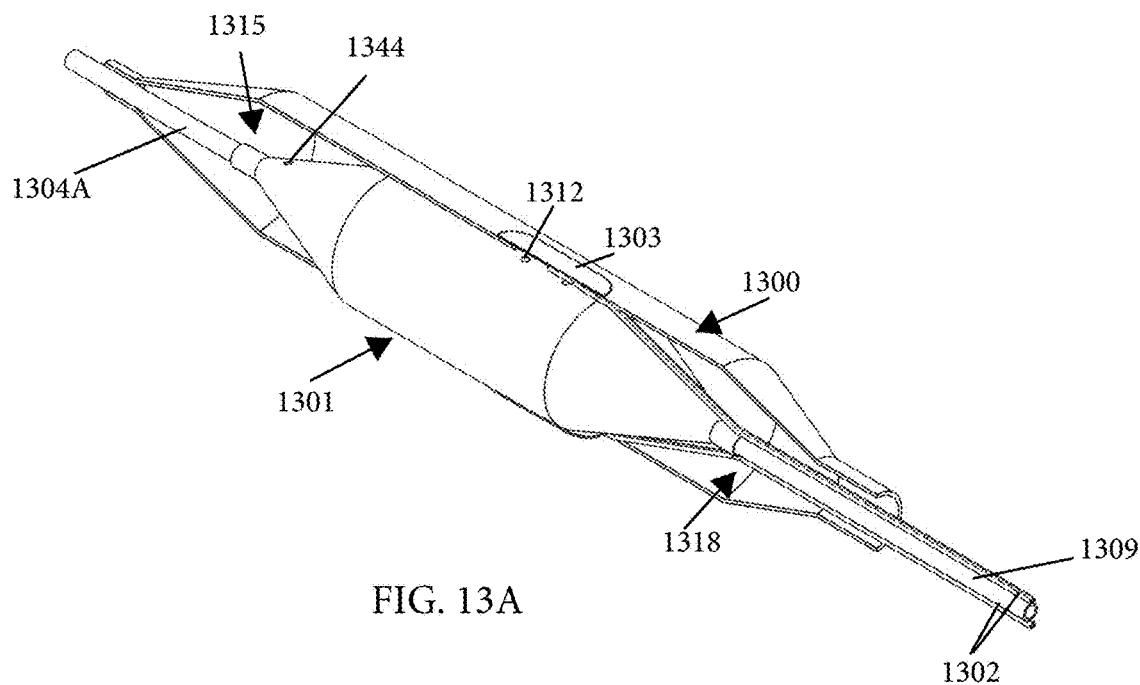
FIG. 13A
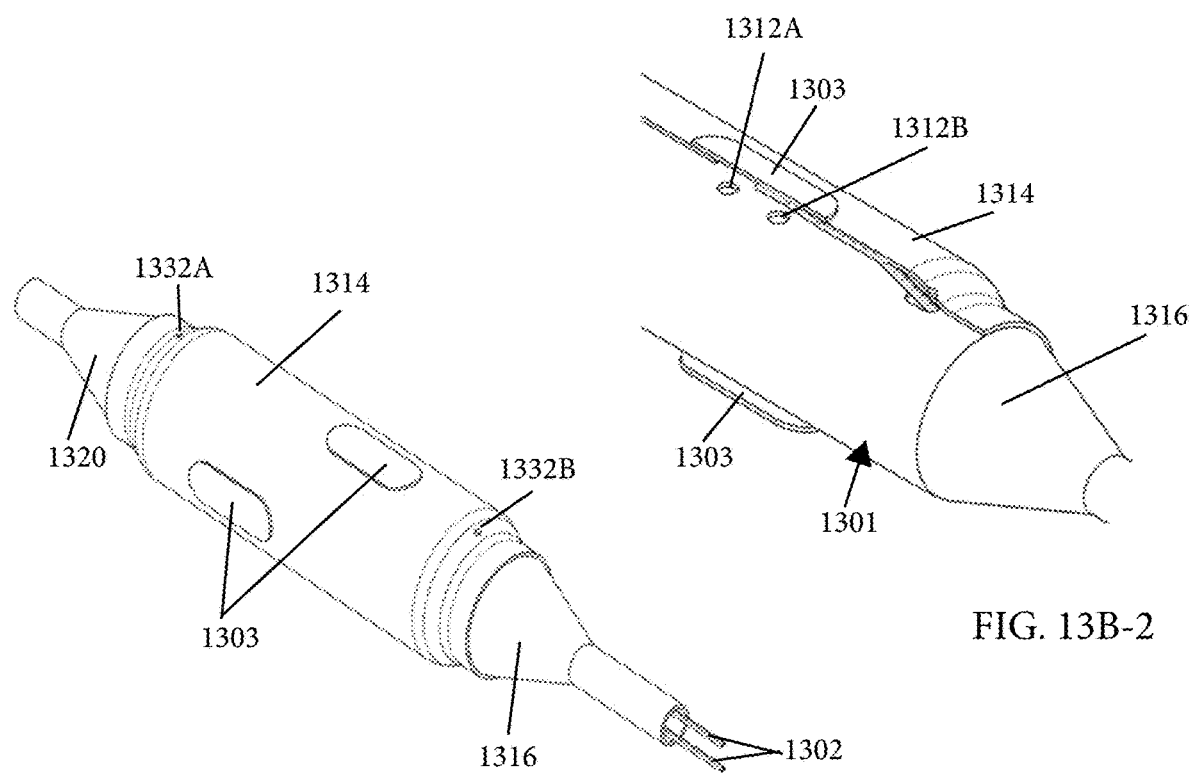
FIG. 13B-1
FIG. 13B-2

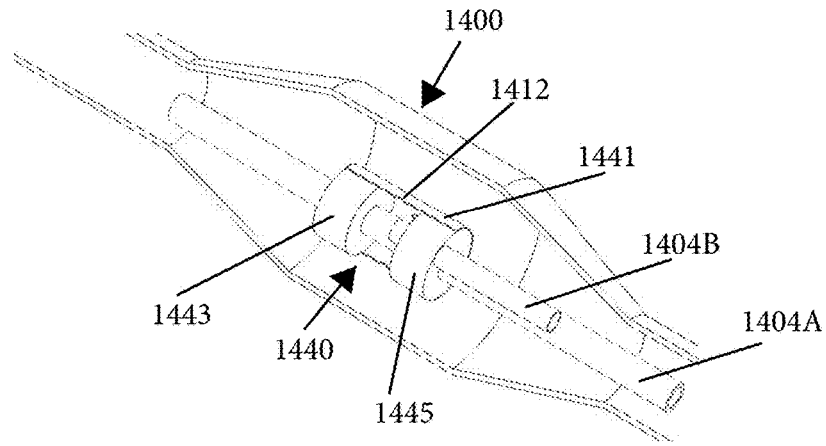
FIG. 14A
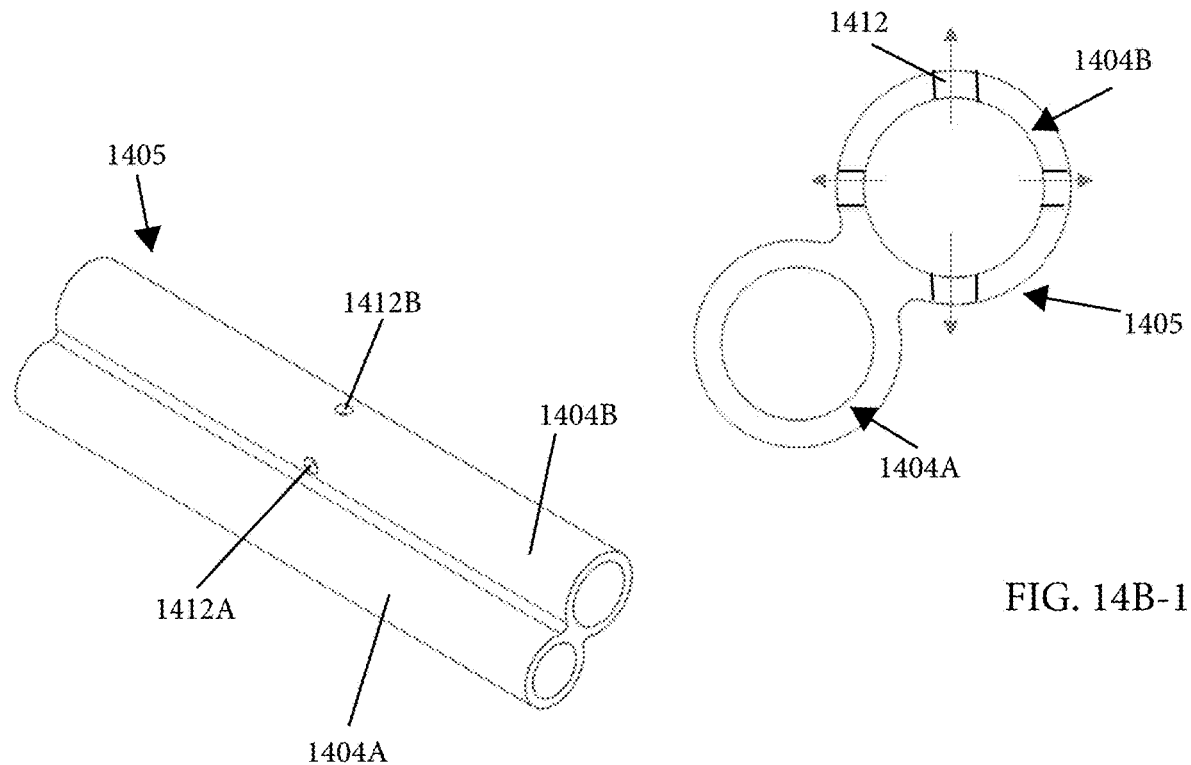
FIG. 14B-1
FIG. 14B-2

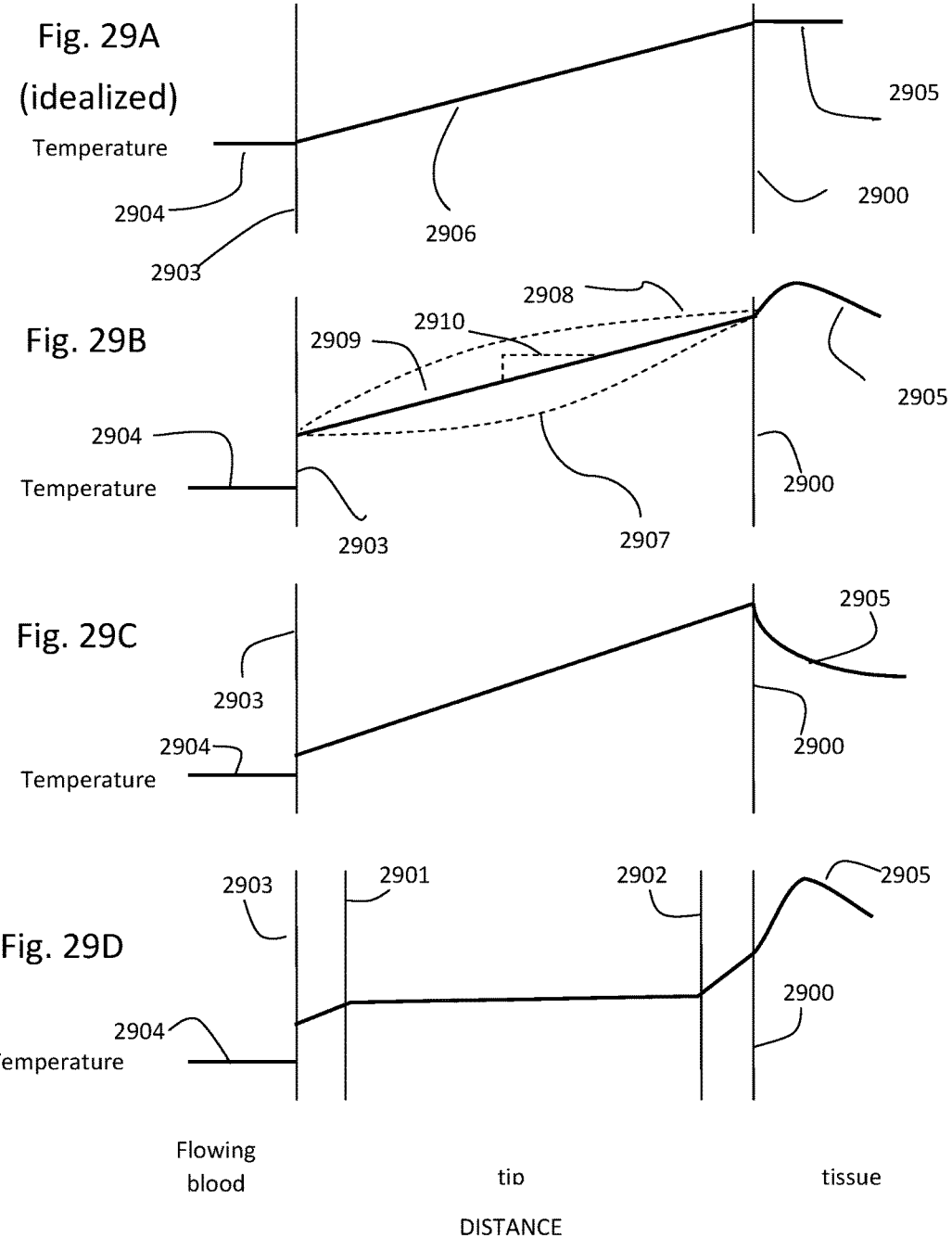

FIG. 34A
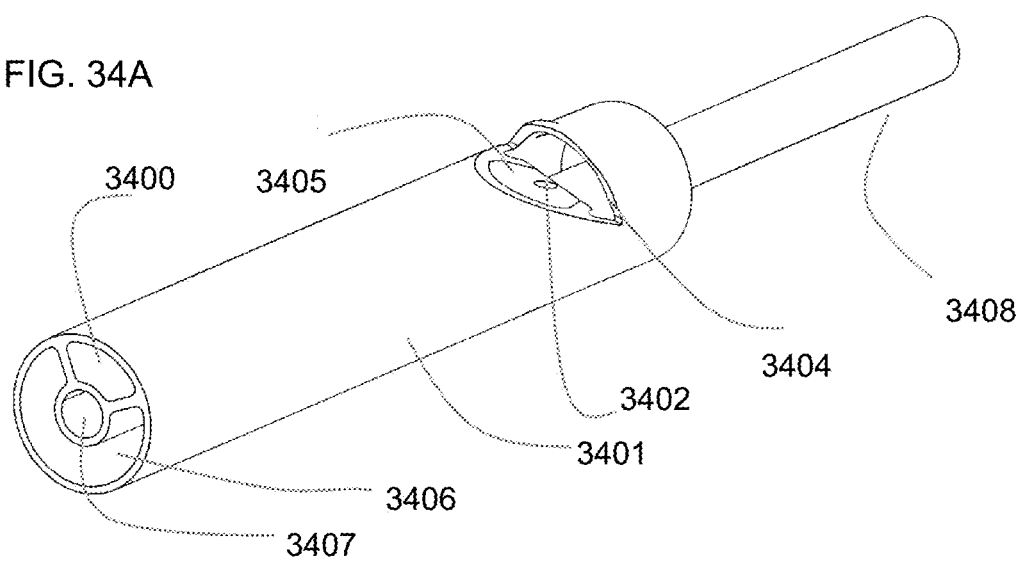
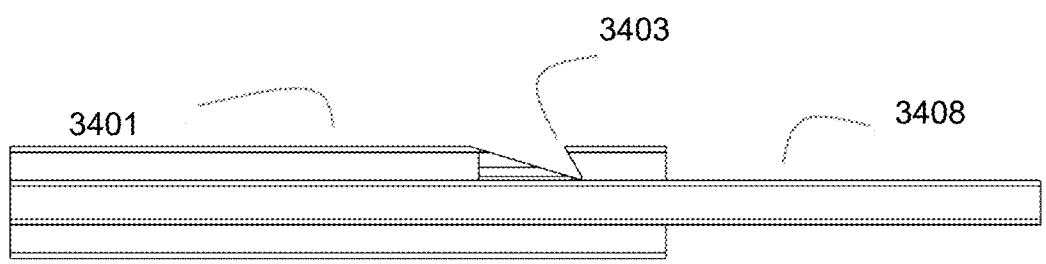
FIG. 34B

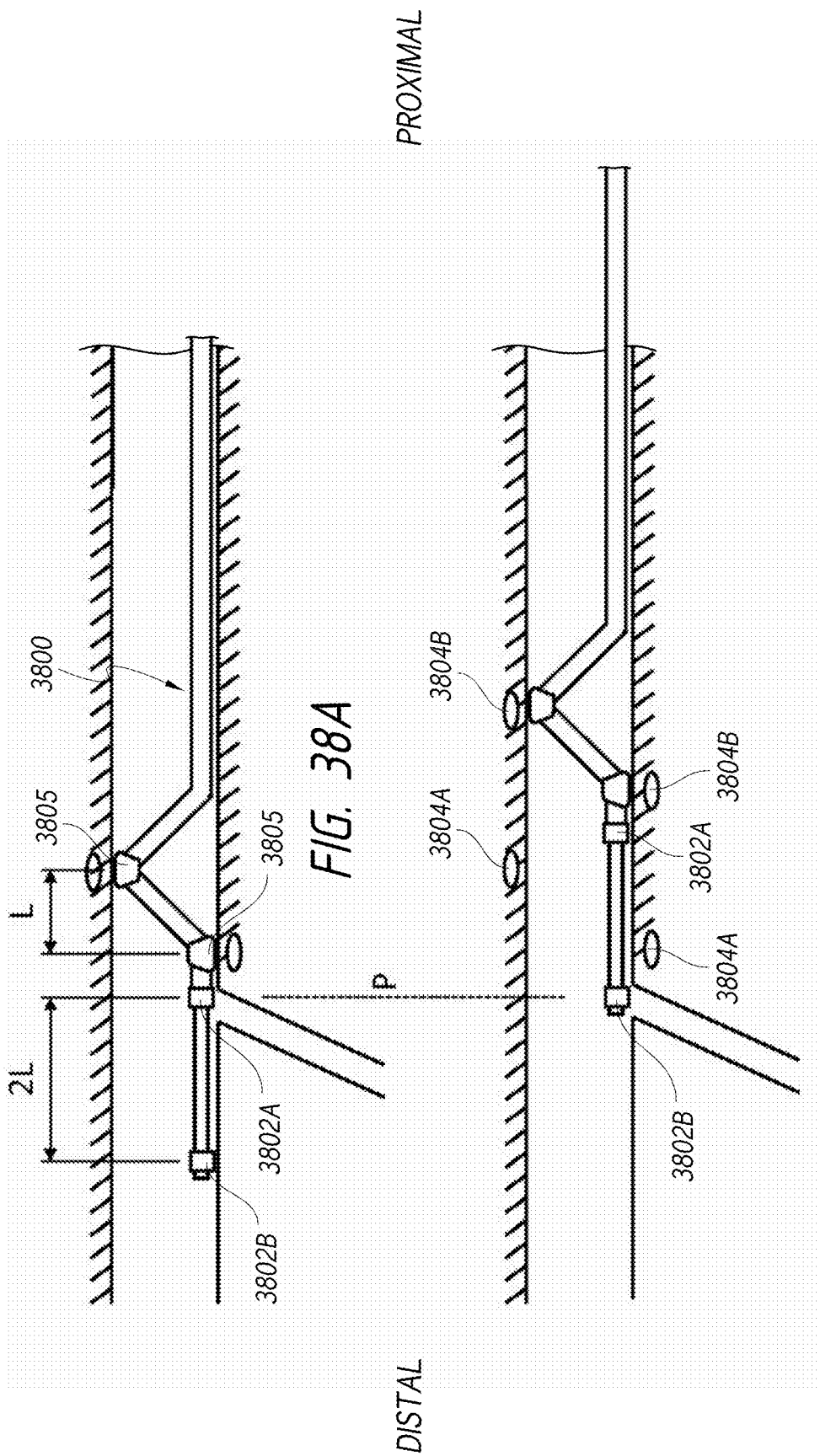

THERAPEUTIC TISSUE MODULATION DEVICES AND METHODS

RELATED APPLICATIONS

This application claims priority to U.S. Provisional Application No. 62/346,990 filed Jun. 7, 2016 and to U.S. Provisional Application No. 62/458,990 filed Feb. 14, 2017, the entire contents of each of which is hereby expressly incorporated by reference herein. This application is also related to PCT Publication No. WO 2016/090175 published on Jun. 9, 2016, the entire content of which is hereby expressly incorporated by reference herein.

FIELD

The disclosure relates generally to therapeutic tissue modulation and, more specifically, to embodiments of devices, systems and methods for therapeutically effecting modulation (e.g., ablation) of targeted nerve fibers of, for example, the hepatic system, to treat metabolic diseases or conditions, such as diabetes mellitus.

BACKGROUND

Chronic hyperglycemia is one of the defining characteristics of diabetes mellitus. Hyperglycemia is a condition in which there is an elevated blood glucose concentration. An elevated blood glucose concentration may result from impaired insulin secretion from the pancreas and also, or alternatively, from cells failing to respond to insulin normally. Excessive glucose release from the liver is a significant contributor to hyperglycemia. The liver is responsible for approximately 90% of the glucose production and 33% of glucose uptake, and derangements in both in type 2 diabetes contribute to hyperglycemia in the fasting and post-prandial states.

Type 1 diabetes mellitus results from autoimmune destruction of the pancreatic beta cells leading to inadequate insulin production. Type 2 diabetes mellitus is a more complex, chronic metabolic disorder that develops due to a combination of insufficient insulin production as well as cellular resistance to the action of insulin. Insulin promotes glucose uptake into a variety of tissues and also decreases production of glucose by the liver and kidneys; insulin resistance results in reduced peripheral glucose uptake and increased endogenous glucose output, both of which drive blood the glucose concentration above normal levels.

Current estimates are that approximately 26 million people in the United States (over 8% of the population) have some form of diabetes mellitus. Treatments, such as medications, diet, and exercise, seek to control blood glucose levels, which require a patient to closely monitor his or her blood glucose levels. Additionally, patients with type 1 diabetes mellitus, and many patients with type 2 diabetes mellitus, are required to take insulin every day. Insulin is not available in a pill form, however, but must be injected under the skin. Because treatment for diabetes mellitus is self-managed by the patient on a day-to-day basis, compliance or adherence with treatments can be problematic.

SUMMARY

Several embodiments described herein relate generally to devices, systems and methods for therapeutically effecting neuromodulation of targeted nerve fibers to treat various medical conditions, disorders and diseases. In some embodiments, neuromodulation of targeted nerve fibers is used to treat, or reduce the risk of occurrence of symptoms associated with, a variety of metabolic diseases. For example, neuromodulation of targeted nerve fibers can treat, or reduce the risk of occurrence of symptoms associated with, diabetes (e.g., diabetes mellitus) or other diabetes-related diseases. The methods described herein can advantageously treat diabetes without requiring daily insulin injection or constant monitoring of blood glucose levels. The treatment provided by the devices, systems and methods described herein can be permanent or at least semi-permanent (e.g., lasting for several weeks, months or years), thereby reducing the need for continued or periodic treatment. Embodiments of the devices described herein can be temporary (and non-implantable), or implantable.

In several embodiments, the invention comprises modulation of the nervous system to treat disorders affecting insulin and/or glucose, such as insulin regulation, glucose uptake, metabolism, etc. In some embodiments, nervous system input and/or output is temporarily or permanently modulated (e.g., decreased). Several embodiments are configured to perform one or a combination of the following effects: ablating nerve tissue, heating nerve tissue, cooling the nerve tissue, deactivating nerve tissue, severing nerve tissue, cell lysis, apoptosis, and necrosis. In some embodiments, localized neuromodulation is performed, leaving surrounding tissue unaffected. In other embodiments, the tissue surrounding the targeted nerve(s) is also treated.

In some embodiments, neuromodulation of targeted nerve fibers as described herein can be used for the treatment of insulin resistance, genetic metabolic syndromes, ventricular tachycardia, atrial fibrillation or flutter, arrhythmia, inflammatory diseases, hypertension (arterial or pulmonary), obesity, hyperglycemia (including glucose tolerance), hyperlipidemia, eating disorders, and/or endocrine diseases. In some embodiments, neuromodulation of targeted nerve fibers treats any combination of diabetes, insulin resistance, or other metabolic diseases. In some embodiments, temporary or implantable neuromodulators may be used to regulate satiety and appetite (e.g., to promote weight loss). In several embodiments, modulation of nervous tissue that innervates (efferently or efferently) the liver is used to treat hemochromatosis, Wilson's disease, non-alcoholic steatohepatitis (NASH), non-alcoholic fatty liver disease (NAFLD), and/or other conditions affecting the liver and/or liver metabolism. In some embodiments, modulation of nervous tissue that innervates (efferently or efferently) the liver (e.g., hepatic denervation) is effective for reducing whole-body sympathetic tone and resulting conditions such as hypertension, congestive heart failure, atrial fibrillation, obstructive sleep apnea, and/or renal failure, etc.

In some embodiments, sympathetic nerve fibers associated with the liver are selectively disrupted (e.g., ablated, denervated, disabled, severed, blocked, injured, desensitized, removed) to decrease hepatic glucose production and/or increase hepatic glucose uptake, thereby aiding in the treatment of, or reduction in the risk of, diabetes and/or related diseases or disorders. The disruption can be permanent or temporary (e.g., for a matter of several days, weeks or months). In some embodiments, sympathetic nerve fibers in the hepatic plexus are selectively disrupted. In some embodiments, sympathetic nerve fibers surrounding (e.g., within the perivascular space of) the portal triad, sympathetic nerve fibers surrounding the common hepatic artery proximal to the proper hepatic artery, sympathetic nerve fibers surrounding the proper hepatic artery, sympathetic nerve fibers in the celiac ganglion adjacent the celiac artery, other sympathetic nerve fibers that innervate or surround the liver, sympathetic nerve fibers that innervate the pancreas, sympathetic nerve fibers that innervate fat tissue (e.g., visceral fat), sympathetic nerve fibers that innervate the adrenal glands, sympathetic nerve fibers that innervate the small intestine (e.g., duodenum, jejunum, ileum), sympathetic nerve fibers that innervate the stomach (or portions thereof, such as the pylorus), sympathetic nerve fibers that innervate brown adipose tissue, sympathetic nerve fibers that innervate skeletal muscle, and/or sympathetic nerve fibers that innervate the kidneys are selectively disrupted or modulated (simultaneously or sequentially) to facilitate treatment or reduction of symptoms associated with hypertension, diabetes (e.g., diabetes mellitus), or other metabolic diseases or disorders. In some embodiments, the methods, devices and systems described herein are used to therapeutically modulate autonomic nerves associated with any diabetes-relevant organs or tissues. For example, with respect to the pancreas and duodenum, the nerves that innervate one or both structures can be neuromodulated (e.g., ablated) in addition to or instead of the nerves that innervate the liver, wherein said neuromodulation affects one or more symptoms/characteristics associated with diabetes or other metabolic diseases or disorders. Such symptoms/characteristics include but are not limited to changes (e.g., increases or decreases) in glucose levels, cholesterol levels, lipid levels, triglyceride levels, norepinephrine levels, insulin regulation, etc. in the blood plasma or liver or other organs. The devices and methods disclosed herein with respect to hepatic modulation (e.g., hepatic denervation) can alternatively or additionally be used for neuromodulating (e.g., denervating) at least portions of the pancreas, duodenum, stomach or other organs and structures.

In accordance with several embodiments, any nerves containing autonomic fibers are modulated, including, but not limited to, the saphenous nerve, femoral nerves, lumbar nerves, median nerves, ulnar nerves, vagus nerves, and radial nerves. Nerves surrounding arteries or veins other than the hepatic artery may be additionally or alternatively be modulated such as, but not limited to, nerves surrounding the superior mesenteric artery, the inferior mesenteric artery, the femoral artery, the pelvic arteries, the portal vein, pulmonary arteries, pulmonary veins, abdominal aorta, vena caves, splenic arteries, gastric arteries, the internal carotid artery, the internal jugular vein, the vertebral artery, renal arteries, and renal veins. Celiac arteries may also be modulated according to several embodiments herein.

In accordance with several embodiments, a therapeutic neuromodulation system is used to selectively disrupt sympathetic nerve fibers. The neuromodulation system can comprise an ablation catheter system and/or a delivery catheter system (e.g., hollow, solid or partially hollow catheter, probe, shaft or other delivery device with or without a lumen). An ablation catheter system may use radiofrequency (RF) energy to ablate sympathetic nerve fibers to cause neuromodulation or disruption of sympathetic communication. In some embodiments, an ablation catheter system uses ultrasonic energy to ablate sympathetic nerve fibers. In some embodiments, an ablation catheter system uses ultrasound (e.g., high-intensity focused ultrasound or low-intensity focused ultrasound) energy to selectively ablate sympathetic nerve fibers. In other embodiments, an ablation catheter system uses electroporation to modulate sympathetic nerve fibers. An ablation catheter, as used herein, shall not be limited to causing ablation, but also includes devices that facilitate the modulation of nerves (e.g., partial or reversible ablation, blocking without ablation, stimulation). In some embodiments, a delivery catheter system delivers drugs or chemical agents to nerve fibers to modulate the nerve fibers (e.g., via chemoablation). Chemical agents used with chemoablation (or some other form of chemically-mediated neuromodulation) may, for example, include phenol, alcohol, or any other chemical agents that cause chemoablation of nerve fibers. In some embodiments, cryotherapy is used. For example, an ablation catheter system is provided that uses cryoablation to selectively modulate (e.g., ablate) sympathetic nerve fibers. In other embodiments, a delivery catheter system is used with brachytherapy to modulate the nerve fibers. The catheter systems may further utilize any combination of RF energy, ultrasonic energy, focused ultrasound (e.g., HIFU, LIFU) energy, ionizing energy (such as X-ray, proton beam, gamma rays, electron beams, and alpha rays), electroporation, drug delivery, chemoablation, cryoablation, brachytherapy, or any other modality to cause disruption or neuromodulation (e.g., ablation, denervation, stimulation) of autonomic (e.g., sympathetic or parasympathetic) nerve fibers. As discussed below, microwave energy or laser energy (or combinations of two, three or more energy sources) are used in some embodiments. In some embodiments, energy is used in conjunction with non-energy based neuromodulation (e.g., drug delivery).

In some embodiments, a minimally invasive surgical technique is used to deliver the therapeutic neuromodulation system. For example, a catheter system (e.g., hollow, solid, partially hollow, catheter, probe, shaft or other delivery device with or without a lumen) for the disruption or neuromodulation of sympathetic nerve fibers can be delivered intra-arterially (e.g., via a femoral artery, brachial artery, radial artery). In some embodiments, an ablation catheter system is advanced to the proper hepatic artery to ablate (completely or partially) sympathetic nerve fibers in the hepatic plexus. In other embodiments, the ablation catheter system is advanced to the common hepatic artery to ablate sympathetic nerve fibers surrounding the common hepatic artery. In some embodiments, the ablation catheter system is advanced to the celiac artery or celiac trunk to ablate sympathetic nerve fibers in the celiac ganglion or celiac plexus (e.g., including nerves downstream thereof). An ablation or delivery catheter system can be advanced within other arteries (e.g., left hepatic artery, right hepatic artery, gastroduodenal artery, gastric arteries, splenic artery, renal arteries, etc.) in order to disrupt targeted sympathetic nerve fibers associated with the liver or other organs or tissue (such as the pancreas, fat tissue (e.g., visceral fat of the liver), the adrenal glands, the stomach, the small intestine, gall bladder, bile ducts, brown adipose tissue, skeletal muscle), at least some of which may be clinically relevant to diabetes. In several embodiments, neuromodulation (e.g., denervation, stripping, stimulation) of the celiac ganglion or modulation of celiac ganglion activity facilitates treatment of hypertension.

In some embodiments, a therapeutic neuromodulation or disruption system is delivered intravascularly, or endovascularly, through the venous system. For example, the therapeutic neuromodulation system may be delivered either through the portal vein or through the inferior vena cava. In some embodiments, the neuromodulation system is delivered percutaneously to the biliary tree to modulate or disrupt sympathetic nerve fibers.

In other embodiments, the neuromodulation system is delivered transluminally or laparoscopically to modulate or disrupt sympathetic nerve fibers. For example, the neuromodulation system may be delivered transluminally either through the stomach or through the duodenum.

In some embodiments, minimally invasive delivery of the neuromodulation system is accomplished in conjunction with image guidance techniques. For example, a visualization device such as a fiberoptic scope can be used to provide image guidance during minimally invasive surgical delivery of the neuromodulation system. In some embodiments, fluoroscopic, computerized tomography (CT), radiographic, optical coherence tomography (OCT), intravascular ultrasound (IVUS), Doppler, thermography, and/or magnetic resonance (MR) imaging is used in conjunction with delivery of the neuromodulation system. In some embodiments, radiopaque markers are located at a distal end of the neuromodulation system to aid in delivery and alignment of the neuromodulation system.

In some embodiments, an open surgical procedure is used to access the nerve fibers to be modulated. In some embodiments, any of the modalities described herein, including, but not limited to, RF energy, ultrasonic energy, HIFU, thermal energy, light energy, electrical energy other than RF energy, drug delivery, chemoablation, cryoablation, steam or hot-water, ionizing energy (such as X-ray, proton beam, gamma rays, electron beams, and alpha rays) or any other modality are used in conjunction with an open surgical procedure to modulate or disrupt sympathetic nerve fibers. Neuromodulation via microwave energy and laser energy are also provided in some embodiments and discussed herein. In other embodiments, nerve fibers are surgically cut (e.g., transected) to disrupt conduction of nerve signals or otherwise cause nerve injury.

In some embodiments, a non-invasive (e.g., transcutaneous) procedure is used to modulate or disrupt sympathetic nerve fibers (e.g., nerves that innervate the liver, nerves within or surrounding the hepatic arteries, the celiac arteries, the gastroduodenal artery, the splenic artery, nerves that innervate the pancreas, and/or nerves that innervate the duodenum). In some embodiments, any of the modalities described herein, including, but not limited, to RF energy, ultrasonic energy, HIFU energy, radiation therapy, light energy, infrared energy, thermal energy, steam, hot water, magnetic fields, ionizing energy, other forms of electrical or electromagnetic energy or any other modality are used in conjunction with a non-invasive procedure to modulate or disrupt sympathetic nerve fibers.

In accordance with some embodiments, the neuromodulation system is used to modulate or disrupt sympathetic nerve fibers at one or more locations or target sites. For example, an ablation catheter system (e.g., comprising an ablation device or methodology described herein, for example ultrasound, RF, cryo, etc.) may perform ablation in a circumferential or radial pattern, and/or the ablation catheter system may perform ablation at a plurality of points linearly spaced apart along a vessel length. In other embodiments, an ablation catheter system performs ablation at one or more locations in any other pattern capable of causing disruption in the communication pathway of sympathetic nerve fibers (e.g., spiral patterns, zig-zag patterns, multiple linear patterns, etc.). The pattern can be continuous or non-continuous (e.g., intermittent). The ablation may be targeted at certain portions of the circumference of the vessels (e.g., half or portions less than half of the circumference). In some embodiments, modulation of (e.g., thermal injury or damage to) the vessel wall is non-circumferential. Ablation or other treatment may be performed in one quadrant, two quadrants, three quadrants or four quadrants of the vessel. In one embodiment, ablation or other treatment is not performed in more than two quadrants of the vessel. In other embodiments, ablation or other treatment is performed in sectors of other increments such as 2, 3, 5 or 6 sections. In some embodiments, the sector may span a radial distance of 90 degrees to 120 degrees. In other embodiments, the sector may span a radial distance of 120 degrees to 240 degrees. In various embodiments, the sectors are radially disposed in increments of approximately 90, 120, 144, or 180 degrees in order to achieve the desired effect.

In accordance with embodiments of the invention disclosed herein, therapeutic neuromodulation to treat various medical disorders and diseases includes neural stimulation of targeted nerve fibers. For example, autonomic nerve fibers (e.g., sympathetic nerve fibers, parasympathetic nerve fibers) may be stimulated to treat, or reduce the risk of occurrence of, diabetes (e.g., diabetes mellitus) or other conditions, diseases and disorders.

In some embodiments, parasympathetic nerve fibers that innervate the liver are stimulated. In some embodiments, parasympathetic nerve fibers that innervate the pancreas, fat tissue (e.g., visceral fat of the liver), the adrenal glands, the stomach (e.g., or portions thereof such as the pylorus), the kidneys, brown adipose tissue, skeletal muscle, and/or the small intestine (e.g., duodenum) are stimulated. In accordance with some embodiments, any combination of parasympathetic nerve fibers innervating the liver, the pancreas, fat tissue, the adrenal glands, the stomach, the kidneys, brown adipose tissue, skeletal muscle, and the small intestine are stimulated to treat, or alleviate or reduce the risk of occurrence of the symptoms associated with, diabetes (e.g., diabetes mellitus) or other conditions, diseases, or disorders. In some embodiments, the organs or tissue are stimulated directly either internally or externally. For example, modulation of tissue (or components of tissue, such as cells, receptors, baroreceptors, etc.) may be accomplished by several embodiments described herein, and may occur with or without modulation of nerves.

In some embodiments, neuromodulation of targeted autonomic nerve fibers treats diabetes (e.g., diabetes mellitus) and related conditions by decreasing systemic glucose. For example, therapeutic neuromodulation of targeted nerve fibers can decrease systemic glucose by decreasing hepatic glucose production. In some embodiments, hepatic glucose production is decreased by disruption (e.g., ablation) of sympathetic nerve fibers. In other embodiments, hepatic glucose production is decreased by stimulation of parasympathetic nerve fibers.

In some embodiments, therapeutic neuromodulation of targeted nerve fibers decreases systemic glucose by increasing hepatic glucose uptake. In some embodiments, hepatic glucose uptake is increased by disruption (e.g., ablation) of sympathetic nerve fibers. In other embodiments, hepatic glucose uptake is increased by stimulation of parasympathetic nerve fibers. In some embodiments, triglyceride or cholesterol levels are reduced by the therapeutic neuromodulation.

In some embodiments, disruption or modulation of the sympathetic nerve fibers of the hepatic plexus has no effect on the parasympathetic nerve fibers surrounding the liver. In some embodiments, disruption or modulation (e.g., ablation or denervation) of the sympathetic nerve fibers of the hepatic plexus causes a reduction of very low-density lipoprotein (VLDL) levels, thereby resulting in a beneficial effect on lipid profile. In several embodiments, the invention comprises neuromodulation therapy to affect sympathetic drive and/or triglyceride or cholesterol levels, including high-density lipoprotein (HDL) levels, low-density lipoprotein (LDL) levels, and/or very-low-density lipoprotein (VLDL) levels. In some embodiments, denervation or ablation of sympathetic nerves reduces triglyceride levels, cholesterol levels and/or central sympathetic drive. For example, norepinephrine levels may be affected in some embodiments.

In other embodiments, therapeutic neuromodulation of targeted nerve fibers (e.g., hepatic denervation) decreases systemic glucose by increasing insulin secretion. In some embodiments, insulin secretion is increased by disruption (e.g., ablation) of sympathetic nerve fibers (e.g., surrounding branches of the hepatic artery). In other embodiments, insulin secretion is increased by stimulation of parasympathetic nerve fibers. In some embodiments, sympathetic nerve fibers surrounding the pancreas may be modulated to decrease glucagon levels and increase insulin levels. In some embodiments, sympathetic nerve fibers surrounding the adrenal glands are modulated to affect adrenaline or noradrenaline levels. Fatty tissue (e.g., visceral fat) of the liver may be targeted to affect glycerol or free fatty acid levels. In some embodiments, insulin levels remain the same or increase or decrease by less than ±5%, less than ±10%, less than ±2.5%, or overlapping ranges thereof. In some embodiments, insulin levels remain constant or substantially constant when a portion of the pancreas is ablated, either alone or in combination with the common hepatic artery or other hepatic artery branch or structure associated with the portal triad. In various embodiments, denervation of nerves innervating the liver (e.g., sympathetic nerves surrounding the common hepatic artery or other structures associated with the portal triad) does not affect a subject's ability to respond to a hypoglycemic event.

In several embodiments, the invention comprises modulation of the nervous system to treat disorders affecting insulin and/or glucose, such as insulin regulation, glucose uptake, metabolism, etc. In some embodiments, nervous system input and/or output is temporarily or permanently modulated (e.g., decreased). Several embodiments are configured to perform one or a combination of the following effects: ablating nerve tissue, heating nerve tissue, cooling the nerve tissue, deactivating nerve tissue, severing nerve tissue, cell lysis, apoptosis, and necrosis. In some embodiments, localized neuromodulation is performed, leaving surrounding tissue unaffected. In other embodiments, the tissue surrounding the targeted nerve(s) is also treated.

In accordance with several embodiments, methods of hepatic denervation are performed with shorter procedural and energy application times than renal denervation procedures. In several embodiments, hepatic denervation is performed without causing pain or mitigates pain to the subject during the treatment. In accordance with several embodiments, neuromodulation (e.g., denervation or ablation) is performed without causing stenosis or thrombosis within the target vessel (e.g., hepatic artery). In embodiments involving thermal treatment, heat lost to the blood stream may be prevented or reduced compared to existing denervation systems and methods, resulting in lower power and shorter treatment times. In various embodiments, the methods of neuromodulation are performed with little or no endothelial damage (e.g., less than 20% ablation of) to the target vessels. In several embodiments, energy delivery is delivered substantially equally in all directions (e.g., omnidirectional delivery). In various embodiments of neuromodulation systems (e.g., catheter-based energy delivery systems described herein), adequate electrode contact with the target vessel walls is maintained, thereby reducing power levels, voltage levels, vessel wall or tissue thermal injury, and treatment times.

In accordance with several embodiments, a method of decreasing blood glucose levels within a subject is provided. The method comprises inserting an RF, ultrasound, etc. ablation catheter (e.g., hollow, solid, partially hollow, catheter, probe, shaft or other delivery device with or without a lumen) into vasculature of the subject and advancing the RF ablation catheter to a location of a branch of a hepatic artery or other structure associated with the portal triad (e.g., the proper hepatic artery or the common hepatic artery). In one embodiment, the method comprises causing a therapeutically effective amount of RF, ultrasound, etc. energy to thermally inhibit neural communication within sympathetic nerves of a hepatic plexus surrounding the common or proper hepatic artery to be delivered intravascularly, or endovascularly, by the ablation catheter to the inner wall of the proper hepatic artery, thereby decreasing blood glucose levels within the subject. In some embodiments, the delivery of the therapeutically effective amount of RF, ultrasound, etc. energy to the common or proper hepatic artery also comprises delivery of energy sufficient to modulate (e.g., ablate, denervate) nerves of the pancreas and/or duodenum, which may provide a synergistic effect. In various embodiments, blood glucose levels decrease by 30-60% (e.g., 40-50%, 30-50%, 35-55%, 45-60% or overlapping ranges thereof) from a baseline level.

In one embodiment, the therapeutically effective amount of RF energy at the location of the inner vessel wall of the target vessel or at the location of the target nerves is in the range of between about 100 J and about 2 kJ (e.g., between about 100 J and about 1 kJ, between about 100 J and about 500 J, between about 250 J and about 750 J, between about 300 J and about 1 kJ, between about 300 J and about 1.5 kJ, between about 500 J and 1 kJ, or overlapping ranges thereof). In one embodiment, the therapeutically effective amount of RF energy has a power between about 0.1 W and about 14 W (e.g., between about 0.1 W and about 10 W, between about 0.5 W and about 5 W, between about 3 W and about 8 W, between about 2 W and about 6 W, between about 5 W and about 10 W, between about 8 W and about 12 W, between about 10 W and about 14 W, or overlapping ranges thereof). The ranges provided herein can be per electrode, per energy delivery location, or total energy delivery. The RF, ultrasound, etc. energy may be delivered at one location or multiple locations along the target vessel or within multiple different vessels. In some embodiments, the RF, ultrasound, etc. energy is delivered sufficient to cause fibrosis of the tissue surrounding the nerves, thereby resulting in nerve dropout. In some embodiments, various electrodes along the length are toggled on or off to customize treatment length.

In accordance with several embodiments, a tissue modulation device (e.g., neuromodulation device adapted for intravascular hepatic neuromodulation) comprises an elongated shaft comprising a proximal end portion and a distal end portion and a balloon positioned at the distal end portion, the balloon being configured to transition from a non-inflated delivery configuration to an inflated deployment configuration. In this embodiment, the balloon comprises a plurality of electrode arrays positioned along an outer surface of the balloon, each of the electrode arrays comprising a plurality of spaced-apart electrodes. In this embodiment, each of the electrode arrays is configured to be connected to a generator by separate connection wires such that each of the electrode arrays is individually controllable (e.g., activated or deactivated). The plurality of electrode arrays are arranged to form a spiral pattern along the outer surface of the balloon. When in the inflated deployment configuration, at least one of the plurality of electrode arrays is adapted to be in contact with a vessel wall (e.g., a common hepatic artery, proper hepatic artery, gastroduodenal artery, splenic artery, celiac artery, renal artery).

In some embodiments, a size of each of the plurality of electrode arrays in its longest aspect is less than or equal to a characteristic length of thermal conduction in body tissue. In some embodiments, the plurality of spaced-apart electrodes in each array or group of electrodes are closely-spaced such that the electrodes are positioned within a region or area having a longest aspect or dimension that is no more than 6 mm (e.g., when the electrode array consists of four electrodes). In various embodiments, each electrode array consists of between two and eight spaced-apart electrodes (e.g., two, three, four, five, six, seven, eight electrodes). Each electrode array may have the same number of electrodes or some electrode arrays may have different numbers of electrodes than others. In various embodiments, the number of electrode arrays or groups ranges from two to eight (e.g., two, three, four, five, six, seven, eight arrays or groups). However, more than eight arrays or groups may be present in other embodiments.

In some embodiments, the electrode arrays are coupled to the outer surface of the balloon by an adhesive. In some embodiments, the electrode arrays are coupled to a flexible substrate. The balloon may comprise a coating covering an entire outer surface of the balloon except for active electrode areas of the electrodes or covering a substantial portion of the outer surface of the balloon and/or electrodes other than the active electrode areas. In some embodiments, a portion of the connection wires spanning from the first electrode to the last electrode in at least one of the plurality of electrode arrays forms a zig-zag pattern. Each of the electrode arrays disposed on the outer surface of the balloon may form the zig-zag pattern of connection wires to reduce overall spacing and to avoid folds of the balloon in a non-inflated configuration (e.g., to reduce overall profile). In some embodiments, the device comprises one or more lesion spacing indicators, or markers, positioned along the distal end portion of the elongated shaft to facilitate controlled spacing of lesion zones. The lesion spacing indicator(s) (e.g., radiopaque markers) may be positioned on a distal extension distal of the balloon, may be positioned proximal of the balloon, and/or may be positioned inside the balloon.

In accordance with several embodiments, a method of ablating nerves surrounding a blood vessel having a controlled lesion spacing pattern comprises inserting a neuromodulation device within the blood vessel. The neuromodulation device comprises a first electrode and a second electrode spaced apart distal of the first electrode along a distal end portion of the neuromodulation device and at least one lesion spacing indicator positioned distal of the second electrode. The method further comprises causing the first electrode to contact an inner wall of the blood vessel at a first contact location and the second electrode to contact the inner wall of the blood vessel at a second contact location, wherein the first contact location and the second contact location are spaced apart axially from each other by a separation distance. The method further comprises causing the first electrode and the second electrode to deliver radiofrequency energy to the inner wall of the blood vessel while at the contact locations. The method also comprises repositioning the neuromodulation device axially within the blood vessel using the at least one lesion spacing indicator and causing the first electrode to contact the inner wall of the blood vessel at a third contact location and the second electrode to contact the inner wall at a fourth contact location, wherein the third contact location and the fourth contact location are spaced apart axially from each other by the separation distance. The neuromodulation device may then be removed from the blood vessel.

In some embodiments, the first location and the second location are in different quadrants of the inner wall of the blood vessel with respect to each other and the third location and the fourth location are in different quadrants of the inner wall of the blood vessel with respect to each other. The first location and the third location may be in the same quadrant and the second location and the third location may be in the same quadrant. For example, the neuromodulation device may be adapted to deflect or otherwise change configurations such that one of the first and second electrodes is in contact with the vessel wall at a first quadrant while the other of the first and second electrodes is in contact with the vessel wall at a second quadrant different from the first quadrant. In some embodiments, the first and second electrodes are configured to come into contact with the vessel wall in quadrants on opposite sides of the vessel wall (e.g., contact locations spaced apart by about 180 degrees). In some embodiments, the first contact location and the second contact location are spaced apart circumferentially by between 120 degrees and 210 degrees. In some embodiments, the first contact location and the second contact location are spaced apart circumferentially by about 90 degrees.

In other embodiments, the first location and the second location are in the same quadrant and the third location and the fourth location are in the same quadrant. For example, the first and second electrodes may be positioned into contact with an inner wall of the blood vessel in a first quadrant and activated to form spaced apart lesion zones in the first quadrant and then the neuromodulation device may be retracted or advanced by a distance using the at least one spacing indicator and the first and second electrodes may be positioned into contact with an inner wall of the blood vessel in a second quadrant different from the first quadrant (e.g., on an opposite side of the vessel circumference).

In some embodiments, the at least one lesion spacing indicator is spaced apart axially from the second electrode by a distance that is equal to the separation distance. In other embodiments, the at least one lesion spacing indicator is spaced apart axially from the second electrode at distance that is twice the separation distance. In embodiments where two spaced-apart lesion spacing indicators positioned distal to the second electrode are used, a proximal lesion spacing indicator may be positioned adjacent the second electrode (e.g., within 2 mm, within 1 mm) and the spacing between the two spaced-apart lesion spacing indicators may be equal to or twice the separation distance. In some embodiments, repositioning the neuromodulation device axially within the blood vessel comprises aligning a distal one of the two lesion spacing indicators with a position of a proximal one of the two lesion spacing indicators prior to repositioning. The separation distance may be between 3 mm and 8 mm (e.g., 3 mm, 4 mm, 5 mm, 6 mm, 7 mm, 8 mm).

In accordance with several embodiments, a neuromodulation system adapted for tissue contact sensing and modulation of tissue comprises a neuromodulation device including an elongated shaft having a proximal end portion and a distal end portion and an electrode assembly positioned at the distal end portion of the elongated shaft. In one embodiment, the electrode assembly comprises an inner electrode element and an outer electrode element separated by an insulation layer, wherein the inner electrode element is concentric within the outer electrode element. The electrode assembly is adapted to apply common mode signals to the inner electrode element and the outer electrode element to cause delivery of radiofrequency power sufficient to ablate tissue and to apply differential mode sensing signals between the inner electrode element and the outer electrode element to generate tissue contact sensing measurements to be received by a processing device adapted to determine a level of tissue contact based on the tissue contact sensing measurements.

The tissue contact sensing measurements may comprise bipolar contact impedance measurements between the inner electrode member and the outer electrode member and/or temperature measurements obtained by one or more thermocouple leads within the inner electrode member. In some embodiments, the system comprises a processing device configured to receive the tissue contact sensing measurements and to determine whether contact exists or a level of tissue contact based on the received tissue contact sensing measurements. The processing device may be configured (e.g., specifically programmed) to generate an output indicative of the level of tissue contact. In some embodiments, the common mode signals have a frequency range between 400 kHz and 650 kHz (e.g., between 400 kHz and 500 kHz, between 450 kHz and 600 kHz, between 550 kHz and 650 kHz, overlapping ranges thereof or any value of or within the recited ranges). In some embodiments, the differential mode sensing signals have a frequency outside of the frequency range of the common mode signals. For example, the differential mode sensing signals have a frequency between 800 kHz and 20 MHz (e.g., between 800 kHz and 1 MHz between 1 MHz and 10 MHz, between 5 MHz and 15 MHz, between 10 MHz and 20 MHz, overlapping ranges thereof or any value of or within the recited ranges). In several embodiments, a ratio of a contact surface area of the outer electrode to a contact surface are of the inner electrode is between 5:1 and 25:1 (e.g., between 5:1 and 10:1, between 10:1 and 25:1, between 10:1 and 20:1, between 15:1 and 25:1, overlapping ranges thereof or any value of or within the recited ranges).

In several embodiments of the invention, the energy-based delivery systems comprise cooling systems that are used to, for example, reduce thermal damage to regions surrounding the target area. For example, cooling may lower (or maintain) the temperature of tissue at below a particular threshold temperature (e.g., at or between 40 to 50 degrees Celsius), thereby preventing or reducing cell necrosis. Cooling balloons or other expandable cooling members are used in some embodiments. In one embodiment, ablation electrodes are positioned on a balloon, which is expanded using cooling fluid. In some embodiments, cooling fluid is circulated through a delivery system (e.g., a catheter system). In some embodiments, cooling fluid (such as pre-cooled saline) may be delivered (e.g., ejected) from a catheter device in the treatment region. In further embodiments, cooling fluid is continuously or intermittently circulated internally within the catheter device to cool the endothelial wall in the absence of sufficient blood flow.

The tissue modulation devices (e.g., neuromodulation devices, ablation catheters) described herein may advantageously cause one or more electrodes to exert sufficient contact pressure on a vessel wall. In various embodiments, the sufficient contact pressure is between about 0.1 g/mm$^2$ and about 100 g/mm$^2$ (e.g., between about 0.1 g/mm$^2$ and about 10 g/mm$^2$, between about 5 g/mm$^2$ and about 20 g/mm$^2$, between about 1 g/mm$^2$ and about 50 g/mm$^2$, or overlapping ranges thereof). In one embodiment, the therapeutically effective amount of RF energy is in the range of between about 300 J and about 1.5 kJ (e.g., about 300 J to about 1 kJ) per target location or total for all target locations.

The therapeutically effective amount of RF energy may have a power level between about 0.1 W and about 14 W (e.g., between about 0.1 W and about 10 W, between about 3 W and about 8 W, between about 3 W and about 10 W) per target location.

In some embodiments, the tissue modulation device (e.g., neuromodulation device) comprises one or more lesion spacing indicators (e.g., radiopaque markers) positioned along the distal end portion of the elongated shaft (e.g., distal of the distal-most electrode) to facilitate controlled spacing of lesion zones. The lesion spacing indicators may be positioned on a distal extension extending beyond the shape-set portion. In one embodiment, the device consists of two spaced-apart lesion indicators. In another embodiment, one of the electrodes functions as one of the spaced-apart lesion-spacing indicators. The lesion-spacing indicators may comprise radiopaque markers visible under fluoroscopy or other imaging technique. The lesion-spacing indicators may be spaced apart at a distance equal to the distance between the first monopolar electrode and the second monopolar electrode when the shape-set portion is in the deployed configuration or at a distance that is twice the distance between the first monopolar electrode and the second monopolar electrode when the shape-set portion is in the deployed configuration. Other distances may be used as desired and/or required.

In accordance with several embodiments, a tissue modulation device (e.g., neuromodulation device adapted for intravascular hepatic neuromodulation) comprises an elongated shaft comprising a proximal end portion and a distal end portion and a balloon positioned at the distal end portion, the balloon being configured to transition from a non-inflated delivery configuration to an inflated deployment configuration. In this embodiment, the balloon comprises a plurality of electrode arrays positioned along an outer surface of the balloon, each of the electrode arrays comprising a plurality of spaced-apart electrodes. In this embodiment, each of the electrode arrays is configured to be connected to a generator by separate connection wires such that each of the electrode arrays is individually controllable (e.g., activated or deactivated). The plurality of electrode arrays are arranged to form a spiral pattern along the outer surface of the balloon. When in the inflated deployment configuration, at least one of the plurality of electrode arrays is adapted to be in contact with a vessel wall (e.g., a common hepatic artery, proper hepatic artery, gastroduodenal artery, splenic artery, celiac artery, renal artery).

In some embodiments, a size of each of the plurality of electrode arrays in its longest aspect is less than or equal to a characteristic length of thermal conduction in body tissue. In some embodiments, the plurality of spaced-apart electrodes in each array or group of electrodes are closely-spaced such that the electrodes are positioned within a region or area having a longest aspect or dimension that is no more than 6 mm (e.g., when the electrode array consists of four electrodes). In various embodiments, each electrode array consists of between two and eight spaced-apart electrodes (e.g., two, three, four, five, six, seven, eight electrodes). Each electrode array may have the same number of electrodes or some electrode arrays may have different numbers of electrodes than others. In various embodiments, the number of electrode arrays or groups ranges from two to eight (e.g., two, three, four, five, six, seven, eight arrays or groups). However, more than eight arrays or groups may be present in other embodiments.

In some embodiments, the electrode arrays are coupled to the outer surface of the balloon by an adhesive. In some embodiments, the electrode arrays are coupled to a flexible substrate. The balloon may comprise a coating covering an entire outer surface of the balloon except for active electrode areas of the electrodes or covering a substantial portion of the outer surface of the balloon and/or electrodes other than the active electrode areas. In some embodiments, a portion of the connection wires spanning from the first electrode to the last electrode in at least one of the plurality of electrode arrays forms a zig-zag pattern. Each of the electrode arrays disposed on the outer surface of the balloon may form the zig-zag pattern of connection wires to reduce overall spacing and to avoid folds of the balloon in a non-inflated configuration (e.g., to reduce overall profile). In some embodiments, the device comprises one or more lesion spacing indicators positioned along the distal end portion of the elongated shaft to facilitate controlled spacing of lesion zones. The lesion spacing indicator(s) (e.g., radiopaque markers) may be positioned on a distal extension distal of the balloon, may be positioned proximal of the balloon, and/or may be positioned within the balloon.

In some embodiments, the method comprises providing cooling to a portion of the common hepatic artery that is or is not being targeted by the RF energy or to the at least one electrode. In one embodiment, cooling comprises infusing saline within the catheter or within the blood flow adjacent the at least one electrode. In one embodiment, cooling comprises obstructing flow upstream of the at least one electrode to increase the arterial flow rate past the at least one electrode, thereby providing convective cooling due to increased blood flow. In some embodiments, flow is diverted or channeled toward the at least one electrode (e.g., from a center of the vessel toward a wall of the vessel).

In accordance with several embodiments, a device for thermally-induced hepatic neuromodulation is provided. The device comprises a catheter body having a proximal end and a distal end and a lumen extending from the proximal end to the distal end. In one embodiment, the catheter body is configured for percutaneous, intravascular placement within a hepatic artery branch. The device may comprise an actuatable portion at the distal end of the catheter body and at least one electrode disposed on the actuatable portion. In some embodiments, the actuatable portion is configured to provide stabilization of the catheter within the hepatic artery branch and to facilitate contact of the at least one electrode with an inner arterial wall of hepatic artery branch. The at least one electrode or transducer may be configured to be activated to deliver thermal energy sufficient to achieve modulation (e.g., denervation, ablation, stimulation) of at least a portion of the hepatic artery branch (e.g., a segment of the common hepatic artery having a length of 30 mm or less, 24 mm or less, 20 mm or less, or between 20 mm and 30 mm). The at least one electrode or transducer may be repositioned and activated at multiple positions along the length of and/or around the circumference of the hepatic artery branch. The at least one electrode or transducer may comprise one or more monopolar electrodes or one or more bipolar electrode pairs. In embodiments involving multiple electrodes or transducers, modulation at different locations or positions may be performed simultaneously or sequentially. In some embodiments, a neuromodulation device consists or consists essentially of only two electrodes or transducers. In some embodiments, a neuromodulation device consists or consists essentially only of four electrodes or transducers. In various embodiments, the electrodes or transducers advantageously facilitate ablation of only two quadrants or sections of the vessel wall instead of all four quadrants. In some embodiments, electrodes or transducers are positioned to maintain 180-degree offset between the electrodes or transducers and to provide spacing between the electrodes or transducers along the length of the vessel, as desired or required. Other numbers of electrodes or transducers (e.g., three electrodes, five electrodes, etc.) and other circumferential offsets (e.g., 30 degrees, 45 degrees, 60 degrees, 72 degrees, 90 degrees, 120 degrees) may be used in other embodiments. In various embodiments, the electrodes or transducers may be spaced circumferentially (or radially) and/or axially (or longitudinally) and may be independently adjustable to adjust circumferential and/or axial spacing of the electrodes (and treatment sites) depending on the vessel, patient, or treatment parameters.

An aspect of the disclosure is directed towards several alternative designs, materials and methods of manufacturing medical device structures and assemblies for an ablation catheter. Accordingly, one illustrative embodiment is an ablation catheter configured to be navigated through a vessel to ablate tissue, the ablation catheter comprising an elongate shaft having a proximal and distal end. An electrode is positioned near the distal end of the elongate shaft, and is configured to transmit radiofrequency energy into a vessel wall. A substantially enclosed space within the electrode (e.g., hollow electrode or cavity) facilitates heat transfer from the vessel wall into the blood stream. In some aspects, an agitator or stirrer is provided to increase fluid flow or circulation within the enclosed fluid space. These structures and assemblies may be incorporated into any of the ablation catheters (e.g., RF energy delivery devices or instruments) described herein.

Some embodiments pertain to a method of ablating perivascular nerves, comprising navigating an ablation catheter through a vasculature to a vessel lumen of a vessel, the ablation catheter including an elongate shaft, having an electrode near the distal end of the elongate shaft and a substantially enclosed space (e.g., hollow cavity) within the electrode. The method further includes causing fluid within the substantially enclosed space to flow within the closed space thereby providing free or forced convective heat transfer that facilitates heat transfer from the vessel wall into the blood stream. This method can be used in conjunction with any of the catheters, devices, instruments, or systems described herein.

In accordance with one embodiment, an ablation catheter comprises a catheter shaft having a proximal end and a distal end and an electrode positioned near the distal end of the catheter shaft and configured to transmit radiofrequency energy into a vessel wall. The electrode comprises a substantially enclosed space that comprises an agitator. The substantially enclosed space is configured to contain fluid to facilitate heat transfer away from the vessel wall. In some embodiments, the catheter comprises an actuator adapted to engage said agitator.

In some embodiments, the substantially enclosed space comprises a plurality of agitators (e.g., two, three, four or more). The substantially enclosed space may be expandable and/or may be formed by a balloon (e.g., compliant or semi-compliant balloon). In some embodiments, the substantially enclosed space is configured to be filled with fluid during use. In some embodiments, the substantially enclosed space is prefilled with fluid during manufacture. The substantially enclosed space may be only substantially enclosed in that it is configured to leak at a relatively slow rate. For example, the substantially enclosed space may be configured to leak fluid at a leakage rate of less than 10 ml/min.

In some embodiments, an ablation catheter configured to be navigated through a vessel to ablate tissue comprises an elongate catheter shaft having a proximal and a distal end, an expandable chamber positioned near the distal end of the shaft, and one more electrodes affixed to the expandable chamber and configured to transmit radiofrequency energy into a vessel wall. The expandable chamber may comprise or contain a substantially closed fluid space configured to facilitate heat transfer away from the vessel wall. In some embodiments, the substantially closed fluid space comprises fluid that is either filled during manufacture or filled at the time of use within the vessel (e.g., after insertion to a desired location within the vessel).

In some embodiments, a catheter comprises an elongate shaft having a proximal end and a distal end, an expandable chamber positioned near the distal end of the elongate shaft, and a valved inlet to the expandable chamber providing restricted flow in a first direction and unrestricted flow in a second direction. In one embodiment, the valved inlet is configured to provide convective flow of fluid within the expandable chamber. In one embodiment, the valved inlet is configured to entrain additional fluid within the expandable chamber.

In accordance with some embodiments, an ablation catheter comprises an elongate shaft having a proximal end and a distal end, a fluid delivery lumen, an expandable chamber positioned near the distal end of the elongate shaft, and an outlet providing restricted flow of fluid through the expandable chamber. The outlet may be an orifice in a catheter lumen or a channel within a balloon waist of a balloon of the ablation catheter.

In accordance with several embodiments, a catheter comprises an elongate shaft having a proximal end and a distal end, a fluid delivery lumen, a chamber positioned near the distal end of the elongate shaft, and a compliance volume configured to allow flow of fluid (e.g., gas or liquid) into and out of the chamber. In some embodiments, the compliance volume is distal to the chamber. In other embodiments, the compliance volume is proximal to the chamber. The compliance volume may be a gas pocket. In various embodiments, the compliance volume may be located within the elongate shaft and/or within the chamber. The compliance volume may comprise a compliant balloon or an elastic mechanical device.

In some embodiments, a method of using an ablation catheter comprising at least a single agitator, a substantially enclosed space and a catheter shaft comprising a proximal end, a distal end, and a thermal element located at the distal end of the catheter shaft comprises inserting the catheter shaft into a vessel lumen (e.g., lumen of a hepatic artery, a renal artery, a gastroduodenal artery, a splenic artery, a mesenteric artery, a branch of a celiac artery) of a patient, heating a tissue adjacent to the vessel lumen of a patient with the thermal element, filling the substantially enclosed space with fluid, and removing heat from the tissue through engaging an agitator to transfer heat throughout the substantially enclosed space adjacent to the thermal element.

In some embodiments, a method of using an ablation catheter comprising at least a single agitator, a substantially enclosed space and a catheter shaft comprising a proximal end, a distal end, and a thermal element located at the distal end of the catheter shaft comprises inserting the catheter shaft into a cardiac structure of a patient, heating a tissue adjacent to the cardiac structure of a patient with the thermal element, filling the substantially enclosed space with fluid, and removing heat from the tissue through engaging an agitator to transfer heat throughout the substantially enclosed space adjacent to the thermal element.

In some embodiments, a system for ablating tissue adjacent the lumen of a vessel in a patient comprises an ablation catheter, a controller configured to regulate power delivery to said ablation catheter, a first cable configured to transmit power from the controller to the ablation catheter, a second electrode configured to be placed in electrical contact with the patient; and a second cable configured to transmit power from the second electrode to the controller. The ablation catheter may comprise an elongate catheter shaft having a proximal and a distal end, a first electrode positioned near the distal end of the catheter shaft and configured to transmit radiofrequency energy into a vessel wall, and a substantially enclosed space within the first electrode. The substantially enclosed space may comprise one or more agitators. In some embodiments, the system comprises a second electrode spaced from the first electrode, the second electrode comprising a substantially enclosed space and one or more agitators within the substantially enclosed space.

In accordance with several embodiments, an ablation catheter comprises a catheter shaft having a proximal end and a distal end and an electrode positioned near the distal end of the catheter shaft and configured to transmit radiofrequency energy into a vessel wall. The electrode comprises a substantially enclosed space that comprises a phase change material. The substantially enclosed space is configured to contain fluid to facilitate heat transfer away from the vessel wall. In some embodiments, the phase change material functions as a heat pump.

In accordance with several embodiments, an ablation balloon catheter is adapted to deliver ablation electrodes to a treatment site and deploy the electrodes into a treatment position. In some embodiments, one or more electrodes with attached electrical conductors are affixed to an expanding balloon assembly mounted near the distal end of a catheter. In some cases, it is beneficial to protect the electrode and electrical conductor from damage during use and to protect a patient from injury due to interaction with the electrode or electrical conductor. In some embodiments, at least a portion of the electrodes and electrical conductors are enclosed by a flexible covering or sleeve. In some embodiments, the flexible covering or sleeve is a cylindrical tube. In other embodiments, the flexible covering or sleeve is a conformal coating.

In accordance with several embodiments, an intraluminal ablation catheter adapted to ablate tissue includes a shaft having a proximal end and a distal end. A multi-lumen balloon is positioned near the distal end of the shaft. The multi-lumen balloon comprises at least one main lumen and at least one accessory lumen. In some embodiments, at least one electrode is affixed to the multi-lumen balloon. The at least one electrode may comprise a surface electrically exposed to the tissue to be ablated or otherwise treated. The catheter also includes electrical conductors passing from the electrode to a power source.

In some embodiments, at least one electrical conductor passes through at least one accessory lumen. At least one accessory lumen may be configured to convey fluid. In one embodiment, the at least one accessory lumen is configured to convey cooling fluid past a hot surface of the balloon while energy is being delivered by the at least one electrode. In some embodiments, the cooling fluid is delivered to an accessory lumen through an infusion lumen. The cooling fluid may be removed from the balloon through a return lumen. In some embodiments, a portion of an electrode assembly is contained within an accessory lumen.

In accordance with several embodiments, a balloon ablation catheter includes a proximal manifold and an elongate shaft having a plurality of lumens. The plurality of lumens includes a guidewire lumen and a fluid infusion lumen. The catheter also includes an expandable member (e.g., balloon) coupled to a distal end of the elongate shaft. The balloon includes a plurality of electrodes coupled thereto. The catheter further includes a plurality of electrical conductors extending from a port of the proximal manifold to each of the plurality of electrodes. In some embodiments, the catheter does not include more than four electrodes. In some embodiments, two electrodes are advantageous because 180 degree offset may be maintained and vessels having short lengths (e.g., common hepatic artery having a length of about 30 mm) may be modulated. In other embodiments, four electrodes are advantageous because of one or more of the following benefits: (i) increased vessel lengths may be treated while still maintaining 90-degree or 180 degree offset; (ii) ability to place multiple electrodes in shortest vessel length while controlling radial or circumferential spacing between two electrodes, (iii) increased ability to adjust electrode placement characteristics in difficult anatomy (e.g., tortuous, short length, severe tapers); allows operator to work around side branches or focal disease sites; (iv) allows operator to perform treatments in multiples of two; (v) reduces treatable territory lost in the vessel due to incomplete treatment (e.g., ablation) cycles; and/or (vi) maintains the ability to radially and/or longitudinally offset space between sets of treatments (e.g., ablations). In some embodiments using four electrodes, treatment may be better controlled (e.g., radial and/or length spacing between electrode pairs may be controlled) and the number of treatment sites or catheter placements may be reduced to perform four treatments (e.g., ablations) compared to devices having more than four electrodes. Using only two electrodes or only four electrodes is viable in several embodiments due to, for example, the increased efficiency of the electrodes and the treatment parameters used. If two electrodes are used, the two electrodes may comprise monopolar electrodes or a bipolar electrode pair. If four electrodes are used, the four electrodes may comprise monopolar electrodes or two bipolar electrode pairs. Electrodes may be toggled on and off to customize treatment (e.g., based on length of desired lesion zone, length of vessel, etc.).

The catheter may include a flexible outer sleeve covering at least a portion of a length of the balloon and at least a portion of the plurality of electrical conductors so as to contain the portion of the plurality of electrical conductors. The flexible outer sleeve may be removably coupled to the balloon such that the outer sleeve may be removed from the balloon prior to expansion or inflation of the balloon. In some embodiments, the flexible outer sleeve is permanently coupled (e.g., bonded, adhered, or otherwise non-removably coupled) to the balloon. In some embodiments, the flexible outer sleeve includes a plurality of fenestrations aligned with at least some of the plurality of electrodes. In some embodiments, the flexible outer sleeve includes one or more openings, slots or holes separate from the fenestrations that are not aligned with any of the electrodes. These one or more openings, slots or holes may advantageously be adapted to provide increased flexibility to the balloon, to facilitate folding and/or to reduce heat.

In some embodiments, the plurality of electrodes is directly bonded (e.g., soldered, welded, adhered with adhesive) to the balloon without the use of flex circuits. A respective one of the plurality of electrical conductors may be bonded (e.g., soldered, welded, adhered with adhesive) to a corresponding one or more of the plurality of electrodes. In some embodiments, one or more of the plurality of electrodes includes a channel along a length of a surface of the electrode adapted to receive an electrical conductor, thereby providing a reduced outer profile. One or more of the electrodes may be curved to conform to an outer surface of the balloon when in an inflated configuration. The balloon may include a plurality of divots, or recesses adapted to receive a respective one of the plurality of electrodes such that an outer diameter of the balloon at each electrode location is no larger than the outer diameter of the balloon adjacent to each electrode.

In some embodiments, the catheter includes a distal tracking segment coupled to a distal end of the expandable member (e.g., balloon). The distal tracking segment may advantageously be adapted to vary a flexibility of the catheter from distal to proximal or from proximal to distal. In some embodiments, at least a portion (e.g., a distal tip) of the distal tracking segment comprises radiopaque material. The distal tracking segment may have a pre-shaped configuration (e.g., as a result of shape memory material that is pre-shaped to a particular shape) or the distal tracking segment may be configured to be shaped by an operator to have a particular desired shape or geometry (e.g., a shape that corresponds to a shape or geometry of vasculature through which a distal end portion of the catheter must traverse. In some embodiments, the fluid infusion lumen includes at least one orifice that is oriented so as to direct a fluid jet directly at a surface of one of the plurality of electrodes.

The catheter may also be coupled to a moveable outer sheath. The moveable outer sheath may be coupled along a length of the elongate shaft of the catheter and may be moveable with respect to the elongate shaft. In some embodiments, translational movement of the moveable outer sheath adjusts a push force on a distal end portion of the catheter or adjusts a flexibility of the elongate shaft of the catheter. The moveable outer sheath may comprise a captive support shaft or guide sheath adapted to deliver (e.g., infuse) fluid or dye to a blood vessel. The sheath may be less than 6 French and may have variable stiffness along its length. The moveable outer sheath may be reinforced with braids or coils. The moveable outer sheath may be adapted to move with respect to the catheter shaft by greater than 5 cm or greater than 10 cm. In some embodiments, the flexible outer sleeve is integrally coupled to the moveable outer sheath. For example, the flexible outer sleeve may be a proximal portion of the moveable outer sheath that is moveable with respect to the elongate shaft such that the outer sleeve may be removed from covering the balloon (and the one or more electrodes of the balloon) prior to expansion or inflation of the balloon.

In accordance with several embodiments, a method of delivering therapeutic energy to tissue using a balloon catheter is provided. The method includes positioning a balloon of a balloon catheter at a first placement location within a vessel (e.g., a common hepatic artery) of a subject from which energy is to be delivered, wherein the balloon comprises one or more energy delivery members (e.g., electrodes, ultrasound transducers or delivery elements) that are configured to be independently activated. The method further includes determining at least one of a position and orientation of each of the one or more energy delivery members at the first placement location. The method also includes causing at least one of the one or more energy delivery members not to be activated at the first placement location based on at least one of the position or orientation of the at least one energy delivery member.

In some embodiments, the method further includes determining, based on a determined position and orientation of each of the one or more energy delivery members, that energy delivery by at least one of the one or more energy delivery members may affect a non-target adjacent structure (e.g., a structure or tissue desired not to be affected or desired not to receive any energy or heat), such as a pancreas, bile duct, portal vein, lymph node, etc.). In some embodiments, the method includes determining, based on the determined position of the one or more energy delivery members, that at least one of the energy delivery members is positioned beyond a boundary (e.g., a proximal or distal end) of the vessel such that energy delivery is customized to a vessel length. For example, the at least one of the energy delivery members determined to be positioned beyond the boundary of the vessel (e.g., at a bifurcation or in a different branch or vessel or outside a length of the vessel) may not be activated when others of the energy delivery members are activated so as not to deliver energy to a location beyond the boundary of the vessel, thereby facilitating customized treatment based on vessel length. The determinations of position and/or orientation may be based on various imaging methods or mechanisms (e.g., fluoroscopy, computerized tomography (CT), radiographic, angiographic, optical coherence tomography (OCT), intravascular ultrasound (IVUS), Doppler, thermography, magnetic resonance (MR) imaging and/or the like).

In accordance with several embodiments, a method of delivering therapeutic energy to tissue using a balloon catheter includes positioning a balloon of a balloon catheter at a first placement location within a vessel of a subject. The balloon may include a plurality of electrodes arranged in an electrode pattern comprised of or consisting of four electrodes. The method includes activating (simultaneously or independently) a first pair of the plurality of electrodes at the first placement location, wherein the first pair of the plurality of electrodes are spaced apart circumferentially and axially along the balloon. The method also includes repositioning the balloon at a second placement location within the vessel of the subject and activating (simultaneously or independently) a second pair of the plurality of electrodes different than the first pair of the plurality of electrodes at the second placement location. The second pair of the plurality of electrodes is spaced apart circumferentially and axially along the balloon from the first pair. The method creates a lesion pattern (e.g., a spiral lesion pattern) that is different than the electrode pattern. In some embodiments, the electrodes of the first pair are spaced apart circumferentially from each other by 90 degrees and the electrodes of the second pair are spaced apart from each other circumferentially by 90 degrees. A first electrode of the first pair and a first electrode of the second pair may be spaced apart circumferentially by 180 degrees and aligned along a plane that is perpendicular to an axis (e.g., longitudinal axis) of the vessel. A second electrode of the first pair and a second electrode of the second pair may also be spaced apart circumferentially by 180 degrees and aligned along a plane that is perpendicular to an axis (e.g., longitudinal axis) of the vessel. In some embodiments, the lesion pattern is adapted to increase perivascular circumferential coverage without causing circumferential coverage along a cross-section of a vessel wall.

In accordance with several embodiments, a method of delivering therapeutic energy to tissue using a balloon catheter is provided. The method includes positioning a balloon of a balloon catheter at a first placement location within a vessel (e.g., common hepatic artery) of a subject. The balloon may include a plurality of electrodes arranged in an electrode pattern comprised of six electrodes. The method includes activating a first triplet of the plurality of electrodes at the first placement location, wherein the first triplet of the plurality of electrodes are spaced apart circumferentially and axially from each other along the balloon. The method also includes repositioning the balloon at a second placement location within the vessel of the subject and activating a second triplet of the plurality of electrodes different than the first triplet of the plurality of electrodes at the second placement location. The second triplet of the plurality of electrodes are spaced apart circumferentially and axially from each other along the balloon. The lesion pattern created by the activation of the first triplet of electrodes and the second triplet of electrodes may advantageously be different than the electrode pattern. In some embodiments, the first triplet of the plurality of electrodes are spaced apart circumferentially from each other by 120 degrees and the second triplet of the plurality of electrodes are spaced apart circumferentially from each other by 120 degrees.

In accordance with several embodiments, an intraluminal ablation catheter adapted for hepatic denervation includes a proximal manifold. The proximal manifold may comprise one or more ports (e.g., coolant fluid infusion port, dye delivery port, guidewire port, balloon inflation port). The catheter may also include an elongate shaft comprising at least one lumen. The elongate shaft comprises a central longitudinal axis extending along its length. The catheter also includes an expandable member (e.g., inflatable balloon) coupled to a distal end portion of the elongate shaft. The expandable member is adapted to transition between a non-expanded (e.g., non-inflated, folded) configuration and an expanded (e.g., inflated, unfolded) configuration. The expandable member comprises or consists of four electrodes. A first electrode and a second electrode of the four electrodes may be located within a first circumferential cross-section along the expandable member at a first axial distance from a distal end of the expandable member and may be located in opposite quadrants from each other (e.g., 180 degrees apart or approximately 180 degrees apart circumferentially) about the central longitudinal axis of the elongate shaft when the expandable member is in the expanded configuration. A third electrode and a fourth electrode of the four electrodes may be located within a second circumferential cross-section along the expandable member at a second axial distance from the distal end of the expandable member and are located in opposite quadrants from each other (e.g., 180 degrees apart or approximately 180 degrees apart circumferentially) about the central longitudinal axis of the elongate shaft when the expandable member is in the expanded configuration. The second axial distance is different from the first axial distance. The catheter also includes means for cooling the four electrodes.

In some embodiments, the third and fourth electrodes are each circumferentially offset from the first and second electrodes such that they are in different quadrants than the first and second electrodes. For example, the third and fourth electrodes may be offset from the first and second electrodes by 90 degrees. In some embodiments, a center point of the first and second electrodes are aligned along a first plane that is substantially perpendicular to the central longitudinal axis of the elongate shaft and a center point of the third and fourth electrodes are aligned along a second plane that is substantially perpendicular to the central longitudinal axis of the elongate shaft. The at least one lumen of the elongate shaft may include a first central guidewire lumen adapted to track a guidewire and at least one fluid delivery lumen in fluid communication with an interior of the balloon and adapted to deliver coolant within the balloon and/or fluid to inflate/deflate the balloon to cause it to transition between the expanded and non-expanded configurations.

The means for cooling may include one or more orifices adapted to direct fluid jets toward at least one of the four electrodes. The orifices may be positioned along an inner balloon within the balloon (which may be referred to as an outer balloon in such embodiments), along a fluid delivery lumen, or along other structures internal to the balloon. In some embodiments, at least one orifice is positioned adjacent each of the four electrodes such that each of the four electrodes is directly cooled. One or more nozzles or eductors may be positioned adjacent the one or more orifices such that each of the one or more nozzles or eductors is configured to direct the fluid jets toward at least one surface of a respective one the four electrodes. In one embodiment, a second balloon (e.g., inner balloon) is located within the balloon (e.g., outer balloon) and the one or more orifices are positioned along the second balloon at a location adjacent one, some or all of the electrodes. In some embodiments, the means for cooling comprises a fluid inlet lumen having an outlet located within the balloon and adjacent to at least one of (e.g., one, some or all of) the four electrodes.

In some embodiments, the balloon includes fenestrations, with each of the four electrodes being located within a respective fenestration. In some embodiments, each of the four electrodes is directly bonded to an outer surface of the balloon without the use of a flex circuit. In some embodiments, the catheter includes one or more lesion spacing indicators (e.g., radiopaque markers) positioned along the elongate shaft to facilitate controlled spacing of lesion zones. The lesion spacing indicator(s) may be positioned distal to the balloon, proximal to the balloon, and/or within the balloon.

In some embodiments, each of the four electrodes includes a channel along a length of a surface of the electrode adapted to receive an electrical conductor. A separate electrical conductor may be coupled to each electrode and may extend from the respective electrode to the proximal manifold. In some embodiments, the catheter further includes a distal tracking segment coupled to a distal end of the expandable member (e.g., balloon) or coupled to a distal end of the elongate shaft or the at least one lumen. The distal tracking segment is adapted to vary a flexibility of the catheter from distal to proximal. A distal tip of the distal tracking segment may comprise radiopaque material. The distal tracking segment may have a pre-shaped configuration or may be configured to be shaped by an operator either prior to insertion or after insertion.

In some embodiments, the balloon includes a plurality of divots, wherein each of the plurality of divots is adapted to receive a respective one of the plurality of electrodes such that an outer diameter of the balloon at each electrode location is no larger than the outer diameter of the balloon adjacent to each electrode. The catheter may also include a moveable outer sheath (e.g., captive support sleeve) coupled along a length of the elongate shaft and moveable with respect to the elongate shaft, wherein translational movement of the moveable outer sheath adjusts a push force on a distal end portion of the catheter or adjusts a flexibility of the elongate shaft.

In some embodiments, the balloon is adapted to be substantially cylindrical when in the expanded configuration such that each of the four electrodes is substantially equidistant circumferentially from each of the other four electrodes when the balloon is in the expanded configuration. In some embodiments, each of the four electrodes is formed of a cluster of two electrode elements positioned circumferentially adjacent to each other and adapted to function as a single monopolar electrode. In some embodiments, a surface area of the cluster of two electrode elements ranges between 5 $mm^2$ and 40 $mm^2$ (e.g., between 5 $mm^2$ and 20 $mm^2$, between 10 $mm^2$ and 40 $mm^2$). In some embodiments, a maximum width of any of the two electrode elements is less than one-fourth of the circumference of the expandable member when in the expanded configuration. The two electrode elements may be positioned to straddle a folding line of the expandable member. In some embodiments, the cluster of two electrode elements has a substantially square aspect ratio. The catheter may advantageously be sized and adapted to be advanced to a location within a hepatic artery (e.g., common hepatic artery).

In accordance with several embodiments, an intraluminal ablation catheter includes a proximal manifold, an elongate shaft comprising at least one lumen and a first balloon coupled to a distal end portion of the elongate shaft, wherein the balloon is adapted to transition between a folded configuration and an expanded, unfolded configuration. The balloon includes or consists of four electrodes positioned along the balloon, with a first electrode and a second electrode of the four electrodes being located in a first circumferential cross-sectional plane along the balloon and located in opposite quadrants from each other around the circumference of the balloon when the balloon is in the expanded, unfolded configuration, and a third electrode and a fourth electrode of the four electrodes being located within a second circumferential cross-sectional plane along the balloon and located in opposite quadrants from each other around the circumference of the balloon when the balloon is in the expanded, unfolded configuration. The second circumferential cross-sectional plane is axially offset from the first circumferential cross-sectional plane. The catheter also includes means for cooling the four electrodes.

In some embodiments, the third electrode and the fourth electrode are located in different quadrants circumferentially than the first electrode and the second electrode when the balloon is in the expanded, unfolded configuration. The third electrode and the fourth electrode may be located in quadrants that are circumferentially offset by 90 degrees from the quadrants in which the first electrode and the second electrode are located when the balloon is in the expanded, unfolded configuration. The first electrode and the second electrode may be located 180 degrees apart circumferentially from each other about a central longitudinal axis of the elongate shaft. The third electrode and the fourth electrode may be located 180 degrees apart circumferentially from each other about the central longitudinal axis of the elongate shaft. In some embodiments, the third and fourth electrodes are each circumferentially offset from the first and second electrodes by 90 degrees when the balloon is in the expanded, unfolded configuration.

In some embodiments, the at least one lumen includes a first central guidewire lumen adapted to track a guidewire and at least one fluid delivery lumen in fluid communication with an interior of the balloon and adapted to deliver coolant and/or other fluid within the balloon. The means for cooling may include one or more orifices adapted to direct fluid jets toward at least one of the four electrodes. The orifices may be positioned along an inner balloon within the balloon (which may be referred to as an outer balloon in such embodiments), along a fluid delivery lumen, or along other structures internal to the balloon. In some embodiments, at least one orifice is positioned adjacent each of the four electrodes such that each of the four electrodes is directly cooled. One or more nozzles or eductors may be positioned adjacent the one or more orifices such that each of the one or more nozzles or eductors is configured to direct the fluid jets toward at least one surface of a respective one the four electrodes. In one embodiment, a second balloon (e.g., inner balloon) is located within the balloon (e.g., outer balloon) and the one or more orifices are positioned along the second balloon at a location adjacent one, some or all of the electrodes. In some embodiments, the means for cooling comprises a fluid inlet lumen having an outlet located within the balloon and adjacent to at least one of (e.g., one, some or all of) the four electrodes.

In some embodiments, the balloon includes fenestrations, with each of the four electrodes being located within a respective fenestration. In some embodiments, each of the four electrodes is directly bonded to an outer surface of the balloon without the use of a flex circuit. In some embodiments, the catheter includes one or more lesion spacing indicators (e.g., radiopaque markers) positioned along the elongate shaft to facilitate controlled spacing of lesion zones. The lesion spacing indicator(s) may be positioned distal to the balloon, proximal to the balloon, and/or within the balloon.

In some embodiments, each of the four electrodes includes a channel along a length of a surface of the electrode adapted to receive an electrical conductor. A separate electrical conductor may be coupled to each electrode and may extend from the respective electrode to the proximal manifold. In some embodiments, the catheter further includes a distal tracking segment coupled to a distal end of the balloon or coupled to a distal end of the elongate shaft or the at least one lumen. The distal tracking segment is adapted to vary a flexibility of the catheter from distal to proximal. A distal tip of the distal tracking segment may comprise radiopaque material. The distal tracking segment may have a pre-shaped configuration or may be configured to be shaped by an operator either prior to insertion or after insertion.

In some embodiments, the balloon includes a plurality of divots, wherein each of the plurality of divots is adapted to receive a respective one of the plurality of electrodes such that an outer diameter of the balloon at each electrode location is no larger than the outer diameter of the balloon adjacent to each electrode. The catheter may also include a moveable outer sheath (e.g., captive support sleeve) coupled along a length of the elongate shaft and moveable with respect to the elongate shaft, wherein translational movement of the moveable outer sheath adjusts a push force on a distal end portion of the catheter or adjusts a flexibility of the elongate shaft.

In some embodiments, the balloon is adapted to be substantially cylindrical when in the expanded configuration such that each of the four electrodes is substantially equidistant circumferentially from each of the other four electrodes when the balloon is in the expanded configuration. In some embodiments, each of the four electrodes is formed of a cluster of two electrode elements positioned circumferentially adjacent to each other and adapted to function as a single monopolar electrode. In some embodiments, a surface area of the cluster of two electrode elements ranges between 5 mm$^2$ and 40 mm$^2$ (e.g., between 5 mm$^2$ and 20 mm$^2$, between 10 mm$^2$ and 40 mm$^2$). In some embodiments, a maximum width of any of the two electrode elements is less than one-fourth of the circumference of the expandable member when in the expanded configuration. The two electrode elements may be positioned to straddle a folding line of the expandable member. In some embodiments, the cluster of two electrode elements has a substantially square aspect ratio. The catheter may advantageously be sized and adapted to be advanced to a location within a hepatic artery (e.g., common hepatic artery).

In accordance with several embodiments, an intraluminal ablation catheter includes a proximal manifold, an elongate shaft comprising at least one lumen, and a first balloon coupled along the elongate shaft, wherein the balloon is adapted to transition between a folded configuration and an expanded, unfolded configuration. The balloon may include four clusters of electrodes each comprising two electrode members positioned circumferentially adjacent to each other and aligned axially along the length of the balloon. Each of the four clusters may be positioned in a different circumferential quadrant of the balloon when in the expanded, unfolded configuration. In some embodiments, each of the four clusters is spaced apart axially from each of the other three clusters. The catheter also includes means for directly cooling the four clusters of electrode members.

In some embodiments, the four clusters of electrode members are positioned such that the clusters collectively form a spiral pattern along a length of the balloon. In some embodiments, each successive cluster moving from a distal end to a proximal end of the balloon is circumferentially offset by 90 degrees or approximately 90 degrees from the previous cluster. In some embodiments, a first two of the four clusters are circumferentially offset from each other by 180 degrees or approximately 180 degrees and wherein a second two of the four clusters are circumferentially offset from each other by 180 degrees or approximately 180 degrees.

In some embodiments, the at least one lumen includes a first central guidewire lumen adapted to track a guidewire and at least one fluid delivery lumen in fluid communication with an interior of the balloon and adapted to deliver coolant and/or other fluid within the balloon. In some embodiments, the means for cooling includes one or more orifices adapted to direct fluid jets toward at least one of the four clusters. The orifices may be positioned along an inner balloon within the balloon (which may be referred to as an outer balloon in such embodiments), along a fluid delivery lumen, or along other structures internal to the balloon. In some embodiments, at least one orifice is positioned adjacent each of the four clusters such that each of the four clusters is directly cooled. One or more nozzles or eductors may be positioned adjacent the one or more orifices such that each of the one or more nozzles or eductors is configured to direct the fluid jets toward at least one of the four clusters. In one embodiment, a second balloon (e.g., inner balloon) is located within the balloon (e.g., outer balloon) and the one or more orifices are positioned along the second balloon at a location adjacent one, some or all of the clusters. In some embodiments, the means for cooling comprises a fluid inlet lumen having an outlet located within the balloon and adjacent to at least one of (e.g., one, some or all of) the four clusters.

In some embodiments, the electrode members of the four clusters are directly bonded to an outer surface of the balloon without the use of a flex circuit. In some embodiments, the catheter includes one or more lesion spacing indicators (e.g., radiopaque markers) positioned along the elongate shaft to facilitate controlled spacing of lesion zones. The lesion spacing indicator(s) may be positioned distal to the balloon, proximal to the balloon, and/or within the balloon.

In some embodiments, each of the electrode members includes a channel along a length of a surface of the electrode member adapted to receive an electrical conductor.

A separate electrical conductor may be coupled to each electrode member or a single electrical conductor may be coupled to all electrode members of an electrode cluster and may extend from the respective electrode to the proximal manifold. In some embodiments, the catheter further includes a distal tracking segment coupled to a distal end of the balloon or coupled to a distal end of the elongate shaft or the at least one lumen. The distal tracking segment is adapted to vary a flexibility of the catheter from distal to proximal. A distal tip of the distal tracking segment may comprise radiopaque material. The distal tracking segment may have a pre-shaped configuration or may be configured to be shaped by an operator either prior to insertion or after insertion.

The catheter may also include a moveable outer sheath (e.g., captive support sleeve) coupled along a length of the elongate shaft and moveable with respect to the elongate shaft, wherein translational movement of the moveable outer sheath adjusts a push force on a distal end portion of the catheter or adjusts a flexibility of the elongate shaft. In some embodiments, the balloon is adapted to be substantially cylindrical when in the expanded configuration such that each of the four clusters is substantially equidistant circumferentially from each of the other four clusters when the balloon is in the expanded configuration. In some embodiments, a surface area of the cluster of two electrode members ranges between 5 mm$^2$ and 40 mm$^2$ (e.g., between 5 mm$^2$ and 20 mm$^2$, between 10 mm$^2$ and 40 mm$^2$). In some embodiments, a maximum width of any of the two electrode members is less than one-fourth of the circumference of the expandable member when in the expanded configuration. The two electrode members of each cluster may be positioned to straddle a folding line of the expandable member. In some embodiments, the cluster of two electrode elements has a substantially square aspect ratio. Each cluster may include three, four, five, six or more than six electrode elements. The catheter may advantageously be sized and adapted to be advanced to a location within a hepatic artery (e.g., common hepatic artery).

Although some embodiments summarized above are described with respect to hepatic neuromodulation, the embodiments herein also contemplate neuromodulation or tissue modulation of regions other than the liver or hepatic vessels. For example, the catheters, devices and systems described herein may also be used for renal denervation (e.g., by modulating the nerves in one or both renal arteries), for glucose or lipid regulation by modulating the nerves that innervate the pancreas, kidney, duodenum, jejunum and/or stomach, for cardiac ablation, for pulmonary tissue or vessel ablation or neuromodulation, as well as other targets and indications described herein. The devices and systems summarized above may be used within vessels other than a hepatic artery, such as a renal artery, a gastroduodenal artery, a celiac artery or a splenic artery. For example, the devices and systems may be used within one or more renal arteries or veins and may be suitable for treating hypertension or other conditions associated with modulation of nerves surrounding the renal vessels. As another example, the devices and systems may be used within a gastroduodenal artery, celiac artery or vessel innervating the pancreas and the neuromodulation device may be suitable for treating one or more symptoms of diabetes. As another example, the devices and systems may be used within a vessel and may be configured to cause modulation of nerves surrounding the vessel sufficient to alter sympathetic tone.

For purposes of summarizing the disclosure, certain aspects, advantages, and novel features of embodiments of the invention have been described herein. It is to be understood that not necessarily all such advantages may be achieved in accordance with any particular embodiment of the invention disclosed herein. Thus, the embodiments disclosed herein may be embodied or carried out in a manner that achieves or optimizes one advantage or group of advantages as taught or suggested herein without necessarily achieving other advantages as may be taught or suggested herein. The methods summarized above and set forth in further detail below describe certain actions taken by a practitioner; however, it should be understood that they can also include the instruction of those actions by another party. Thus, actions such as "delivering a neuromodulation catheter within a hepatic artery" include "instructing the delivery of a neuromodulation catheter within a hepatic artery." With respect to the drawings, elements from one figure may be combined with elements from the other figures.

BRIEF DESCRIPTION OF THE DRAWINGS

FIG. 7 illustrates an embodiment of an electrode assembly.

FIG. 13A is a partial sectional view of a distal end portion of an embodiment of a balloon ablation device.

FIGS. 13B-1 and 13B-2 is a perspective and partial cutaway view, respectively, of a distal end portion of another embodiment of a balloon ablation device.

FIGS. 13O-1 and 13C-2 is a partial section view and an enlarged partial section view, respectively, of a distal end portion of another embodiment of a balloon ablation device.

FIG. 14A is a partial section view of an embodiment of a cooling assembly inside of a balloon of a balloon ablation device.

FIGS. 14B-1 and 14B-2 show a perspective view and an end view, respectively, of an embodiment of a multi-lumen cooling assembly.

FIGS. 16A-1 to 16A-3 show an isometric, side and cross-sectional view of an embodiment of a multi-lumen ablation balloon assembly.

FIGS. 16C-1 and 16C-2 show cross sectional views of embodiments of a multi-lumen extrusion suitable for making multi-lumen ablation balloon components.

FIGS. 16D-1, 16D-2, 16E-1 and 16E-2 show cross sectional views through a central portion of multi-lumen ablation balloon components.

FIGS. 17A, 17B-1, 17B-2 and 17C show various views of an embodiment of a composite multi-lumen balloon ablation device.

FIG. 29A is a graph illustrating the temperature distribution at various parts of an idealized thermal element and tissues.

FIG. 29B is a graph illustrating the temperature distribution at various parts of a thermal element and adjacent tissues of a substantially solid electrode.

FIG. 29C is a graph illustrating the temperature distribution at various parts of a thermal element and adjacent tissues of a substantially solid electrode, but having lower thermal conductivity compared to FIG. 29B.

FIG. 29D is a graph illustrating the temperature distribution of a fluid filled electrode, according to an aspect of the disclosure.

FIG. 34A shows an embodiment of a whistle-like catheter having a jet apparatus configured to entrain fluid with a high velocity, low flow jet.

FIG. 34B shows a cross-sectional view of the embodiment of FIG. 34A.

FIGS. 38A and 38B schematically illustrate embodiments of ablation catheters having lesion spacing indicators adapted to control lesion spacing.

DETAILED DESCRIPTION

Introduction

Figure 1A:
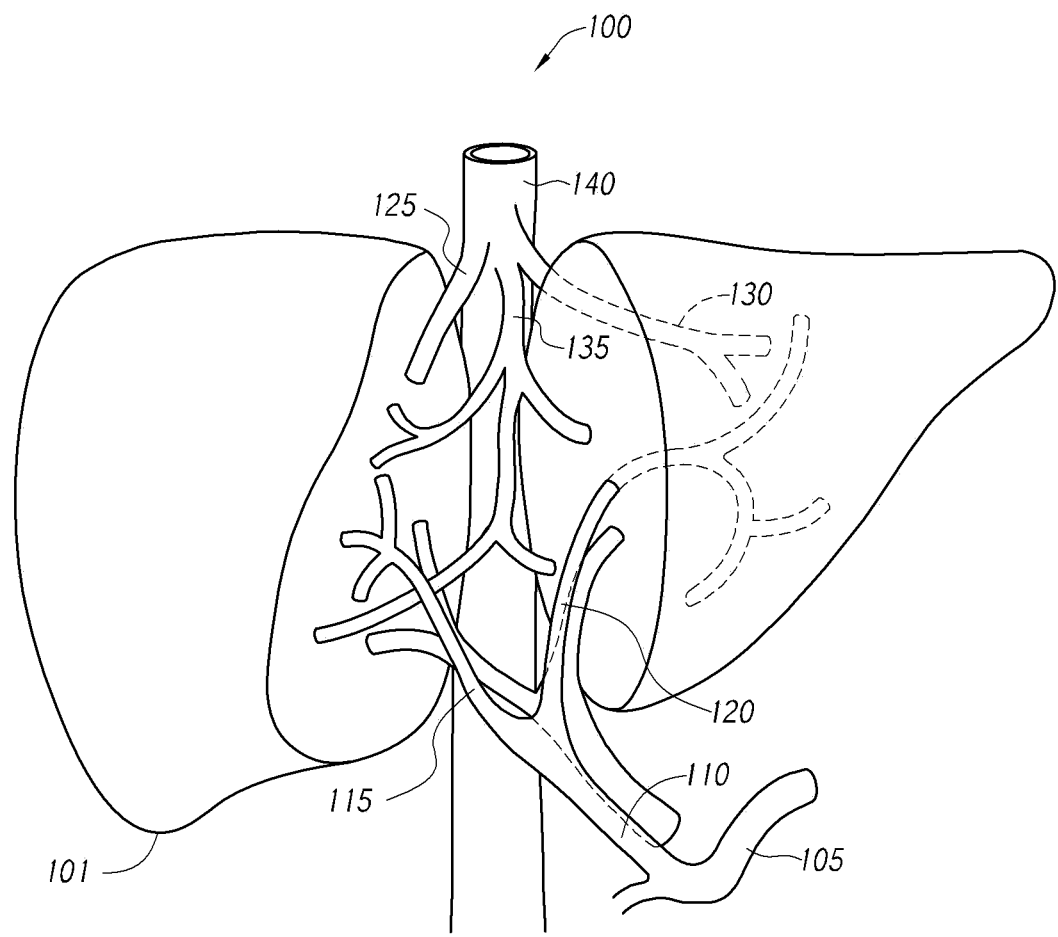
FIG. 1A illustrates the anatomy of a target treatment location including the liver and hepatic blood supply, in accordance with an embodiment of the invention.

Embodiments of the invention described herein are generally directed to therapeutic neuromodulation of targeted nerve fibers to treat, or reduce the risk of occurrence or progression of, various metabolic diseases, conditions, or disorders, including but not limited to diabetes (e.g., diabetes mellitus). While the description sets forth specific details in various embodiments, it will be appreciated that the description is illustrative only and should not be construed in any way as limiting the disclosure. Furthermore, various applications of the disclosed embodiments, and modifications thereto, which may occur to those who are skilled in the art, are also encompassed by the general concepts described herein. Although several figures set forth below are described with respect to hepatic neuromodulation, the embodiments herein also contemplate neuromodulation or tissue modulation of regions other than the liver or hepatic vasculature. For example, the catheters, devices and systems described herein may also be used for renal denervation (e.g., by modulating the nerves in one or both renal arteries), for glucose or lipid regulation by modulating the nerves that innervate the pancreas, duodenum, jejunum and/or stomach, for cardiac ablation, for pulmonary tissue or vessel ablation or neuromodulation, as well as other targets and indications described herein.

The autonomic nervous system includes the sympathetic and parasympathetic nervous systems. The sympathetic nervous system is the component of the autonomic nervous system that is responsible for the body's "fight or flight" responses, those that can prepare the body for periods of high stress or strenuous physical exertion. One of the functions of the sympathetic nervous system, therefore, is to increase availability of glucose for rapid energy metabolism during periods of excitement or stress, and to decrease insulin secretion.

The liver can play an important role in maintaining a normal blood glucose concentration. For example, the liver can store excess glucose within its cells by forming glycogen, a large polymer of glucose. Then, if the blood glucose concentration begins to decrease too severely, glucose molecules can be separated from the stored glycogen and returned to the blood to be used as energy by other cells. The liver is a highly vascular organ that is supplied by two independent blood supplies, one being the portal vein (as the liver's primary blood supply) and the other being the hepatic arteries (being the liver's secondary blood supply).

The process of breaking down glycogen into glucose is known as glycogenolysis, and is one way in which the sympathetic nervous system can increase systemic glucose. In order for glycogenolysis to occur, the enzyme phosphorylase must first be activated in order to cause phosphorylation, which allows individual glucose molecules to separate from branches of the glycogen polymer. One method of activating phosphorylase, for example, is through sympathetic stimulation of the adrenal medulla. By stimulating the sympathetic nerves that innervate the adrenal medulla, epinephrine is released. Epinephrine then promotes the formation of cyclic AMP, which in turn initiates a chemical reaction that activates phosphorylase. An alternative method of activating phosphorylase is through sympathetic stimulation of the pancreas. For example, phosphorylase can be activated through the release of the hormone glucagon by the alpha cells of the pancreas. Similar to epinephrine, glucagon stimulates formation of cyclic AMP, which in turn begins the chemical reaction to activate phosphorylase.

Another way in which the liver functions to maintain a normal blood glucose concentration is through the process of gluconeogenesis. When the blood glucose concentration decreases below normal, the liver will synthesize glucose from various amino acids and glycerol in order to maintain a normal blood glucose concentration. Increased sympathetic activity has been shown to increase gluconeogenesis, thereby resulting in an increased blood glucose concentration.

The parasympathetic nervous system is the second component of the autonomic nervous system and is responsible for the body's "rest and digest" functions. These "rest and digest" functions complement the "fight or flight" responses of the sympathetic nervous system. Stimulation of the parasympathetic nervous system has been associated with decreased blood glucose levels. For example, stimulation of the parasympathetic nervous system has been shown to increase insulin secretion from the beta-cells of the pancreas. Because the rate of glucose transport through cell membranes is greatly enhanced by insulin, increasing the amount of insulin secreted from the pancreas can help to lower blood glucose concentration. Neuromodulation (e.g., denervation, ablation or stimulation) of sympathetic and/or parasympathetic nerves surrounding other organs or tissues (such as the pancreas, small intestine, duodenum, and/or portions of the stomach) may also be performed in combination with modulation of nerves innervating the liver to treat diabetes or the symptoms associated with diabetes (e.g., high blood glucose levels, high triglyceride levels, high cholesterol levels, low insulin secretion levels). Several embodiments described herein are adapted to modulate (e.g., ablate, stimulate, etc.) the parasympathetic system alone or in conjunction with the sympathetic system. In some embodiments, one system is activated and the other deactivated. Alternatively, both systems can be activated or deactivated. In some embodiments, stimulation of the parasympathetic nerves innervating the pancreas is combined with denervation of sympathetic nerves innervating the liver to treat diabetes or the symptoms associated with diabetes (e.g., high blood glucose levels, high triglyceride levels, high cholesterol levels, low insulin secretion levels). Stimulation and/or denervation of sympathetic and/or parasympathetic nerves surrounding other organs or tissues (such as the pancreas, duodenum and/or portions of the stomach) may also be performed in combination.

FIG. 1A illustrates a liver 101 and vasculature of a target hepatic treatment location 100. The liver may be innervated along structures of or associated with the portal triad (e.g., hepatic arteries), along which both sympathetic and parasympathetic nerve fibers may course. The vasculature includes the common hepatic artery 105, the proper hepatic artery 110, the right hepatic artery 115, the left hepatic artery 120, the right hepatic vein 125, the left hepatic vein 130, the middle hepatic vein 135, and the inferior vena cava 140. In the hepatic blood supply system, blood enters the liver by coursing through the common hepatic artery 105, the proper hepatic artery 110, and then either of the left hepatic artery 120 or the right hepatic artery 115. The right hepatic artery 115 and the left hepatic artery 120 (as well as the portal vein, not shown) provide blood supply to the liver 101, and directly feed the capillary beds within the hepatic tissue of the liver 101. The liver 101 uses the oxygen provided by the oxygenated blood flow provided by the right hepatic artery 115 and the left hepatic artery 120. Deoxygenated blood from the liver 101 leaves the liver 101 through the right hepatic vein 125, the left hepatic vein 130, and the middle hepatic vein 135, all of which empty into the inferior vena cava 140.

Figure 1B:
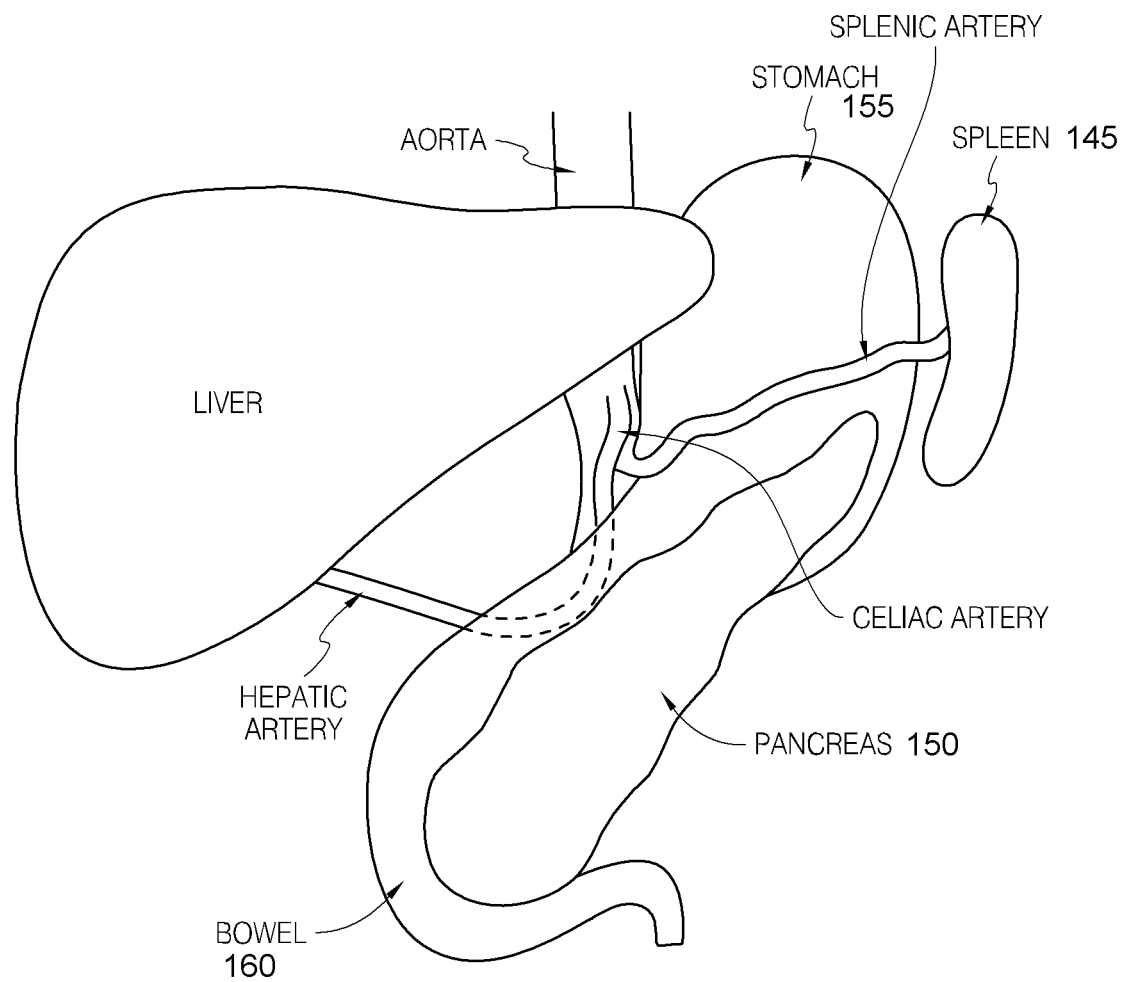
FIG. 1B illustrates the anatomy of a target treatment location including the liver and hepatic blood supply, in accordance with an embodiment of the invention.

FIG. 1B illustrates a liver 101 and target vasculature of hepatic neuromodulation methods and systems to treat diabetes or symptoms associated with diabetes or glucose production. The target vasculature may include a hepatic artery 105, which branches off from a celiac artery 210 originating at the abdominal aorta 205. The hepatic artery 105 supplies blood to the liver. The splenic artery 235 is also illustrated, which also branches off from the celiac artery 210 to provide blood to the spleen 145. Other organs or dense structures positioned adjacent the hepatic artery 105 may include the pancreas 150, the stomach 155, and portions of the bowel 160 (including the small intestine). Systems and methods may be provided to identify locations along the hepatic artery 105 that are in close proximity to adjacent structures (e.g., organs) which may influence glucose production and to modulate tissue at or near the identified locations (e.g., delivering energy using radiofrequency, ultrasound or microwave energy delivery devices sufficient to modulate nerves that innervate the liver and/or other adjacent structures that may influence glucose production (such as the pancreas 150, stomach 155, and/or small intestine 160)). The modulation provided may be sufficient to reduce glucose levels (e.g., blood glucose levels), lipid levels, cholesterol levels, etc. In various embodiments, portions of multiple adjacent structures (e.g., organs) may be denervated or otherwise modulated (either from a single location or from multiple locations along a portion of the hepatic artery 105 or arteries connected or adjacent to the hepatic artery 105, such as the celiac artery 210, splenic artery 235, and gastroduodenal artery). Several embodiments of the invention are particularly advantageous in that disruption of sympathetic nerves that innervate organs that influence glucose production and storage may be performed consistently regardless of anatomical variations between subjects.

Figure 1C:
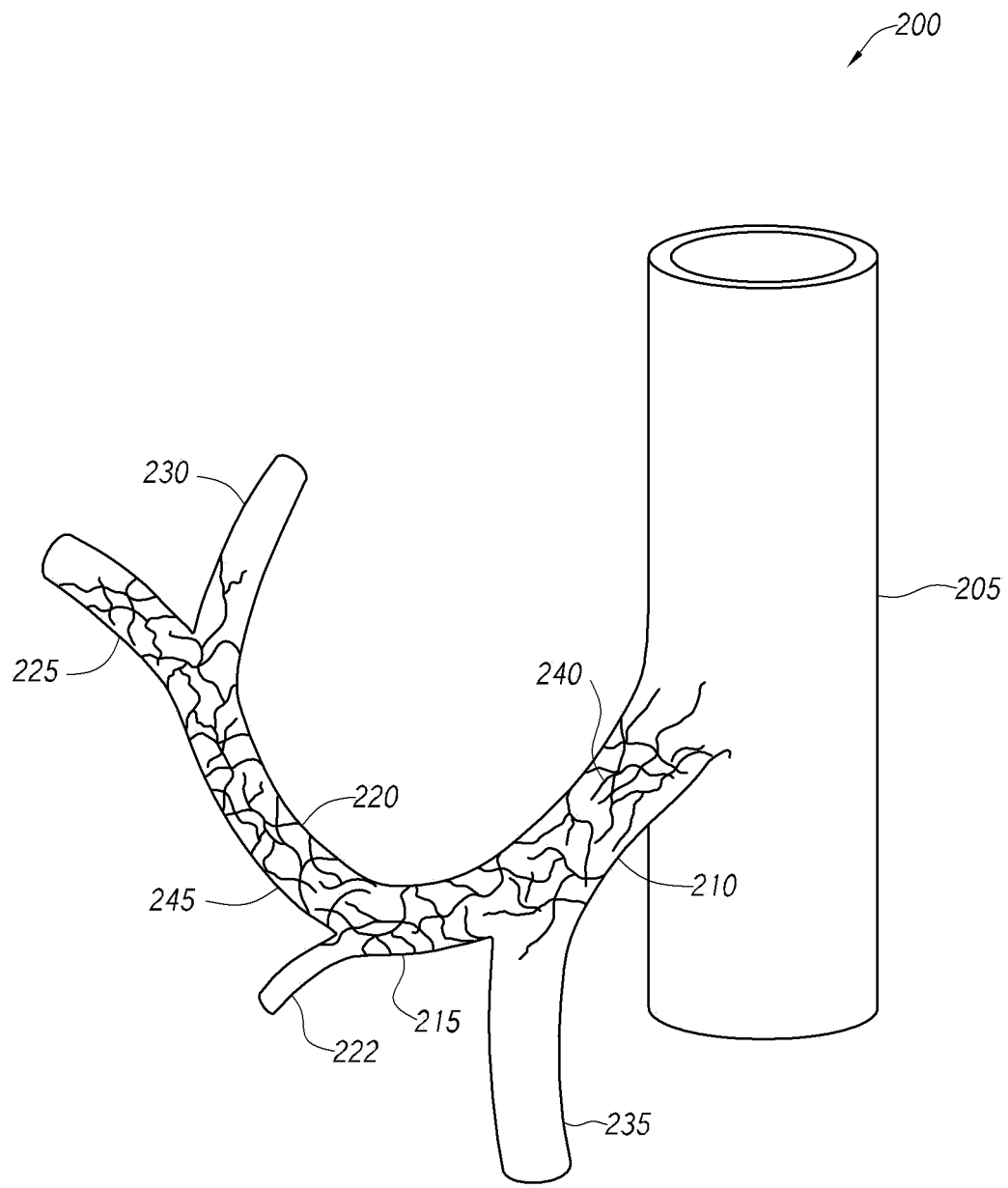
FIG. 1C illustrates various arteries supplying blood to the liver and its surrounding organs and tissues and nerves that innervate the liver and its surrounding organs and tissues.

FIG. 1C illustrates various arteries surrounding the liver and the various nerve systems 200 that innervate the liver and its surrounding organs and tissue. The arteries include the abdominal aorta 205, the celiac artery 210, the common hepatic artery 215, the proper hepatic artery 220, the gastroduodenal artery 222, the right hepatic artery 225, the left hepatic artery 230, and the splenic artery 235. The various nerve systems 200 illustrated include the celiac plexus 240 and the hepatic plexus 245. Blood supply to the liver is pumped from the heart into the aorta and then down through the abdominal aorta 205 and into the celiac artery 210. From the celiac artery 210, the blood travels through the common hepatic artery 215, into the proper hepatic artery 220, then into the liver through the right hepatic artery 225 and the left hepatic artery 230. The common hepatic artery 215 branches off of the celiac trunk, or artery 210. The common hepatic artery 215 gives rise to the gastric and gastroduodenal arteries. The nerves innervating the liver may include portions of the celiac plexus 240 and the hepatic plexus 245. The celiac plexus 240 wraps around the celiac artery 210 and continues on into the hepatic plexus 245, which wraps around the proper hepatic artery 220, the common hepatic artery 215, and may continue on to the right hepatic artery 225 and the left hepatic artery 230. The nature of the neuroanatomy in these regions (e.g., the proximity of neural structures to the arterial lumen) is amenable to endovascular approaches for disrupting sympathetic nervous activity, including but not limited to endovascular ablation. In some anatomies, the celiac plexus 240 and hepatic plexus 245 adhere tightly to the walls (and some of the nerves may be embedded in the adventitia) of the arteries supplying the liver with blood, thereby rendering intra-to-extra-vascular neuromodulation particularly advantageous to modulate nerves of the celiac plexus 240 and/or hepatic plexus 245. In several embodiments, the media thickness of the vessel (e.g., hepatic artery) ranges from about 0.1 cm to about 0.25 cm. In some anatomies, at least a substantial portion of nerve fibers of the hepatic artery branches are localized within 0.5 mm to 1 mm from the lumen wall such that modulation (e.g., denervation) using an endovascular approach is effective with reduced power or energy dose requirements. In some (but not all) embodiments where radiofrequency energy is used, low-power or low-energy (e.g., less than 10 W of power output and/or less than 1 kJ of energy delivered to the inner wall of the target vessel or to the target nerves) intravascular energy delivery may be used because the nerves are tightly adhered to or within the outer walls of the arteries supplying the liver with blood (e.g., hepatic artery branches).

With continued reference to FIGS. 1A, 1B, and 1C, the hepatic plexus 245 is the largest offset from the celiac plexus 240. The hepatic plexus 245 is believed to carry primarily afferent and efferent sympathetic nerve fibers, the stimulation of which can increase blood glucose levels by a number of mechanisms. For example, stimulation of sympathetic nerve fibers in the hepatic plexus 245 can increase blood glucose levels by increasing hepatic glucose production. Stimulation of sympathetic nerve fibers of the hepatic plexus 245 can also increase blood glucose levels by decreasing hepatic glucose uptake. Therefore, by disrupting (e.g., blocking, terminating, denervating, ablating) sympathetic nerve signaling in the hepatic plexus 245, blood glucose, triglyceride, norepinephrine, lipid (e.g., lipoprotein), and/or cholesterol levels can be decreased or reduced. In some embodiments, blood glucose levels are reduced from baseline by 10-80% (e.g., 10-20%, 20-30%, 30-40%, 40-50%, 50-60%, 60-70%, 70-80%, 30-60%, 40-70%, 20-50%, or overlapping ranges thereof). Triglyceride, norepinephrine, lipid and/or cholesterol levels may also be reduced by similar amounts.

In several embodiments, any of the regions (e.g., arteries, nerves) identified in FIGS. 1A, 1B, and 1C may be modulated according to embodiments described herein. Alternatively, in one embodiment, localized therapy is provided to the hepatic plexus, while leaving one or more of these other regions unaffected. In some embodiments, multiple regions (e.g., of organs, arteries, nerve systems) shown in FIGS. 1A, 1B, and 1C may be modulated in combination (simultaneously or sequentially), which may provide one or more synergistic effects. For example, in some embodiments, methods of metabolic neuromodulation treatment involve forming ablation lesions in the common hepatic artery as well as in the celiac, splenic and/or other portions or branches of the hepatic artery (e.g., proper hepatic artery, left hepatic artery, right hepatic artery) to facilitate denervation of complementary metabolic organs and structures (e.g., pancreas, stomach, duodenum) in addition to the liver, even in the instance of a shortened common hepatic artery and/or unusual branch vessel anatomy. In some embodiments, if a subject has a short common hepatic artery (e.g., less than 30 mm), ablation of other vessels or portions of the hepatic artery may be desired and/or required to achieve an effective treatment. In other embodiments, treatment of complementary metabolic organs and structures by delivering energy in the celiac artery, splenic artery, gastroduodenal artery and/or other portions of the hepatic artery (e.g., proper hepatic artery, right hepatic artery, left hepatic artery) may advantageously provide one or more synergistic effects. Although several access/delivery devices are described herein that are configured for (e.g., in shape, size, flexibility, etc.) the hepatic artery, such access/delivery devices can also be used for other arteries and vessels, and in particular, other tortuous vasculature. In addition, although devices may be described herein as neuromodulation catheters or devices and described with respect to modulation (e.g., ablation) of nerves, the catheters or other devices may be used to modulate other types of tissue (e.g., tissue lining an organ or vessel, muscle tissue, endothelial tissue, connective tissue, submucosal tissue).

Figure 2A:
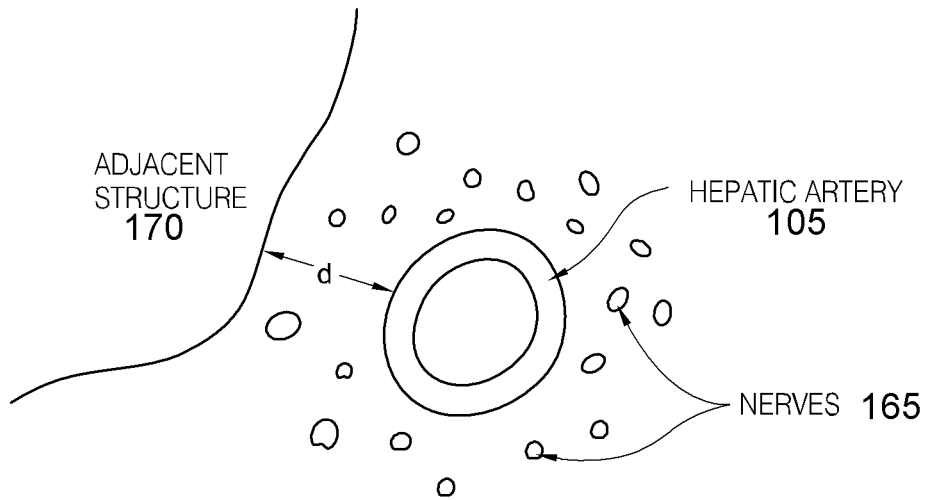
FIGS. 2A and 2B illustrate examples of distribution of nerves surrounding a hepatic artery, as influenced by presence of an adjacent dense structure.
Figure 2B:
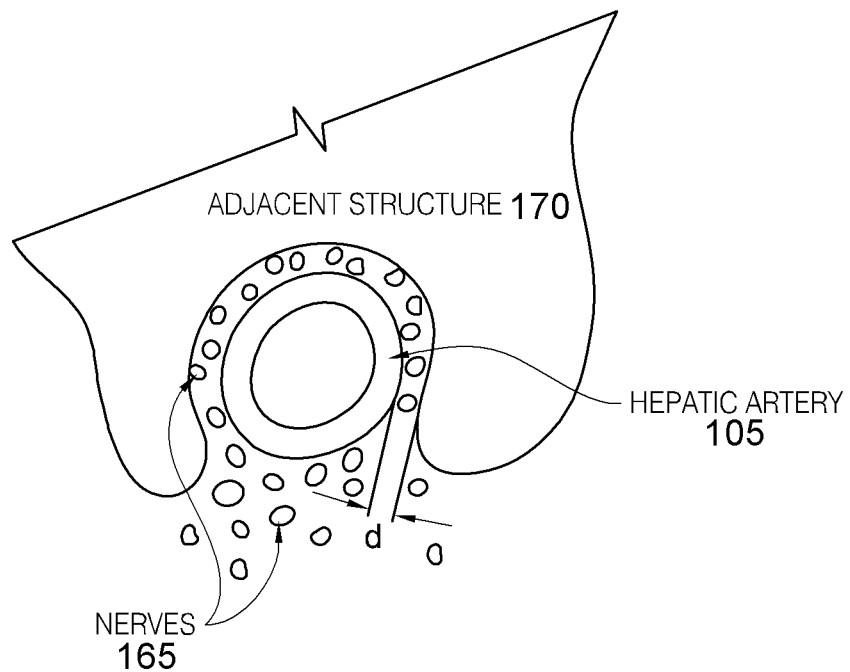

Sympathetic nerves may be distributed around the hepatic arteries (or other arteries, such as the celiac artery, the splenic artery, the gastroduodenal artery), and several embodiments of the invention are adapted to treat these vessels. The hepatic artery passes by many adjacent structures from its origin at the celiac artery to its termination at the liver. The distance that the nerves are away from the hepatic artery or the density of nerves can be influenced by the proximity of adjacent dense structures, such as the liver, pancreas, stomach, small intestine). In accordance with several embodiments, it may be advantageous to modulate tissue at locations along the hepatic artery that are in sufficiently close proximity (e.g., less than 1 cm away from the inner wall of the hepatic artery) to adjacent dense structures (e.g., liver, pancreas, stomach, small intestine, muscle, and/or connective tissue). For example, locations along the hepatic artery that are close to adjacent structures may be associated with highly dense concentrations of nerves, the modulation of which could reduce glucose levels or provide other effects associated with treatment of diabetes in an efficient and effective manner. FIG. 2A illustrates a schematic representation of distribution of nerves 165 surrounding a hepatic artery 105 with limited adjacent structure 170 influence (e.g., where the adjacent dense structure 170 is greater than 1 cm away from the inner wall of the hepatic artery 105) and FIG. 2B illustrates a schematic representation of distribution of nerves 165 surrounding a hepatic artery 105 with significant adjacent structure 170 influence (e.g., wherein the adjacent dense structure 170 is less than 1 cm away from the inner wall of the hepatic artery 105). As can be seen, the distribution of nerves 165 in FIG. 2B is very highly concentrated around the hepatic artery 105 due to the limited space between the hepatic artery 105 and the adjacent structure 170. The illustrated example may represent an area of the hepatic artery 105 that is generally encapsulated by the pancreas.

The anatomy of the vascular branches distal of the celiac plexus may be highly disparate between subjects. In accordance with several embodiments, systems and methods are provided to identify locations along the hepatic artery 105 where the hepatic artery 105 is in close proximity to (e.g., less than 1 cm, less than 5 mm from) an adjacent dense structure 170 and to provide energy to the identified locations in a manner that disrupts the nerves 165 surrounding the hepatic artery 105 (e.g., nerves 165 between the medial layer of the hepatic artery 105 and the adjacent dense structure 170). In some embodiments, the locations where the hepatic artery 105 is in close proximity to an adjacent dense structure 170 are matched with locations determined to be ideal candidates for neuromodulation (e.g., locations having a proper vessel diameter, sufficient treatment length without much tortuosity, etc.). In some embodiments, treatment may be adjusted based on a determined location of an adjacent structure (e.g., pancreas, portal vein, bile duct, lymph nodes). For example, if an adjacent structure is determined to be a heat sink, treatment parameters may be adjusted to deliver additional energy or dose at a particular location within a vessel to accommodate for the presence of the adjacent structure that will sink a portion of the heat generated by the energy delivery. As another example, if an adjacent structure is determined to be reflective, treatment parameters may be adjusted to deliver additional or less energy or dose at a particular location within a vessel. In another example, treatment may be adjusted such that therapeutic treatment (e.g., energy) is not provided at all (e.g., a particular electrode located adjacent a structure desired to be avoided is not activated) at a particular location within a vessel. Additional details regarding adjustment of treatment In some abnormal but fairly common patient anatomies, the right hepatic artery 225 and/or the left hepatic artery 230 (the arteries supplying blood to the liver from the celiac offshoot of the aorta 205 that are immediately adjacent the liver) may not branch off of the proper hepatic artery 220 as illustrated in FIG. 1C. Instead, the patient may have a "replaced" right and/or left artery that branches off of a different artery originating from the celiac artery that is not downstream of the common hepatic artery 215. For such patient anatomies, ablation or denervation of the common hepatic artery 215 may not result in a desired treatment outcome because not all of the nerves innervating the liver would be ablated or otherwise denervated or modulated. In still other abnormal but fairly common patient anatomies, a patient may have one or more accessory arteries that function as an extra right hepatic artery or left hepatic artery. The accessory artery or arteries may also be surrounded by nerves that innervate the liver. Accordingly, for such patient anatomies with replaced and/or accessory right and/or left hepatic arteries, denervation or other modulation may need to be effected at multiple locations (e.g., at the common hepatic artery and one or more other vascular locations) such that complete denervation of the nerves innervating the liver are affected (e.g., ablated or otherwise modulated). Additional details regarding treatment adjustment based on adjacent structures will be provided below.

Figure 3:
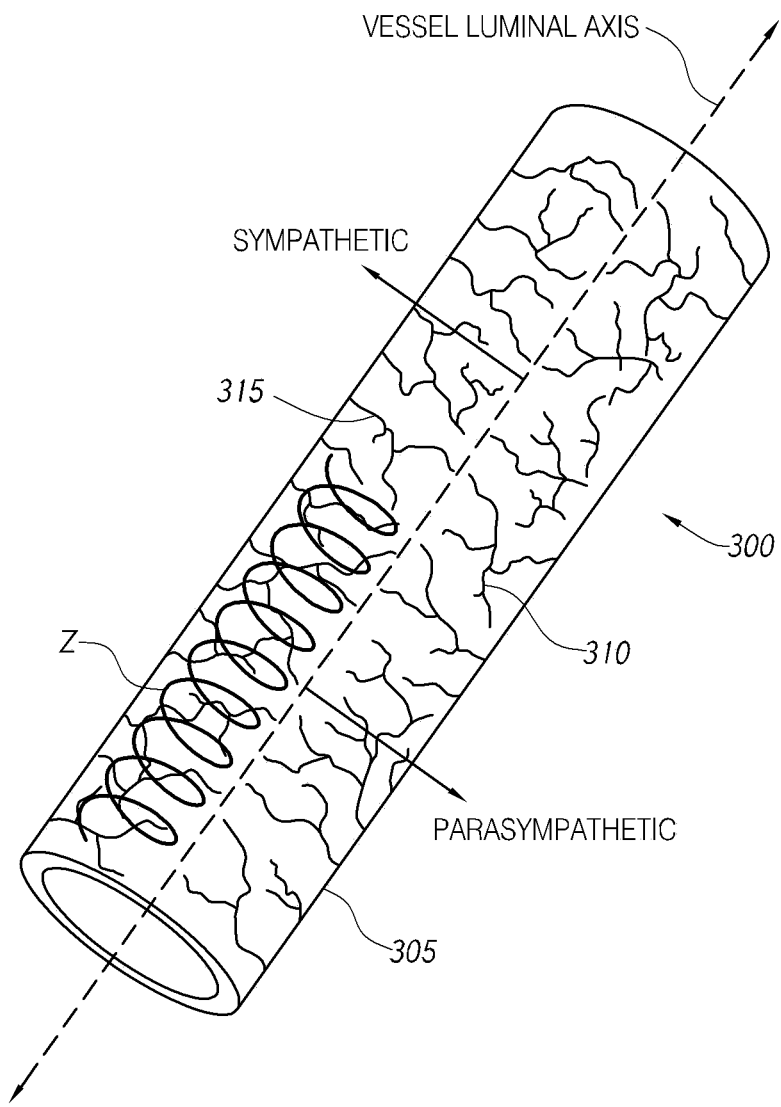
FIG. 3 illustrates a schematic drawing of a common hepatic artery and nerves of the hepatic plexus.

FIG. 3 is a schematic illustration of the nerve fibers of the hepatic plexus 300. A portion of the common hepatic artery 305 (or, alternatively, the proper hepatic artery) is shown with the hepatic plexus 300 wrapping around the artery. Some of the nerve fibers of the hepatic plexus may be embedded within the perivascular space (e.g., adventitia) of the common hepatic artery 305 (or proper hepatic artery), or at least tightly adhered to or within the outer vascular walls. As shown, there is a vessel lumenal axis that follows the center of the artery lumen. The hepatic plexus 300 is comprised of parasympathetic nerves 310 and sympathetic nerves 315. In some anatomies, the parasympathetic nerves 310 tend to course down one half of the circumference of an artery and the sympathetic nerves 315 tend to course down the other half of the artery.

As shown in FIG. 3, the portion of the common hepatic artery 305 is roughly cylindrical, with parasympathetic nerves 310 innervating approximately a 180° arc of the cylinder, and the sympathetic nerves of the hepatic plexus 315 innervating the opposite approximately 180° arc of the cylinder. In some anatomies, there is very little overlap (if any) between the parasympathetic nerves 310 and the sympathetic nerves 315 of the hepatic plexus. Such discretization may be advantageous in embodiments where only sympathetic nerves 315 or parasympathetic nerves 310 of the hepatic plexus are to be modulated. In some embodiments, modulation of the sympathetic nerves 315 of the hepatic plexus may be desirable while modulation of the parasympathetic nerves 310 of the hepatic plexus may not be desirable (or vice-versa).

In some embodiments, only selective regions of the perivascular space (e.g., adventitial layer) of target vasculature is modulated. In some subjects, parasympathetic and sympathetic nerves may be distributed distinctly on or within the adventitial layer of blood vessels. For example, using an axis created by the lumen of a blood vessel, parasympathetic nerves of the hepatic plexus may lie in one 180 degree arc of the adventitia while sympathetic nerves may lie in the other 180 degree arc of the adventitia, such as shown in FIG. 3. Generally, the sympathetic nerve fibers tend to run along the anterior surface of the hepatic artery, while the parasympathetic nerve fibers are localized toward the posterior surface of the hepatic artery. In these cases, it may be advantageous to selectively disrupt either the sympathetic or the parasympathetic nerves by modulating nerves in either the anterior region or the posterior region, respectively.

In some subjects, sympathetic nerve fibers may run along a significant length of the hepatic artery, while parasympathetic nerve fibers may join toward the distal extent of the hepatic artery. Research has shown that the vagus nerve joins the liver hilus near the liver parenchyma (e.g., in a more distal position than the nerves surrounding the hepatic arterial tree). As the vagal nerves are parasympathetic, the nerves surrounding the hepatic artery proximally may be predominantly sympathetic. In accordance with several embodiments, modulation (e.g., ablation) of the proper hepatic artery towards its proximal extent (e.g., halfway between the first branch of the celiac artery and the first branch of the common hepatic artery) is performed when it is desired to disrupt sympathetic nerves in the hepatic plexus. Ablation of the proximal extent of the hepatic artery could advantageously provide the concomitant benefit of avoiding such critical structures as the bile duct, pancreas and portal vein (which approaches the hepatic artery as it courses distally towards the liver), in accordance with one embodiment of the invention.

In one embodiment, only the anterior regions of the hepatic artery are selectively modulated (e.g., ablated). In one embodiment, approximately 180 degrees of the arterial circumference (which may include the corresponding adventitial layer) is ablated. In some embodiments, it is desirable to ablate in the range of about 60° to about 240°, about 80° to about 220°, about 100° to about 200°, about 120° to about 180°, about 140° to about 160°, or overlapping ranges thereof. In some embodiments, the portion of the vessel wall not being targeted opposite the portion of the vessel wall being targeted is actively cooled during the modulation procedure.

In embodiments in which only selective portions of the vessel wall are to be treated, a zig-zag, overlapping semicircular, spiral, lasso, or other pattern of ablation may be used to treat only selective regions of nerve tissue in the adventitia or other perivascular space. An example of a spiral ablation pattern Z, in accordance with one embodiment, is shown in FIG. 3. In some embodiments, one or more ablation electrodes having an inherent zig-zag, spiral or other pattern are used. In some embodiments, a single point ablation electrode (regardless of electrode pattern) is advanced longitudinally and circumferentially about substantially 180 degrees of the vessel circumference to ablate in a zig-zag, spiral or other pattern, thereby selectively ablating only approximately 180 degrees of the vessel wall and the accompanying nerve tissues. In some embodiments, other patterns of electrode configurations are used. In some embodiments, other patterns of ablation electrode movement (regardless of inherent conformation) are used. In some embodiments, lesion zones are created that do not overlap with each other. In various embodiments, lesion zones are spaced apart axially and/or radially (circumferentially).

In some embodiments, where only selective regions of the vessel wall are to be modulated (e.g., ablated or stimulated) it may be helpful to have a high degree of device (e.g., catheter) control, stability and/or precision. To achieve the control necessary for a high degree of precision, a guide catheter may be used to engage the osteum of a nearby branch (e.g., the branch of the common hepatic artery off of the celiac artery, or celiac trunk) to provide a constant reference point from which to position an energy delivery (e.g., ablation) catheter. Alternatively, the catheter (e.g., probe) could also be anchored in other branches, either individually or simultaneously, to further improve control and/or stabilization. Simultaneous anchoring may be achieved by means of a compliant, inflatable balloon (e.g., having a shape and size configured to match an osteum or another portion of a particular vessel), which may substantially occlude the vascular lumen (e.g., osteum), thereby anchoring the catheter and providing increased stability. Such an approach may obviate the need for angiography to map the course of treatment, including the concomitant deleterious contrast agent and x-ray exposure, because treatment guidance can be performed relative to a reference angiogram, with distance of the neuromodulation catheter from the guide catheter measured outside of the patient. In some embodiments, the inflatable balloon may have a size and shape configured to engage multiple ostia or to be anchored in multiple branches (simultaneously or sequentially). In some embodiments, occlusion of a vessel results in increased arterial blood flow at a target location, thereby providing more effective convective cooling. In one embodiment, a balloon catheter is configured to deliver a controlled amount of energy within a defined region of an arterial wall irrespective of low and/or variable flow within the artery (e.g., hepatic artery).

The anatomy of the vascular branches distal of the celiac plexus may be highly disparate between subjects and variations in the course of the sympathetic and parasympathetic nerves tend to be associated predominantly with branches distal of the celiac plexus, rather than being associated with any specific distance distally along the hepatic artery. In some embodiments, a neuromodulation location is selected based on a position relative to the branching anatomy rather than on any fixed distance along the hepatic artery in order to target the sympathetic nerve fibers; for example, within the common hepatic artery and about 1 cm-6 cm (e.g., about 2 cm-3 cm, or substantially at the midpoint of the common hepatic artery) from the branching of the celiac axis or 1 mm-1 cm (e.g., 1 mm, 2 mm, 3 mm, 4 mm, 5 mm, 6 mm, 7 mm, 8 mm, 9 mm, 1 cm) from the branching of the splenic artery or from the branching of the gastroduodenal artery.

Parasympathetic and sympathetic nerve fibers tend to have opposing physiologic effects, and therefore, in some embodiments, only the sympathetic nerve fibers and not the parasympathetic nerve fibers are disrupted (e.g., denervated, ablated) in order to achieve the effects of reducing endogenous glucose production and increasing hepatic and peripheral glucose storage. In some embodiments, only the parasympathetic nerve fibers and not the sympathetic nerve fibers are stimulated in order to achieve the effects of reducing endogenous glucose production and increasing hepatic and peripheral glucose storage. In some embodiments, the sympathetic nerve fibers are denervated while the parasympathetic nerve fibers are simultaneously stimulated in order to achieve the effects of reducing endogenous glucose production and increasing hepatic and peripheral glucose storage. In some embodiments, the denervation of the sympathetic nerve fibers and the stimulation of the parasympathetic nerve fibers are performed sequentially.

In accordance with several embodiments, methods of therapeutic neuromodulation for preventing or treating disorders (such as diabetes mellitus) comprise modulation of nerve fibers (e.g., the sympathetic nerve fibers of the hepatic plexus). In one embodiment, neuromodulation decreases hepatic glucose production and/or increases hepatic glucose uptake, which in turn can result in a decrease of blood glucose levels, triglyceride levels, lipid levels, norepinephrine levels, and/or cholesterol levels. Disruption of the nerve fibers can be effected by ablating, denervating, severing, destroying, removing, desensitizing, disabling, reducing, crushing or compression, or inhibiting neural activity through, blocking, or otherwise modulating (permanently or temporarily) the nerve fibers or surrounding regions. In some embodiments, the disruption is carried out using one or more energy modalities that are delivered for example, intravascularly, extravascularly, or noninvasively (e.g., transcutaneously) from an extracorporeal location. Energy modalities include, but are not limited to, acoustic or sound energy such as ultrasonic energy, unfocused ultrasound, focused ultrasound such as high-intensity or low-intensity focused ultrasound, microwave energy, radiofrequency (RF) energy, thermal energy (e.g., cryoenergy, heat provided by a hot fluid or gas, such as steam), electrical energy, infrared energy, laser energy, phototherapy or photodynamic therapy (e.g., in combination with one or more activation agents), plasma energy, ionizing energy delivery (such as X-ray, proton beam, gamma rays, electron beams, and alpha rays), mechanical energies delivered by cutting or abrasive elements, cryoablation, and chemical energy or modulation (e.g., chemoablation), or any combination thereof. In some embodiments, the disruption of the sympathetic nerve fibers is carried out by chemicals or therapeutic agents (for example, via drug delivery), either alone or in combination with an energy modality. In various embodiments different energy modalities may be used in combination (either simultaneously or sequentially).

In some embodiments, a catheter system is configured to extravascularly and selectively disrupt target nerves. In some embodiments, a catheter is advanced through a cardiovascular system to the target site. The catheter may be passed transluminally to the extravascular space or may create a virtual space between the vascular media and adventitia of the vessel. In some embodiments, the catheter, once positioned at the desired location is activated to selectively modulate or disrupt the target nerve or nerves. The selective disruption may be accomplished or performed through chemo-disruption, such as supplying any type of nerve destroying agent, including, but not limited to, neurotoxins or other drugs detrimental to nerve viability. In some embodiments, selective disruption is performed through energy-induced disruption, such as thermal or light ablation (e.g., radiofrequency ablation, ultrasound ablation, or laser ablation). In one embodiment, a camera or other visualization device (e.g., fiberoptic scope) is disposed on a distal end of the catheter to ensure that nerves are targeted and not surrounding tissue. If a target location is adjacent the branch between the common hepatic artery and the proper hepatic artery, a less acute catheter bend may be required due to the angulation between the bifurcation of the common hepatic artery and the proper hepatic artery. In some embodiments, the catheter comprises a side port, opening or window, thereby allowing for delivery of fluid or energy to denervate or ablate nerves with the longitudinal axis of the catheter aligned parallel or substantially parallel to the target vessel portion. In some embodiments, the catheter or probe is inserted percutaneously and advanced to the target location for extravascular delivery of energy or fluid.

In accordance with several embodiments disclosed herein, the invention comprises modulation of nerve fibers instead of or in addition to nerve fibers in the hepatic plexus to treat diabetes or other metabolic conditions, disorders, or other diseases. For example, sympathetic nerve fibers surrounding (e.g., within the intima, media, perivascular space (e.g., adventitia) of the common hepatic artery proximal to the proper hepatic artery or other branch of the hepatic artery, sympathetic nerve fibers surrounding the celiac artery (e.g., the celiac ganglion or celiac plexus, which supplies nerve fibers to multiple organs including the pancreas, stomach, and small intestine), sympathetic nerve fibers that innervate the pancreas, sympathetic nerve fibers that innervate the adrenal glands (e.g., the renal plexus or suprarenal plexus), sympathetic nerve fibers that innervate the gut, bowel, stomach or small intestine (e.g., the duodenum or jejunum), sympathetic nerve fibers that innervate brown adipose tissue, sympathetic nerve fibers that innervate skeletal muscle, the vagal nerves, the phrenic plexus or phrenic ganglion, the gastric plexus, the splenic plexus, the splanchnic nerves, the spermatic plexus, the superior mesenteric ganglion, the lumbar ganglia, the superior or inferior mesenteric plexus, the aortic plexus, or any combination of sympathetic nerve fibers thereof may be modulated in accordance with the embodiments herein disclosed. In some embodiments, instead of being treated, these other tissues are protected from destruction (e.g., ablation or denervation) during localized neuromodulation of the hepatic plexus. In some embodiments, one or more sympathetic nerve fibers (for example, a ganglion) can be removed (for example, pancreatic sympathectomy). The nerves (sympathetic or parasympathetic) surrounding the various organs described above may be modulated in a combined treatment procedure (either simultaneously or sequentially), which may provide one or more synergistic effects.

In some embodiments, modulation of the nerves (e.g., sympathetic denervation) innervating the stomach results in reduction of ghrelin secretion and greater satiety, decreased sympathetic tone leading to increased motility and/or faster food transit time, thereby effecting a "neural gastric bypass." In some embodiments, modulation of the nerves (e.g., sympathetic denervation) innervating the pylorus results in decreased efferent sympathetic tone, leading to faster transit time and effecting a "neural gastric bypass." In some embodiments, modulation of the nerves (e.g., sympathetic denervation) innervating the duodenum results in disrupted afferent sympathetic activity leading to altered signaling of various receptors and hormones (e.g., gut hormones, GLP-1, gastric inhibitory peptide (GIP), cholecystokinin (CCK), peptide YY (PYY), 5-hydroxytryptamine (5-HT)), thereby causing increased insulin secretion and insulin sensitivity, and/or decreased efferent sympathetic tone leading to faster transit time, thereby effecting a "neural duodenal bypass."

In some embodiments, modulation of the nerves (e.g., sympathetic denervation) innervating the pancreas results in decreased efferent sympathetic tone, thereby causing improvement in beta cell function (e.g., increased beta cell insulin production and beta cell mass), improvement in insulin secretion, and/or decreased alpha cell glucagon production. In some embodiments, modulation of the afferent sympathetic nerves innervating the liver results in a reduction of sympathetic tone in the beta cells and/or reflexive decreased sympathetic tone to the pancreas (thereby augmenting insulin secretion), to the gastrointestinal tract (e.g., duodenum), thereby causing a secondary hormonal or neural improvement in pancreatic beta cell function (an indirect result of hepatic sympathetic tone reduction due to afferent neural disruption and a reflex loop involving the pancreas, an indirect result of increased hepatic glycogen accumulation leading to a central nervous system response increasing beta cell function, or a reduction in system glucose levels leading to a reduced beta cell toxicity), and/or to the muscle. In some embodiments, modulation of the afferent sympathetic nerves innervating the liver results in an increase in a hepatokine hormone with systemic effects (e.g., hepatic insulin sensitizing substance). In some embodiments, stimulation of the common hepatic branch of the vagus nerves could result in similar effects.

In accordance with several embodiments, the branches of the forks between the common hepatic artery, the proper hepatic artery and the gastroduodenal artery are advantageously simultaneously or sequentially targeted (e.g., with RF energy) because sympathetic nerves supplying the liver and pancreas are generally tightly adhered to or within the walls of these arteries. Forks between other arteries or vessels may similarly be simultaneously or sequentially be targeted (e.g., with RF energy). In some embodiments, coiled electrodes opposing the artery walls are used.

Several embodiments of the invention are particularly advantageous because they include one, several or all of the following benefits: (i) enables effective electrode cooling in targeted vessel (ii) consistent and maintained contact with vessel walls while maintaining ample surface area for electrode cooling; (iii) fewer treatment locations due to increased efficacy; (iv) ability to effectively treat a short vessel length such as the common hepatic artery; (v) reduction in sympathetic tone, blood glucose, cholesterol and/or triglyceride levels, (vi) reduction in lipid and/or norepinephrine levels in the liver, pancreas, and/or duodenum; (vii) confirmation of treatment efficacy; (viii) denervation of multiple organs or tissue structures from a single location; (ix) effective denervation of nerves in a perivascular region while maintaining minimal heating of, or thermal injury to, the inner vessel wall; (x) higher likelihood of successful neuromodulation due to modulation of areas of high nerve density or concentration; (xi) increased circumferential vessel coverage with reduced axial vessel length coverage, (xii) reduced contact pressure of the electrode(s) on the vessel wall; and/or (xiii) increased dose-response rate.

In some embodiments, a catheter system comprises an ablation device coupled to a generator (for example, pulse-generating device or power generator). For example, the ablation device may be an ablation catheter. The ablation catheter may have a proximal end portion and a distal end portion. In some embodiments, the distal end portion (e.g., treatment portion) of the ablation catheter comprises one or more electrodes (e.g., one electrode, two electrodes, three electrodes, four electrodes, five electrodes, six electrodes, more than six electrodes). In some embodiments, the ablation catheter consists of only two electrodes. In other embodiments, the ablation catheter consists of only four electrodes. The one or more electrodes can be positioned on an external surface of the ablation catheter or can extend out of the distal end portion of the ablation catheter. In some embodiments, the electrodes are all activated as monopolar electrodes. In some embodiments, the electrodes comprise one or more active electrodes and one or more return electrodes that cooperate to form bipolar electrode pairs. In some embodiments, the distal end portion of the ablation catheter comprises at least one bipolar electrode pair and at least one monopolar electrode. One or more electrically conductive wires (for example, thermocouple wires) may connect one or more electrodes located at the distal end of the ablation catheter to the generator (for example, pulse-generating device). In some embodiments, multiple electrodes can extend from the ablation catheter on an expandable member (e.g., balloon) to provide multiple energy delivery locations or points within a vessel (e.g., a hepatic artery, a renal artery) or other body lumen or within an organ (e.g., pancreas, stomach, small intestine).

In some embodiments, the generator (for example, pulse-generating device) applies power or delivers electrical (e.g., radiofrequency (RF)) signals or pulses to the electrodes located at or near the distal end portion of the ablation catheter. The electrodes may be positioned to deliver RF energy in the direction of sympathetic nerve fibers in the hepatic plexus to cause ablation due to thermal energy. In some embodiments, the electrodes are positioned on top of reflective layers or coatings to facilitate directivity of the RF energy away from the ablation catheter. In various embodiments, the electrodes are curved or flat. The electrodes can be dry electrodes or wet electrodes. In some embodiments, a catheter system comprises one or more probes with one or more electrodes. For example, a first probe can include an active electrode and a second probe can include a return electrode. In some embodiments, the distal ends of the one or more probes are flexible. The ablation catheter can comprise a flexible distal end portion. Variable regions of flexibility or stiffness along a catheter length are provided in some embodiments. In various embodiments, a first flexible portion is actuated to have a first bend shape configured to conform to a first anatomical bend (e.g., a first bend of a hepatic artery branch) and a second flexible portion is actuated to have a second bend shape configured to conform to a second anatomical bend (e.g., a second bend of a hepatic artery branch).

In some embodiments, a plurality of electrodes are spaced apart longitudinally with respect to a center axis of the ablation catheter (e.g., along the length of the ablation catheter). In some embodiments, a plurality of electrodes are spaced apart radially around a circumference of the distal end of the ablation catheter. In some embodiments, a plurality of electrodes are spaced apart both longitudinally along a longitudinal axis of the ablation catheter and radially around a circumference of the ablation catheter from each other. In various embodiments, the electrodes are positioned in various other patterns (e.g., spiral patterns, checkered patterns, zig-zag patterns, linear patterns, randomized patterns). In some embodiments, various electrodes along the length are toggled on or off (e.g., according to a monopolar activation scheme) to customize treatment length.

One or more electrodes can be positioned so as to be in contact with the inner walls (e.g., intima) of the blood vessel (e.g., common hepatic artery or proper hepatic artery) at one or more target ablation sites adjacent the autonomic nerves to be disrupted or modulated, thereby providing intravascular energy delivery. In some embodiments, the electrodes are coupled to expandable and collapsible structures (e.g., self-expandable or mechanically expandable) to facilitate contact with an inner vessel wall. The expandable structures can comprise coils, springs, prongs, tines, scaffolds, wires, stents, balloons, cages, baskets and/or the like. The expandable electrodes can be deployed from the distal end of the catheter or from the external circumferential surface of the catheter. The catheter can also include insulation layers adjacent to the electrodes or active cooling elements. In some embodiments, cooling elements are not required. In some embodiments, the electrodes can be needle electrodes configured to penetrate through a wall of a blood vessel (e.g., a hepatic artery) to deliver energy extravascularly to disrupt sympathetic nerve fibers (e.g., the hepatic plexus). For example, the catheter can employ an intra-to-extravascular approach using expandable needle electrodes having piercing elements. The electrodes can be disposable or reusable.

In some embodiments, the catheter includes electrodes (either individual electrodes or multiple electrodes (e.g., a pair or cluster) effectively functioning as a single electrode) having a surface area of about 1 to about 20 mm$^2$, about 2 to about 5 mm$^2$, about 1 to about 15 mm$^2$, about 5 to about 20 mm$^2$, about 7.5 to about 17.5 mm$^2$, about 6 to about 16 mm$^2$, about 10 to about 15 mm$^2$, about 4 mm$^2$ to about 30 mm$^2$, overlapping ranges thereof, less than about 5 mm$^2$, greater than about 20 mm$^2$, 4 mm$^2$, or about 12.5 mm$^2$. In some embodiments, the catheter relies only on direct blood cooling. In some embodiments, the surface area of the electrodes is a function of the cooling available to reduce thrombus formation and endothelial wall damage. In some embodiments, lower temperature cooling is provided. The temperature of the cooling fluid provided may vary from below freezing temperatures to room temperature. In some embodiments, higher electrode surface areas are used, thereby increasing the amount of energy delivered to the perivascular space, including electrode surface areas of about 5 to about 120 mm$^2$, about 40 to about 110 mm$^2$, about 50 to about 100 mm$^2$, about 60 to about 90 mm$^2$, about 70 to about 80 mm$^2$, overlapping ranges thereof, less than 5 mm$^2$, or greater than 120 mm$^2$. In some embodiments, the electrodes comprise stainless steel, copper, platinum, gold, nickel, nickel-plated steel, magnesium, or any other suitably conductive material.

In accordance with several embodiments, methods of hepatic denervation are performed with shorter procedural and energy application times than renal denervation procedures. In several embodiments, hepatic denervation is performed without causing pain or mitigates pain to the subject during the treatment. In accordance with several embodiments, neuromodulation (e.g., denervation or ablation) is performed without causing stenosis or thrombosis within the target vessel (e.g., hepatic artery). In embodiments involving thermal treatment, heat lost to the blood stream may be prevented or reduced compared to existing denervation systems and methods, resulting in lower power and shorter treatment times. In various embodiments, the methods of neuromodulation are performed with little or no endothelial damage (e.g., less than 20% ablation of) to the target vessels. In several embodiments, energy delivery is delivered substantially equally in all directions (e.g., omnidirectional delivery). In various embodiments of neuromodulation systems (e.g., catheter-based energy delivery systems described herein), adequate electrode contact with the target vessel walls is maintained, thereby reducing power levels, voltage levels, vessel wall or tissue thermal injury, and treatment times.

Balloon Catheters

Balloon ablation catheters having a plurality of electrodes may be used to effect hepatic denervation. In some embodiments, lower power and longer duration ablations are used for ablation procedures involving occlusion within the hepatic arteries than for ablation procedures in other arteries, such as the renal arteries. Such treatment may be uniquely possible because of the liver's dual source blood supply. Balloon ablation of the hepatic vessels (e.g., common hepatic artery) may employ full occlusion for a substantial period of time, not previously possible or not previously attempted in other locations for safety reasons (e.g., to avoid potential stroke due to ischemia). In some embodiments, balloons may be inflated and used for ablation in the range of about 1 to about 10 minutes, about 10 minutes to about 20 minutes, about 20 minutes to about 60 minutes, about 15 minutes to about 45 minutes, about 10 minutes to about 40 minutes, about 15 minutes, about 20 minutes, about 25 minutes, about 30 minutes, about 35 minutes, about 40 minutes, about 45 minutes, about 50 minutes, about 55 minutes, about 60 minutes. Longer ablation times may have several advantages in accordance with several embodiments. First, longer exposure times mean that lower treatment temperatures may be used because tissue and nerve death is a function of both temperature and time. In some embodiments, temperatures are used in the ranges of about 30° C. to about 80° C., about 40° C. to about 70° C., or about 50° C. to about 60° C. In one embodiment, temperatures greater than 45° C. and less than 60° C. are used. The term "balloon" as used herein describes an expandable, fully or partially enclosed structure. Examples are provided of several balloon structures comprised of single or multiple components. When describing the configuration of the balloon assembly, descriptions of "inner", "outer", "proximal", "distal" and other terms are used for clarity but are not intended to be limiting.

In some embodiments, the vessel (e.g., arterial) lumen is simultaneously protected by infusing a low temperature coolant through the balloon cavity (thereby keeping the intima cool) while focusing RF energy and thermal heating at the level of the adventitia or perivascular space (where the target nerves are located). Balloon occlusion may facilitate improved contact and contact pressure between the electrodes disposed on the outside of the balloon and the arterial wall. Balloon occlusion may advantageously compress the tissues of the vessel wall and thereby reduce the distance from the electrode(s) to the target nerves, which improves the efficiency of thermal energy delivery to the target nerves. In some embodiments, less contrast/imaging agent may be required by using a balloon catheter because an occluding device is reliably and accurately positioned (and maintains that position once in place), and serves as a reliable marker of device and therapy placement. Additionally, when a balloon engages the vascular wall, heating of the blood is avoided entirely (because energy is transferred directly from the electrode(s) to the vessel wall without directly contacting the blood), thereby reducing the risk of vapor bubble formation or thrombosis (e.g., clot formation).

In some embodiments, the neuromodulation catheter (e.g., ablation catheter) designs described herein advantageously provide effective modulation of nerves innervating branches of the hepatic artery or other vessel without causing, or at least minimizing endothelial damage, if desired. For example, the catheters described herein can occlude the hepatic artery (e.g., using a balloon) and then circulate coolant in the region of the ablation (e.g., within the lumen of the balloon). In some embodiments, the catheters provide the unique advantage of both higher power net energy offered through larger electrode surface area (which may be enabled by the larger electrode sizes that can be manufactured on a balloon) and increased deposition time (which may be permitted by the ability to occlude flow to the hepatic artery for longer periods of time). In accordance with several embodiments, the increase in energy density through higher power mitigates the risk of damage to the endothelial wall by the flow of coolant within the balloon.

In accordance with several embodiments, catheters, such as a hepatic neuromodulation catheter, having one or more features to improve electrode cooling are provided.

Although various embodiments are described herein in the context of hepatic access, the catheters described herein may also be used to access other locations within a patient's body and/or for other purposes (e.g., renal denervation procedures). Some embodiments are intended for use in cardiac ablation. Various cardiac ablation embodiments provide focal, linear, substantially straight or curved lesions. Various ablation targets comprise left or right cardiac atrium, left or right cardiac ventricle, cardiac septum, valvular annulus, pulmonary vein, and/or ostium of pulmonary vein. Some embodiments are steerable. Still other embodiments are useful for treating conditions including: uterine fibroids, benign prostate hyperplasia, prostate cancer, esophageal lesions or conditions, and/or pulmonary or bronchial conditions.

Energy delivery catheters may comprise balloon catheters configured to modulate nerves or other tissue. In some embodiments, a balloon catheter comprises a catheter body and at least one distal balloon. The catheter body may comprise a lumen configured to continuously infuse saline or other fluid into the balloon. In some embodiments, the distal balloon comprises one or more hydrogel portions spaced around the circumference of the distal balloon. In one embodiment, if saline is used, any water that vaporizes from the surface of the distal balloon is replenished by diffusion from the balloon lumen, thereby preventing or inhibiting free saline to travel into the vessel interface and reducing any undesired effects of saline infusion.

In some embodiments, a target ablation region is pre-cooled prior to treatment (e.g., ablation). For example, precooling may be performed using cold infusion techniques (e.g., iced saline infused directly into the vessel) or using a chilled balloon (e.g., with coolant delivered by a pump from a fluid reservoir). In some embodiments, blood flow may also be restricted during pre-cooling to increase residence time and achieve desired heat transfer. The pre-cooling of the ablation region may advantageously lower the initial temperature for the ablation and allow more power to be delivered locally, thereby enabling steeper temperature gradients and deeper, tighter lesions. The pre-cooling may also result in lower conductivity in the cooled region, further concentrating power into locally heated regions. In one embodiment, a balloon having one or more electrodes is inserted to a target ablation site within a blood vessel or organ (e.g., within a common hepatic artery). Coolant may be circulated through the balloon for a period of time (e.g., 20-60 seconds, 30-50 seconds, 20-40 seconds, 30 seconds) prior to initiating ablation via the one or more electrodes. The temperature of the coolant (e.g., in a syringe, IV bag or other fluid reservoir) may range from below freezing temperatures to room temperature (e.g., 0 degrees Celsius to 25 degrees Celsius, −20 degrees Celsius to 10 degrees Celsius, −10 degrees Celsius to 30 degrees Celsius, overlapping ranges thereof, or any value within the recited ranges). In some embodiments, the pre-cooling of the target ablation site may advantageously allow for delivery of ablative energy at a higher power level than if the target ablation site was not pre-cooled, thereby enabling deeper and/or more narrow lesions to be formed. Such cooling may decrease collateral injury to the nerve fibers not intended for treatment. In many embodiments, cooling is not used.

Some strategies for increasing lesion depth during ablation procedures have focused on actively cooling the surface of the electrode (e.g., using infused saline, internally circulated and/or chilled fluid). In some embodiments, electrode cooling allows deeper lesions to be formed without vaporizing the tissue adjacent to the electrode. In some applications, when cooling, it is difficult to have feedback about the peak temperature reached by the tissues, since the typical practice of placing a thermocouple within the electrode will measure a temperature that is biased by the cooling itself, and thus may not be representative of the peak temperature reached by the more distant tissues.

One embodiment for measuring the adventitia peak tissue temperature in an endovascular ablation of the hepatic artery is as follows. A thermocouple, thermistor or other temperature-measurement device may be placed at a location within the hepatic artery and used to measure the wall temperature at a distance of about 5 mm (as a shortest path) from the surface of the electrode, for electrode sizes between 1 mm and 2 mm in diameter. Studies have shown that measuring the wall temperature at such a distance is a fair approximation of the peak temperature reached within the adventitia.

With electrode cooling, the thermocouple within the electrode measures a temperature that is driven by the cooling itself, which may be much lower than the temperature reached by more distal tissues. Thus, for a temperature-controlled ablation, this measurement may not be useful in indicating the temperature reached by the adventitia, where the nerves are located. As a consequence, in one embodiment, the nerves can fail to be ablated if the heat provided is not sufficient to cause ablation within a certain time period, or there can be collateral damage if the heat is excessive. In accordance with several embodiments, a temperature-controlled neuromodulation (e.g., ablation) is desirable, as if one controls the electrical output (e.g., voltage, current, or power), the heat transferred to the tissues depends on a limited number of variables, such as contact force and impedance, thereby reducing the variability of the therapeutic effect. The placement of remote probes placed at discrete locations within the target tissue to address any shortcomings with cooled electrode strategies may be undesirable in several embodiments because they would require transvascular placement, thereby increasing the risk of the procedure.

In accordance with several embodiments, an intraluminal or endovascular catheter is adapted to deliver ablative radio frequency energy through a plurality of electrodes disposed on or within an expandable member (e.g., non-compliant inflatable balloon), the catheter further including means for cooling of the electrodes to provide augmented heat transfer at the electrode surface. The ablation catheter is advantageously adapted to create a continuous circumferential "donut"", checkerboard, or "spiral" lesion with discrete footprints, such that circumferential perivascular ablation occurs without causing circumferential ablation of the vessel wall (e.g., arterial wall of the common hepatic artery).

In some embodiments, the plurality of electrodes consists of four electrodes arranged in a 2-and-2 pattern or configuration on the balloon, with the first pair of electrodes being positioned on opposite or substantially opposite sides of the circumference of the balloon (e.g., 180 degrees or approximately 180 degrees apart from each other around the circumference of the balloon) in a first circumferential cross-section (e.g., cross-sectional plane having a width equal to or just larger than the length of the electrodes) and the second pair of electrodes being positioned on opposite or substantially opposite sides of the circumference of the balloon (e.g., 180 degrees or approximately 180 degrees apart from each other around the circumference of the balloon) in a second circumferential cross-section (e.g., cross-sectional plane having a width equal to or just larger than the length of the electrodes) that is offset axially and/or circumferentially (e.g., 90 degrees or approximately 90 degrees offset circumferentially, 180 degrees, 120 degrees, 45 degrees, or another circumferential offset) from the first circumferential cross-section of the first pair of electrodes. In some embodiments, the electrodes of the first pair are in opposite quadrants about a central longitudinal axis of the balloon from each other but generally aligned axially along the length of the balloon and the electrodes of the first pair are in opposite quadrants about a central longitudinal axis of the balloon from each other but generally aligned axially along the length of the balloon.

Several embodiments of the invention provide for efficient heat transfer from the balloon, electrode(s) and surrounding tissue to the coolant fluid circulated through the balloon assembly (e.g., an inner and outer balloon separated by an annular gap). This advantageously reduces peak tissue temperature during the ablation procedure. Convective heat transfer at a surface can be described by a heat transfer coefficient. A convective heat transfer coefficient is defined as $H=Nu*K/D$, where H is a heat transfer coefficient (W/mm$^{2\circ}$ C.), K is a thermal conduction coefficient (W/m° C.), D is a hydraulic diameter or characteristic length and Nu is a dimensionless number known as the Nusselt number. It is known empirically that fully developed laminar flow in a circular pipe has a Nusselt number of approximately 4. For example, given a segment of a 5 mm diameter balloon surface 1 cm long, the convective heat transfer across the surface is approximately 0.077 W/° C. The restricted or directed flow of coolant provided by embodiments described herein results in a reduced characteristic length of between 0.01 mm and 1.0 mm for the hydraulic diameter D in the previous equation. This characteristic length may represent the boundary layer for turbulent flow or a restricted flow channel at or adjacent an electrode surface provided by the gap between the inner balloon and the outer balloon. This may advantageously result in an improved heat transfer coefficient of more than fivefold, in accordance with several embodiments of the invention.

The means for cooling may advantageously result in augmented heat transfer, or a high velocity gradient at the heat transfer surface of the electrodes caused by turbulent flow. The means for cooling may comprise (but is not limited to one of the following): directed fluid cooling via one or more jets directed towards a surface of each electrode, mechanical stirring (e.g., paddles, fluidic oscillators, flappers, electromechanical oscillators, inertial agitators), heat pumps, ducts integrated into the balloon wall without jets, composite tubes (e.g., elastomeric matrix), and multi-lumen extrusions. In some embodiments, the means for cooling comprises one or more orifices or openings in an expandable manifold (e.g., a balloon) or a fluid lumen, with the orifices or openings positioned to direct a jet of fluid that impinges on a surface of an electrode. Jets may include a nozzle or an eductor adapted to entrain fluid. The jet(s) may be directed toward one or more electrode surfaces. Multiple jets may be provided for each electrode. In some embodiments, the means for cooling comprises a narrow channel with a relatively small hydraulic diameter that discharges proximate or adjacent to an electrode. In some embodiments, the means for cooling provides annular flow between coaxial lumens or between balloons arranged in a balloon-within-a-balloon manner.

In accordance with several embodiments, the plurality of electrodes are directly mounted to a balloon. The balloon catheter may comprise an outer balloon and an inner balloon arranged in a coaxial manner (balloon-in-balloon), with the plurality of electrodes disposed on the outer balloon (e.g., directly on outer surface or within divots formed within the outer surface) or within through-holes or openings extending through the wall of the outer balloon. The balloon may comprise a single full inner balloon with a partial outer balloon sleeve or conformal coating surrounding the inner balloon, with the electrodes being disposed on or within the outer sleeve or conformal coating.

In some embodiments, an outer balloon is adapted to support four electrodes (either four individual electrodes or four pairs of electrodes adapted to function as four individual electrodes). The wall thickness of the outer balloon may range from about 0.01 mm to about 0.03 mm (e.g., 0.013 mm to 0.025 mm, 0.02 mm to 0.03 mm, overlapping ranges thereof, or any value within the recited ranges). The outer balloon may range from about 10 mm to about 50 mm in length (e.g., 20 mm to 50 mm, 10 mm to 30 mm, overlapping ranges thereof, or any value within the recited ranges) and from about 3 mm to about 8 mm in diameter. In one embodiment, the outer balloon is 0.02 mm thick, 5 mm in diameter, and 20 mm long. The outer balloon may be provided with a proximal cone and a proximal waist to facilitate attachment to a catheter shaft. The inside diameter of the proximal waist of the outer balloon may be between about 1 mm and about 2.5 mm (e.g., between 1 mm and 2 mm, between 1 mm and 1.5 mm, between 1.5 mm and 2 mm, between 1.5 mm and 2.5 mm, overlapping ranges thereof, 1.6 mm, or any value within the recited ranges). In some embodiments, the outer balloon is provided with a distal cone and a distal waist for attachment to a distal catheter shaft. In other embodiments, the distal edge of the outer balloon is bonded to the body of an inner balloon. The outer balloon may be provided with openings to permit the passage of electrode lead wires into the ablation catheter. The wires may comprise bifilar, multi-filar or individual lead wires. Additional openings may be provided in the outer balloon for discharge of cooling fluid into the vasculature proximal and/or distal to the balloon assembly. Suitable materials for the outer balloon include, for example, PET, Nylon, PEBA, Polyolefin, polyurethane and copolymers thereof. The inner surface of the electrode(s) may optionally be electrically insulated.

In some embodiments, an inner balloon is disposed within the outer balloon and is adapted to provide fluid delivery orifices or jets proximate the plurality of electrodes. Suitable materials for the inner balloon include, for example, PET, Nylon, PEBA, Polyolefin, polyurethane and copolymers thereof. The wall thickness of the inner balloon may range from about 0.01 mm to about 0.05 mm (e.g., 0.013 mm to 0.025 mm, 0.01 mm to 0.03 mm, 0.02 mm to 0.05 mm, overlapping ranges thereof, or any value within the recited ranges). The inner balloon may range from about 5 mm to about 50 mm in length (e.g., 20 mm to 50 mm, 10 mm to 30 mm, overlapping ranges thereof, or any value within the recited ranges) and from about 2 mm to about 7.5 mm in diameter. In one embodiment, the inner balloon is 0.02 mm thick, 4.5 mm in diameter, and 15 mm long. In some embodiments, the inner balloon diameter is 0.5 mm smaller than the outer balloon. The inner balloon may be provided with a proximal cone and a proximal waist and a distal cone and a distal waist to for attachment to a catheter shaft. The inside diameter of the proximal waist and the distal waist of the inner balloon may range from about 0.5 mm to about 2.5 mm (e.g., between 1 mm and 2 mm, between 0.5 mm and 1.5 mm, between 1.5 mm and 2 mm, between 1.5 mm and 2.5 mm, overlapping ranges thereof or any value within the recited ranges). In one embodiment, the inside diameter of the inner balloon proximal waist is substantially the same as the inside diameter of the outer balloon waist. The inner balloon may be provided with auxiliary orifices or jets to provide fluid flow through the gap between inner balloon and the outer balloon. In some embodiments, spacers are provided to maintain a minimum gap between the inner balloon and the outer balloon. In some embodiments, this minimum gap ranges from about 0.05 mm to about 0.5 mm (e.g., 0.05 mm, 0.10 mm, 0.15 mm, 0.20 mm, 0.25 mm, 0.30 mm, 0.35 mm, 0.40 mm, 0.45 mm, 0.50 mm, or any sub-range within the recited overall range).

In accordance with several embodiments, a plurality of orifices are provided in the inner balloon to direct fluid towards the inner surface of the electrodes on or within the outer balloon. In some embodiments, the fluid exits the orifice as a high velocity jet. Orifice diameter may range from about 0.025 mm to about 0.20 mm (0.025 mm to 0.075 mm, 0.050 mm to 0.10 mm, 0.075 mm to 0.15 mm, 0.10 mm to 0.20 mm, overlapping ranges thereof, or any value within the recited ranges). The flow rate of the jets may be less than 12 mL/min/electrode. In one embodiment, the flow rate of coolant fluid through an orifice is about 0.1 mL/s and the pressure drop across the orifice is about 500 kPa. Jet velocity may range from about 5 m/s to about 50 m/s (e.g., 5 m/s to 30 m/s, 15 m/s to 30 m/s, 15 m/s to 40 m/s, 20 m/s to 40 m/s, 35 m/s to 50 m/s, overlapping ranges thereof, 22 m/s, or any value within the recited ranges). In some embodiments, there are two or more orifices per electrode. The distance from the orifice to the electrode may range from about 0.10 mm to about 2.0 mm (e.g., between 0.10 mm and 0.50 mm, between 0.50 mm and 1.0 mm, between 0.50 mm and 1.5 mm, between 1.0 mm and 2.0 mm, between 0.10 mm and 1.0 mm, overlapping ranges thereof, or any value within the recited ranges). The inner balloon may further comprise auxiliary orifices or jets to provide fluid flow through the gap between the inner balloon and outer balloon. The total flow rate through the auxiliary orifices may be a small fraction (e.g., less than 10% of the total electrode flow (0.1*4*0.1 ml/s=0.04 ml/s) of the flow rate of the direct electrode cooling jets. In one embodiment, a single auxiliary orifice is provided at the distal end of the outer balloon. The diameter of this auxiliary orifice may be about 0.05 mm while the pressure drop across the auxiliary orifice is substantially equal to that of the direct electrode cooling orifices.

In some embodiments, the ablation catheter is provided with a shaft of approximately 1 meter in length. The shaft may be comprised of a plurality of lumens. Some lumens provide for passage of electrode wires. Other lumens may provide for delivery and discharge of cooling fluid. Another lumen may provide for passage of a guide wire. The guide wire lumen may range from about 0.2 mm to about 1.0 mm in diameter (e.g., from 0.2 mm to 0.5 mm, from 0.3 mm to 0.6 mm, from 0.4 mm to 0.8 mm, from 0.5 mm to 1.0 mm, overlapping ranges thereof, 0.43 mm, or any value within the recited ranges). Suitable materials for a guide wire lumen may include, but are not limited to, PTFE, HDPE, blends of PTFE and polyimide and other materials. In some embodiments, one or more (e.g., one, two, three, four) fluid inlet lumens and one or more fluid discharge lumens (e.g., one, two, three, four) are provided. In one embodiment, the guide wire lumen comprises a PEEK fiber braid reinforced polyimide tube having a PTFE/Polyimide composite inner layer and PEBA outer layer. The wall thickness of the guide wire lumen may be less than 0.076 mm. In some embodiments, the inside diameter of inlet and discharge lumens range from about 0.3 mm to about 0.8 mm. In one embodiment, the inside diameter of the inlet and discharge lumens is about 0.6 mm. Suitable materials for inlet and discharge lumens include, but are not limited to, polyimide, polyolefin, nylon, polyester, PEBA, Polyethylene, PTFE, polyurethane, and the like. In some embodiments, one or more lumens are provided for passage of the electrode wires. In one embodiment, the electrode wire lumens are comprised of polyimide tubes of 0.025 mm wall thickness. More than one electrode wire may be passed through a single electrode wire lumen. In one embodiment, a pair of bifilar electrode wires are passed through each of two electrode wire lumens. In some embodiments, an air gap is provided between electrode wires and at least part of the lumen to reduce capacitive coupling.

In some embodiments, a catheter fluid path is provided from an inlet port through an inlet lumen into an inner balloon through an orifice into a space between an inner and outer balloon through a proximal fluid space between the cones of an internal and external balloon, through a discharge lumen out through an outlet port. In some embodiments, an external control system provides and controls fluid flow though the catheter fluid path. In some embodiments, the external end of the shaft terminates in a manifold assembly comprising an inlet port, an outlet port, a guide wire port and an electrode wire extension cable.

Suitable coolants for an ablation catheter system include, but are not limited to, water, saline, physiologic salt solutions, non-ionic colloids such as dextran or glucose, etc. In one embodiment, the coolant is physiologic saline (e.g., 0.9% sodium chloride).

The plurality of electrodes may have an exposed, electrically conductive surface affixed to the outer balloon. As described above, in one embodiment, four electrodes are provided in 2 pairs. A first pair of electrodes may be positioned diametrically opposed to each at a first axial location along the outer balloon, a second pair of electrodes diametrically opposed to each other are positioned at a second axial location along the outer balloon, with the first and second pair of electrodes being offset 90 degrees with respect to each other. In another embodiment, the electrodes are positioned such that each of the 4 electrodes is equidistant from each of the other electrodes. In some embodiments, the electrodes are 1 to 2 mm wide and 3 to 8 mm long. In one embodiment, the electrodes are 1.5 mm wide and 6 mm long. In some embodiments, the electrode width is selected as a ratio of the balloon diameter such that electrode width=(balloon circumference/N)−A, where N is the number of folded faces on the wrapped balloon and A is an allowance for balloon folding. In one embodiment, electrode width=(5 mm*π/8)−0.5 mm=1.5 mm.

In some embodiments, the intraluminal ablation catheter is provided with a plurality of clusters of electrodes. In a particular embodiment, four clusters of electrodes are spaced axially and circumferentially along the axis of the outer balloon. Each cluster is comprised of a pair of electrodes placed side by side in a transverse plane along the outer balloon. In some embodiments, each electrode element in the pair is 4 mm long and 1.5 mm wide. Clusters may be distributed 5 mm on center along the length of the balloon leaving a 1 mm gap between each cluster. The gap between the elements of a cluster may range from about 0.1 mm to 0.5 mm (e.g., 0.1 mm, 0.2 mm, 0.3 mm, 0.4 mm, 0.5 mm). In some embodiments, the total surface area of a cluster is between about 4 and 30 mm$^2$ (e.g., between 8 and 18 mm$^2$, between 6 and 16 mm$^2$, between 12 and 20 mm$^2$, between 8 and 20 mm$^2$, overlapping ranges thereof, or any value within the recited ranges). In other embodiments, the electrode elements of a cluster may be staggered so as to overlap axially with electrode elements of adjacent clusters.

Electrode wires may be provided to connect the electrode elements to a RF generator. Electrode wires may be comprised of 40 gauge bifilar type T thermocouple wires. In some embodiments, the thermocouple wires are insulated with multiple layers of polymers selected from a group including, but not limited to, Teflon, PTFE, polyimide, PET polyester, nylon polyurethane, Butvar, PVDF, PFA, polyethylene, TFE copolymers, etc.). In some embodiments, 40 gauge thermocouple wire has conductor diameters of 0.0031 in (0.079 mm). Overall dimensions of the insulated wire may be 0.1 mm×0.2 mm. Type T thermocouple wire is comprised of a copper conductor and a constantan conductor. In this case, the copper wire carries most of the RF electrical current while the differential potential measured between the copper and constantan conductors indicates the temperature at a thermocouple junction proximate the electrode. Other temperature measurement and conductor assemblies include copper, gold, silver, tin and other alloys and wires connected to thermistors may be located proximate one or more of the electrodes.

In some embodiments, electrode spacing markers (e.g., lesion spacing indicators as described in more detail below) may be placed on the catheter shaft to guide the placement of the catheter during an ablation procedure. These markers may be placed on the catheter shaft proximal to the electrodes or on a distal shaft extension beyond the electrodes. In one embodiment, the markers are placed on a distal shaft extension with the same center-to-center spacing as the electrodes (e.g., 6-8 mm). The distal shaft extension may be 1 cm to 5 cm long (e.g., 3 cm) and may include radiopaque markers comprised of segments of platinum 10% Iridium alloy tube 1.5 mm long and having a wall thickness of approximately 0.04 mm. The diameter of the markers may be selected to be flush or nearly flush with the outer surface of the shaft extension (e.g., about 1 mm in diameter).

In some embodiments, the distal shaft extension is configured to provide a gradually increasing flexural rigidity along its length to facilitate tracking of the balloon ablation catheter through tortuous vascular anatomy. In one embodiment, the shaft diameter increases from 0.7 mm to 1.5 mm along its length, providing a corresponding change in stiffness from approximately 10 gmf*cm$^2$ to 100 gmf*cm$^2$. In some embodiments, the distal shaft extension is comprised of braid-reinforced thermoplastic elastomer (e.g., non-electrically conductive PEEK). In one embodiment, the shaft is comprised of a PEEK braid-reinforced polyimide tube coated with PEBA. The distal shaft extension may be about 1 cm to about 5 cm in length (e.g., 1 cm to 4 cm, 2 cm to 4 cm, 3 cm to 5 cm, overlapping ranges thereof, or any value within the recited ranges). The inner layer of the distal shaft extension may be an extension of the catheter shaft guide wire lumen. The Outer layers of the distal shaft extension may be a series of elastomeric tubing sections becoming incrementally stiffer from distal to proximal. Tubing segment durometers may range from 35D to 50D to 70D durometer. The inner guide wire lumen layer may be slit towards the distal end to further reduce stiffness. Other combinations of fibers and matrix may also be used. In some embodiments, the reinforcing fibers are non-electrically conductive in order to reduce capacitive coupling. Some embodiments of the distal shaft extension provide substantial elastic recovery after deflection to a radius of curvature of less than 2 cm.

In accordance with several embodiments, the intraluminal ablation catheter comprises a slideably-coupled auxiliary proximal shaft (e.g., captive sliding sleeve). In some embodiments, the auxiliary proximal shaft advantageously provides enhanced support for accessing tortuous anatomy and acute vascular side branches. In some embodiments, the auxiliary proximal shaft advantageously provides for delivery of angiographic dye to a vessel upstream from a side branch to provide angiographic visualization of the side branch to facilitate vascular access. In some implementations, the sleeve is a reinforced polymer tube of wall thickness ranging from 0.075 mm to 0.25 mm. An annular gap of 0.25 mm to 0.5 mm may be provided between the proximal auxiliary shaft and the catheter shaft. In one embodiment, the proximal auxiliary shaft has a 2 mm outer diameter and the proximal auxiliary shaft is comprised of PEEK fiber reinforced polyimide tube having a PTFE/Polyimide composite inner surface and an outer surface coated with PEBA with a wall thickness of 0.1 mm, resulting in an inner diameter of 1.8 mm. In combination with a catheter shaft outer diameter of 1.25 mm, this provides an annular clearance of 0.75 mm to provide for dye delivery. In some embodiments, the distal portion of the auxiliary shaft is curved.

In accordance with several embodiments, an intraluminal ablation catheter system is provided comprising an intraluminal ablation catheter having a plurality of electrodes, a connecting cable, an RF generator adapted to deliver power to the plurality of electrodes, a temperature measurement system, a fluid delivery system, a fluid pressure monitoring system and a user interface. In some embodiments, the system provides for independent power delivery to a plurality of electrodes. In another embodiment, the system is configured to interrupt or adjust power delivery based on fluid delivery pressure or flow and electrode temperature measurements.

Figure 4:
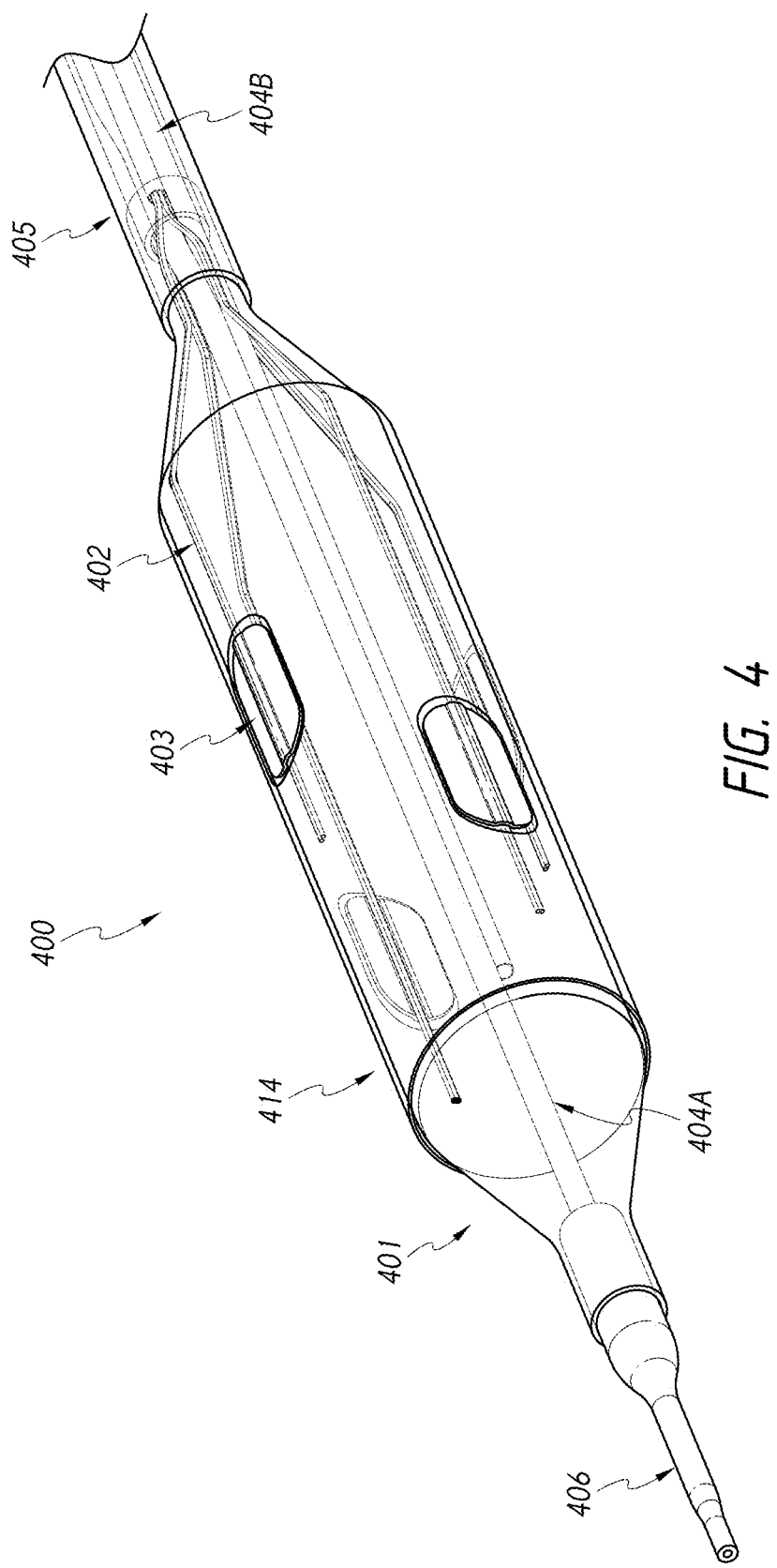
FIG. 4 illustrates a perspective, partially see-through view of a distal end portion of an embodiment of a balloon catheter.

FIG. 4 illustrates an embodiment of a distal portion of a balloon catheter 400. Although the balloon catheter 400 is advantageously designed to effect denervation from within a hepatic artery (e.g., common hepatic artery), the balloon catheter 400 and the features disclosed in connection therewith may also be adapted for denervation or other treatment of other arteries, veins, vasculature, lumens, organs or tissue. The distal portion of the balloon catheter 400 illustrated in FIG. 4 includes the portion of the catheter involved in effecting treatment (e.g., denervation) and/or diagnostics at a particular location within a body of a subject (e.g., within a common hepatic artery). The balloon catheter 400 includes a balloon 401, multiple wire conductors 402, multiple electrodes 403, one or more lumens 404 and an elongate shaft 405 (only a distal end of which is shown). The balloon catheter 400 optionally includes a distal tracking segment 406 distal of the balloon 401. The elongate shaft 405 extends from a proximal end of the balloon 401 to a proximal manifold (not shown). The elongate shaft 405 may have a length sized such that the balloon 401 may be positioned in a hepatic artery (e.g., common hepatic artery, proper hepatic artery, left hepatic artery, right hepatic artery), gastroduodenal artery, superior mesenteric artery or splenic artery when inserted through an access location in a radial artery or a femoral artery. The balloon catheter 400 may incorporate structures or features of any embodiments disclosed in this subsection or elsewhere in this disclosure.

The one or more lumens 404 may include a guidewire lumen 404A that extends from the proximal manifold through the elongate shaft 405, through the balloon 401 and through the distal tracking segment 406 if present. In some embodiments, the guidewire lumen 404A is centrally located within the elongate shaft 405 and/or the balloon 401 (e.g., aligned along a central longitudinal axis). The guidewire lumen 404A is adapted to receive a guidewire so that the balloon catheter 400 can be advanced over the guidewire to a desired location (e.g., a location within a common hepatic artery) within a subject. The guidewire lumen 404A may be sized so as to track a 0.014" guidewire. In one embodiment, the balloon catheter 400 is sized so as to be delivered through a 7 French guide catheter. For example, the elongate shaft 405 may be sized to have a 5 French outer diameter and the balloon 401 may be sized to have a 6 French profile. The one or more lumens 404 may also include an inflation lumen 404B adapted to facilitate inflation or expansion of the balloon 401. The fluid delivered through the inflation lumen 404B may also be adapted to facilitate or provide cooling (e.g., to obtain a desired convective heat transfer at the balloon surface). The inflation lumen 404B may extend from a port of the proximal manifold to a location within the balloon 401. The elongate shaft 405 may also include one or more additional inflow or outflow lumens to regulate flow rates and/or to facilitate cooling and/or to infuse dyes. In various embodiments, a first inflow lumen infuses fluid (e.g., gas or liquid) into the balloon 401 and a second outflow lumen removes fluid out of the balloon 401 and back to the proximal manifold. Any of the cooling mechanisms, structures or features described herein may be implemented in the balloon catheter 400. For example, the balloon 401 may be cooled by mechanical stirrers activated by a drive mechanism or by jets generated by one or more orifices in the one or more cooling lumens. Shrouds may be provided around one or more of the orifices to improve efficiency. In various embodiments, fluid infusion or cooling systems comprise an open circuit such that fluid is slowly leaked out (e.g., via weeping through one or more discharge ports or openings) of the balloon 401 or a closed circuit such that the fluid is recirculated and does not exit through the balloon 401.

As shown in FIG. 4, the balloon catheter 400 may consist of two pairs of two electrodes arranged in a 2×2 pattern, with two electrodes being positioned at the same or generally the same first axial distance along the length of the balloon and on opposite or substantially opposite sides of the balloon (e.g., 180 degrees or about 180 degrees apart from each other around the circumference of the balloon when the balloon is in an expanded configuration) and the other two electrodes positioned at the same or generally the same second axial distance along the length of the balloon and on opposite or substantially opposite sides of the balloon (e.g., 180 degrees or about 180 degrees apart from each other around the circumference of the balloon when the balloon is in an expanded configuration). As shown, the second pair of electrodes at the second axial distance may be positioned 90 degrees or about 90 degrees offset circumferentially from each of the electrodes of the first pair. The balloon catheter 400 may consist of four electrodes 403 spaced apart around a circumference of the balloon 401, with each electrode spaced 90 degrees circumferentially apart from each adjacent electrode and each electrode spaced apart longitudinally from each adjacent electrode as well so as to form an overall spiral configuration. Various electrode shapes, electrode patterns, electrode fabrication and processing features and methods, electrode mounting features and methods, wire routing methods, and balloon materials and folds that may be implemented in conjunction with the balloon catheter 400 or any other balloon catheter embodiments will be described further herein.

The electrodes 403 may be composed of materials including stainless steel, gold (e.g., 22 carat or 24 carat gold), platinum, platinum alloys, platinum iridium alloys (e.g., Pt10Ir) or combinations of the same. Other metals or alloys may also be used as desired and/or required. In accordance with several embodiments, the electrodes 403 may advantageously be shaped and sized so as to maximize surface area while not exceeding a dimension required to allow for balloon folding. For example, a width of an individual electrode may be constrained by folding requirements of a balloon (e.g., quad-fold, tri-fold, bi-fold) for a given balloon diameter. A width (e.g., radial dimension) of each electrode may range from 0.5 mm to 2.5 mm (e.g., 0.5 mm to 1.5 mm, 1.0 mm to 2.0 mm, 1.5 mm to 2.5 mm, 0.5 mm to 2.0 mm, overlapping ranges thereof, or any value within the recited ranges) for a balloon catheter designed to have a 6 French profile. As one example, for a 5 mm diameter balloon, a width (e.g., radial dimension) of each electrode may be constrained to about 1.5-1.6 mm. In some embodiments, each electrode has an oblong, generally oval shape (as illustrated, for example, in FIG. 4) so as not to exceed a desired width to allow for balloon folding. In accordance with several embodiments, a length (e.g., longitudinal dimension) of each electrode may range from 2 mm to 10 mm (e.g., 2 mm to 4 mm, 3 mm to 5 mm, 2 mm to 6 mm, 3 mm to 5 mm, 3 mm to 6 mm, 4 mm to 6 mm, 4 mm to 8 mm, 6 mm to 10 mm, overlapping ranges thereof, or any value within the recited ranges). The length may be constrained by tissue conductivity variability and a desire for reasonably uniform current density across the electrode. Although the electrodes 403 are illustrated as being generally flat and ovular in FIG. 4, the electrodes 403 may have other shapes adapted to produce a more uniform or optimum distribution of current density so as to avoid hot spots at the edges or center of the electrodes 403. The more uniform current density provides an improved distribution of thermal energy, or heat conduction, observed by the tissue.

Figure 5A:
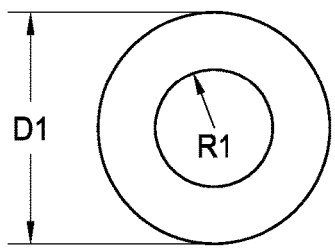
FIGS. 5A-5E are schematic drawings illustrating various embodiments of electrode shapes.
Figure 5B:
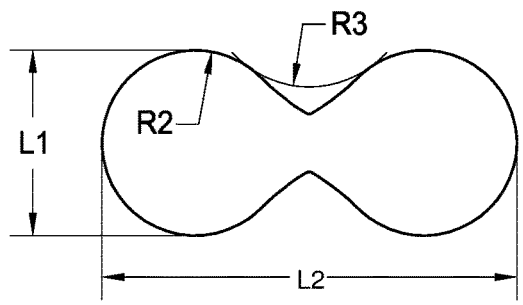
Figure 5C:
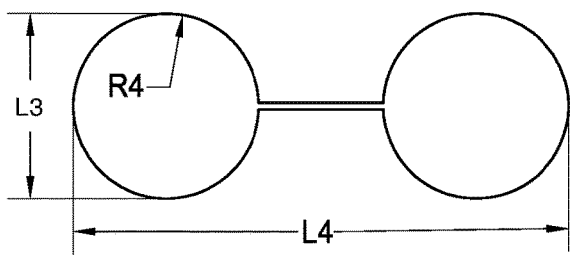
Figure 5D:
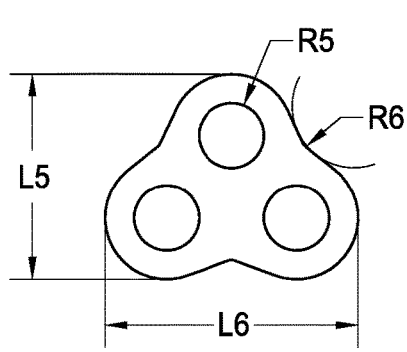
Figure 5E:
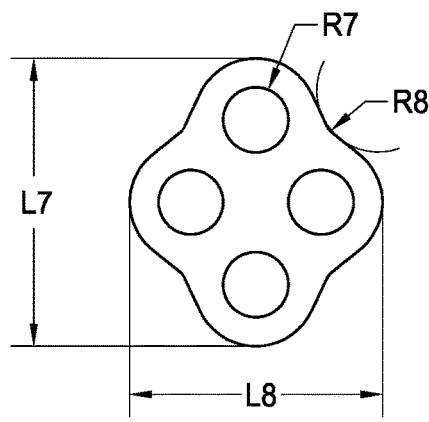

In accordance with several embodiments, the electrodes 403 are shaped so as to maximize energy delivery while minimizing peak tissue temperature. Various electrode shapes are illustrated in FIGS. 5A-5E. FIG. 5A illustrates a donut- or ring-shaped electrode (similar to a washer). FIG. 5B illustrates a dogbone-shaped electrode. FIG. 5C illustrates a dumbbell-shaped electrode. FIG. 5D illustrates a tricomb-shaped electrode and FIG. 5E illustrates a honeycomb-shaped electrode. Although illustrated as a two-dimensional electrode that would allow for adhesion to a surface, the dogbone- and dumbbell-shaped electrodes could be extended to a third dimension. In various embodiments, electrode thickness ranges from 0.0005 inches to 0.0020 inches (e.g., from 0.0005 inches to 0.0010 inches, from 0.0010 to 0.0015 inches, from 0.0005 inches to 0.0015 inches, from 0.0010 inches to 0.0020 inches, overlapping ranges thereof, or any value within the recited ranges).

With reference to FIG. 5A, a diameter D1 of the electrode may range from 0.1 inches to 0.2 inches (e.g., 0.10, 0.11, 0.12, 0.13, 0.14, 0.15, 0.16, 0.17, 0.18, 0.20, 0.10 inches to 0.16 inches, or any other value within the recited ranges). The radius R1 may range from 0.05 inches to 0.10 inches (e.g., 0.05, 0.06, 0.07, 0.08, 0.09, 0.10, or any other value within the recited range). With reference to FIG. 5B, the length L1 may range from 0.05 inches to 0.15 inches (e.g., 0.05, 0.06, 0.07, 0.08, 0.09, 0.10, 0.11, 0.12, 0.13, 0.14, 0.15, 0.06 inches to 0.11 inches, or any other value within the recited ranges), the length L2 may range from 0.10 inches to 0.25 inches (0.10 inches to 0.20 inches, 0.15 inches to 0.25 inches, 0.12 inches to 0.235 inches, overlapping ranges thereof, 0.21 inches, or any value within the recited ranges), the radius R2 may range from 0.05 inches to 0.15 inches (e.g., 0.05, 0.06, 0.07, 0.08, 0.09, 0.10, 0.11, 0.12. 0.13, 0.14, 0.15, or any other value within the recited range), and the radius of curvature R3 may vary depending on the values of the other dimensions (for L1=0.10", L2=0.21" and R2=0.10", R3 may be 0.002"). With reference to FIG. 5C, the length L3 may range from 0.02 inches to 0.12 inches (e.g., 0.02, 0.03, 0.04, 0.05, 0.06, 0.07, 0.08, 0.09, 0.10, 0.11, 0.12, 0.04 inches to 0.08 inches, or any other value within the recited ranges), the length L4 may range from 0.10 inches to 0.25 inches (0.10 inches to 0.20 inches, 0.15 inches to 0.25 inches, 0.13 inches to 0.20 inches, overlapping ranges thereof, 0.13 inches, or any value within the recited ranges), and the radius R4 may range from 0.03 inches to 0.12 inches (e.g., 0.03, 0.04, 0.05, 0.06, 0.07, 0.08, 0.09, 0.10, 0.11, 0.12, 0.04 to 0.08 inches, or any other value within the recited range). With reference to FIG. 5D, the length L5 may range from 0.05 inches to 0.25 inches (e.g., 0.08 inches to 0.20 inches, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, or any other value within the recited ranges). The length L6 may be the same dimension as L5 or may be different but within the same range as L5. The radius R5 may range from 0.005 inches to 0.04 inches (e.g., 0.010 inches to 0.035 inches, 0.005 inches to 0.010 inches, 0.015 inches to 0.025 inches, 0.020 inches to 0.040 inches, overlapping ranges thereof, 0.015 inches, or any other value within the recited ranges) and the radius of curvature R6 may be equal to L5 divided by 4. With reference to FIG. 5E, the length L7 may range from 0.05 inches to 0.25 inches (e.g., 0.09 inches to 0.20 inches, 0.06 inches to 0.12 inches, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, or any other value within the recited ranges). The length L8 may be the same dimension as L7 or may be different but within the same range as L7. The radius R7 may range from 0.005 inches to 0.10 inches (0.005 inches to 0.08 inches, 0.015 inches to 0.025 inches, 0.02 inches to 0.04 inches, 0.03 inches to 0.06 inches, 0.04 inches to 0.07 inches, 0.05 inches to 0.10 inches, overlapping ranges thereof, 0.01 inches, or any other value within the recited ranges) and the radius of curvature R8 may be equal to L8 divided by 4.

In some embodiments, masking, insulation or cutouts of a central region of an elongated electrode may advantageously reduce local current density. While peak current density often occurs near the ends of elongated electrodes, peak tissue temperature can still occur near the central region of the electrode. Further displacement of current towards the ends of the electrode may advantageously reduce local current density in the hottest regions and provide a more moderate temperature profile. The electrodes 403 may have rounded ends to provide a more even and uniform current distribution.

Figure 6A:
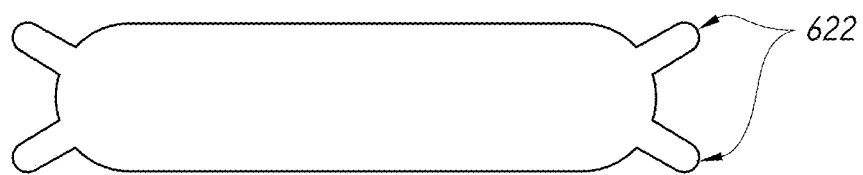
FIGS. 6A-6D are schematic drawings illustrating various embodiments of electrode edge features.
Figure 6B:
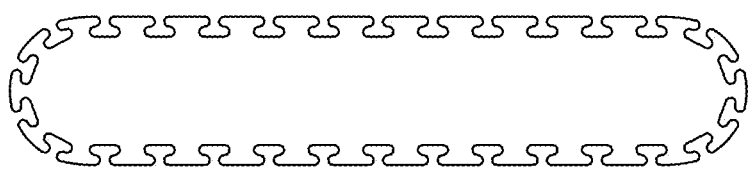
Figure 6C:
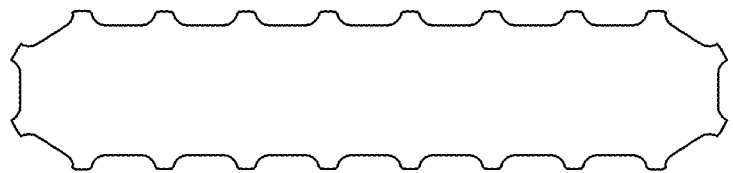
Figure 6D:
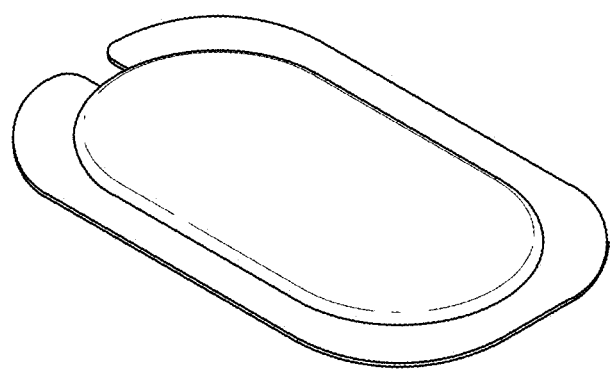

The electrodes 403 may include features to facilitate security of attachment to the balloon (e.g., improve bond strength, allow for adhesive backfill), to facilitate strain relief, to provide covering overlap, to provide a smooth transition from the balloon, and/or to increase flexibility. Such features may include anchor tabs 622 (such as illustrated, for example, in FIG. 6A), edge features such as holes, slots, scallops, serrations and slits (as illustrated, for example, in FIGS. 6B and 6C), tapered edges or flanges (such as illustrated in FIG. 6D), and/or a convex profile. The edge features (e.g., holes, slots, scallops, serrations and slits) may also allow for wire access.

Figure 6E:
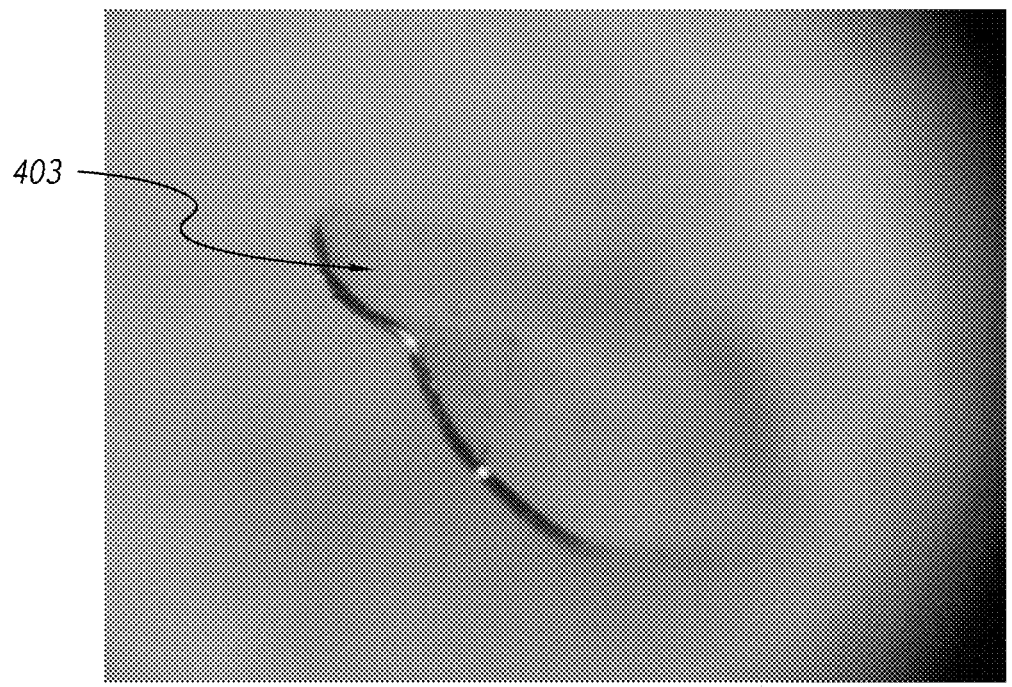
FIG. 6E is a side view of an embodiment of an electrode showing its curved profile.
Figure 6F:
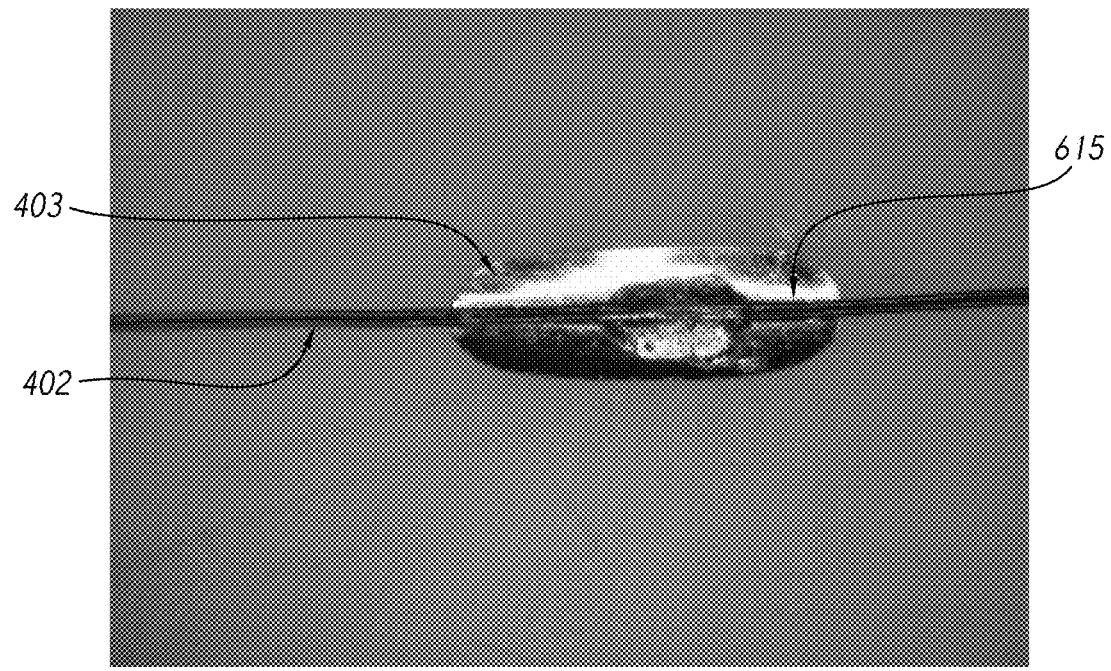
FIG. 6F illustrates an embodiment of an electrode having a channel for receiving wire conductors and shows the wire conductors bonded to the electrode.

In accordance with several embodiments, the electrodes 403 are fabricated and mounted so as to reduce or eliminate any raised profiles, thereby reducing the likelihood of removal of the electrodes 403 during delivery, retrieval or other use. In various embodiments, the electrodes are curved so as to conform to the curved outer surface of the balloon when inflated, such as illustrated in FIG. 6E. By fitting the electrode to the radius of the balloon, the edge profile is significantly decreased. The electrodes 403 may also be filleted, ramped and/or streamlined with a suitable material like an adhesive along one or more edges to reduce edge profiles, especially the proximal edges that may encounter resistance, friction, during withdrawal or retrieval of the balloon due to abuse or kinking of the balloon 401 or elongate shaft 405. In accordance with several embodiments, adhesive provided under the electrode(s) creates a fillet. As illustrated in FIG. 6F, a channel 615 may be created or formed along the entire underside of each electrode to receive a wire conductor instead of just running the wire conductor along the underside of the electrode, thereby reducing the outer profile, and thickness, of the electrodes. The optional distal tracking segment 406 may include a funnel that extends over a portion of the balloon 401.

Figure 6G:
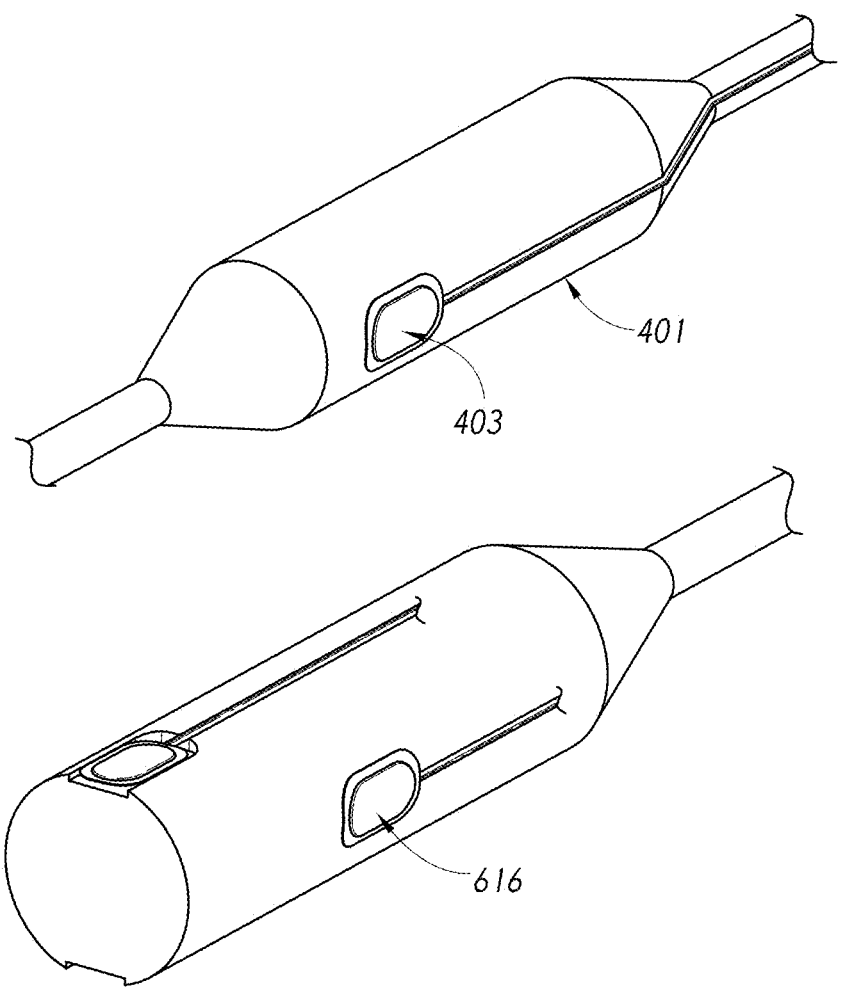
FIG. 6G includes a schematic perspective view and section view of an embodiment of a balloon having divots or recesses adapted to receive electrodes.

With reference to FIG. 6G, in some embodiments, a balloon 401 of a balloon catheter may include receptor divots 616 formed into the balloon wall, thereby creating a recess or well into which an electrode 403 can be attached below the normal outer surface of the balloon 401, thereby reducing or minimizing the outer profile of the balloon 401 at the location of the electrodes 403. The divots, or wells, 616 may advantageously protect the edges of the electrode that are now recessed below the outer surface of the balloon, thereby protecting the electrode from mechanical forces during folding and intravascular delivery. In accordance with several embodiments, each electrode is bonded to the bottom of the well and not to the outer edges of the well, thereby allowing the electrode to rise from the divot, or well, during balloon deployment and expansion. An added benefit is that the electrode will get closer to the vascular wall when it rises. In this application, the closer to the vessel wall the electrode comes the better the treatment potential is. Upon balloon depressurization, the electrode will then return into its recessed position allowing for a smooth retrieval. In various embodiments, the wire conductors can be routed over the balloon surface or in a formed channel and then bonded in place. In alternative embodiments, the wire conductors, or conductive wires 402, are routed through a balloon surface at the bottom of the well for an inter balloon circuit orientation.

The electrodes 403 may be formed from a wire, rod, foil, sheet or tube by stamping, forging, and/or swaging methods. The electrodes 403 can be produced, for example, by means of punching the desired shape from a thin sheet of material or through 3D printing the geometry. In some embodiments, the electrodes 403 are formed using laser cutting methods. The edges of the electrodes 403 may be formed by a secondary stamping operation. For example, use of a compliant die material may provide tapered edges. The channel 615 for receiving the conductor wire may be formed, for example, by pressing the wire/electrode assembly on a compliant die base, thereby providing precise, conformal apposition between the wire and electrode components. In accordance with several embodiments, the electrodes 403 are advantageously applied and/or mounted to the balloon 401 without using flex circuits or printing technology. By not using flex circuits, the footprint of the electrode/wire assembly can be advantageously reduced compared to flex circuit constructions.

Figure 6H:
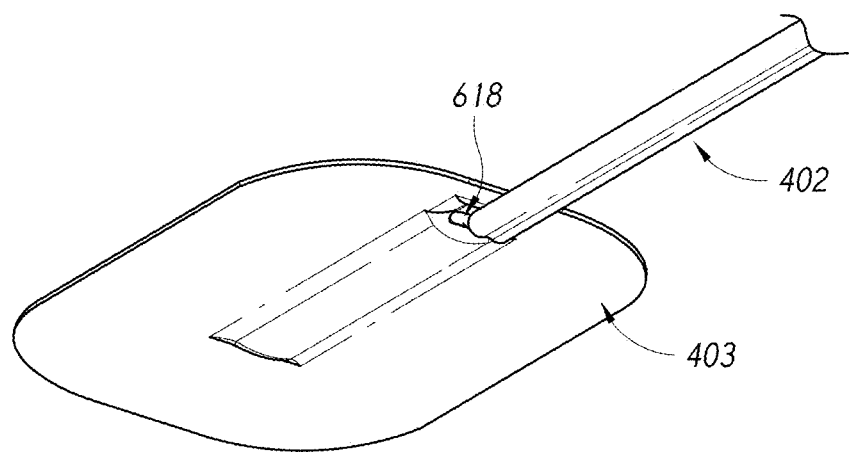
FIG. 6H illustrates an embodiment of attachment of conductor wires to an electrode.

The electrode 403 may be attached to the conductive wire, or transmission wire, by a variety of means, including soldering, welding (e.g., laser, electron beam, resistance, spot welding), and/or conductive epoxy. With reference to FIG. 6H, in one embodiment, the conductive wire(s) 402 may be inserted into a hole 618 in an electrode blank or tube prior to forming or swaging into the electrode 403. Moderate heat applied during the forming may promote diffusion or metallic bonding. The conductive wires 402 may be stripped and/or tinned with solder prior to attachment to the electrode 403. The electrodes and/or conductive wires may be textured on one side to promote bonding. The texture may be applied, for example, by stamping, etching, embossing or other methods. In some embodiments, the conductive wires 402 are pressed, stamped, twisted, folded, rolled or otherwise formed prior to attachment to reduce thickness and increase strength. In some embodiments, only a short portion of the conductive wire 402 (e.g., a portion less than the entire length of the electrode length) is stripped and attached to the electrode 403 (as shown, for example, in FIG. 6F), thereby preserving the insulation material along the conductive wire 402 for a majority of the length of the wire along the electrode surface. The conductive wire 402 and/or electrode 403 may be overcoated so as to provide a wider, cleaner bond area.

The conductive wires 402 may be an integral part of the electrode 403. Electrode and wire segments of integral structure may be cut, stamped, pressed, forged, or machined or etched from a substantially homogeneous wire, film or blank. An exposed portion of the electrode 403 may be plated with gold, platinum or other noble or biocompatible metal. The wire/electrode base material may be copper, constantan, gold, platinum, stainless steel or other alloys or metals.

With reference to FIG. 7, in some embodiments, an electrode 403 may be partly copper and partly constantan. In some embodiments, there may be copper and constantan layers. The layers may be formed from metal foil. In some embodiments, the copper and constantan layers form a top side and a bottom side with respect to the electrode surface. In other embodiments, the copper and constantan conductors 732 are substantially side by side and coincident with a common surface. In some embodiments, the electrode/wire assembly includes a termination region 734 providing sites 735 for connecting extension wires. In some embodiments, the electrode 403 is comprised of a flex circuit.

The conductive wires, wire conductors, or transmission wires 402, may extend from the electrodes 403 to a port of the proximal manifold. The conductive wires 402 are adapted to activate and power the electrodes 403. The conductive wires 402 may be constructed from metal foil bonded to a temporary carrier film and etched into a desired pattern. The temporary carrier film may have metal foil applied to both sides. At least one side may be a highly conductive material such as copper, gold, silver or alloys thereof. Another layer of metal may be made from different thermoelectric properties.

In some embodiments, a process of bonding the electrode and conductive wire assemblies to the balloon comprises applying one or more of the electrode/wire assemblies to the carrier film, applying adhesive to the electrode/wire assemblies, bonding the electrode/wire assemblies to the balloon, removing the carrier film, and applying conformal coating to the balloon and electrode/wire assemblies. The temporary carrier film itself may comprise one or more of the following materials: polyethylene glycol (PEG), polyethylene oxide (PEO), polyvinyl alcohol (PVOH), polyvinyl acetate (PVAc) and blends and copolymers thereof. The temporary and/or removable adhesives used for the conductive wires may include acrylics, PVAc, PVOH, and/or the like.

The conductive wires 402 may comprise thermocouple wires (e.g., T-type thermocouples comprises of a copper positive wire and a negative constantan wire). In some embodiments, the conductive wires 402 are configured as separate, individually insulated wires. In some embodiments, the conductive wires 402 are configured as bifilar or multifilar wires encapsulated, joined together and electrically insulated from each other. The encapsulants and insulator materials may include polyimide, nylon, polyurethane or other polymeric materials. Encapsulant may be used to bond wires to substrate by use of solvents or heat. The encapsulant may be selected to have a different melting point or solvent resistance than the underlying wire insulation in order to preserve the electrical insulation of the wires. Multifilar wires may be separated near the distal end of the catheter to be routed to separate electrodes.

In some embodiments, one or more electrodes and one or more electrical conductors, or conductive wires, are positioned at least partially between a balloon and a flexible sleeve. Referring back to FIG. 4, in accordance with several embodiments, the balloon catheter 400 includes a sleeve, or covering 414 that extends over at least a portion of the balloon 401. In some embodiments, the sleeve 414 advantageously protects one or more of the electrodes 403 and at least a portion of one or more electrical conductors 402 from damage during use and protect the patient from injury due to interaction with the electrode or electrical conductor. The inner diameter of the sleeve 414 may be sized to match or be substantially close to the outer diameter of the balloon 401. The method and material used in sleeve creation may be dependent on device performance requirements. Materials for the sleeve 414 could include polyurethanes, nylon, Polyethylene Terephthalate (PET) or others. The sleeve 414 can be a cylinder that extends along all or a portion of the main body of the balloon 401 or can be formed with a balloon matching waist that extends along the proximal waist or the distal waist of the balloon 401. The sleeve 414 in the embodiment shown in FIG. 4 includes a proximal balloon matching waist and extends to the start of the distal cone of the balloon 401. In some embodiments, the sleeve 414 is sized and adapted to extend over a full length of the balloon 401. In some embodiments, the sleeve 414 is sized and adapted to extend over a partial length of the balloon 401 (such as just over a proximal cone or waist of the balloon) so as to capture and contain the conductive wires 402. In some embodiments the balloon 401 and sleeve 414 comprise overlapping, or telescoping, balloon segments or portions that are nested, with one overlapping the other. For example, although the balloon 401 illustrated in FIG. 4 extends from the elongate shaft 405 to the distal tracker 406, the balloon 401 could instead only extend from the distal tracker 406 to a position that overlaps with a distal edge of the sleeve 414. In another embodiment, the balloon 401 is the proximal segment or portion and the sleeve 414 is the distal segment or portion. The balloon 401 and sleeve 414 may be bonded together so that inflation pressure inside the balloon 401 is maintained. In some embodiments, the sleeve 414 is not permanently bonded or attached to the balloon 401 such that the sleeve 414 can be removed from the balloon 401 prior to expansion or inflation of the balloon 401.

Figures 1, 8A:
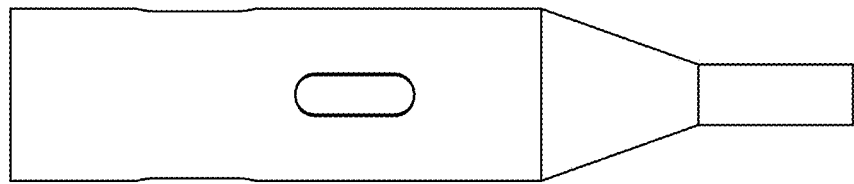
FIGS. 8A-1 and 8A-2 illustrate side and perspective views of an embodiment of a sleeve having windows or fenestrations adapted to align with electrodes on a balloon catheter.
Figures 2, 8A:
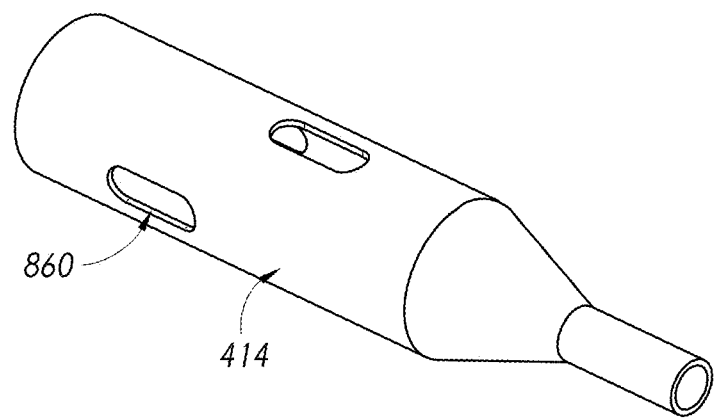

With reference to FIGS. 8A-1 and 8A-2, in some embodiments, the sleeve 414 includes windows or fenestrations 860 positioned at desired locations of one or more of the electrodes 403 of the balloon 401. The windows or fenestrations 860 may be precision mounted and aligned before assembly based on a desired electrode pattern. In some embodiments, the windows or fenestrations 860 are sized to be larger than the electrodes, which may allow the gap to be filled with elastomeric adhesive material so as to provide increased securement and strain relief. In other embodiments, the windows or fenestrations 860 are sized to be smaller than the electrodes, which may also provide enhanced strain relief and secure attachment. In some embodiments, the balloon 401 includes temporary supports to align electrodes in the windows, such as adhesives, strippable tube/film, wrap, PVOH and/or a tube. The sleeve 414 may include additional extra holes or slotted windows to aid in flexibility, folding, reduce bulk, etc.

In some embodiments, the flexible covering or sleeve 414 is a cylindrical tube. In other embodiments, the flexible covering or sleeve 414 is a conformal coating. In some embodiments, the conformal coating is a polymer coating. Examples of suitable materials for the polymer coating include: polyurethane, silicone (e.g., PDMS), acrylates, epoxy, nylon, PEBA, Polymethylmethacrylate, Styrene Isobutadiene Styrene block copolymers, UV cure adhesives, hot melt adhesives, combinations of the same, and/or the like. Some suitable conformal coating materials are applied as a solution in a solvent. Other suitable conformal coating materials are provided as liquids and cure in place after they are applied. Other suitable conformal coating materials are applied as a powder or a film. In some embodiments, the conformal coating is applied is applied by spraying, dipping, painting, wiping, rolling electrostatic spraying or powder coating and the like. In some embodiments, a tie layer or primer is applied to a balloon and/or electrode and electrical conductor before application of the coating.

Figure 8B:
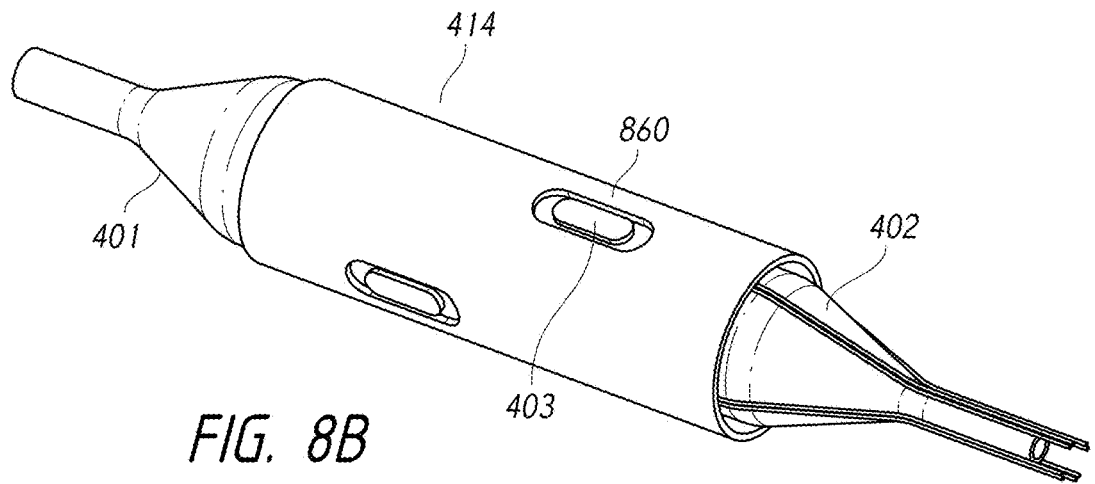
FIGS. 8B-8F illustrate embodiments of sleeves of a balloon catheter.
Figure 8C:
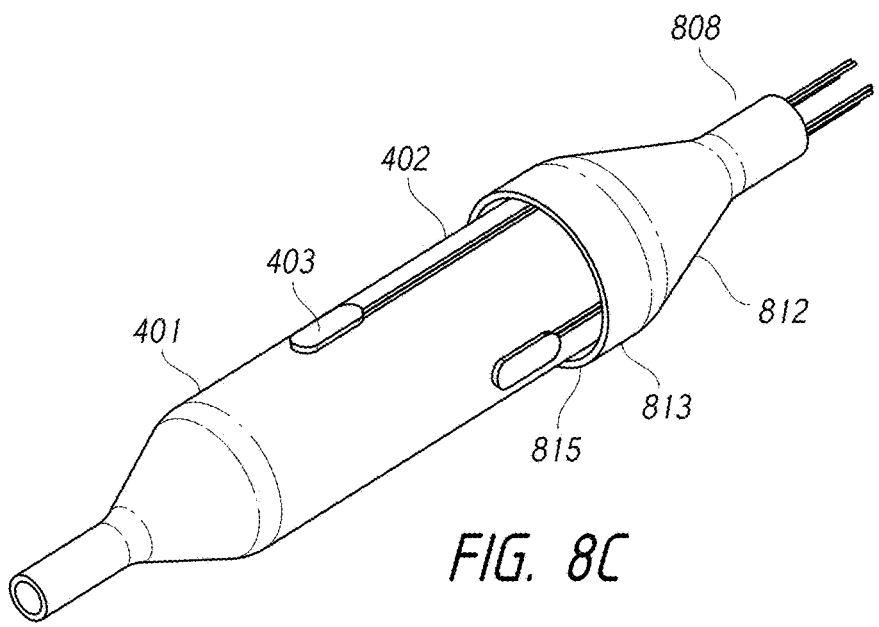

FIG. 8B illustrates a balloon 401 with at least one electrode 403 and at least one electrical conductor 402. A substantially cylindrical flexible sleeve 414 is provided to enclose at least a portion of the one or more electrical conductors 402. An opening, window or fenestration 860 is provided in the sleeve 414 to expose the electrode 403 to the adjacent tissue. In some embodiments, multiple electrodes 403 and fenestrations 860 are provided, as shown in FIGS. 8C-8G. As shown in FIG. 8C, the sleeve 414 may be waistless.

FIG. 8C illustrates an embodiment of an expandable ablation balloon 401 having at least one electrode 403 and at least one electrical conductor 402. In some embodiments, a short, flexible outer sleeve 414 comprising a waist 808, cone, 812 and short body 813 is provided to cover the proximal portion of the electrical conductor 402. In some embodiments, a distal edge 815 of the sleeve 414 is proximal to the most proximal electrode.

Figure 8D:
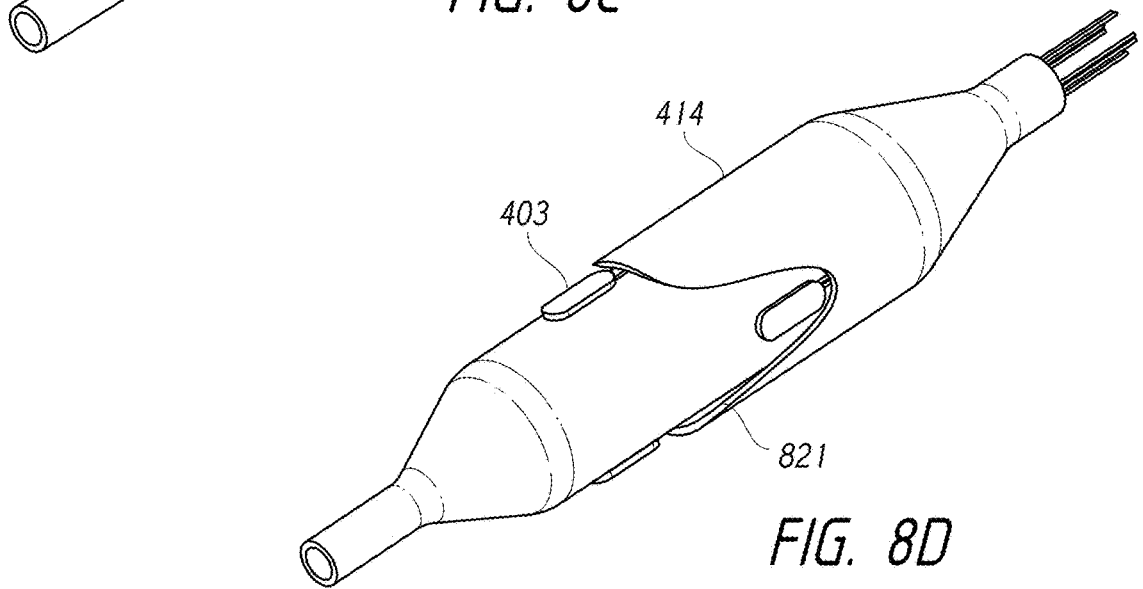

FIG. 8D illustrates an embodiment of a balloon catheter in which the outer sleeve 414 has a scalloped or contoured edge 821 that is configured to cover all or substantially all of a plurality of the electrical conductors 402 and/or electrodes 403.

Figure 8E:
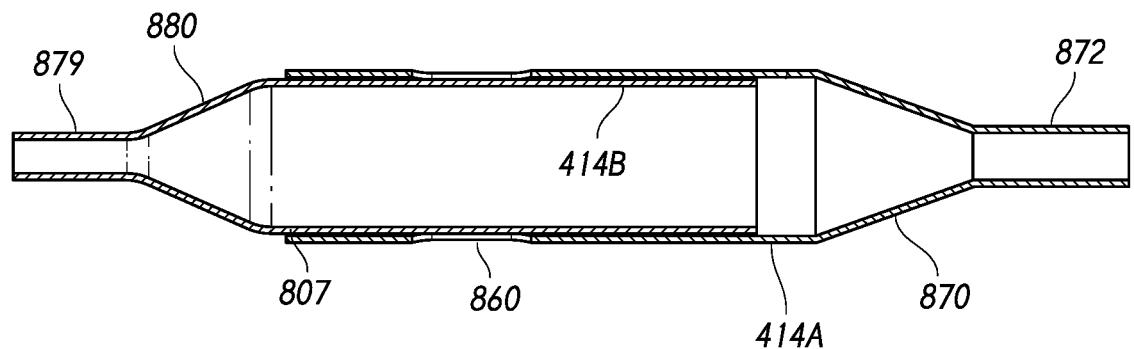

FIG. 8E illustrates an embodiment of an ablation balloon assembly comprised of a proximal sleeve, or outer sleeve 414A and a distal sleeve, or inner sleeve 414B. In some embodiments, the proximal sleeve 414A and the distal sleeve 414B overlap to form a substantially enclosed balloon space. In other embodiments, the proximal sleeve 414A and distal sleeve 414B are joined together by a bond 807. The outer sleeve 414A may have fenestrations 860 to provide exposure of the electrodes (not shown) to the surrounding tissue. In some embodiments, the proximal sleeve 414A has a proximal cone 870 and a proximal waist 872 and the distal sleeve 414B has a distal waist 879 and a distal cone 880. In several embodiments, the electrical conductors (not shown) pass between the outer sleeve and the inner sleeve. In some embodiments, the outer sleeve 414A has a distal edge and the inner sleeve 414B has a proximal edge. In some embodiments, the outer sleeve 414A has a proximal edge and the inner sleeve 414B has a distal edge.

Figure 8F:
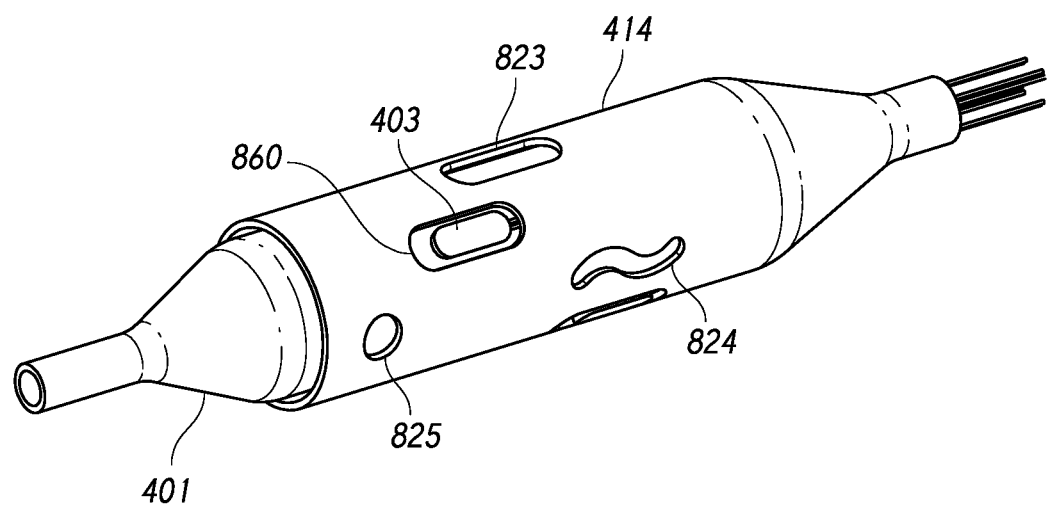

FIG. 8F illustrates an embodiment of a balloon catheter having a balloon 401 and an outer sleeve 414 with multiple fenestrations 860 and electrodes 403. In some embodiments, the outer sleeve 414 is provided with slots 823, holes 825 and/or irregularly-shaped fenestrations 824 not associated with electrodes in order to reduce bulk, improve flexibility and/or facilitate manufacturing.

Suitable materials for balloons and sleeves include, for example: PET, PEBA, nylon, polyolefin, polyester, polyurethane and the like. Suitable bonding materials include epoxy, polyurethane adhesives, acrylic adhesives, silicone, Room Temperature Vulcanization (RTV), hot melt and ultraviolet (UV) cure materials. In some embodiments, it is advantageous to bond the inner balloon or sleeve to the outer sleeve by pressurizing the balloon to obtain the desired fit between inner and outer layers. In other embodiments, it is advantageous to form the outer sleeve from a heat shrink or similar material that can be caused to relax onto an inner layer.

The sleeve 414 may be directly bonded to the balloon 401 using one or more of the following methods or mechanisms: (i) automated dispensing and positioning; (ii) dispense, spray, calendar, paint, dip, stencil; (iii) press onto balloon and cure; (iv) re-blowing and curing, (v) high tack, high Viscosity (ranges) pressure-sensitive adhesive (PSA) and (vi) back fill. The sleeve 414 may be adhered or solvent-bonded to the balloon 401. In some embodiments, methods of forming or bonding the sleeve 414 to the balloon 401 could include applying heat shrink to a properly-sized mandrel or spray formed on a similar mandrel. The sleeve 414 may be attached to the balloon with the electrodes 403 surface mounted and the wire conductors 402 routed internally on the sleeve 414. The sleeve 414 may be slid over the balloon and attached to the balloon surface with adhesive or solvent bonding, the wire conductors 402 are then routed through the elongate shaft. The electrodes 403 may be directly bonded to the sleeve 414. In some embodiments, the sleeve 414 is pressed onto the balloon 401 and cured. Laminating the sleeve 414 to the balloon 40 may comprise full or partial lamination.

Referring back to FIG. 4, the conductive wires 402 are positioned between the sleeve 414 and the balloon 401. As shown in FIG. 4, a distal terminus, or end, of the conductive wires 402 may extend distal of the electrode 403 to which it is connected, thereby providing increased holding power or a ramp. In some embodiments, one, some or all of the conductive wires 402 extend through an aperture in the balloon surface below the electrode or adjacent an edge of the electrode 403 to which they are connected and then run internally within the balloon 401 toward the elongate shaft 405. This internal wiring embodiment provides the advantages of balloon flexibility and concealment of the wires within the balloon 401, thereby protecting them from mechanical damage. As one example of a method of providing internal routing of a conductive wire, a small hole is made in a vascular balloon, the conductive wire is then inserted through the hole and out through the balloon waist. Adhesive may then be applied to the bottom (underside facing the balloon) of the electrode 403. Next, the inserted wire end is then pulled until the base of the electrode meets the surface of the balloon. Any excess adhesive is flowed out from under the electrode, thereby forming a fillet, and then the adhesive is cured, thereby securing the electrode 403 in place and sealing the wire hole in the balloon 401.

In some embodiments, the conductive wires 402 extend proximally from the electrodes along an external surface of the balloon 401 and enter through a surface of a proximal cone of the balloon as it tapers toward the outer diameter of the elongate shaft 405. The entry location may be at a top, or distal end (the end with the largest cross-sectional dimension), of the cone, at a bottom, or proximal end (the end with the smallest cross-sectional dimension), of the cone or any location along the cone. In some embodiments, the conductive wires 402 extend proximally from respective electrodes 403 along an external surface of the balloon 401 and enter the elongate shaft 405 within the balloon waist or at a location of a proximal bond with the elongate shaft 405 just proximal of the balloon waist. The external wiring embodiments provides the advantages of the balloon remaining intact and the balloon being able to be inflated during application of power to the electrodes (thereby improving positioning). The conductive wires 402 can be adjusted in the process to ensure that they run straight and that the adhesive over the wires creates a positive fold bias. External routing and attachment of the conductive wires 402 may be accomplished by tensioning the conductive wire in fixturing that can be elevated. With the electrode base up, adhesive may be applied to the bottom (underside facing the balloon) of the electrode 403, the electrode 403 is then lifted to the balloon 401 which is correctly positioned above the electrode 403. In some embodiments, the adhesive is then cured and tension is released from the wire. The wire may then be run in a straight line on the balloon and covered with adhesive that is then cured.

In some embodiments, a flex circuit electrode design is used. The flex circuit electrode design may include a first polymer layer, a thermocouple layer, a second polymer layer, a conductive layer and a third polymer layer. Gold plating may be applied to the exposed conductive layer after the other layers are laminated together.

In various embodiments, the balloon 401 comprises a non-compliant balloon. The material of the balloon 401 may comprise a low compliance material such as PET, nylon, polyurethane (50D-72D), polyolefin copolymer, surlyn, ionomer, polyether block amide (PEBA), polyimide or a higher compliance material such as polyvinyl chloride (PVC), lower durometer polyurethane (30A-50D), silicone, kraton, EVA, or low durometer PEBA. The balloon 401 may be folded using a bifold, trifold, quadfold or mushroom folding configuration, such as illustrated in FIGS. 9A-9D, respectively. For embodiments using a combined sleeve and balloon, the balloon may comprise a comparatively non-compliant substrate like PET and the outer sleeve may comprise a more compliant material that is very thin and flexible (e.g., Bionate 55D or Bionate 80A).

Figure 9A:
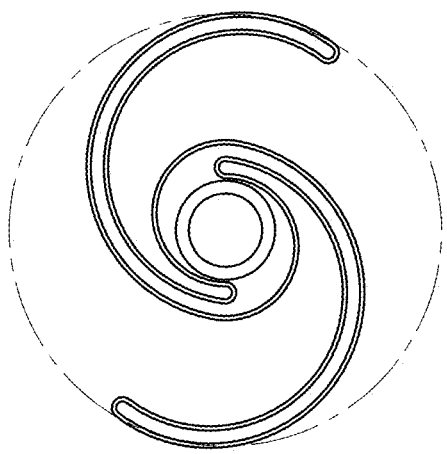
FIGS. 9A-9E schematically illustrate various embodiments of balloon folding configurations.
Figure 9B:
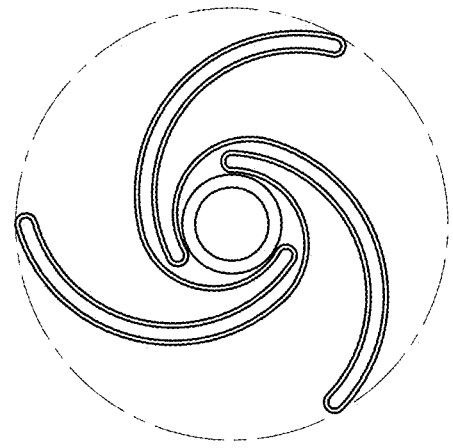
Figure 9C:
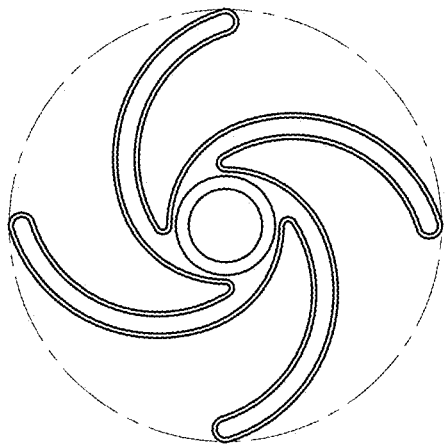
Figure 9D:
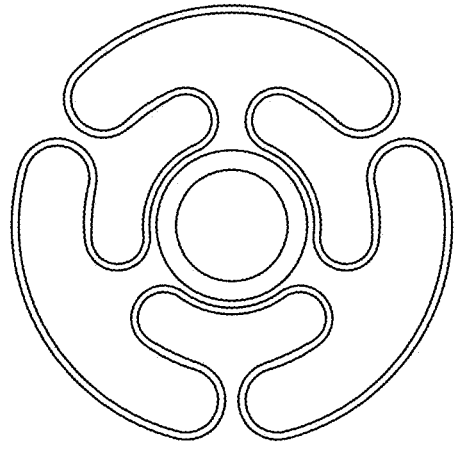
Figure 9E:
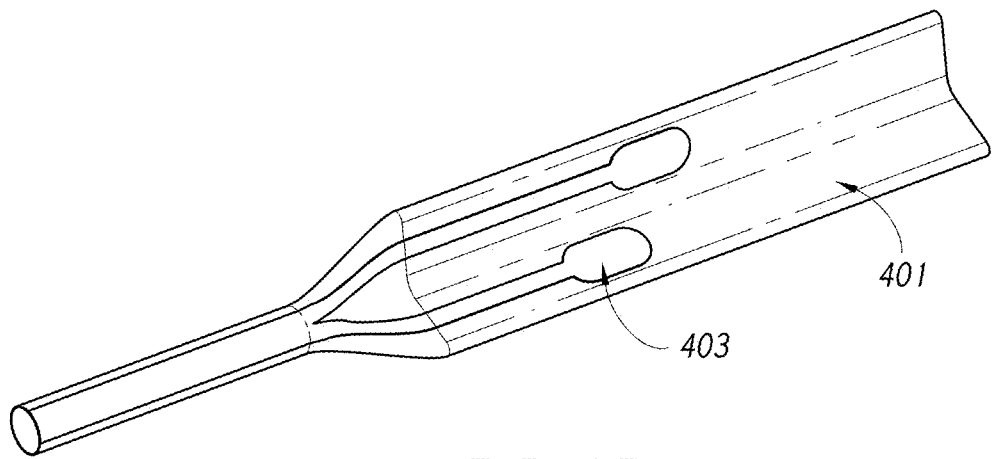

Various electrode patterns may be used for the electrodes on the balloon catheter (e.g., balloon catheter 400). In some embodiments, the electrodes are aligned along two, three or four axes to facilitate folding (e.g., bifold, trifold, quadfold). In some embodiments, the balloon includes circumferentially distributed adjacent pairs of electrodes connected in parallel. The electrodes may advantageously be positioned on a balloon so as to facilitate folding, as shown schematically in FIG. 9E. It may be particularly advantageous for as many electrodes as possible to lie on an outer surface of a fold when in a folded configuration.

Figure 10A:
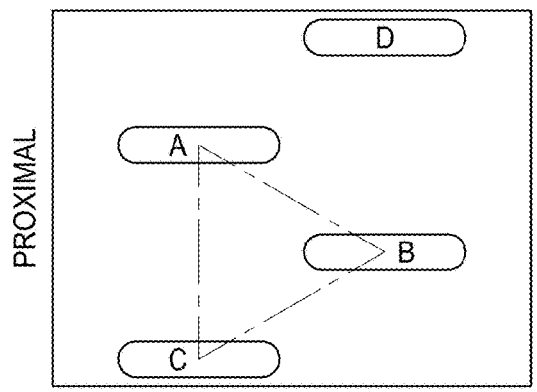
FIGS. 10A-10F schematically illustrate various embodiments of electrode patterns.
Figure 10B:
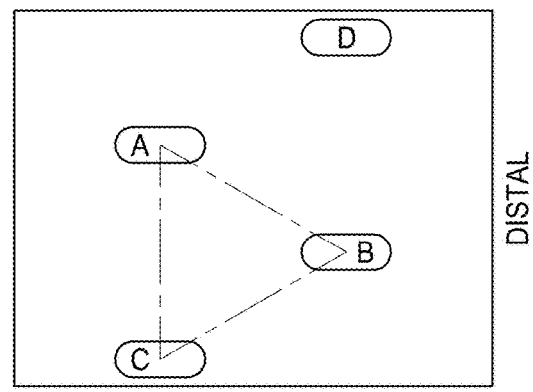

In some embodiments (such as schematically shown in FIGS. 10A and 10B), the balloon 401 comprises an electrode pattern consisting of four electrodes each spaced apart circumferentially by 90 degrees or about 90 degrees. As schematically shown in FIGS. 10A and 10B, the electrodes that are 180 degrees apart from each other (A and C, B and D) may be aligned axially along a length of the balloon or sleeve, such that there are multiple rows of pairs of electrodes spaced 180 degrees apart. The two proximal electrodes (A and C) are axially spaced apart from the two distal electrodes (B and D) at a spacing distance h. The spacing distance h may vary as desired and/or required. As shown in FIG. 10A and FIG. 10B, the electrodes may be positioned to have an equilateral configuration so as to advantageously provide equal spacing between all electrode pairs (AB, BC, CD, DA, AC, BD). The electrode spacing may be governed by the equation $h=\pi*D \tan(60°)/4$, when measured from centroid or proximate edges. The electrode spacing may be adapted to facilitate uniform power delivery between electrode pairs. In some embodiments, the distal edges of the proximal electrodes (A and C) and the proximal edges of the distal electrodes (B and D) do not overlap and are spaced at a distance of between 0.1 mm and 5 mm (e.g., between 0.1 mm and 1 mm, between 0.5 mm and 1.5 mm, between 1 mm and 2 mm, between 1.5 mm and 3 mm, between 2.5 mm and 4 mm, between 3 mm and 5 mm, between 1 mm and 2.5 mm, overlapping ranges thereof, or any values within the recited ranges).

Figure 10C:
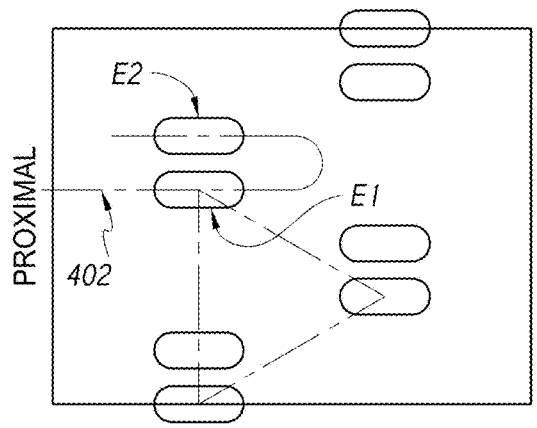

As schematically shown in FIG. 10C, each electrode may be replaced with a cluster of electrodes that are wired together so as to function as a single electrode. This embodiment facilitates a longer radial electrode dimension than axial electrode dimension, which may in turn advantageously result in increased perivascular circumferential ablation, while still preserving the ability to fold the balloon along fold lines as desired during assembly. As illustrated in FIG. 10C, the conductive wire 402 may be coupled (e.g., bonded) to a first electrode E1 of a cluster of electrodes and may then extend beyond the edge of the first electrode E1 and loop back and be coupled (e.g., bonded) to the second electrode E2 of the cluster of electrodes. This wiring configuration may be repeated for the other clusters of electrodes. Each cluster may include two, three, four or more electrodes.

Figure 10D:
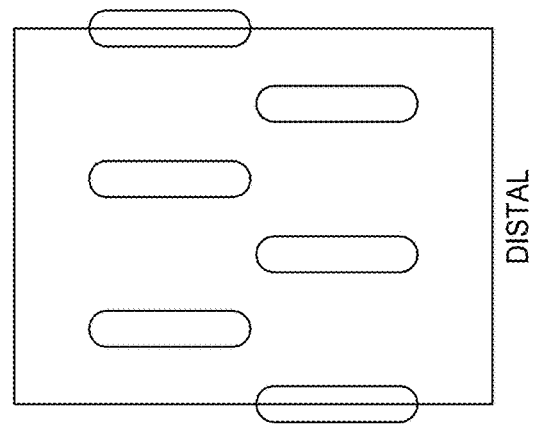

In some embodiments, the electrode pattern includes a 3×3 matrix of electrodes arranged on the balloon (as shown, for example, in the schematic drawing of FIG. 10D) instead of a 2×2 matrix (e.g., multiple rows of triplets instead of pairs). Each electrode may be spaced apart circumferentially from each adjacent circumferential electrode by 60 degrees or about 60 degrees. Each of the proximal electrodes may be spaced apart circumferentially from each other by approximately 120 degrees around a circumference of the balloon or sleeve and each of the distal electrodes may be spaced apart circumferentially from each other by approximately 120 degrees around a circumference of the balloon or sleeve. The proximal electrodes and the distal electrodes may be axially spaced apart from each other similar to as described above in connection with the 2×2 matrix pattern.

Figure 10E:
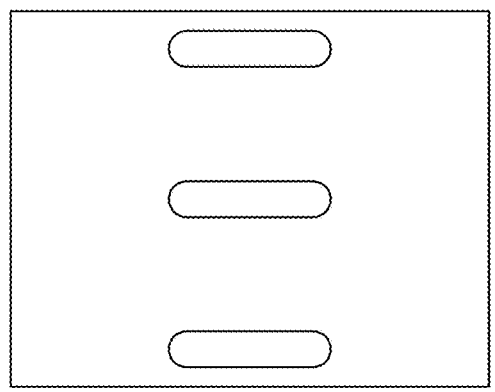
Figure 10F:
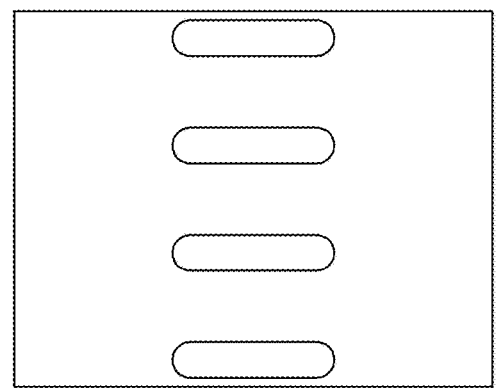

In other embodiments, the electrode pattern may consist of a planar pattern of three electrodes spaced apart circumferentially by 120 degrees or about 120 degrees (as shown in FIG. 10E) or a planar pattern of four electrodes spaced apart circumferentially by 90 degrees or about 90 degrees (as shown in FIG. 10F). Of course, other numbers of electrodes, patterns or arrangements or spacing could also be used as described elsewhere herein.

Figures 11A, 11B:
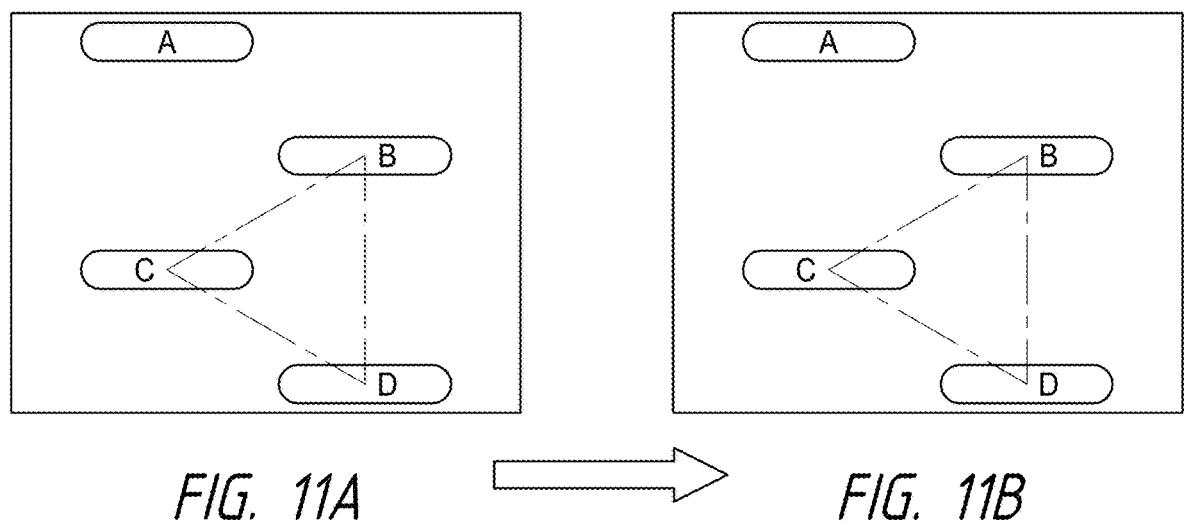
FIGS. 11A and 11B schematically illustrates an embodiment of a translational stepping method.

In some embodiments, the electrodes are simultaneously powered, or activated, such that the lesion pattern corresponds to the electrode pattern. In other embodiments, the electrodes are independently powered, or activated, (and deactivated). The balloon catheter may be translated to multiple locations within a single artery or other vessel branch and the electrodes may be activated (simultaneously or independently) at the multiple locations. All of the electrodes may be activated simultaneously or a combination of electrodes may be activated simultaneously. Independent activation (and deactivation) of electrodes may advantageously facilitate different lesion patterns to be achieved using a single electrode pattern. For example, with reference to FIGS. 11A and 11B, electrodes A and B may be activated (either simultaneously or individually) at a first placement location within a vessel (e.g., a common hepatic artery) and then the balloon may be translated to a second placement location and electrodes C and D may be activated (either simultaneously or individually) at the second location, thereby effecting a "spiral" lesion pattern in which each successive lesion site is spaced apart both axially and circumferentially. This translational stepping method may advantageously provide increased perivascular circumferential treatment (e.g., ablation) over the length of the vessel while limiting the footprint of the medial or vessel wall injury in any cross section. The translational stepping method may also advantageously provide improved positioning accuracy because the balloon catheter does not need to be rotated. In accordance with several embodiments, the translational stepping method may be performed without requiring a "spiral" electrode pattern and using single plane imaging.

Independent activation (and deactivation) of individual electrodes may also facilitate therapy that is customized based on vessel length or based on vessel location and/or electrode placement location in a manner so as to avoid adjacent structures that are desired to be avoided. For example, if a particular electrode is positioned at a location that is beyond an end of a vessel desired to be treated or too close to an end of a vessel desired to be treated, that electrode may not be activated. In addition, if an electrode is determined to be at a position within a vessel that is facing toward an adjacent structure or tissue that is not desired to be affected, that electrode may not be activated at that treatment location or the treatment parameters of the energy delivered by that electrode may be adjusted (e.g., lower power level, shorter duration). When delivering therapy within a vessel, one or more of the electrodes may not be activated so as to avoid damaging non-target perivascular organs or structures (e.g., pancreas, portal vein, bile duct, lymph nodes). As one example, when a balloon catheter is positioned in a common hepatic artery, one or more electrodes determined to be oriented caudally (in a direction of the pancreas) may not be activated when the balloon catheter is positioned in a distal segment of the common hepatic artery but may be activated when the balloon catheter is positioned in a proximal segment of the common hepatic artery. The electrodes may also be independently sensed to provide feedback.

In accordance with several embodiments, a method of activating therapy delivery members (e.g., electrodes, transducers) may include determining a location of an adjacent structure or tissue that is desired not to be targeted by the therapy. The method may also include determining a position and orientation of each of the therapy delivery members at a particular treatment location within a vessel. The method may also include determining whether any of the therapy delivery members are likely to affect the adjacent structure or tissue if activated at the particular treatment location. If it is determined that one or more of the therapy delivery members are likely to affect the adjacent structure or tissue, the method may include not activating the one or more therapy delivery members at the particular treatment location or adjusting parameters of the treatment for (e.g., limiting power applied to) the one or more therapy delivery members at the particular treatment location.

In accordance with several embodiments, it can be particularly advantageous for the electrodes on a balloon catheter adapted for perivascular denervation to have large surface area to optimize lesion depth and lesion width while limiting peak tissue temperature to prevent steam pops. Steam pops occur when water in tissue boils, potentially causing mechanical disruption of the arteries or other vessels. However, electrode width is constrained by balloon folding or recovery requirements while electrode length is constrained by the flexibility requirements as well as available vessel length and desired number of lesions with limited overlap. As indicated in connection with the pattern illustrated in FIG. 10C, electrodes may be positioned in pairs or groups (e.g., clusters) side by side in a circumferential direction. The electrodes within each pair or group are adapted to effectively function as a single monopolar electrode having a larger surface area in some implementations by activating the electrodes simultaneously (e.g., in parallel) in a monopolar manner. Each pair of electrodes can be driven and controlled separately or in parallel. In some embodiments, the plurality of groups of electrodes are positioned apart axially and circumferentially along the balloon shown in FIG. 12A such that no pair or group of electrodes is positioned at the same axial position along the length, thereby facilitating balloon folding and reduced overall outer circumferential dimension when the balloon is folded. The small gaps between each electrode of the pair may also advantageously facilitate balloon folding. In accordance with several embodiments, the substantially square aspect ratio resulting from the electrode pair arrangement provides efficient tissue heating.

Figure 12A:
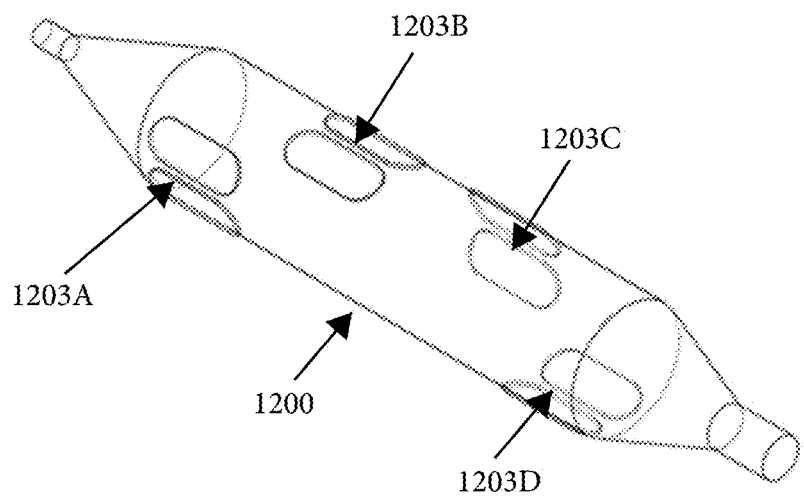
FIG. 12A is a perspective view of an embodiment of a balloon of an ablation device having a plurality of pairs of electrodes.
Figure 12B:
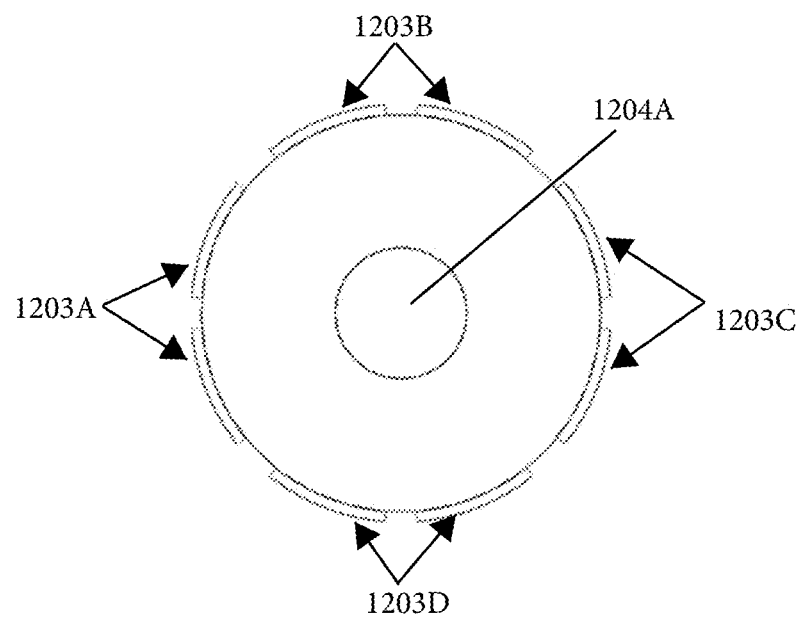
FIG. 12B is a side cross-sectional view of the balloon of FIG. 12A.

FIG. 12A illustrates an embodiment of an electrically-insulating electrode support structure (e.g., balloon) 1200 of a balloon catheter comprising a plurality of clusters of electrode members or elements 1203A-1203D. Each cluster of electrode members or elements 1203 can be activated to effectively function as a single electrode. As illustrated, each successive axially adjacent cluster or grouping of electrode members moving from proximal to distal is spaced about ninety degrees circumferentially from the previous cluster or grouping of electrode members such that the collective clusters form a spiral pattern around the circumference of the balloon and so as to facilitate folding and reduced overall circumferential dimension of the folded balloon. FIG. 12B illustrates a cross-section view of the support structure 1200 of the balloon catheter of FIG. 12A. As shown best in FIG. 12B, an optional guidewire lumen 1204A extends through the balloon 1200 of the balloon catheter such that the balloon catheter may be advanced over a guidewire. The spacing between adjacent electrodes in each cluster of electrodes 1203 may range from about 0.1 mm to about 1 mm (e.g., 0.2 mm to 0.5 mm, 0.3 mm to 0.6 mm, 0.5 mm to 1 mm, overlapping ranges thereof, or any value within the recited ranges). The center-to-center distance between adjacent axial clusters of electrodes (e.g., between cluster 1203A and 1203B) may range from about 3 mm-8 mm (e.g., 4 mm to 6 mm, 3 mm to 5 mm, 4 mm to 8 mm, overlapping ranges thereof, or any value within the recited ranges). The axial length of each electrode in each cluster may range from about 3 mm to about 8 mm (e.g., 4 mm to 6 mm, 3 mm to 5 mm, 4 mm to 8 mm, overlapping ranges thereof, or any value within the recited ranges) and the circumferential width of each electrode in each pair may range from about 0.5 mm to about 3 mm (e.g., 0.5 mm to 1.5 mm, 1 mm to 2 mm, 1 mm to 3 mm, overlapping ranges thereof, or any value within the recited ranges). The distance between the proximal edge of the proximal-most cluster 1203D and the distal edge of the distal-most cluster 1203A may range from about 10 mm to about 50 mm (e.g., 10 mm to 30 mm, 15 mm to 25 mm, 20 mm to 50 mm, 25 mm to 45 mm). The surface area covered by each cluster of electrodes may range from about 5 mm$^2$ to about 50 mm$^2$ (e.g., 4 mm$^2$ to 30 mm$^2$, 6 mm$^2$ to 18 mm$^2$, 5 mm$^2$ to 20 mm$^2$, 15 mm$^2$ to 30 mm$^2$, 20 mm$^2$ to 50 mm$^2$, overlapping ranges thereof, or any value within the recited ranges). It should be appreciated that the distances between electrodes may vary depending on balloon length and diameter.

As described in connection with other balloon catheter embodiments herein, the balloon catheters described herein (e.g., balloon catheter 400) may incorporate cooling systems. In some embodiments, the cooling systems utilize a balloon inflation lumen within the catheter delivery system. For example, the balloon inflation lumen may be used to inflate the balloon and a weep hole or leak in the balloon may allow for fluid to exit the balloon in a controlled manner (e.g., about 10 mL/min) so as to control balloon pressure and fluid flow rates (as described in more detail elsewhere). In various embodiments, the location of the weep hole is in a position on the balloon to create the greatest mixing of incoming fluids with electrode warmed fluids, and is also in a location where the out flow cannot be occluded. The resulting warmed fluid may be discharged downstream into the vasculature. In some embodiments, the balloon inflation lumen discharges cooling fluid (e.g., saline or water) directly into a distal portion of the balloon with a return lumen located at the proximal end of the balloon. This cooling system is adapted to maintain proper inflation pressure by controlling the discharge flow rate at a proximal manifold assembly. In some embodiments, directional ports are located along the balloon inflation lumen inside the balloon. These directional ports can be directed to optimize cooling and warm fluid mixing, or they can be positioned to spray directly at each electrode's back side. These embodiments could also utilize an outflow-controlled discharge at the proximal manifold assembly. For embodiments in which spray jets are directed at the electrode(s), cooling fluid may be delivered at high pressure through the balloon inflation lumen or another delivery lumen. The cooling fluid may be discharged from the balloon inflation lumen or other delivery lumen through an orifice at high velocity directed towards the interior surface of a respective ablation electrode. In several embodiments, the jet(s) will entrain additional fluid within the balloon. The jet(s) may advantageously impinge on an interior surface of an electrode, thereby providing high velocity gradients and efficient convective heat transfer from the electrode to the surface. The tissue proximate the luminal surface of the electrode has the highest intensity of RF heating and therefore benefits from more efficient heat transfer. Additional circulation of fluid throughout the interior of the balloon may provide additional cooling to other tissue regions. Coolant fluid (e.g., saline or water) may be discharged from the balloon into the vessel or removed via a lumen in the catheter shaft.

In accordance with several embodiments, cooling systems or techniques may be implemented using two balloons (e.g., an outer balloon sleeve and an inner balloon or an outer balloon and an inner balloon as described and illustrated herein). FIG. 13A is a partial sectional view of a distal portion of an ablation device having a first balloon 1301 substantially inside of a second balloon 1300. In some embodiments, electrodes 1303 are mounted on, or supported by, the second, outer balloon 1300 and the first, internal balloon 1301 is adapted to supply cooling via one or more openings or ports (e.g., jet orifices) 1312 in the internal balloon 1301. The cooling port(s) 1312 may advantageously be aligned with (e.g., located directly beneath) each of the electrodes 1303. For example, each electrode may have one or more cooling ports 1312 positioned and adapted to direct cooling fluid that particular electrode. Proximity of the cooling ports (e.g., jet orifices) 1312 to the cooled electrode surface advantageously ensures accurate alignment and permits larger orifice diameter and lower pressures and flow rates. Multiple cooling ports or jets 1312 can be used to cool larger electrodes 1303. Metal electrode surface and solder joints may be directly exposed to the cooling jets for better heat transfer. The cooling ports (e.g., jet orifices) 1302 may have a diameter between about 0.05 mm and about 0.25 mm (e.g., between 0.05 mm and 0.10 mm, between 0.07 mm and 0.15 mm, between 0.10 mm and 0.20 mm, between 0.15 mm and 0.25 mm, overlapping ranges thereof, or any value within the recited ranges).

The cooling fluid may enter into the inner balloon 1301 through a fluid inlet 1309 and be directionally sprayed or weeped at a sufficient flow rate to provide a desired cooling effect to the outer balloon 1300 and the electrodes 1303. For example, the flow rate per electrode may range from 0.1-1.0 ml/sec. In some implementations, fluid supplied from the inner balloon 1301 is directed at each electrode 1303 and exhausted from the outer balloon 1300 in a continuous flow loop. The inner balloon 1301 may advantageously be adapted to act both as an inflation device and a pressure reservoir. In some embodiments, the inner balloon 1301 has a higher pressure than the pressure in the outer balloon 1300. The outer balloon pressure may be a function of flow rate, orifice resistance, outlet resistance and/or externally applied back pressure.

In some embodiments, the gap between the inner and outer balloons 1300,1301 is between about 0.05 mm and about 1.5 mm (e.g., between 0.05 mm and 0.50 mm, between 0.10 mm and 0.60 mm, between 0.25 mm and 0.75 mm, between 0.2 mm and 0.3 mm, between 0.5 mm and 1.0 mm, between 0.75 mm and 1.5 mm, overlapping ranges thereof, about 0.25 mm, or any value within the recited ranges). In accordance with several embodiments, small inter balloon gaps, thin electrically insulating coatings (e.g. Parylene) and low conductivity solutions advantageously limit cross talk between channels. Gaps and proximal and distal cones of the balloons may function as manifolds for collecting or distributing coolant fluid. For example, the embodiment of FIG. 13A includes a distal fluid space 1315 between the distal end of the inner balloon 1301 and the distal end of the outer balloon 1300 and a proximal fluid space 1318 between the proximal end of the inner balloon 1301 and the proximal end of the outer balloon 1300.

In some embodiments, one or more auxiliary orifices 1344 at the proximal or distal ends of the inner balloon 1301 prevent fluid stasis that would allow portions of the outer balloon 1300 to heat up. The auxiliary orifice(s) 1344 may provide fluid circulation through the substantially annular space between the inner balloon 1301 and the outer balloon 1300. Coolant may discharge from the outer balloon 1300 at the distal end and/or the proximal end or at any other location along the outer balloon 1300 (e.g., the middle). In some embodiments, conductive wires 1302 may run to the electrodes 1303 between the inner balloon 1301 and the outer balloon 1300. The inner balloon 1301 and the outer balloon 1300 may be comprised of one or more polymeric materials, such as polyethylene, PET, nylon Pebax, PEBA, polyolefin, polyurethane, and/or the like.

In various embodiments, the inner balloon 1301 is partially or entirely contained within the outer balloon 1300. In some embodiments, a proximal and/or distal waist of the inner balloon lies within the cone or body region of the outer balloon. In some embodiments, the inner and outer balloons may be attached to a common shaft of the ablation device (e.g., ablation catheter). The balloon catheter may comprise a guidewire lumen 1304A extending within the shaft to facilitate over-the-wire delivery.

FIGS. 13B-1 and 13B-2 illustrate perspective and cutaway views of a distal portion of an ablation device comprised of an inner balloon 1301 and an outer balloon sleeve 1314. The outer balloon sleeve 1314 extends along a portion of the length of the inner balloon 1301 and forms an annular space with the inner balloon 1301. In some embodiments, one or more irrigation, or discharge, orifices 1332A, 1332B at the proximal and/or distal ends of the outer balloon sleeve 1314 prevent fluid stasis that would allow portions of the outer balloon sleeve 1314 to heat up. The orifice(s) 1332 may provide fluid circulation through the substantially annular space between the inner balloon 1301 and the outer balloon sleeve 1314. Coolant may discharge from the outer balloon sleeve 1314 at the distal end and/or the proximal end (e.g., through discharge orifices 1332A, 1332B) or at any other location along the outer balloon sleeve 1314 (e.g., the middle). In some embodiments, conductive wires 1302 run to the electrodes 1303 between the inner balloon 1301 and the outer balloon sleeve 1314. The inner balloon 1301 includes a proximal cone 1316 and a distal cone 1320. The outer balloon sleeve 1314 may be bonded to the inner balloon 1301 at its proximal and distal ends and/or at other locations along the outer balloon sleeve 1314. As with the embodiment shown in FIG. 13A, the inner balloon includes one or more openings or ports (e.g., jet orifices 1312A, 1312B) 1312 adapted to direct jets of coolant fluid toward the surface of the electrode 1303. The openings or ports 1312 may be positioned adjacent to each of the electrodes 1303.

Figures 1, 13C:
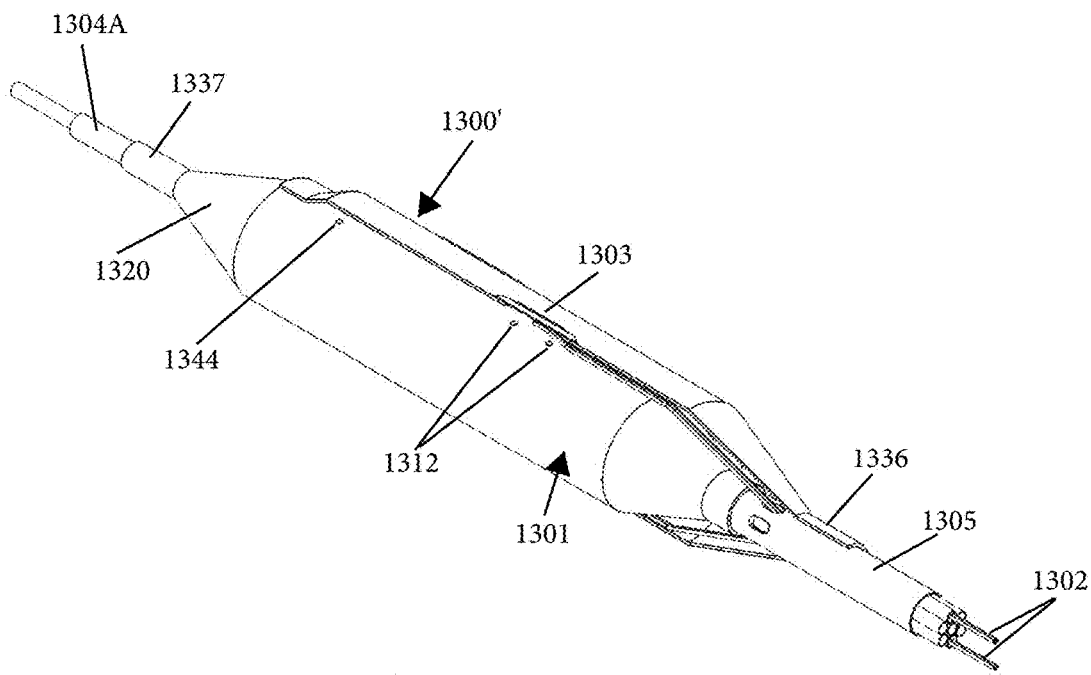
Figures 2, 13C:
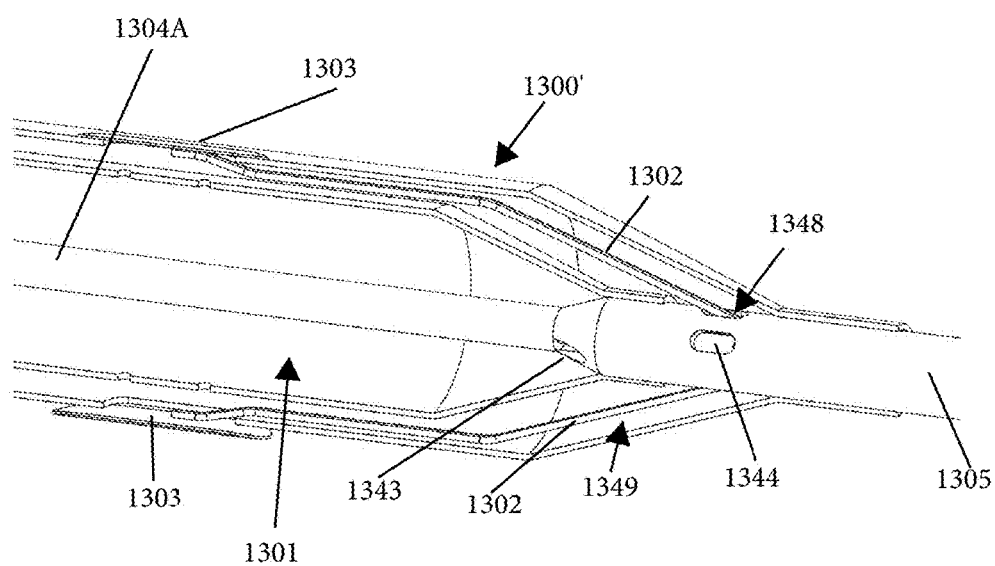

FIGS. 13C-1 and 13C-2 illustrate partial section views of a distal portion of an ablation device comprising an inner balloon 1301 partially enclosed by a partial outer balloon 1300'. The inner balloon 1300 includes a distal auxiliary orifice 1344 and may include other auxiliary orifices along its length. The inner balloon includes a proximal cone and a distal cone 1320. The ablation device includes a central guide wire lumen 1304A. The proximal waist of the inner balloon 1301 and the proximal waist 1336 of the outer balloon 1300' may be bonded or otherwise coupled to a shaft 1305 of the ablation device. The distal waist 1337 of the inner balloon 1301 may also be bonded to the shaft 1305 and the distal end (e.g., edge) of the outer balloon 1300' may be bonded to the inner balloon 1301 at a location proximal to the distal cone 1320 of the inner balloon 1301. The inner balloon 1301 comprises one or more irrigation or cooling orifices 1312 adapted to direct fluid jets toward each of the electrodes 1303 positioned along the outer balloon 1300'. As shown in FIG. 13C-1, the shaft 1305 of the catheter may have a plurality of lumens 1304. Some lumens 1304 may be advantageously occluded and/or provided with side windows to direct fluid in the desired direction. In some embodiments, the shaft 1305 is a multi-lumen extrusion. In other embodiments, the shaft 1305 is a bundle of individual lumens. In some embodiments, the bundle of individual lumens is enclosed in a sleeve. For example, the bundle of individual lumens may be encased in a sleeve that has been partially melted (reflowed) or solvent cast or coated onto the bundle. In some embodiments, the sleeve interpenetrates the bundle. In some embodiments, the shaft 1305 has a transition zone within the balloon.

FIGS. 13C-2 is an enlarged partial section view of the ablation device of FIGS. 13C-1. As shown, the shaft 1305 comprises an inlet lumen 1343 through which cooling fluid is introduced into the inner balloon and a discharge lumen 1346 through which fluid exits the ablation device into the bloodstream. The shaft 1305 includes one or more openings 1348 through which electrode wires 1302 extend and run along the annular space between the inner and outer balloons to a respective electrode 1303. As shown, the ablation device may include a proximal fluid space or gap 1349 between the proximal cones of the inner and outer balloons. In various embodiments, an enlarged opening is provided in the outer balloon 1300' to allow for the electrode wire 1302 joint to penetrate into the inter-balloon gap. This provides a better fit between the electrode 1303 and the outer balloon 1300'. Spacers may be provided to ensure appropriate fluid flow and gap at each electrode 1303.

In accordance with several embodiments, a central guidewire lumen of the ablation device may prevent optimum placement of central cooling orifices or ports for circumferentially-spaced electrodes. Accordingly, a substantially coaxial array of cooling orifices or ports may be provided instead. FIG. 14A is a partial section view of an embodiment of an annular jet assembly 1440 inside of an ablation balloon 1400 comprising multiple irrigation orifices or openings 1412 adapted to provide multiple jets of fluid directed towards a plurality of electrodes without being blocked or interrupted by a guidewire lumen 1404A. The annular jet assembly 1440 comprises a distal endcap 1443 and a proximal endcap 1445 that are coaxially aligned with the guidewire lumen 1404A and extend around the circumference of the guidewire lumen 1404A. A cylindrical covering or surface 1441 extends between the distal endcap 1443 and the proximal endcap 1445. The cooling orifices or ports are disposed at various locations in the cylindrical covering or surface 1441 so as to direct jets of fluid toward the one or more electrodes (not shown) of the ablation device. Coolant fluid may be provided via a coaxial (not shown) or eccentrically placed (as shown in FIG. 14A) inlet lumen 1404B. Coolant fluid may be distributed in an annular cavity around the guidewire lumen 1404A.

In some embodiments, the catheter shaft 1405 of the ablation device comprises a plurality of partial annular lumens. FIGS. 14B-1 and 14B-2 show an end view and an oblique view, respectively, of a multi-lumen shaft 1405 comprising a central guidewire lumen 1404A and an eccentric fluid inlet lumen 1404B comprising a plurality of jet discharge orifices or openings 1412A, 1412B arranged around a circumference of the fluid inlet lumen 1404B that are adapted to deliver jets of fluid in a plurality of directions. In some embodiments, the fluid delivery lumen 1404B loops or coils (not shown) around the guidewire lumen 1404A to present an orifice or port in the direction of each electrode.

Figure 15A:
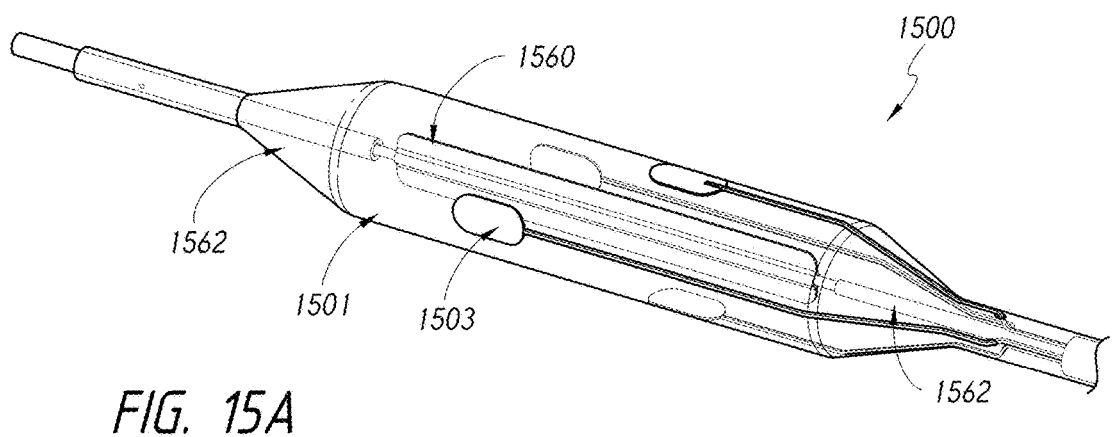
FIGS. 15A and 15B illustrate a distal portion and a proximal portion, respectively, of a balloon ablation catheter.
Figure 15B:
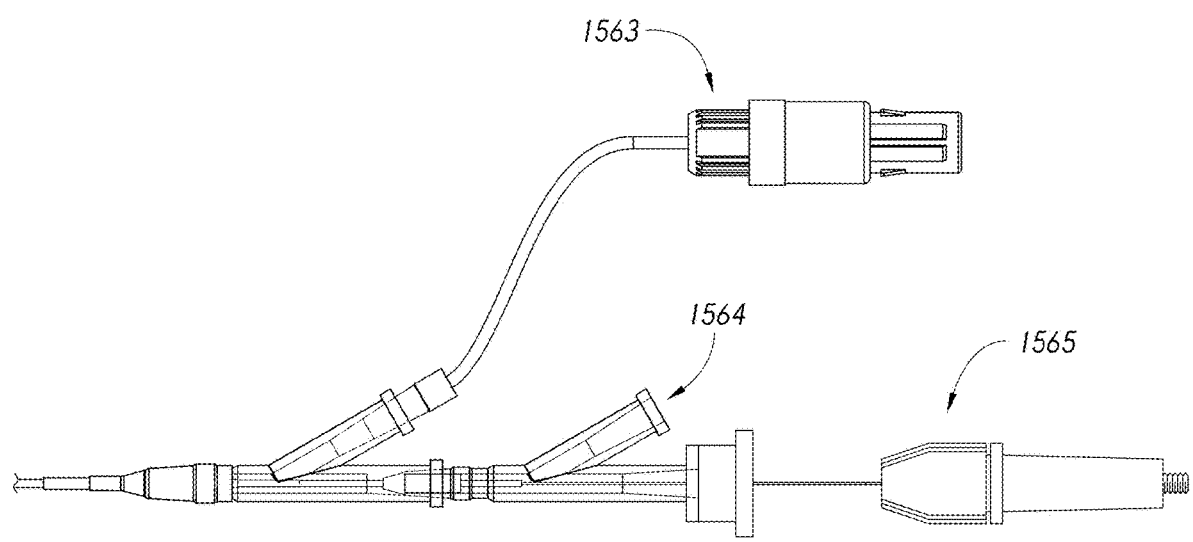

FIG. 15A illustrates an embodiment of a balloon catheter 1500 having an impeller or paddle 1560 to induce cooling of electrodes 1503 by mixing of fluid within a balloon 1501. The impeller 1560 may be constructed from a suitable material and attached to a sufficiently long drive shaft using adhesive or mechanical attachment means. A shaft of the impeller 1560 may be supported by bushings 1562 at each balloon waist, thereby ensuring stable impeller rotation for fluid displacement and electrode cooling. The balloon 1501 may be attached to a delivery shaft having electrical isolation circuitry 1563, an inflation manifold 1564 and an impeller drive system 1565, such as illustrated in FIG. 15B. The impeller or paddle 1560 may be finger-driven by a user or mechanically driven. The impeller or paddle 1560 may be rotatably and/or translationally driven.

Figures 1, 16A:
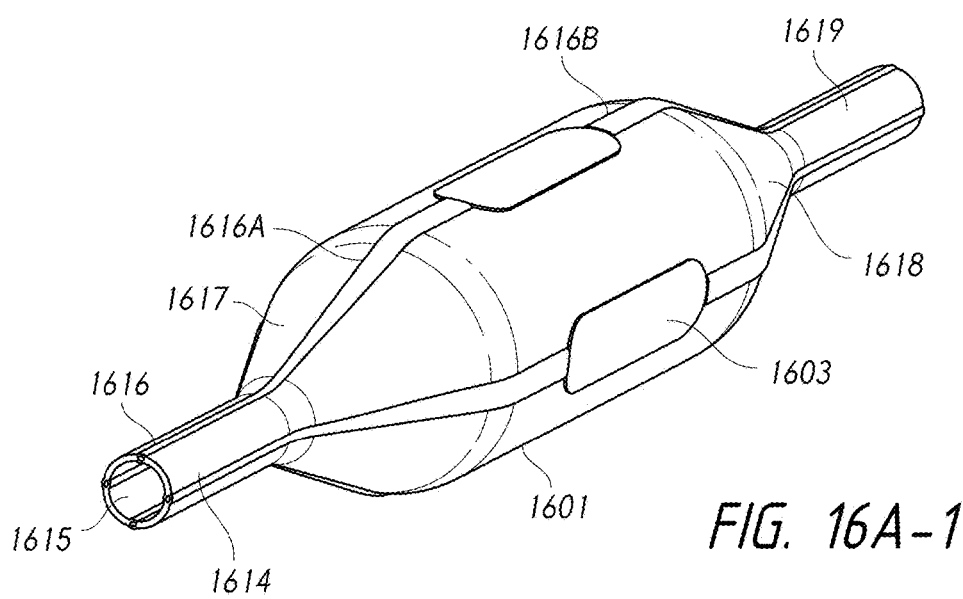
Figures 2, 16A:
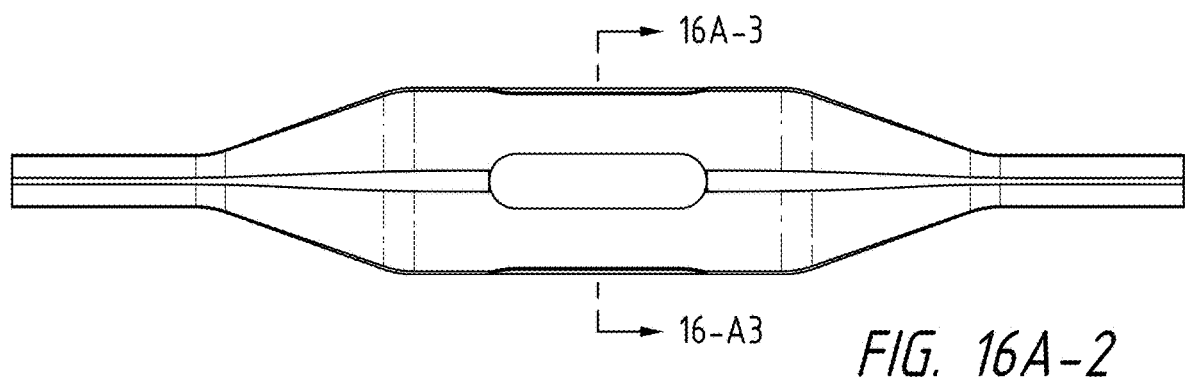
Figures 3, 16A:
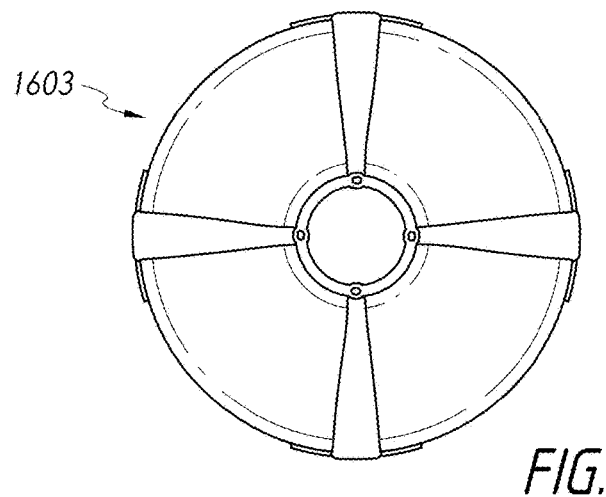

FIGS. 16A-1 to 16A-3 illustrate various views of an embodiment of a distal treatment portion of a multi-lumen balloon ablation catheter 1600. The multi-lumen balloon ablation catheter 1600 includes a multi-lumen balloon 1601 at or near the distal end of an elongate shaft (not shown). The multi-lumen balloon 1601 is constructed with at least one accessory lumen 1616 placed within or adjacent to the balloon wall. At least one electrode 1603 is positioned on the multi-lumen balloon 1601 so that in the deployed state, a face of the electrode 1603 is electrically exposed to the surrounding tissue. An electrical conductor (not shown) extends from the electrode 1603 through at least part of an accessory lumen 1616, connecting to an RF generator via the elongate shaft of the balloon ablation catheter 1600.

In some embodiments, a substantially noncompliant balloon may have distinct regions including a proximal waist 1614, a proximal cone 1617, a main body 1613, a distal cone 1618, and a distal waist 1619. In some embodiments, a main lumen 1615 extends through the center of the balloon 1601. In other embodiments, the main lumen 1615 may be offset from the center of the structure. In still other embodiments, more than one main lumen 1615 may be provided.

In some embodiments, the at least one accessory lumen 1616 extends continuously through the length of the balloon. In some embodiments, the at least one accessory lumen 1616 is occluded, fused, or removed from a portion of balloon 1601. In some embodiments, an opening is made through the side wall of the accessory lumen 1616. Such openings may allow the passage of fluid or electrical conductors. In some embodiments, the accessory lumen 1616 may be divided into a proximal accessory lumen 1616A and a distal accessory lumen 1616B. In some embodiments, the proximal accessory lumen 1618 may enclose an electrical conductor and the distal accessory lumen 1619 may permit the flow of fluid.

Figure 16B:
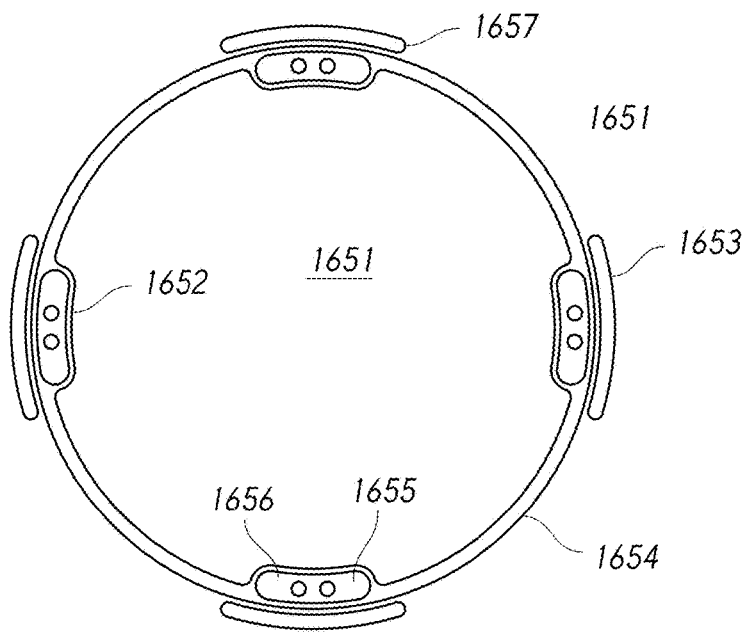
FIG. 16B shows a cross sectional view through the central portion of a multi-lumen ablation balloon assembly.

FIG. 16B shows a cross sectional view through the central portion of an embodiment of a multi-lumen ablation balloon catheter in its deployed state. A main lumen 1651 is pressurized to inflate the balloon 1601 and bring an electrode surface 1653 to its intended position relative to the biological tissue. In some embodiments, the one or more electrodes 1603 are bought into direct contact with the tissue. In other embodiments, the electrodes 1603 may be positioned at a distance from the tissue. In one embodiment, an electrode is affixed to the outer surface 1654 of the ablation balloon by adhesive bonding 1657. In another embodiment, a portion of the electrode 1603 is contained and/or bonded within an accessory lumen 1652 (e.g., accessory lumen 1616). In another embodiment, an electrical conductor extending from the electrode is bonded into the accessory lumen (e.g., accessory lumen 1616).

In some embodiments, a first electrical conductor 1655 passes from a first electrode, through an accessory lumen to a first power source. In some embodiments, a second electrical conductor 1656 passes from a first or second electrode to a sensor or second power source. In some embodiments, the first and second electrical conductors 1655, 1656 form a thermocouple. In some embodiments, the electrical conductor(s) enter the accessory lumen 1652 through an opening in the outer wall of the accessory lumen 1652 proximate the electrode. In other embodiments, the electrical conductor(s) enter the accessory lumen 1652 through an opening beneath the electrode. In some embodiments, a portion of the outer wall of the accessory lumen is removed to permit the proximal and distal portions of the electrode or electrical conductor to be inserted. In some embodiments, there are multiple openings in the accessory lumen. For example, ports may be provided to allow fluid to pass into and out of the accessory lumen(s).

In some embodiments, an accessory lumen has a substantially open lumen. In other embodiments, an accessory lumen is flattened or compressed. In some embodiments, an accessory lumen conforms around an electrical conductor. In some embodiments, the accessory lumen is compressed and/or bonded to itself and/or an electrical conductor. In some embodiments, bonding is provided only at the ends or selected locations along its length.

During thermal ablation procedures, some regions of tissue may become undesirably hot. It has been found that the hottest regions of tissue often occur near an electrode. In accordance with several embodiments, the multi lumen balloon catheter 1600 is configured to absorb heat from the surrounding tissue and transport it to a cooler region of the body or remove it from the body altogether. In one such embodiment, at least a portion of an accessory lumen is configured to convey cooling fluid (e.g., saline or water) past a hot surface of the balloon. In another embodiment, cooling fluid is delivered to the accessory balloon lumen via an infusion lumen in the elongate shaft. In some embodiments, the cooling fluid is delivered into a main balloon lumen from which it enters an accessory lumen. In some embodiments, cooling fluid enters the distal accessory lumen and conveyed past the hot inner balloon surface region to thereby provide convective cooling to the electrode(s). In other embodiments, the cooling fluid enters an accessory lumen proximate the hot interior balloon surface region and is discharged through a proximal or distal accessory lumen into the blood vessel.

The multi-lumen ablation balloon 1601 may be formed from an extruded thermoplastic tubing. Suitable materials for multi-lumen ablation balloons may be selected from a list including, but not limited to, Polyester Terepthalate (PET), polyethylene, High Density Polyethylene, nylon, Polyether block amide (PEBA) polyurethane and other materials. Extruded tubing may be prepared for molding be heating and stretching segments of the tube. Blow molding may be accomplished by heating and pressurizing the tubing inside of a mold. In some embodiments, the molded balloon is cooled before removal from the mold. Molding of multi-lumen balloons may also be accomplished using thermoset polymer materials and reinforced composite materials. Molding parameters (such as pressure, temperature, tension, time and other parameters) may be adjusted to achieve the desired balloon dimensions and properties.

In some embodiments, only the main lumen of the balloon is pressurized during forming. In other embodiments, both main and accessory lumens are pressurized equally. In still other embodiments, the main lumen and accessory lumens are pressurized to different pressures. In one embodiment, fluid may be passed through one or more lumens to affect the temperature of the adjacent material during forming.

Figures 1, 16C:
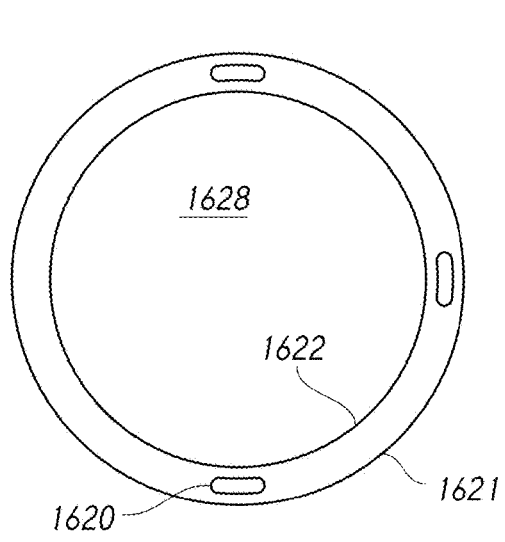
Figures 2, 16C:
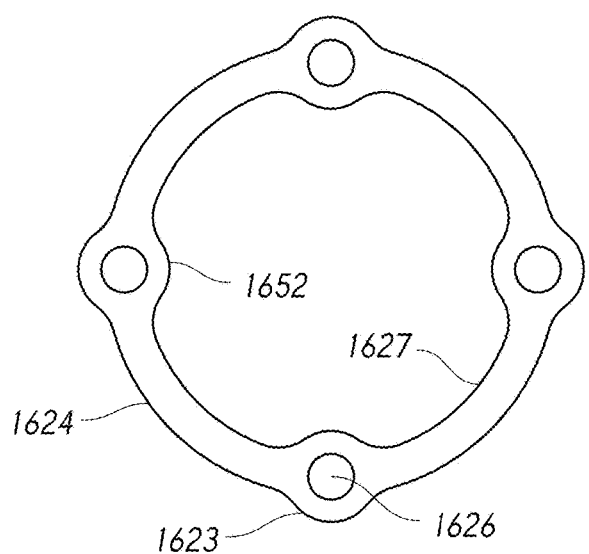

FIGS. 16C-1 shows a cross sectional view of a multi-lumen extrusion suitable for making a multi-lumen ablation balloon component. The extrusion includes a main lumen 1628 and at least one accessory lumen 1620. One skilled in the art will recognize that tubing suitable for blow molding will be topologically similar to the desired end product, but is generally smaller in diameter and of greater wall thickness compared to the final product. The tubing embodiment illustrated in FIGS. 16D-1 has an accessory lumen of elongated aspect ratio and lies substantially within the wall of the main tube between an outer surface 1621 and an inner surface 1622, thereby resulting in a thinner wall in the accessory lumen 1620 compared to the main lumen 1628. Another tubing embodiment shown in FIGS. 16C-2 has an accessory lumen 1626 of generally circular cross section and wall thickness comparable to that of the main lumen 1628, resulting in a protrusion 1625 from an inner surface 1627 and/or a protrusion 1623 from an outer surface 1624. Other embodiments of balloon tubing have the accessory lumen 1620 displaced towards or away from the center of the main lumen 1628. In some embodiments, a plurality of accessory lumens are regularly spaced along the perimeter of the main lumen. In other embodiments, a plurality of accessory lumens are unevenly distributed along the perimeter of the main lumen. In some embodiments, there are a plurality of main lumens.

Figures 1, 16D:
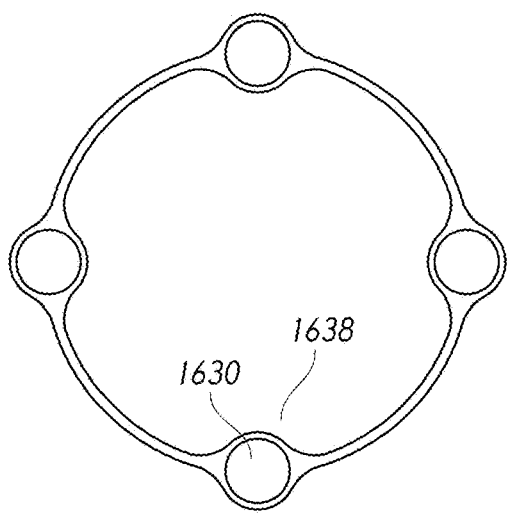
Figures 2, 16D:
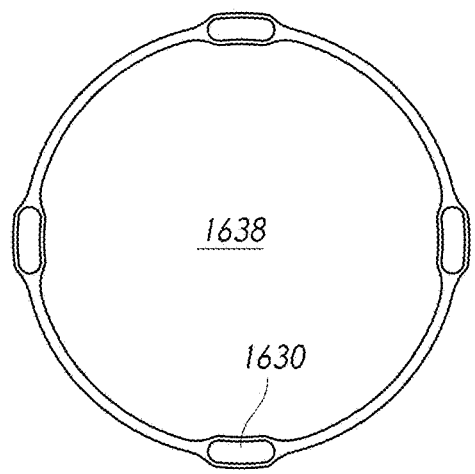
Figures 1, 16E:
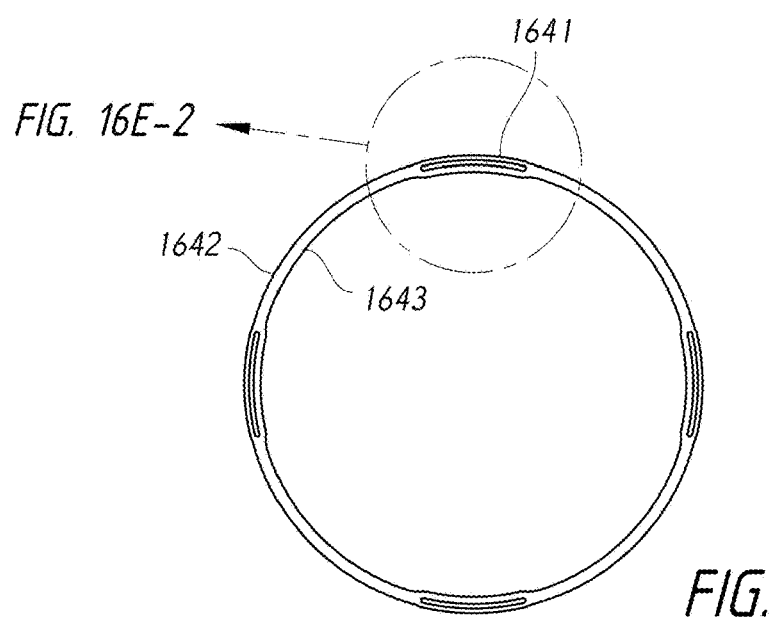
Figures 2, 16E:
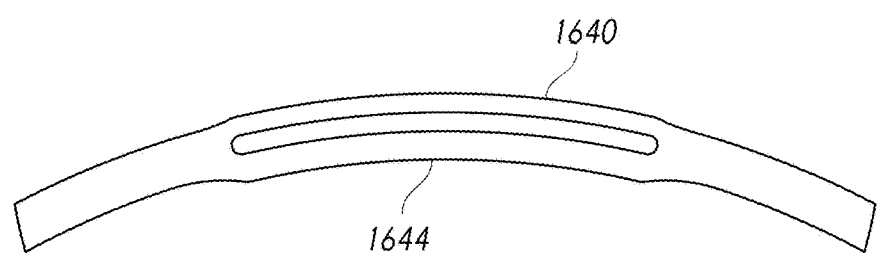

FIGS. 16D-1 shows a cross sectional view through the central portion of a multi-lumen ablation balloon component where blow molding was accomplished by pressurizing both a main lumen 1638 and accessory lumen(s) 1630. FIGS. 16D-2 shows a cross sectional view through the central portion of another multi-lumen ablation balloon component where blow molding was accomplished by pressurizing the main lumen 1638 such that the accessory lumen(s) 1630 have become elongated. FIGS. 16E-1 shows a cross sectional view through the central portion of a multi-lumen ablation balloon component when the main lumen 1643 is under pressure. FIGS. 16E-2 shows a detail cross sectional view through the central portion of a multi-lumen ablation balloon component when the main lumen 1643 is under pressure. An accessory lumen 1641 may be substantially flattened in at least a portion of its length. In some embodiments, the accessory lumen 1641 may be in contact with electrical conductors (not shown). In some embodiments, the accessory lumen 1641 may be bonded to electrical conductors. The wall thickness 1642 of some embodiments of a main balloon lumen suitable for ablation is in the range of 0.0001 inches to 0.010 inches (e.g., from 0.0005 inches to 0.002 inches, from 0.0002 inches to 0.005 inches, from 0.0001 inches to 0.001 inches, from 0.001 inches to 0.008 inches, from 0.005 inches to 0.010 inches, overlapping ranges thereof, or any value within the recited ranges). In various embodiments, the suitable range of accessory balloon lumen diameter is from 0.1 mm to 3.5 mm (e.g., from 0.5 mm to 2.0 mm, from 0.5 mm to 2.5 mm, from 1.0 mm to 2.5 mm, from 1.0 mm to 1.5 mm, from 1.0 mm to 3.0 mm, from 1.5 mm to 2.5 mm, from 1.5 mm to 3.0 mm, from 2.5 mm to 3.5 mm, overlapping ranges thereof or any value within the recited ranges). In some embodiments, the inner accessory lumen wall 1644 is substantially the same thickness as the outer accessory lumen wall 1640. In other embodiments, the inner accessory lumen wall 1644 is different than the outer accessory lumen wall 1640. In various embodiments, the suitable range of main balloon diameters is from 1 mm to 25 mm (e.g., from 1 mm to 5 mm, from 1.5 mm to 6 mm, from 2 mm to 8 mm, from 4 mm to 10 mm, from 5 mm to 15 mm, from 8 mm to 20 mm, from 10 mm to 15 mm, from 10 mm to 20 mm, from 15 mm to 20 mm, overlapping ranges thereof, or any value within the recited ranges). The number of accessory lumens may be one, two, three, four, five, six, seven, eight, nine, ten or more than ten, as desired or required.

In some embodiments, a multi-lumen ablation balloon may be compliant so that it stretches and elongates during deployment and recovery. Compliant balloons, while lacking the well-defined features described for the non-compliant balloon, still exhibit the functional behaviors described herein. Materials suitable for manufacturing compliant multi-lumen ablation balloons include silicone, polydimethylsiloxane, low durometer polyurethane, kraton and the like.

Figure 17A:
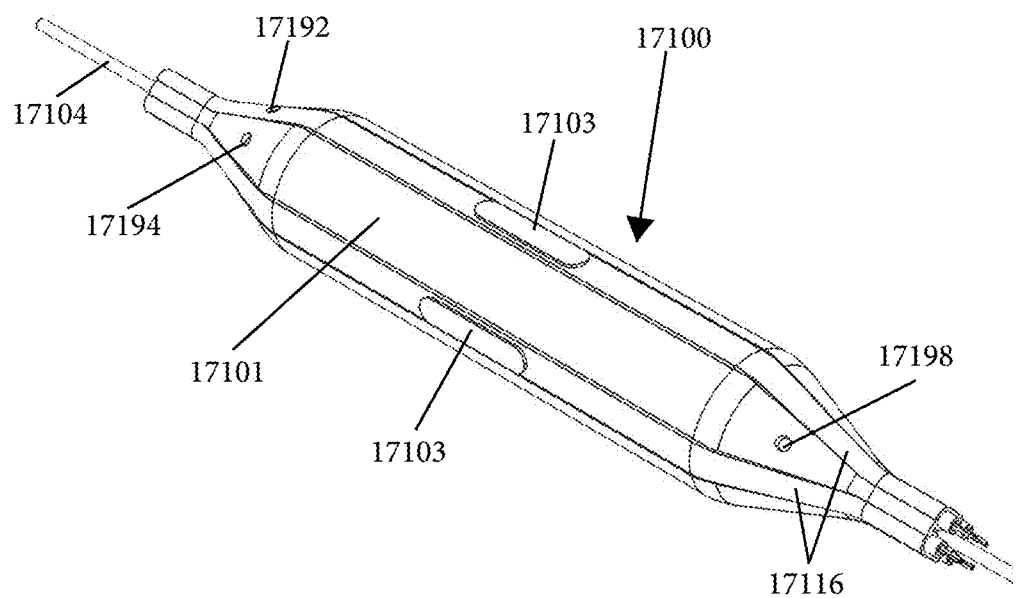
Figures 1, 17B:
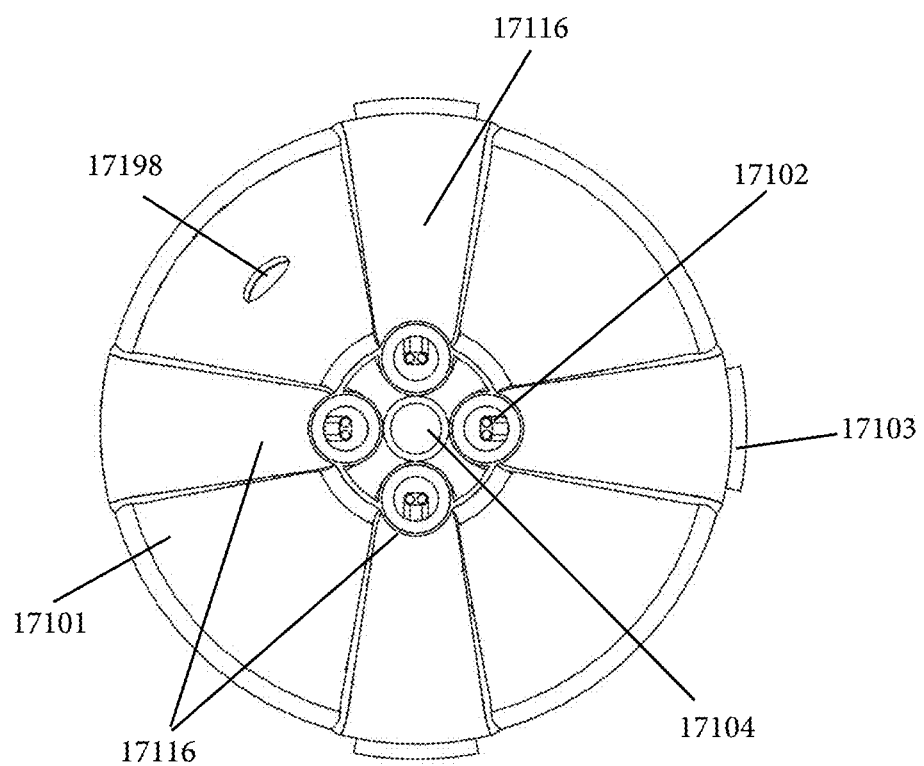
Figures 2, 17B:
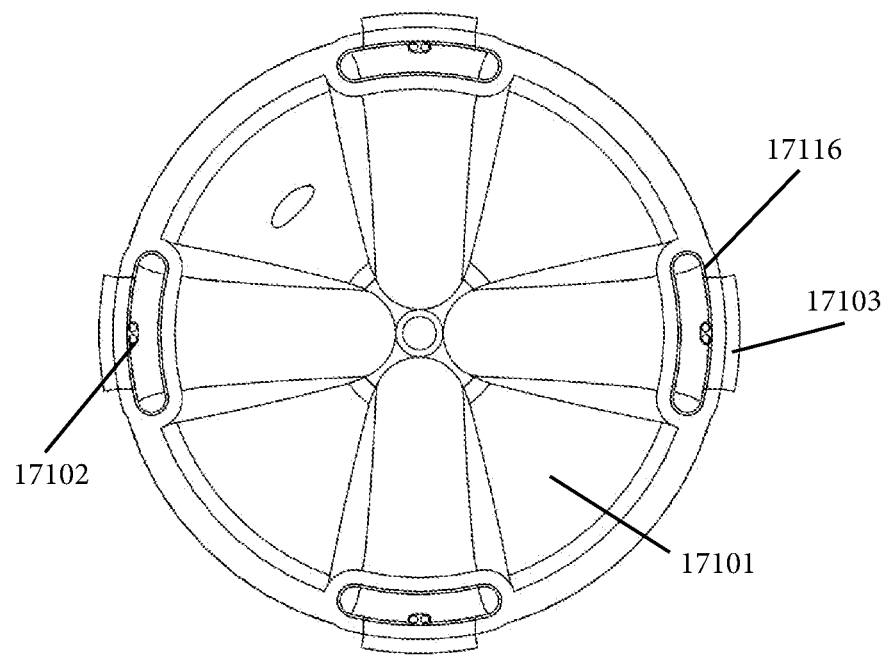
Figure 17C:
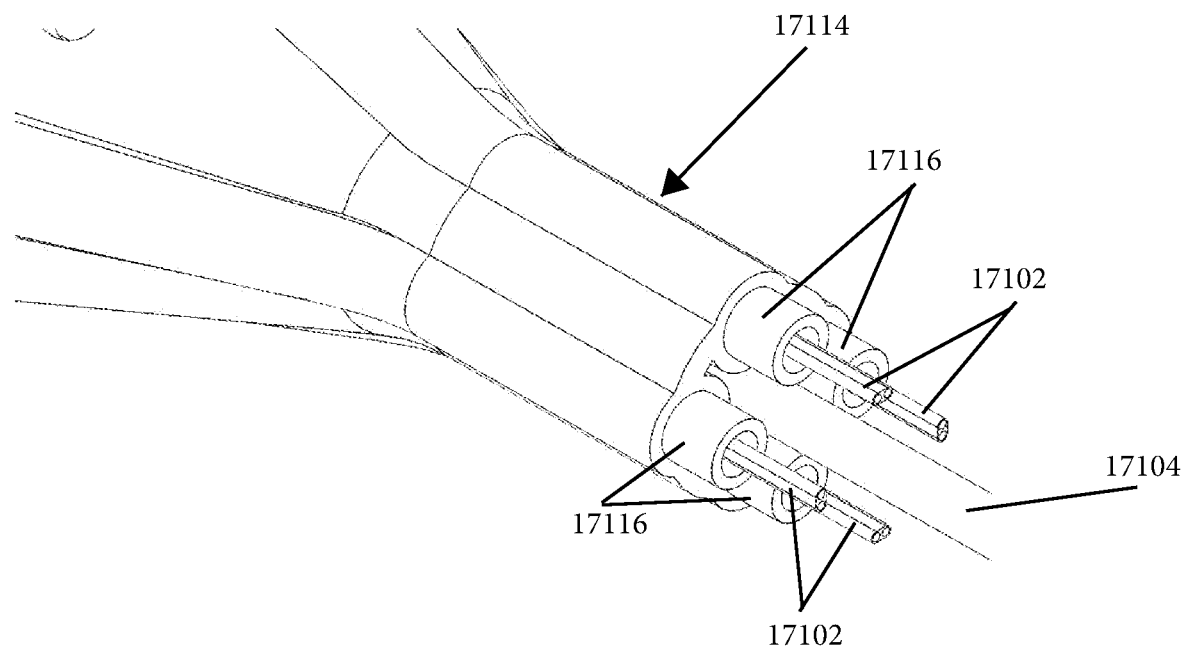

FIGS. 17A, 17B-1, 17B-2 and 17C illustrate a perspective view, an end view, a transverse section view, and an enlarged perspective view of a proximal end, respectively, of an embodiment of a multi-lumen ablation catheter 17100. In the depicted embodiments, the catheter 17100 is a composite structure comprised of a plurality of individual lumens 17116 adapted for irrigation and as a conduit for electrode wires. The plurality of individual lumens 17116 is substantially encased in an elastomeric material adapted to maintain the shape and orientation of the individual lumens. The elastomeric encapsulant structure may form a balloon 17101. As illustrated, the plurality of individual lumens 17116 comprises four lumens spaced apart equally around the central guidewire lumen 17104. An electrode 17103 is disposed at a location along a length of each lumen 17116 so that each lumen 17116 may provide cooling to the electrode positioned along its length. The balloon 17101 comprises a distal external balloon discharge orifice 17194 and a proximal external balloon discharge orifice 17198. FIG. 17C shows an enlarged oblique view of a proximal end 17114 of the composite multi-lumen balloon ablation catheter 17100. As shown, electrode wires 17102 extend within and along each of the respective lumens 17116 to electrically couple each respective electrode to an energy source (e.g., generator). Each lumen 17116 comprises a lumen wall separating the lumen from the balloon 17101. The individual lumens 17116 may be blow molded to provide variable diameter and wall thickness. One, some or all of the lumens 17116 may include an external lumen discharge orifice 17192. FIGS. 17A-17C may incorporate any of the structural or functional features of the multi-lumen balloon components of FIGS. 16A-16E-2 except that the catheter 17100 is a composite structure instead of separately extruded lumens.

In some embodiments, one or more of the individual lumens 17116 may terminate at a point proximal to the distal end of the balloon 17101. For example, the individual lumen may terminate just distal to an electrode 17103 or at the top of a distal cone of the balloon or at a point in between the electrode 17103 and the distal cone. In some embodiments, an electrode 17103 may be affixed to the external surface of an individual lumen 17116. In other embodiments, an electrode 17103 may be placed inside of an individual lumen 17116 with an opening or fenestration provided in the individual lumen providing electrical contact between the electrode and tissue. In some embodiments, a distribution chamber or manifold is provided at the proximal end of the balloon 17101 to provide fluid communication between the plurality of individual balloon lumens 17116 and the catheter shaft fluid delivery lumen(s). In some embodiments, an individual lumen is in direct fluid communication with a catheter shaft fluid delivery lumen. In another embodiment, an individual balloon lumen is a continuation of a catheter shaft fluid delivery lumen.

Accessing the common hepatic artery with a therapeutic device and/or accessories can be difficult due to the geometry/tortuosity of the celiac artery. In a large percentage of humans, the celiac artery branches off the aorta in a downward direction (caudal). The angle of the takeoff can be quite abrupt, resulting in the celiac artery appearing to be parallel to the aorta. The celiac artery feeds the common hepatic artery and the splenic artery, which are typically located above (cranial of) the celiac artery/aortic junction. Therefore, in cases where a downward going celiac artery is present, the celiac artery is required to abruptly change direction from caudal to cranial as it rises superiorly toward the liver. The vessel accomplishes this by forming an acute bend of about 180 degrees, redirecting the blood superiorly and cranially toward the common hepatic artery/splenic artery bifurcation. The takeoff from the celiac artery to the common hepatic artery commonly also requires a change in vessel direction to the patient's right side to reach the liver. In cases in which the aorta is accessed from the femoral artery, the geometry and tortuosity can require multiple abrupt 'U-turns' and bends to be traversed to gain access to the therapeutic site along the common hepatic artery.

In accordance with several embodiments of inventions described herein, the anatomic challenges described above can be overcome and can provide procedural success when conventional therapeutic devices and access equipment may result in procedural failure because the conventional device or access tool is unable to traverse the celiac artery and advance into the common hepatic artery. For example, embodiments described herein include improvements that can be added to a therapeutic device (e.g., balloon catheter 400 or any other catheter or therapeutic device described herein) to enhance the ability of the therapeutic device to abruptly change direction and traverse a 'U-turn' or acute bend without losing guide catheter or guide sheath positioned in the ostium or body of the celiac artery. In accordance with several embodiments, systems and methods described are adapted to access the aorta from a radial artery. Access from the radial artery eliminates the first U-turn as the aorta is approached from a cranial direction above the celiac artery takeoff instead of from a caudal direction below the celiac artery takeoff as is the case when using a femoral artery approach.

Embodiments described herein may advantageously provide one or more of the following advantages or benefits: (i) enables an operator to traverse a patient's tortuous anatomy and provide therapy for chronic disease or acute disease crisis; (ii) enables an operator to traverse the patient's tortuous anatomy and provide intended therapy in a reduced (e.g., minimum) amount of time; enables an operator to traverse the patient's tortuous anatomy and provide intended therapy while reducing (e.g., minimizing) the use of additional devices and accessories, thereby reducing (e.g., minimizing) costs of the overall procedure; and (iv) enables the operator to traverse the patient's tortuous anatomy and provide an ability to visualize branches of distal anatomy when flow conditions prevent dye flowing from guide catheter or guide sheath to fill the intended vessel for visualization.

Figure 18A:
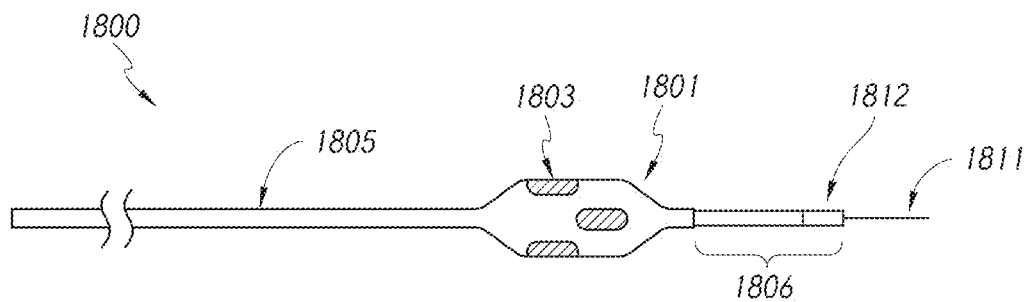
FIGS. 18A and 18B illustrate embodiments of a distal shaft extension segment, or unit, adapted to be coupled to a therapeutic device to facilitate access through tortuous vasculature.
Figure 18B:
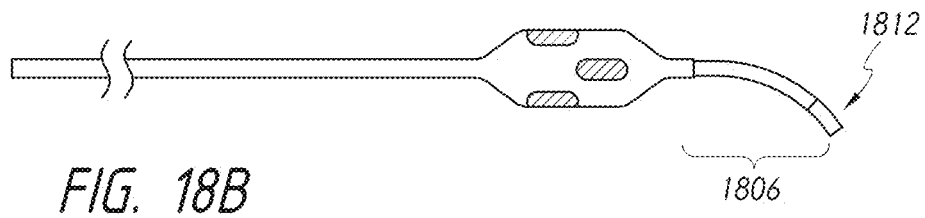

FIGS. 18A and 18B illustrate a distal portion of an embodiment of a therapeutic device 1800 that includes a distal shaft extension segment, or unit 1806. The illustrated therapeutic device 1800 is a balloon ablation catheter having a proximal elongate shaft 1805 and a balloon 1801 with a plurality of electrodes 1803 that is coupled to the proximal elongate shaft 1805. The shaft extension unit 1806 is positioned distal of a distal balloon waist of the balloon 1801. The shaft extension segment 1806 is adapted to gradually change the flexibility of the therapeutic device 1800 from distal to proximal, thereby enabling a smooth flexibility transition as the device 1800 traverses an abrupt turn (e.g., a 90 degree turn or even a U-turn, or 180 degree turn). In some embodiments, the therapeutic device 1800 is an over-the wire device adapted to be delivered over a guide wire 1811 and thus the guidewire 1811 extends through a guidewire lumen of the shaft extension unit 1806. In some embodiments, the therapeutic device 1800 is adapted to have a steerable distal end portion and may not be an over-the-wire device. In such embodiments, the shaft extension segment 1806 may not have a guidewire lumen.

In some embodiments, the distal shaft extension unit 1806 is constructed to be shapeable by the operator. For example, the shaft extension unit 1806 may comprise a slotted hypotube with shape memory material that would allow the operator to customize the desired shape to a patient's anatomy. In some embodiments, the distal shaft extension unit 1806 comprises a shape memory material and is pre-shaped to have a particular shape or geometry when in pre-shaped (e.g., unconstrained) condition. For example, the shape or configuration of the distal shaft extension segment 1806 may be pre-shaped to correspond to a particular known anatomical turn, thereby directing the therapeutic device through the anatomical turn. The pre-shaped condition, or configuration, may be changed by the guidewire 1811. For example, if the guidewire 1811 is within the distal shaft extension segment 1806, then the distal shaft extension segment 1806 may be straight or substantially straight (such as shown in FIG. 18A). If the guidewire is not within the distal shaft extension segment 1806, then the distal shaft extension segment 1806 may have the desired pre-shaped geometry (such as shown in FIG. 18B).

In some embodiments, a distal tip 1812 of the distal shaft extension segment 1806 is radiopaque. The radiopaque distal tip 1812 may be a metallic band or coil or structure made of platinum, platinum iridium alloy, gold, gold alloy or other material that is attached to a distal end of the distal shaft extension segment 1806. In some embodiments, the radiopaque distal tip 1812 is comprised of a polymer (e.g., Pebax®) that is blended with a radiopaque material such as tungsten and formed into a radiopaque band or segment attached to the distal shaft extension unit 1806. The distal tracking segment 406 discussed above may incorporate any of the features described herein with respect to the distal shaft extension segment 1806. The distal shaft extension segment 1806 may be incorporated in any of the balloon catheter embodiments described herein.

Figure 19A:
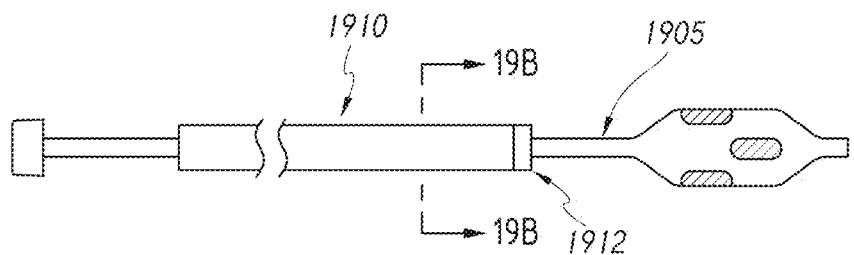
FIGS. 19A and 19B illustrate an embodiment of a moveable outer sheath adapted to be coupled to an elongate shaft of a therapeutic device to facilitate access through tortuous vasculature.

In accordance with several embodiments, a moveable outer shaft (e.g., captive support and fluid delivery shaft) is provided that may be coupled to an elongate shaft of a therapeutic device, such as the balloon catheter 400 or other ablation catheters or therapeutic devices described herein. FIG. 19A illustrates an embodiment of a moveable outer shaft 1910 coupled along an elongate shaft 1905 of a therapeutic device. The moveable outer shaft 1910 may be adapted to be moved distally and/or proximally along the elongate shaft 1905 of the therapeutic device. As the moveable outer shaft 1910 is moved, the flexibility of the therapeutic device changes and/or the ability of the device to transmit a push force to a distal segment or end portion of the device (e.g., the portion with the balloon or other treatment member). For example, as the moveable outer shaft 1910 is moved toward the distal end of the therapeutic device, the flexibility of the distal segment decreases and/or the push capability of the device increases.

Figure 19B:
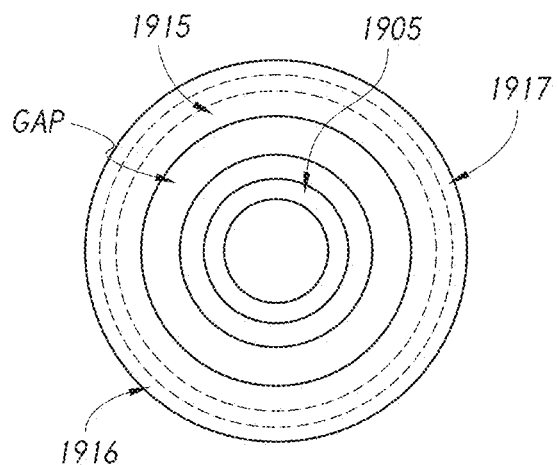

The moveable outer shaft 1910 may be constructed in a manner such that it is kink resistant. In some embodiments, the outer shaft 1910 includes multiple layers of polymer tubes and polymer and/or metallic braids and coils to form a composite tube. FIG. 19B is a cross-section view that illustrates the layers of the moveable outer shaft 1910 surrounding a space (labeled GAP) between the elongate shaft 1905 and the moveable outer shaft 1910. The moveable outer shaft 1910 may include an inner lubricious layer 1915 comprised of a material such as polytetrafluoroethylene (PTFE), fluorinated ethylene propylene (FEP), or high-density polyethylene (HDPE). The moveable outer shaft 1910 may also include a kink-resistant middle layer 1916 comprised of stainless steel, nitinol, tungsten, Kevlar, liquid crystal polymer, and/or the like. An outer layer 1917 of the moveable outer shaft 1910 may comprise, for example, Pebax®, polyimide, nylon, polyester, and/or the like. In some embodiments, the moveable outer shaft 1910 only includes two composite layers (e.g., a kink-resistant layer and an outer layer without the inner lubricious layer) or consists of a single non-composite layer.

In several embodiments, at least a distal tip or segment 1912 of the moveable outer shaft 1910 is radiopaque. The radiopaque distal tip 1912 may be a metallic band or coil or structure made of platinum, platinum iridium alloy, gold, gold alloy or other material that is attached to a distal end of the moveable outer shaft 1910. In some embodiments, the radiopaque distal tip 1912 is comprised of a polymer (e.g., Pebax®) that is blended with a radiopaque material such as tungsten and formed into a radiopaque band or segment attached to the moveable outer shaft 1910. The moveable outer shaft 1910 may be shapeable or deflectable using a pull-wire construction or by changing the pitch of a coil construction by torqueing the coil. In some embodiments, the moveable outer shaft is pre-shaped by heat setting a polymer composite construction or by incorporating metallic structures that are shape set by heat.

In accordance with several embodiments, the moveable outer shaft 1910 may advantageously be utilized to provide fluid communication from outside of the body to a distal end of the moveable outer shaft and/or to a lumen of the therapeutic device. For example, the moveable outer shaft 1910 can be attached to an end of a hypotube that enables fluid communication to a shaft lumen. In some embodiments, a fluid communication port is attached in a concentric fashion to the shaft lumen utilizing a mobile adjustable valve (such as a Tuohy-Borst valve or adapter).

In some embodiments, the moveable outer shaft 1910 incorporates an expandable structure such as a balloon so that it can anchor the therapeutic device to the artery and/or guide catheter or guide sheath while still enabling the distal tip of the therapeutic device to be advanced further into the vasculature. The expandable structure could form a fluid communication pathway from the internal diameter of the guide catheter or guide sheath to the internal diameter of the moveable outer sheath structure. In some embodiments, the moveable outer shaft 1910 is coupled to or integral with a sleeve or sheath (e.g., sleeve 414, 1314) that is adapted to be removed from covering electrodes on a balloon prior to expansion or inflation of the balloon (e.g., balloon 401).

Figure 20A:
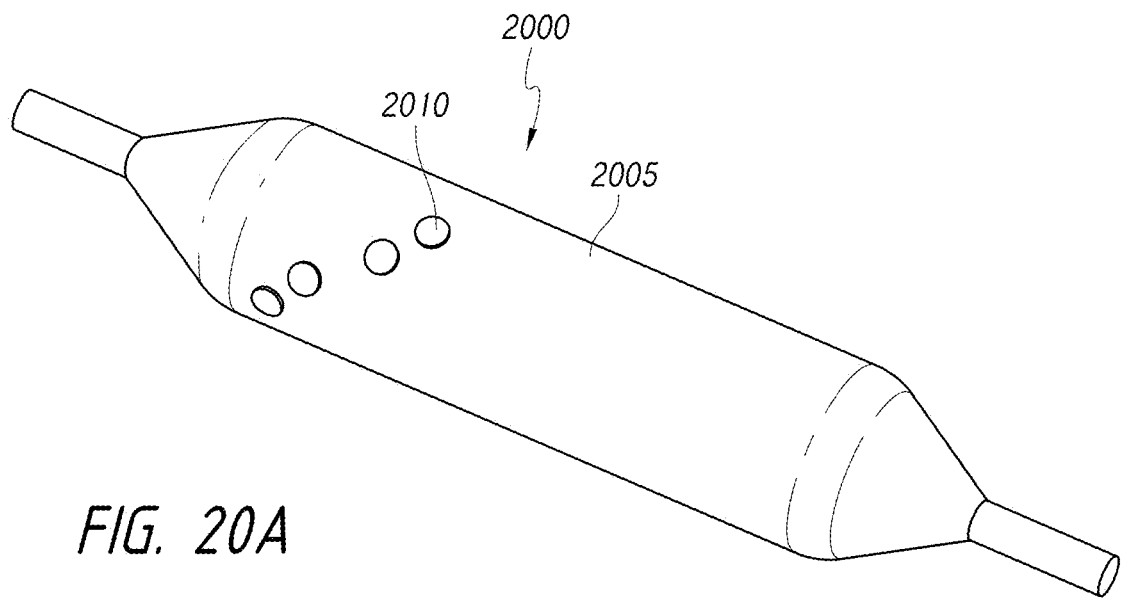
FIGS. 20A-20E, 21, and 22A-22C illustrate various embodiments of balloon ablation devices.

FIG. 20A illustrates a schematic representation of an embodiment of a radiofrequency energy delivery device 2000 comprising a balloon 2005. The balloon 2005 is adapted to be partially or substantially occlusive and comprises multiple electrodes 2010 positioned at one or more locations along the outer surface of the balloon 2005. The balloon 2005 may be sized to cover the entire length of the vessel (e.g., common hepatic artery) to be treated (e.g., ablated or denervated) or may be shorter in order to treat a portion of the vessel. In one embodiment, the balloon 2005 is 5 mm in diameter by 20 mm long; however other balloons may range from 3 mm to 8 mm (e.g., 3 mm, 3.5 mm, 4 mm, 4.5 mm, 5 mm, 5.5 mm, 6 mm, 6.5 mm, 7 mm, 7.5 mm, 8 mm) in diameter and from 10 mm to 40 mm (e.g., from 10 mm to 20 mm, from 15 mm to 25 mm, from 20 mm to 30 mm, from 25 mm to 35 mm, from 30 mm to 40 mm) in length as desired or required based on vessel length. The electrodes 2010 may be comprised of a single electrode element or member or may be comprised of one or more arrays of a plurality of separate electrode elements (e.g., clusters or groups of four electrodes). For example, at least one array of electrode elements may be proximate an area of tissue in thermal communication such that RF power delivered via the electrodes 2010 acts to heat a substantially continuous volume of tissue. If generally circular, the electrodes 2010 may be from 0.5 mm to 3 mm in diameter (e.g., from 0.5 mm to 1 mm, from 1 mm to 1.5 mm, from 1.5 mm to 2 mm, from 2 mm to 2.5 mm, from 2.5 mm to 3 mm, overlapping ranges thereof, or any value of or within the recited ranges). The at least one array of electrodes may be linear, zig zag, curved, rectangular, polygonal, or circular. Other shapes and patterns may also be used as desired or required. The individual electrodes 2010 comprising the array may be from 0.1 mm to 2 mm (e.g., from 0.1 mm to 0.5 mm, from 0.3 mm to 1 mm, from 0.5 mm to 1.5 mm, from 0.8 mm to 2 mm, overlapping ranges thereof, or any value of or within the recited ranges) in their narrowest aspect and from 0.5 mm to 10 mm (e.g., from 0.5 mm to 2.5 mm, from 2 mm to 4 mm, from 3 mm to 5 mm from 0.5 mm to 5 mm, from 3 mm to 6 mm, from 4 mm to 8 mm, from 5 mm to 10 mm, overlapping ranges thereof, or any value of or within the recited ranges) in their longest aspect. In some embodiments the longest aspect of the electrode elements may be from 5 mm to 20 mm. In some embodiments, 0.5 W-3 W (e.g., 0.5 W, 1 W, 1.5 W, 2 W, 2.5 W, 3 W) of RF power may be delivered though the electrode or electrodes. The electrode surface area (of either individual electrodes or pairs or arrays of electrodes activated to function as a single electrode) may range from 1 $mm^2$ to 20 $mm^2$ (e.g., from 1 $mm^2$ to 3 $mm^2$, from 2 $mm^2$ to 4 $mm^2$, from 3 $mm^2$ to 6 $mm^2$, from 3 $mm^2$ to 9 $mm^2$, from 2 $mm^2$ to 10 $mm^2$, from 8 $mm^2$ to 16 $mm^2$, from 10 $mm^2$ to 20 $mm^2$, overlapping ranges thereof, or any value of or within the recited ranges).

Figure 20B:
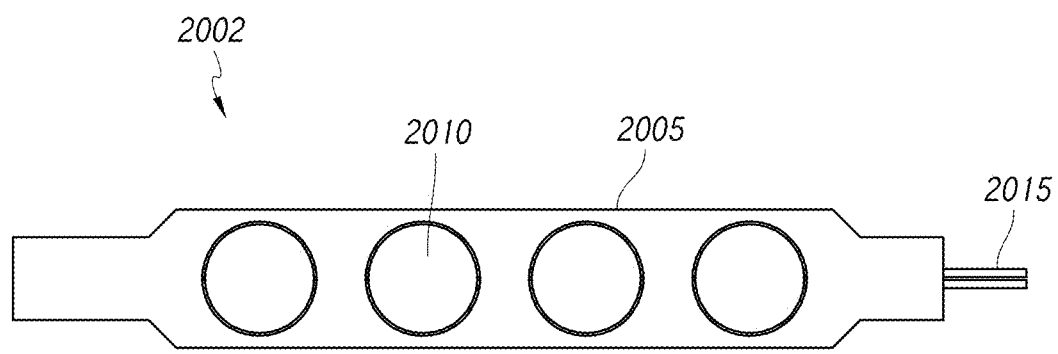
Figure 20C:
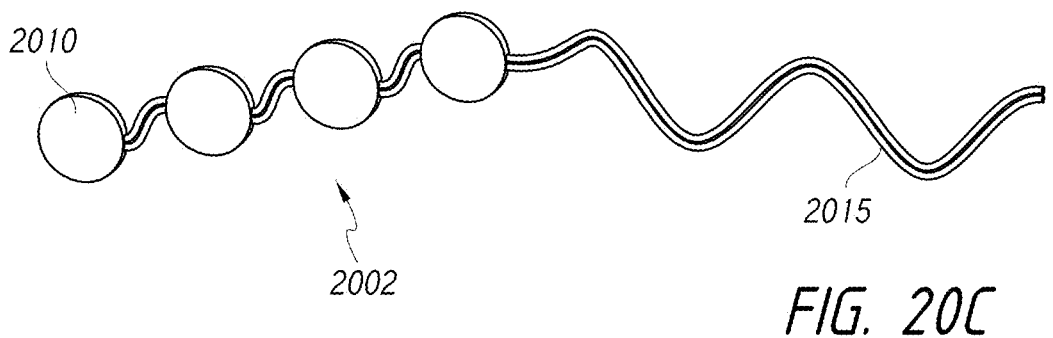

In various embodiments, electrodes or arrays of electrodes may be affixed to the balloon 2005 along with one or more connecting wires 2015. Two embodiments of electrode arrays with connecting wires are illustrated in FIGS. 20B and 20C. In accordance with various embodiments, the connecting wires 2015 supply RF current to the electrode(s) 2010. In some embodiments, the connecting wires 2015 carry a signal for measuring the temperature. In some embodiments, the connecting wires 2015 carry both RF current for ablation or other treatment and signals to measure temperature. In some embodiments, the connecting wires 2015 form a thermocouple (e.g. bifilar thermocouple). The balloon 2005 may consist of two, three, four, five, six or more than six electrode arrays. Each array may consist of two, three, four, five, six, seven, eight or more than eight electrodes.

Figures 1, 20D:
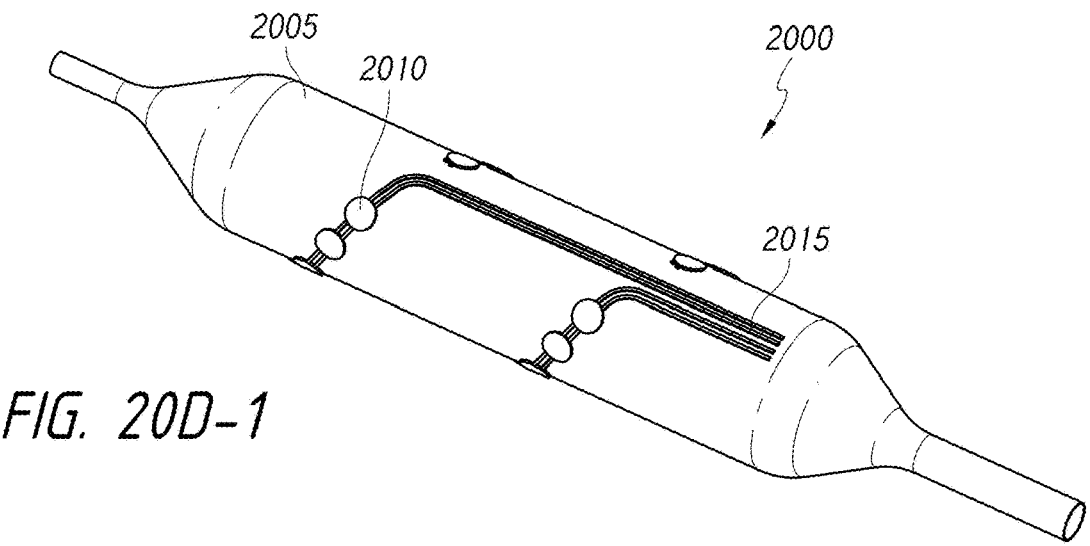
Figures 2, 20D:
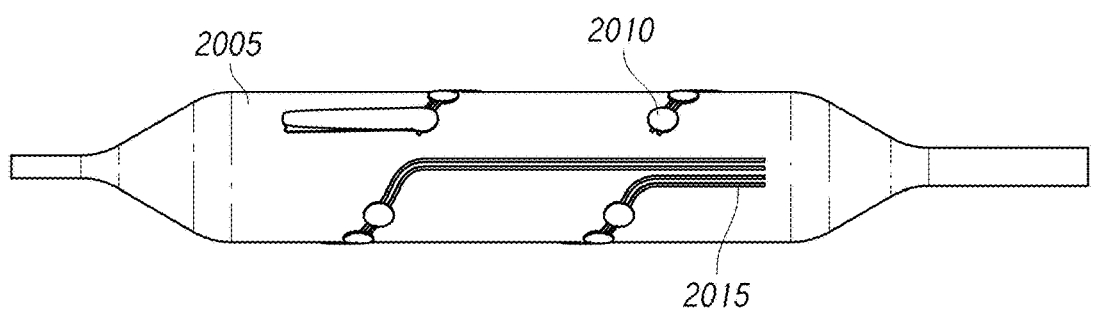

In some embodiments, the electrodes 2010 together with their one or more connecting wires 2015 are affixed to the balloon with adhesives such as epoxy, cyanoacrylate, silicone, acrylic, polyamide, polyurethane, pressure sensitive adhesive, and hot melt adhesives. In one embodiment, the entire balloon and electrode assembly, except for active electrode areas, may be encapsulated in a coating. In another embodiment, the coating covers only portions of the balloon and electrode assembly. FIG. 20B illustrates an embodiment of an electrode array 2002 comprising an adhesive body 2020 that is adapted to be adhered to the balloon 2005. In other embodiments, the electrodes may be attached directly to the balloon 2005. FIG. 20C illustrates an electrode array having a zig-zag arrangement with the connecting wires 2015 coupled between each individual electrode. The zig-zag arrangement may advantageously reduce the spacing between the electrodes and reduce the overall size or array occupied by the electrode array while maintaining a generally spiral pattern. In some embodiments, the electrodes of the electrode array are affixed to a flexible substrate. In some embodiments, the electrodes, connecting wires and flexible substrate together comprise a flex circuit. FIG. 20D illustrates an embodiment of a balloon catheter 2000 having a plurality of electrode arrays 2002 comprising electrodes 2010 and connecting wires 2015 arranged in a spiral pattern around the outer surface of the balloon 2005. The connecting wires 2015 may be coupled to a source of RF power or energy (such as a generator). Each electrode array or group of electrodes may have separate connecting wires such that each electrode array or group is individually controllable by an RF power source.

In accordance with several embodiments, a balloon of a balloon electrode catheter includes at least one group of diagonally or circumferentially oriented electrodes formed of a plurality of electrode elements connected in parallel, where the size of the electrode group in its longest aspect is less than or equal to a characteristic length of thermal conduction or diffusion in tissue. Larger lesions require more power, therefore greater electrode surface area is required to keep current density within acceptable levels (for example, >3 mm$^2$). However, large electrodes (for example, >1.5 mm in a largest aspect) degrade flexibility, trackability and foldability of balloons. Circumferential or diagonal orientation of electrodes may further interfere with balloon folding; however, the electrodes may be positioned so as to be arranged around folds. In accordance with several embodiments, closely-spaced electrode arrays as illustrated and described in connection with FIGS. 20A-20O create locally inhomogeneous current density near the electrodes (e.g., near field) and current density evens out at farther distances from the electrode (e.g., far field). In addition, thermal conduction within the tissue tends to even out temperature within the near field. When electrodes are closely spaced and the length of the electrode is not too long, current density distribution over the electrode surface is predictable and a single temperature measurement can represent the temperature of the entire electrode. For example, temperature may still vary, but in a predictable fashion. In accordance with several embodiments, "closely-spaced" means that the total electrode area is in a region that is no more than 6 mm-8 mm in its longest aspect.

Figure 20E:
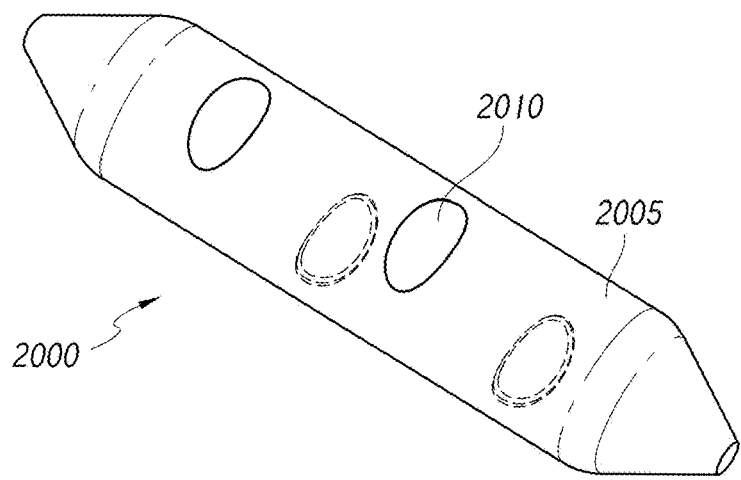

FIG. 20E illustrates an embodiment of a balloon 2005 of a balloon catheter 2000 comprising four individual electrode members offset by 180 degrees from each other and spaced apart longitudinally along the surface of the balloon 2005 so as to provide a desired ablation or treatment pattern designed to provide increased perivascular treatment while reducing vessel wall injury or damage. In some embodiments, the electrodes 2005 exhibit a circumferential aspect ratio. In some embodiments, the array of electrodes is oriented in a diagonal direction with respect to the axis of the artery or other body lumen, thereby increasing the circumferential extent of the lesion while avoiding interference between the electrodes 2010 when the balloon 2005 is in a collapsed, deflated configuration. Greater frequency and extent of ablated tissue increases the degree of neuromodulation or other tissue modulation (e.g., ablation, denervation). The degree of circumferential orientation to the electrode of an electrode array is reflected by the shape of the lesion created by the heating generated by the electrode. Staggered, oblique lesions can advantageously be packed tightly (for example, spaced apart by between 2 mm and 8 mm, e.g., 2 mm, 3 mm, 4 mm, 5 mm, 6 mm, 7 mm, 8 mm) along the vessel to increase the circumferential coverage of the lesion without overlapping lesions.

The electrodes of the balloon catheters (e.g., balloon catheters 400, 2000) may be circular, rectangular or oblong. In some embodiments, the electrodes may be disk shaped. In one embodiment, the electrodes may be comprised of metals selected from a list including, without limitation, gold, platinum, stainless steel, layered composites of gold or platinum, gold or platinum plated base metals such as copper, stainless steel, nickel. In some embodiments, the connecting wires 2015 are continuous with the electrode(s) 2010. In other embodiments, the connecting wires 2015 may be attached to the electrode(s) 2010 by means such as welding, soldering, crimping, or swaging.

In some embodiments, the balloon material is of a low compliance material selected from a list of materials comprising, without limitation: PET, polyester, polyolefin, nylon, high durometer polyurethane and polyether block amide. In some embodiments, the balloon material is comprised of a compliant material such as low durometer polyurethane, kraton, latex, silicone, and/or thermoplastic elastomer.

Balloon ablation catheter systems may be advantageous for denervating nerves surrounding (e.g., within a wall of, such as within the intima, media or adventitia of) the hepatic artery branches in that the hepatic artery branches (e.g., common hepatic artery) can be occluded by one or more balloons and then coolant can be circulated in the region of the ablation (e.g., through a lumen of a balloon). In various embodiments, balloon ablation catheters advantageously facilitate both higher power net energy through larger electrode surface area (enabled, for example, by large electrode sizes that can be included on a balloon) and increased deposition time (which may be permitted by the ability to occlude flow to the hepatic artery for longer periods of time). In some embodiments, the risk of damage to the endothelial wall is mitigated by the flow of coolant even with an increase in energy density through higher power. Accordingly, higher power energy delivery (e.g., about 40 to 50% higher power) may be used than denervation systems used for denervation of other vessels or organs without risk of damage to the endothelial region of the hepatic artery due to maintained less than hyperthermic temperatures up to 1 mm from the lumen of the hepatic artery.

In some embodiments, an actively-cooled balloon catheter is used to ablate target vasculature. A pump sufficient to deliver high flow coolant to the cooling element may be used to facilitate the active cooling. In several embodiments, the range of drive pressures to deliver an appropriate flow rate (e.g., between about 100 and 500 mL/min) of coolant into a 4 to 6 Fr balloon catheter to maintain an appropriate temperature is between about 25 and about 150 psi. The flow rate may be adjusted on the basis of the actual temperature inside the balloon. In some embodiments, the desired coolant temperature in the balloon is between about 5° C. and about 10° C. In some embodiments, temperature-measurement devices (e.g., thermocouples) are included inside the balloon to constantly monitor the coolant temperature. The pump output may be increased or decreased based on the difference between the desired temperature and the actual temperature of the coolant.

Figure 21:
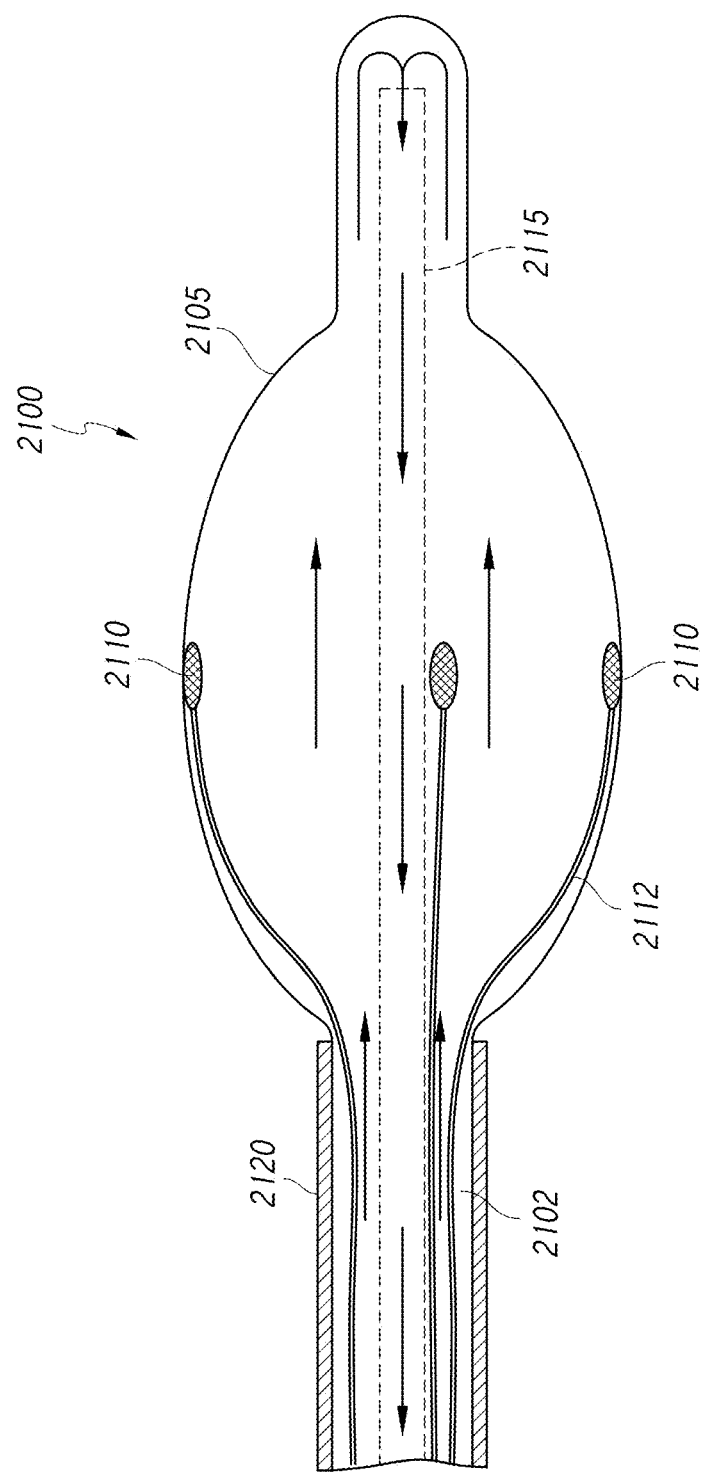

FIG. 21 illustrates an embodiment of an actively-cooled balloon catheter 2100. The balloon catheter comprises a main shaft 2102 having a lumen, a balloon 2105 coupled to a distal end of the main shaft 2102 and in fluid communication with the lumen, a plurality of electrodes 2110 disposed around the circumference of the balloon 2105, electrode leads 2112 coupled to the electrodes 2110 and extending to a proximal end of the main shaft 2102, and an outlet tube 2115. Nonconductive coolant solution may be pumped into an inlet of the balloon 2105 by a pump (not shown) and the nonconductive coolant solution may exit the balloon 2105 through the outlet tube 2115. The main shaft 2102 may comprise an insulating sheath or cover 2120 to prevent or inhibit heat transfer. The nonconductive coolant solution may advantageously provide cooling to the electrodes 2110 on the balloon 2105, while also shielding adjacent tissues from RF energy. Any of the structural and functional features of the balloon catheter 2100 may be incorporated into the other balloon catheters or ablation devices described herein.

Figures 22A, 22B, 22C:
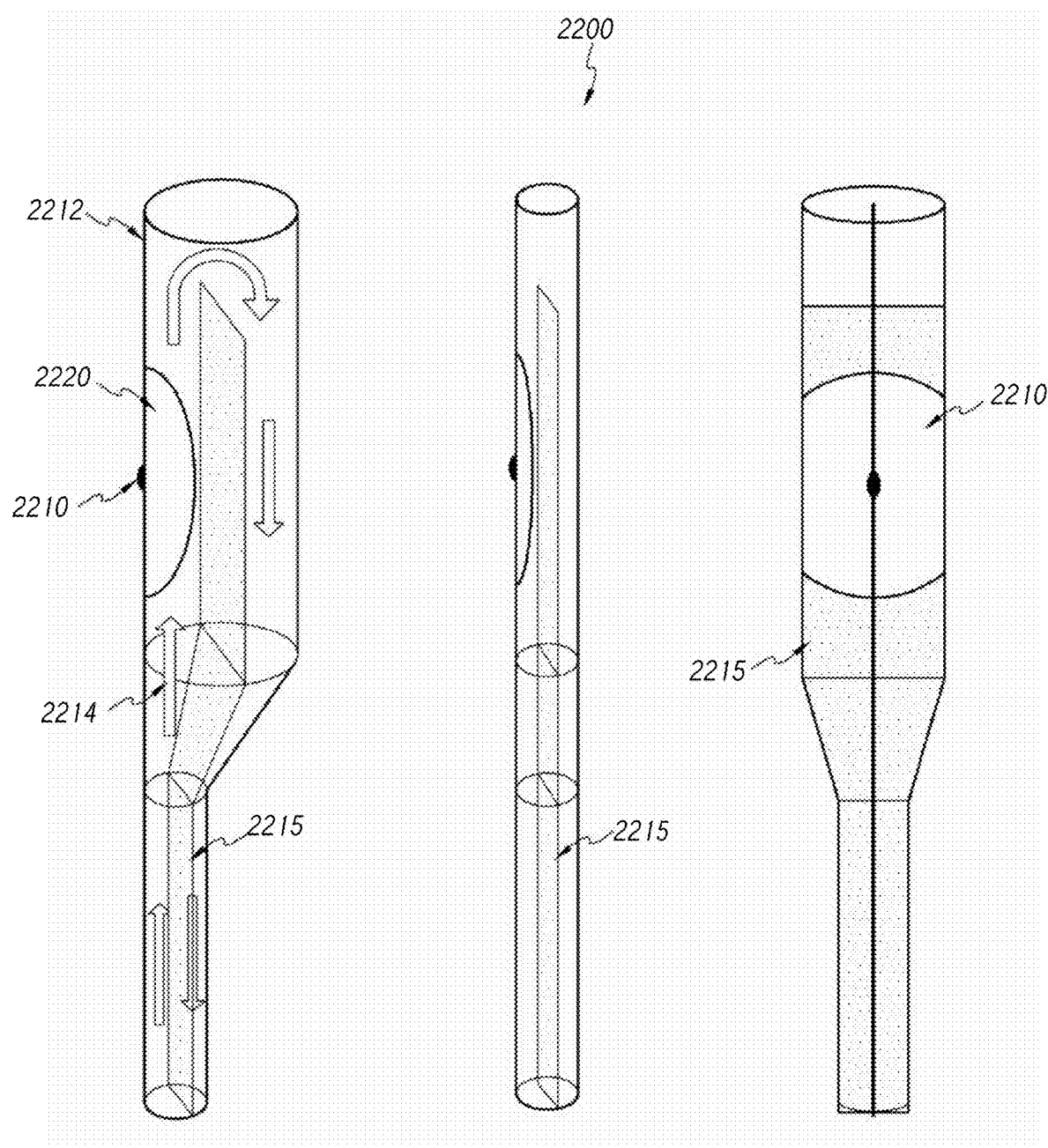

FIGS. 22A-22C illustrate a distal end portion of another embodiment of a balloon catheter 2200 configured to provide cooling to an electrode 2210 of the balloon catheter 2200. In the illustrated embodiment, the balloon catheter 2200 is a tube comprising a balloon 2212 that expands when infused with coolant, pulling taut an internal diaphragm 2215 which directs the flow 2214 (illustrated by arrows) of the coolant from at least one inlet to at least one outlet. A circular surface centered on the electrode 2210 may comprise a heat conducting surface 2220, while the rest of the catheter 2200 may comprise a heat-insulating material configured to prevent or inhibit warming of the coolant 2214 while traveling to a target ablation area. When the cooling balloon 2212 is infused with coolant, the balloon 2212 expands, thereby pressing the electrode 2210 and the cooling balloon 2212 against the vessel wall. In one embodiment, the coolant cools the vessel wall at the target ablation area, thereby preventing against or reducing the likelihood of excessive vessel wall damage. Any of the structural and functional features of the balloon catheter 2200 may be incorporated into the other balloon catheters or ablation devices described herein.

Figure 23:
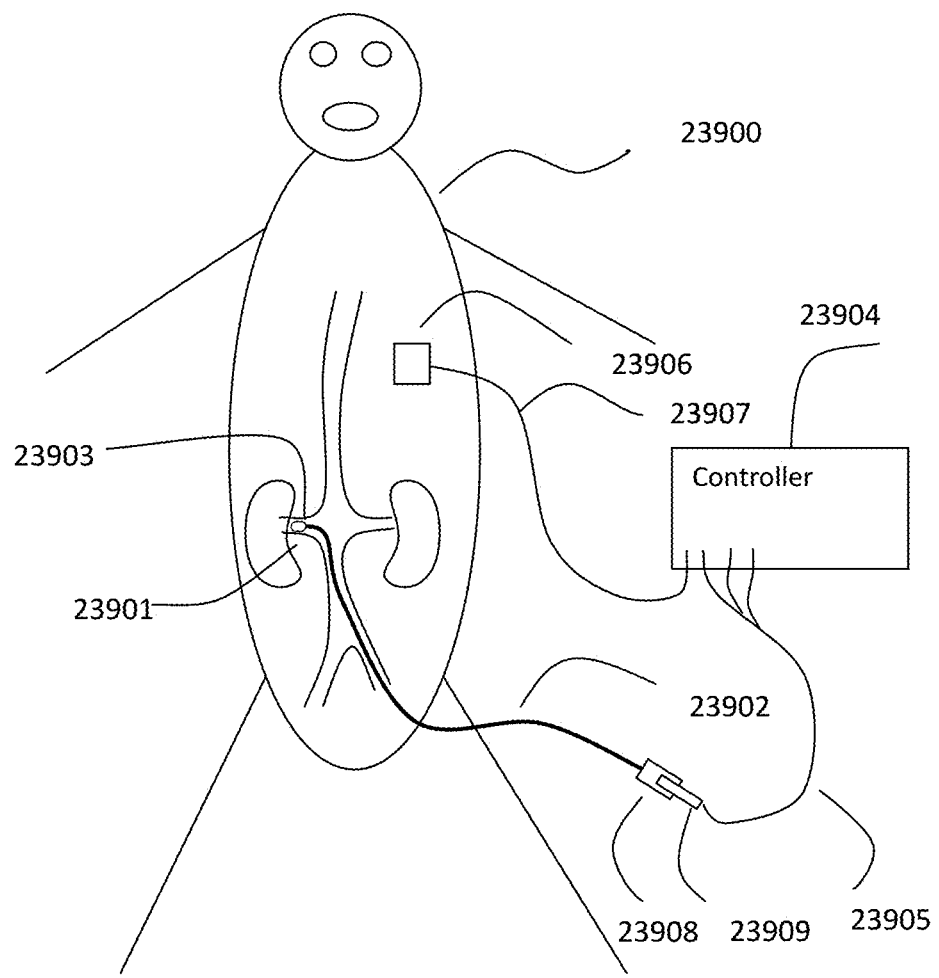
FIG. 23 is a schematic view illustrating an embodiment of a system for delivering ablation energy into a human body.

As illustrated in FIG. 23, the disclosure provides methods and systems to treat a patient 23900 by modulating (e.g., ablating) tissue adjacent to a vessel lumen 23901. The illustrated embodiment of a treatment system comprises an ablation catheter 23902 carrying one or more electrodes 23903 at its distal end to ablate tissue by passing radiofrequency energy into the tissue. The ablation catheter 23902 comprises an elongated catheter shaft having a proximal end and a distal end. A first electrode 23903 may be positioned at or near the distal end of the elongated catheter shaft and configured to transmit radiofrequency energy into tissue adjacent to the vessel lumen 23901. The first electrode 23903 may comprise a substantially enclosed hollow space adapted to be filled with fluid (e.g., liquid or gas). The treatment system further comprises a controller 23904 (e.g., RF generator having one or more processing devices) configured to regulate power delivery to the ablation catheter 23902, a first cable 23905 configured to transmit power from the controller 23904 to the ablation catheter 23902, a second electrode 23906 configured to be placed in electrical contact with the patient 23900, and a second cable 23907 configured to transmit power from the second electrode 23906 to the controller 23904 when in use.

In some embodiments, the system includes connectors 26908 and 23909 to couple the cable(s) 23905 to the ablation catheter 23902. In some embodiments of the system, the second electrode 23906 may be located along and mounted on the shaft of the ablation catheter 23902 proximal or distal to the first electrode 23903. In this case, the first cable 23905 and second cable 23907 may be combined into a single cable. Although illustrated within a renal vessel, the ablation catheter 23902 may be adapted to be delivered to and positioned within a vessel associated with the liver, pancreas, spleen, small intestine, cardiac structure (such as left or right ventricle, left or right atrium, atrial appendage, pulmonary veins, pulmonary arteries, valvular annulus or cardiac septum) and/or other organ or tissue (such as the common hepatic artery, gastroduodenal artery, superior mesenteric artery, splenic artery, or a branch of the celiac artery).

Figure 24:
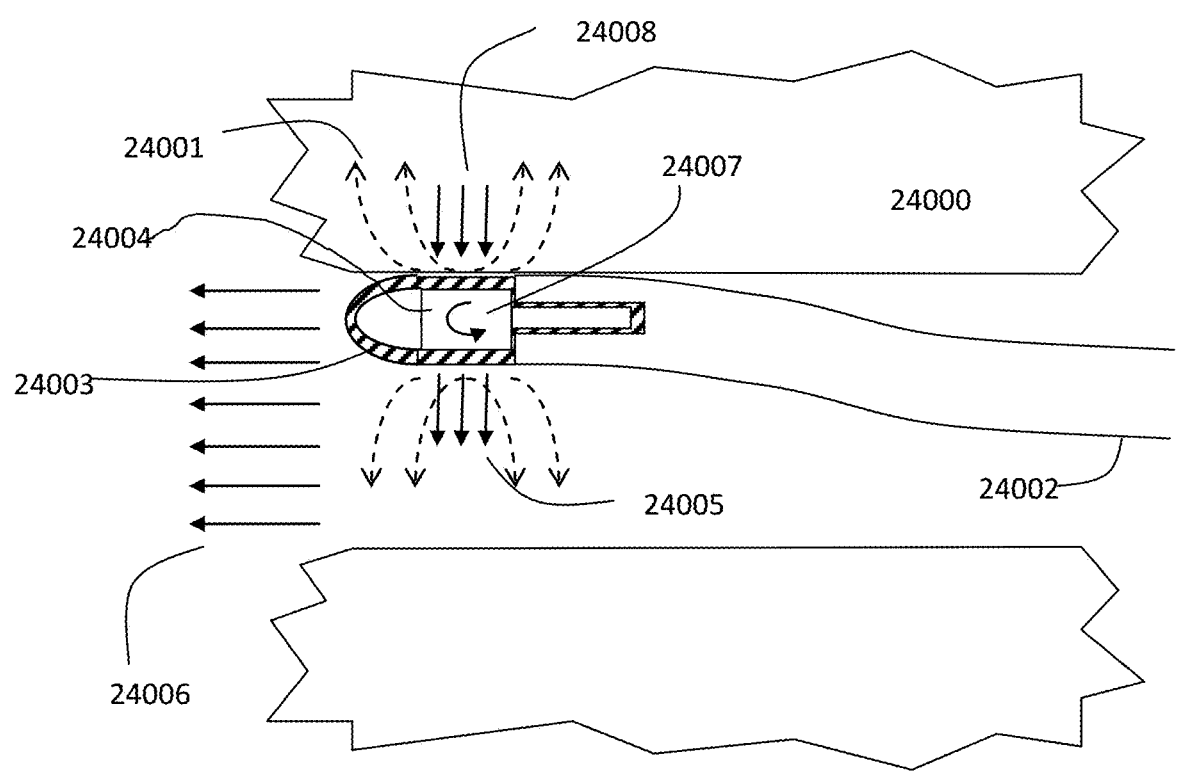
FIG. 24 is a schematic view of a distal end of an embodiment of an ablation catheter depicting mass and heat transfer at an ablation site.

In various embodiments, a means of facilitating heat transfer from the tissue to the blood stream and of reducing of the electrode's internal temperature is achieved through internal cooling. In some embodiments, radiofrequency energy delivery devices (e.g., RF ablation catheters) comprise multiple electrodes, with each electrode having a hollow cavity adapted to be filled with fluid to facilitate cooling (e.g., convective cooling). In an embodiment shown in FIG. 24, an ablation catheter 24002 configured to be navigated for insertion into a body space, such as a blood vessel, may comprise an elongated shaft having a proximal end and a distal end. An electrode 24003 positioned near the distal end of the elongated shaft may be configured to transmit radiofrequency energy 24001 into a vessel wall 24000. A substantially enclosed space 24004 within the electrode 24003 is configured to be filled with fluid to facilitate heat transfer from the vessel wall into the blood stream. In another embodiment, the heat is transferred to other, cooler tissue regions. In one embodiment, an extension of the substantially enclosed space 24004 may provide for increased area to further facilitate cooling. The substantially enclosed space 24004 may comprise a hollow cavity within the electrode 24003.

The cold surfaces (i.e. surfaces in contact with flowing blood) of the electrode 24003 may be configured to be larger than and remote from the hot surfaces (i.e. electrically conducting surfaces in contact with tissue) of the electrode 24003. The cold surfaces and the hot surfaces may generally be radially opposed surfaces of the electrode 24003. The cold surfaces may also be displaced axially along the catheter 24002 to provide greater surface area along the blood environment 24006. The substantially enclosed space 24004 may be prefilled with fluid during manufacture or filled by a clinical professional during use. The fluid within the substantially enclosed space 24004 may be configured to contact both the hot surfaces and the cold surfaces to allow the fluid to circulate (as shown by circulation arrow 24007) between the hot surfaces and the cold surfaces, thereby providing convective heat transfer through the electrode 24003.

In use, the ablation catheter 24002 may be advanced into a vessel (e.g., hepatic artery or other branch of the celiac artery) with an electrode 24003 positioned adjacent to targeted tissue 24000 to be ablated or otherwise modulated. Radiofrequency energy 24001 may be transmitted through the electrode 24003 and dissipated in the tissue 24000 adjacent to the electrode 24003. The tissue 24000 may then be subjected to an increased current density and experience an increase in heating. A portion of that heat 24008 that is generated in the tissue 24000 may then be thermally conducted back into the electrode 24003. The heat 24008 conducts through the hot surfaces of the electrode 24003. Heat 24008 is transferred from the electrode wall to the internal fluid within the space 24004 by convection. The fluid within the substantially enclosed space 24004 provides convective heat transfer by circulating within the substantially enclosed space 24004, thereby carrying heat from the hot surfaces to the cold surfaces. In turn, the fluid transfers heat to the cold surfaces. The resultant heat 24005 is then transferred across the cold surfaces through conduction and, ultimately, transferred into the blood 24006 through convection. Any of the structural and functional features of the ablation catheter 24002 (e.g., fluid-filled electrodes) may be incorporated into the other balloon catheters or ablation devices described herein.

Figure 25:
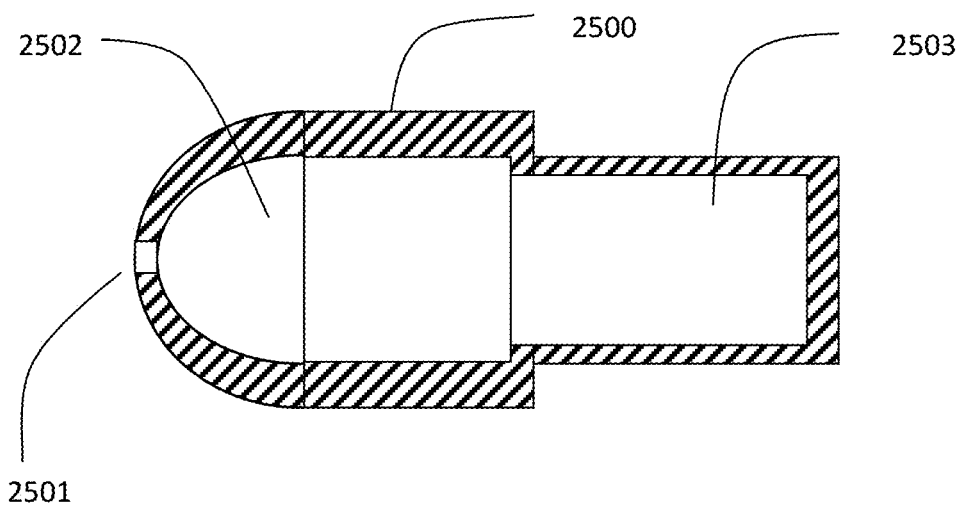
FIG. 25 is a schematic representation of an embodiment of a thermal element with a substantially enclosed fluid space.

FIG. 25 illustrates aspects of an electrode configuration, in accordance with an embodiment of the invention. For example, the wall of the electrode 2500 is configured to be thin and the fluid chamber is configured to be large. In some embodiments, the wall thickness of the electrode 2500 is less than 0.020 inches thick (e.g., less than 0.020 inches thick, less than 0.015 inches thick, less than 0.010 inches thick, 0.001-0.002 inches thick, 0.005-0.010 inches thick, 0.010-0.020 inches thick, 0.015 inches to 0.020 inches thick, overlapping ranges thereof, or any value within the recited ranges). In some embodiments, at least some portions of the wall may be greater than 0.020 inches thick. The diameter of the electrode 2500 may be in the range of 1-2 mm. In some embodiments, the diameter is between 2-4 mm. In other embodiments, the diameter is greater than 4 mm. The material of the electrode 2500 may be selected to provide high thermal and electrical conductivity, biocompatibility and corrosion resistance. Suitable materials include, but are not limited to: platinum, platinum-iridium alloys, gold, stainless steel, cobalt alloys, Inconel, MP35N, Elgiloy, palladium and/or other metals and alloys. The external surfaces of the electrode 2500 may be highly polished to reduce protein fouling. The internal surfaces may be smooth or textured in order to increase heat transfer.

In some embodiments, the electrode 2500 comprises a filler hole 2501 through which fluid may be introduced into the substantially enclosed space 2502. In some embodiments, the space, or cavity, is prefilled and the filler hole 2501 is then sealed. In some embodiments, a small filler tube or nozzle is provided for filling the substantially enclosed space 2502 at the point of use. The filler hole 2501 may be left open, provided it is small enough to prevent substantial loss of the fluid or mixing of blood with the fluid. In some embodiments, there is a second hole to allow gas to escape during the filling process. In some implementations, the fluid is introduced under vacuum to facilitate complete filling. In some implementations, filling may be accomplished through channels or spaces within the catheter shaft.

Figure 26:
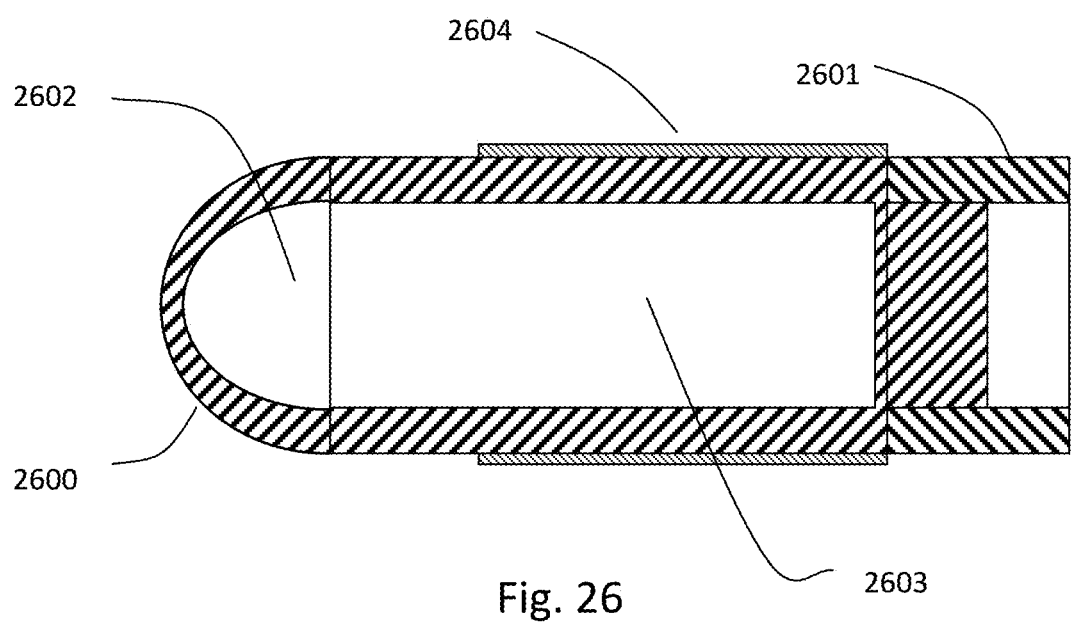
FIG. 26 is a schematic representation of an embodiment of a thermal element having an extended substantially enclosed fluid space, part of which is covered with an electrically insulating material.

In some embodiments, the substantially enclosed space 2502 corresponds to the length of the electrode 2500. In some embodiments, the substantially enclosed space 2502 includes an extension 2503 beyond the electrically conductive portion of the electrode 2500 configured to provide increased cold surface area to facilitate cooling. FIG. 26 illustrates an example of an electrode 2600 mounted on a distal end portion of an ablation catheter shaft 2601. The electrode 2600 has a substantially enclosed space 2602 and an extension 2603. The substantially enclosed space 2602 may be electrically insulated from the body by insulation 2604 to reduce or eliminate heating of the extension 2603 proximate to the heated tissue. This provides additional cold surface area for increased heat transfer to the blood.

The fluid within the electrode may be any suitable fluid. The fluid may be selected according to viscosity, heat capacity, thermal stability, lack of corrosiveness, sterilization compatibility and biocompatibility. In various embodiments, the fluid's viscosity is less than 100 cP. In some embodiments, the fluid's viscosity is less than 10 cP. In some embodiments, the fluid's viscosity is less than 2 cP. The fluid's heat capacity may be greater than about 4 J/gm. In some embodiments, the fluid's heat capacity may be greater than about 1 J/gm. The fluid may be thermally stable, sterilizable, non-corrosive and/or nontoxic. Examples of suitable fluids include, but are not limited to, water, saline, alcohol, dimethyl sulfoxide, and glycerol. Mixtures of fluids may be used. Dispersions of particles or other fluids may be used to further increase heat transfer. Examples of particles include colloidal silver, oils, salts, sugars, and/or the like.

In various embodiments, the motion of the fluid may be passive (e.g., free convection). In order to provide convective heat transfer, the fluid flows across the hot and cold surfaces. Free convection occurs due to thermal expansion of the fluid. Under the influence of gravity, the hot, less dense fluid tends to rise while the cold denser material tends to fall. This may advantageously cause circulation patterns to develop by free convection without requiring an active circulation mechanism. Any of the structural and functional features of the electrodes 2500, 2600 may be incorporated into the electrodes of the other balloon catheters or ablation devices described herein.

Figure 27:
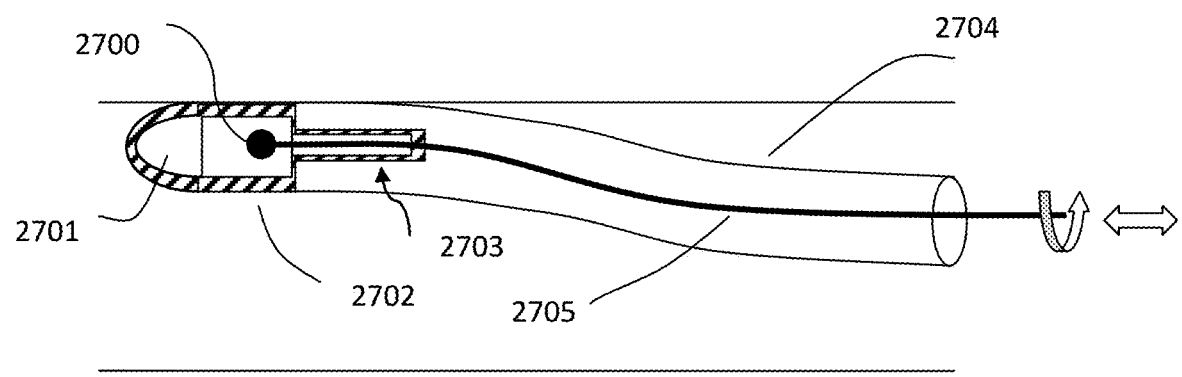
FIG. 27 is a schematic view illustrating an embodiment of an agitator located within a thermal element.

In some embodiments, the motion of the fluid is forced though the use of means such as a mechanical stirring element, or agitator 2700. FIG. 27 details an embodiment of an ablation catheter that includes an agitator 2700 positioned within a substantially enclosed space 2701 to facilitate convective heat transfer within the electrode 2702 beyond what is provided by free convection alone. The agitator 2700 may be configured to provide high velocity gradients at the interior surfaces, thereby increasing the convection coefficient and increasing fluid circulation within the electrode 2702 between the hot surfaces and the cold surfaces. The circulation pattern may be generally rotational along the axis of the electrode 2702. In some embodiments, the interior surface of the electrode 2702 or the agitator 2700 may be shaped in a way that provides a component of circulation in an axial direction. There may include an extension 2703 of the substantially enclosed space 2701 to provide larger surfaces for heat transfer.

In various embodiments, the agitator 2700 is an isolated stirrer configured to move relative to the substantially enclosed space 2701. The agitator 2700 may have fins, vanes or grooves or other texture features to increase fluid velocity. There may be an extended or remote reservoir or extension 2703 of the fluid space to provide larger surfaces for heat transfer. The agitator 2700 may be generally spherical or ball shaped. In some implementations, the agitator 2700 may be elongate. Any of the structural and functional features of the ablation catheter of FIG. 27 (e.g., agitator 2700) may be incorporated into the other balloon catheters or ablation devices described herein.

Figure 28:
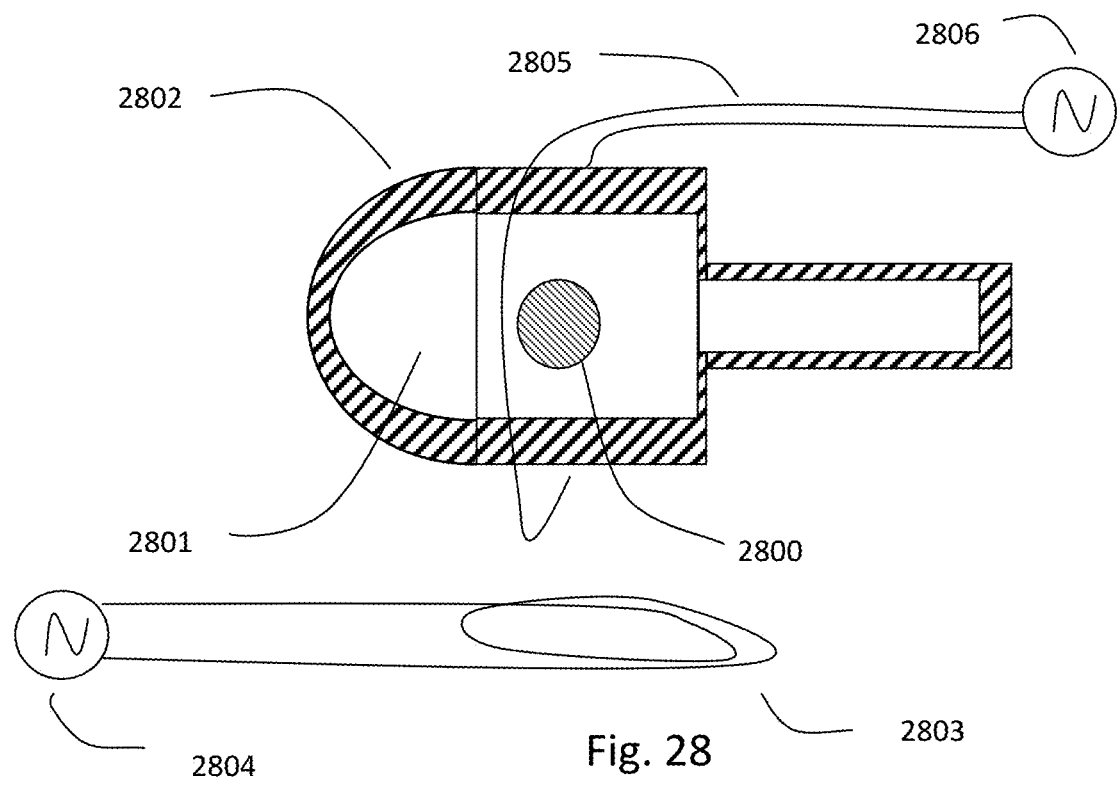
FIG. 28 is a schematic view illustrating an embodiment of an agitator located within a thermal element and associated driving elements.

FIG. 28 illustrates an embodiment of an ablation catheter in which an agitator 2800 is an isolated stirrer configured to move relative to a substantially enclosed space 2801 within an electrode 2802. Examples of various aspects of isolated agitators 2800 include:

a) The agitator 2800 may be a ball of predetermined shape having different density from the fluid located within the substantially enclosed space 2801, whereby movement of the reservoir, either through natural physiologic motion or by some active means will cause the ball to move within the substantially enclosed space 2801 due to the inertia of the agitator 2800, thereby causing the fluid to flow.

b) The ball may be a bubble.

c) The bubble may be an immiscible fluid, examples of which include: oils, water, fats, triglycerides, liquid indium alloys, gallium, gas etc.
d) The immiscible fluid may be a solution or suspension of higher density compared to the surrounding fluid. Examples of solutes or dispersions include salts, sugars, chelated iodine salts such as radiographic contrast media, glass, metal polymer or ceramic nanoparticles, etc.
e) The agitator 2800 may be comprised of magnetic material driven by electromagnetic fields generated inside or outside the body. Examples of magnetic materials include: ferrite, iron, cobalt or nickel and alloys thereof. In some implementations, the electromagnetic fields may be generated by coils 2803 placed in, on or near the patient. Coils 2803 may be powered by a controller 2804.
f) The magnetic agitator 2800 may be comprised of magnetic material driven by electromagnetic fields generated within the catheter proximate the agitator 2800. The internally generated magnetic fields may be generated by coils 2805 placed proximate the electrode 2802. Coils 2805 may be powered by a controller 2806 placed outside the body.
g) The ball or bubble may be a ferro-fluid. Ferro-fluid is a magnetic liquid that can be influenced by magnetic fields.
h) The agitator 2800 may be driven by acoustic fields generated by an acoustic or ultrasonic transducer. The transducer may be incorporated into the catheter proximate the electrode 2802. In other embodiments, the transducer may be external to the body.
i) Acoustic fields may act directly on the fluid urging it to flow by ultrasonic streaming. Ultrasonic streaming is a phenomenon whereby irreversibilities in the motion of the fluid molecules under the influence of an acoustic field cause macroscopic flow to occur.
j) The agitator may be a fluid jet.

In the illustrated embodiment of FIG. 27, the catheter includes a singular agitator 2700. In other embodiments, the catheter may incorporate multiple agitators to further promote heat transfer and electrode cooling. In various embodiments (e.g., as shown in FIG. 27), the agitator 2700 may be externally activated. In this example, an elongate catheter 2704 may have a proximal and a distal end, an electrode 2702 located near the distal end, a substantially enclosed space 2701 located within the electrode 2702, and an agitator 2700 located within the substantially enclosed space 2701. The agitator 2700 may be attached to a coupling element 2705. The coupling element 2705 may extend through the catheter shaft 2704 to connect to an external drive source or actuator (not shown). The actuation of the agitator 2700 may be either rotary motion or axial translation. Various aspects include one or more of the following:

a) The catheter 2704 may have a temperature sensing component. The temperature sensing component may provide the agitation of the fluid.
b) The agitator 2700 may be driven by a separate shaft.
c) The agitator 2700 may be large or small in relation to the size of the substantially enclosed space 2701. There may be fins or texture on the surfaces of the substantially enclosed space 2701 to increase convective heat transfer.
d) The agitator 2700400 may be a wire, coil, cable or shaft rotated or translated, driven by an actuator.
e) The actuator may be proximate the agitator 2700.
f) The actuator may be a linear or rotary micro motor.
g) The actuator may be outside the body.
h) The actuator may be driven by fields transmitted or generated outside the body.
i) The agitator 2700 and/or catheter shaft 2704 may comprise one or more temperature measurement elements (e.g., thermistor, RTD, thermocouple, optical sensor, etc.).
j) The actuator may be an ultrasonic actuator.

In one embodiment, the electrode 2802, closed fluid space and fluid may together be configured to function as a heat pipe. Suitable heat pipe fluids include water, alcohol, fluorocarbons, perfluoro crown ethers, Freon, certain organic solvents (e.g., dimethyl sulfoxide), mercury, and/or the like. The heat pipe may operate under a partial vacuum to achieve the desired operating temperature range. The heat pipe itself may be designed to direct or channel the condensed fluid from the cold surface back towards the hot surface. This may be accomplished by grooving, texturing patterning or coating the interior surfaces of the heat pipe. There may also be a separate channel or conduit for returning the condensed liquid. Condensed liquid may also be transported through a porous media region or wick within a portion of the heat pipe. Any of the structural and functional features of the ablation catheters of FIG. 28 (e.g., agitator 2800 and the heat pipe configuration) may be incorporated into the other balloon catheters or ablation devices described herein.

FIGS. 29A-29D illustrates the effect of the various heat transfer mechanisms on temperature and heat transfer from the tissue to the blood. The heavy lines represent temperature vs. distance across an electrode. The vertical lines represent boundary surfaces including the tissue-to-electrode interface 2900, the electrode-to-internal fluid interfaces 2901 and 2902 and the electrode-to-blood interface 2903.

Heat transfer can be characterized by heat flux, which is heat transferred across a surface per unit area, measured in Watts/mm². Heat flux is proportional to the product of thermal conductivity and temperature gradient. Thus, the combination of high thermal gradient, high thermal conductivity and high surface area provides increased heat transfer. In general, the temperature gradient is a function of part geometry as well. Platinum and its alloys are known to have high, but finite, thermal conductivity. High temperature gradients are provided when a large temperature drops occurs over a short distance. Given sufficiently high flow rates, convective heat transfer is more efficient than conduction. Convective heat transfer is characterized by a convection coefficient expressed in watts/mm²/degree Celsius. In fact, convective heat transfer across a surface actually occurs over a small boundary layer distance in the fluid adjacent to the surface. Thus, the temperature may appear to be discontinuous at the surface, as shown FIGS. 29B, 29C, and 29D.

FIG. 29A illustrates the temperature distribution of a simplified, idealized electrode represented as infinite plates of homogeneous materials with uniform temperature in the blood 2904 and tissue 2905. It can be seen that in this case the temperature 2906 varies linearly across the electrode, providing a constant thermal gradient solely by the temperature of the tissue and blood.

FIG. 29B illustrates the temperature distribution for a realistic solid electrode. In this case, the temperature of the tissue is determined by a balance between RF heating of the tissue and the heat transferred out of the tissue. Heat transfer occurs partly through the electrode by thermal conduction, the rate of which is governed by the thermal conductivity of the electrode material and the geometry of the electrode. The temperature distribution along a path across the electrode

2907, 2908, 2909 may be non-linear and the thermal gradient 2910 will be non-constant. So long as the RF power dissipation in the tissue is not too high, the temperature of the tissue at the tissue electrode interface 2900 may be lower than the peak temperature deeper in the tissue.

FIG. 29C illustrates the effect on tissue temperature when the solid electrode device is caused to deliver a higher amount of power compared to FIG. 29B. In this case, heat transfer across the electrode is insufficient to prevent overheating of the tissue proximate the electrode.

FIG. 29D illustrates the temperature profile of an embodiment of a fluid-filled ablation catheter electrode of the type disclosed herein. In this example, the internal convective heat transfer of the fluid-filled space provides higher temperature gradients across the walls of the electrode, thereby increasing heat transfer, resulting in lower tissue temperature at the electrode interface or higher allowable RF power levels.

In some embodiments, the substantially enclosed space is an expandable space. In some embodiments, the expandable space is formed by a balloon. In some embodiments, the balloon is configured to facilitate flow of the heat transfer fluid within the space. In some embodiments, the balloon expands to substantially occlude a blood vessel. In some embodiments, the substantially enclosed space of the ablation catheter is not within the electrodes but within a balloon on which the electrodes are mounted.

Figure 30A:
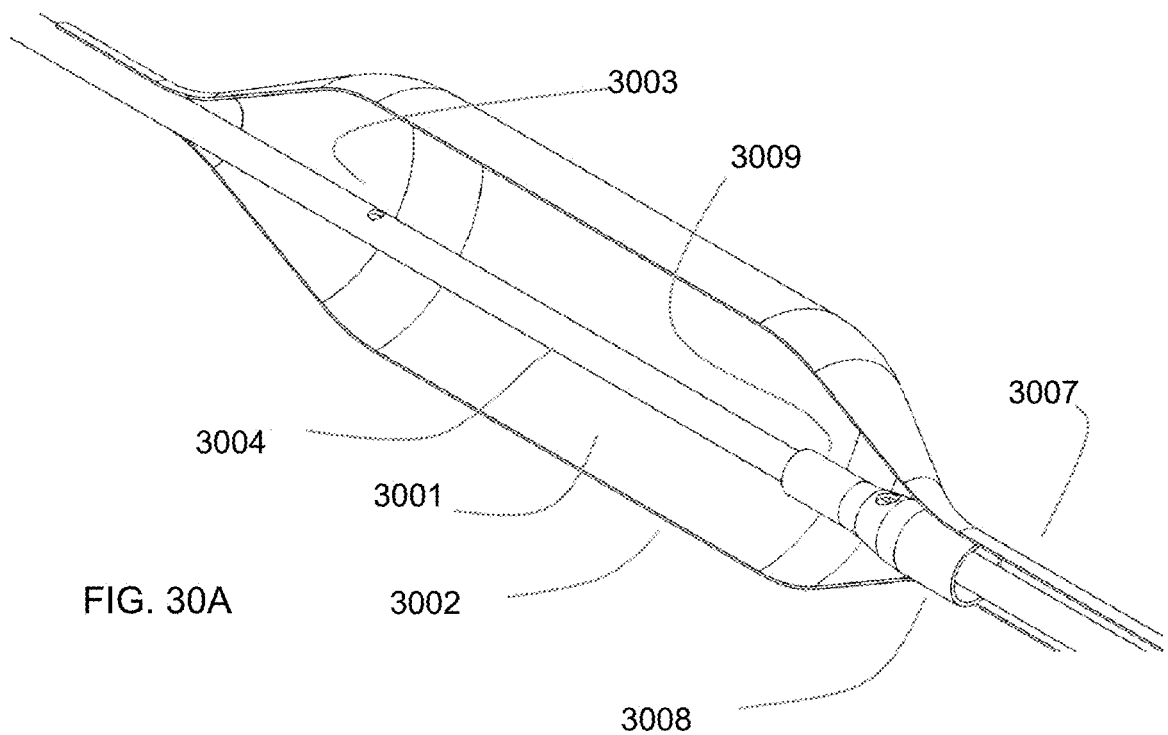
FIG. 30A is a section view of an embodiment of a balloon catheter having a proximal jet valve and a distal bleeder hole.
Figure 30B:
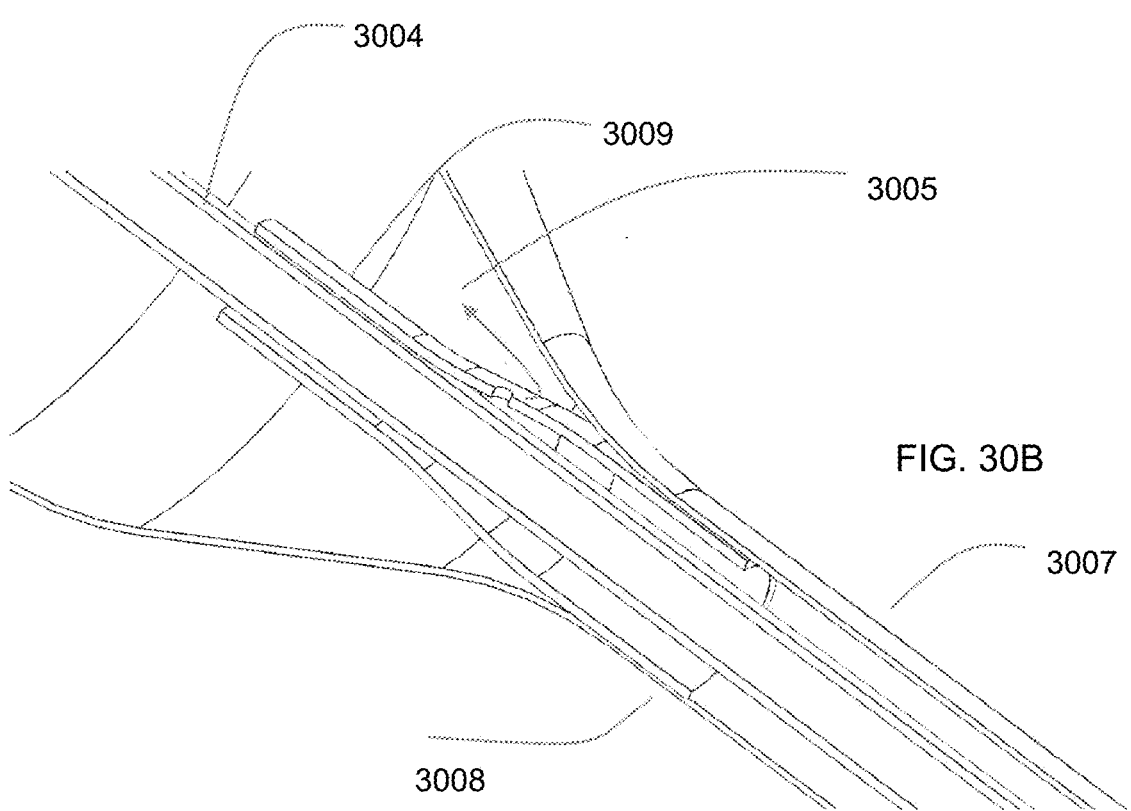
FIG. 30B is a magnified view of the proximal jet valve of FIG. 30A.

FIGS. 30A and 30B show an embodiment of a balloon ablation catheter. In some embodiments, a substantially enclosed space 3001 within a balloon 3002 is allowed to leak fluid at a controlled rate. In some embodiments, the rate of heat transfer by the fluid leak is smaller than the rate of heat transfer from the balloon 3002 to the surrounding tissue. In other embodiments, the rate of heat transfer from the balloon 3002 to the surrounding tissue is in addition to the heat transferred via the fluid leak. In some embodiments, the leak is provided by an opening 3003 in a guidewire lumen 3004 extending through the balloon 3002.

In some embodiments, fluid is pulsed through an inlet jet 3005 at higher velocity than if the same average flow rate were delivered at a constant rate. In some embodiments, flow is provided by a high velocity, low flow rate jet. The jet may be configured to cause circulation substantially throughout the balloon 3002. The circulating flow may be alternately injected and removed through the same lumen (e.g., lumen 3007). FIGS. 30A and 30B show an embodiment having a valve 3008 provided to partially obstruct the delivery lumen 3007 during injection to provide a high velocity, low flow jet while allowing low resistance evacuation of the balloon 3002 during deflation. In some embodiments, the valve 3008 is a flap or conical valve that substantially seals the lumen 3007 during injection but deforms or collapses during deflation to provide reduced resistance. In some embodiments, a valve waist 3009 is mounted on the guidewire lumen 3004 extending through the balloon 3002.

In some embodiments, the high velocity jet is provided by an orifice. The size of the orifice may be less than 0.01 inch, 0.001 to 0.005 inch, 0.005 to 0.010 inch, or greater than 0.01 inch. In some embodiments the orifice is not circular. A non-circular orifice may have a hydraulic diameter of less than 0.01 inch, 0.001 to 0.005 inch, 0.005 to 0.010 inch, or greater than 0.01 inch. The balloon ablation catheter of FIGS. 30A and 30B may comprise multiple ablation elements (e.g., electrodes) positioned along an outer surface of the balloon 3002 (not shown). In accordance with several embodiments, the orifice(s) may be positioned to direct the jet(s) directly toward a back surface of the electrode(s). For example, separate orifices may be positioned to direct a separate jet at each individual electrode. Any of the structural and functional features of the ablation catheter of FIGS. 30A and 30B (e.g., jets, orifices, valves, lumens) may be incorporated into the other balloon catheters or ablation devices described herein.

Figure 31:
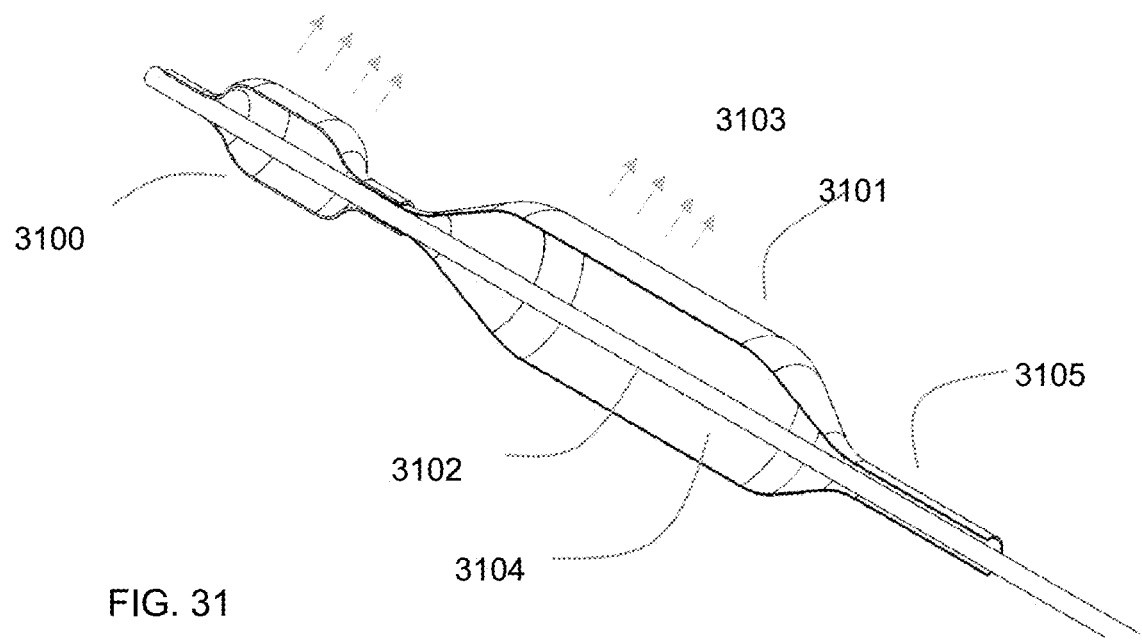
FIG. 31 is an illustration of an embodiment of a balloon catheter system having a distal expansion chamber.

FIG. 31 illustrates an embodiment of a balloon ablation catheter having a distal expansion chamber 3100. The balloon 3101 supports the ablation elements (not shown), which may include multiple electrodes, as shown, for example, in FIGS. 4 and 12A-12E. The balloon ablation catheter includes a guidewire lumen 3102. In some embodiments, the balloon 3101 inflates to contact tissue 3103, thereby fully obstructing blood flow through a vessel. In other embodiments, the balloon 3101 substantially (but not completely) obstructs blood flow through a vessel. Fluid 3104 is delivered through a fluid delivery lumen 3105. In some regions, heat is conducted from hot tissue into the balloon fluid 3104 having an intermediate temperature less than the hot tissue temperature. In other regions, heat is conducted from the balloon fluid 3104 to cooler tissue areas. The distal expansion chamber 3100 may expand and contract to accommodate balloon fluid 3104 to provide convection within the balloon 3101. In some embodiments, additional heat transfer may occur between the expansion chamber 3100 and the tissue 3103.

In some embodiments, pulsed delivery of fluid causes the balloon 3101 to increase and decrease in volume. In some embodiments, the expansion chamber 3100 is provided to contain the fluid 3104 and/or reduce pressure and diameter fluctuations. In some embodiments, the expansion chamber 3100 maintains the balloon 3101 at a constant diameter to maintain contact of the ablation elements mounted thereon with tissue. The expansion chamber 3100 may be provided distally, proximally, internally or externally to the balloon 3101. In one embodiment, the expansion chamber 3100 is a separate compliant balloon. In some embodiments, the expansion chamber 3100 is within the elongate shaft. In some embodiments, compliance is provided by a compressible material within a balloon 3101. The compressible material may be a gas such as air, $CO_2$, $N_2$, $N_2O$, $NO_2$, propane, octane, heptane, fluorocarbons, Freon, and/or other compressible compounds or mixtures. In some embodiments, the gas is contained in a vessel or balloon 3101. In some embodiments, the gas is a bubble in direct contact with the heat transfer fluid. Any of the structural and functional features of the ablation catheter of FIG. 31 may be incorporated into the other balloon catheters or ablation devices described herein.

Figure 32:
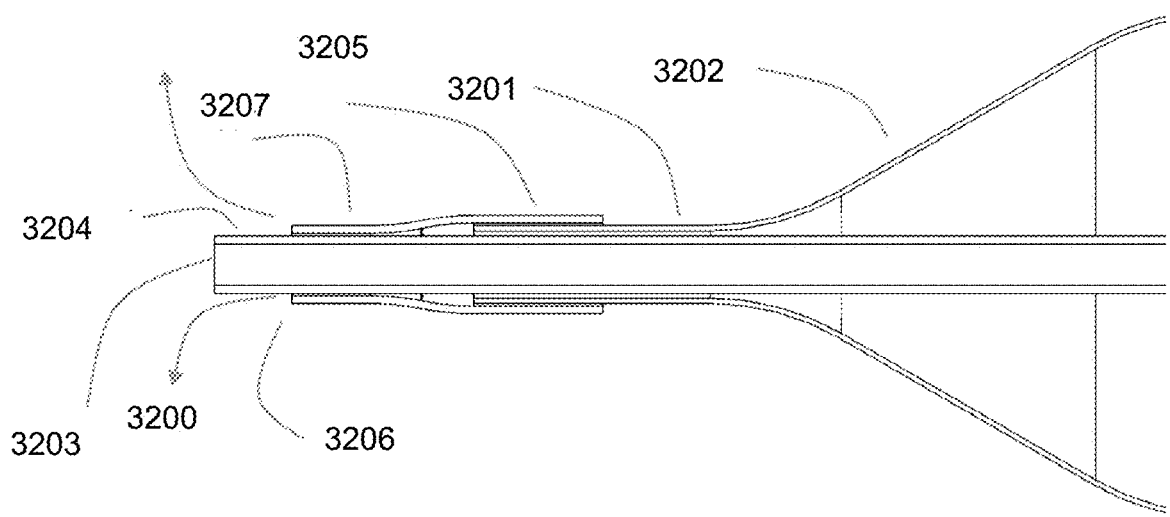
FIG. 32 is section view of an embodiment of a distal bleeder valve.
Figure 33A:
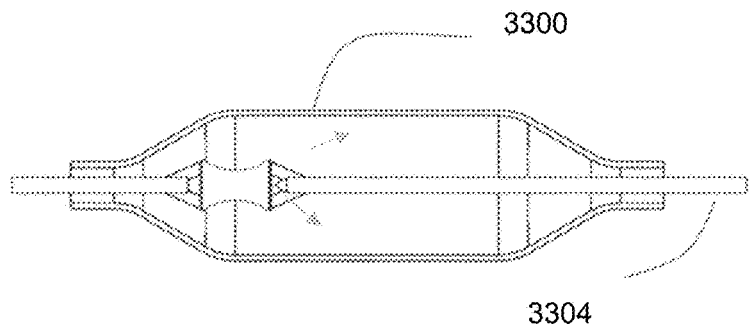
FIG. 33A provides a section view of an embodiment of a fluid entraining element in a balloon.
Figure 33B:
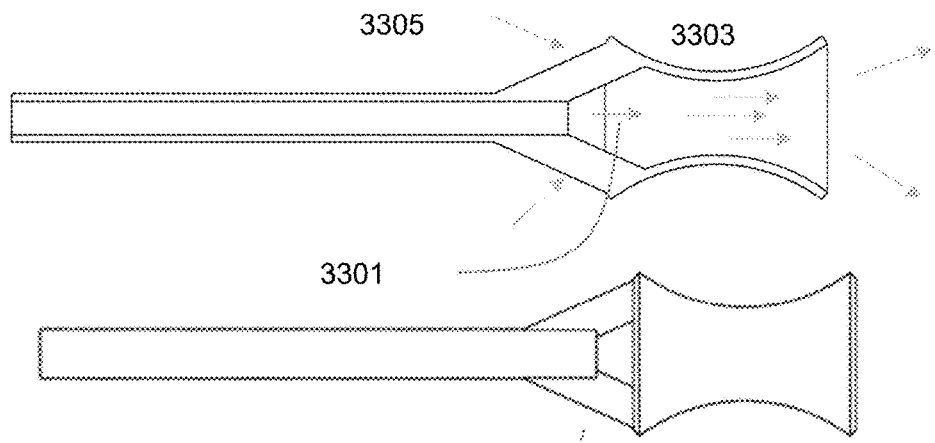
FIG. 33B shows a section view of an embodiment of a fluid entrainment element.
Figure 33C:
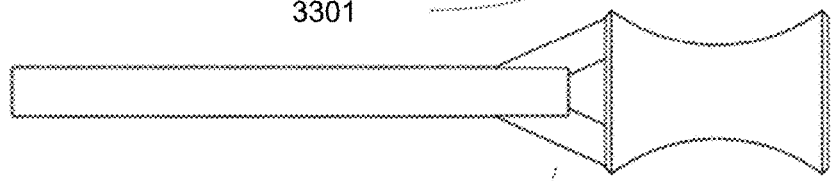
FIG. 33C shows an embodiment of a fluid entrainment element on a delivery lumen.
Figure 33D:
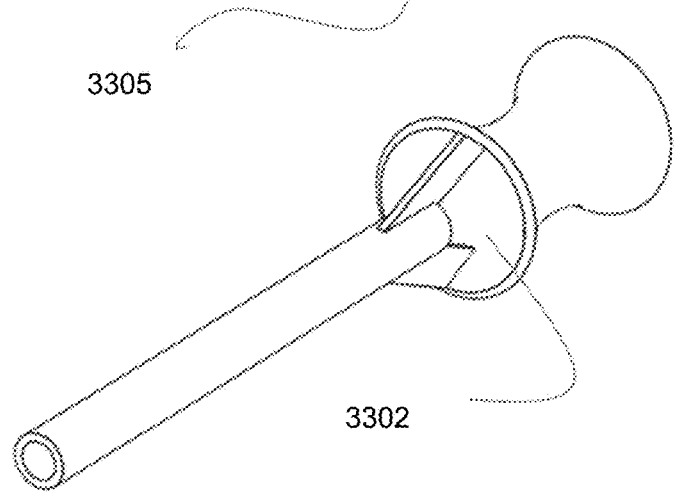
FIG. 33D shows a perspective view of an embodiment of a fluid entrainment element.

FIG. 32 is a section view of a distal bleeder valve. In some embodiments, a controlled fluid leak 3200 is provided by adaptation of a distal waist 3201 or distal bond of the balloon 3202. In other embodiments, the controlled leak is provided by an opening 3203 in the guidewire lumen 3204. Fluid passing through said leak may pass out the opening 3203 of the guidewire lumen 3204 or proximally through the guidewire lumen 3204 into the body or allowed to exit the body. In some embodiments, a valve is provided to control the rate and/or direction of flow of fluid through the guidewire lumen 3204. In some embodiments, the fluid is collected to recirculate through the system. The valve may be a separate element with an overlapping section 3205. In other embodiments, the valve may be integral with the balloon 3202. In some implementations, the valve may form a sliding interface 3206. The valve may have a necked region 3207, as shown in FIG. 32. Any of the structural and functional features of the distal bleeder valve of FIG. 32 may be incorporated into the other balloon catheters or ablation devices described herein.

Some configurations lack the spontaneous blood flow that contributes to cooling of non-obstructive ablation systems. An example of the energy balance associated with one embodiment of a balloon ablation system is shown in Table 1 below (the values are non-limiting values and may vary as desired and/or required).

TABLE 1

| Property/Characteristic | Value | Units | Notes |
| --- | --- | --- | --- |
| $H_2O$ specific heat | 4.2 | J/gmC | Reference: CRC Handbook of Chemistry and Physics, $82^{nd}$ ed. (2001), page 6-3 |
| $H_2O$ density | 1 | gm/ml | Reference: CRC Handbook of Chemistry and Physics, $82^{nd}$ ed. (2001), page 6-5 |
| balloon length | 20 | mm | L typical |
| balloon diameter | 6 | mm | D = 2r typical |
| balloon volume | 0.57 | $cm^2$ | $V = L * \pi * r^2$ |
| balloon electrode power | 1.5 | W | P typical |
| duration | 120 | s | $\Delta t$ typical |
| total energy | 180 | J | $E = P * \Delta t$ |
| % heat transferred back to balloon | 50% | | |
| net balloon energy | 90 | J | $E_{net} = E *$ % balloon absorption |
| body temperature | 37 | C | typical, perfusate temperate may be lower |
| max allowable balloon temperature | 45 | C | threshold for injury |
| change in balloon temperature | 8 | C | $\Delta T$ typical |
| change in balloon enthalpy | 19.0 | J | $\Delta H = \rho * v * Cp * \Delta T$ |
| balloon heat transfer rate | 0.6 | W | $Q = \Delta H / \Delta t$ |
| max heat transfer required | 71.0 | J | $\Delta E = Q * \Delta t = E - \Delta H$ |
| max perfusion required | 2.1 | mL | $V = q * \Delta t = (E - \Delta H)/(\rho * Cp * \Delta T)$ |
| max flow rate required | 0.018 | mL/s | q |

Lower volumes and flow rates are inherently safer and therefore require less sophisticated control and safety systems. Uncontrolled manual injections of less than about 10-20 mL are common and generally considered to be safe. While this flow rate is sufficient to carry excess heat away from the balloon, conventional perfusion systems do not provide sufficient stirring or agitation at low flow rates to equalize temperature throughout the balloon. Several embodiments of the catheters disclosed herein advantageously provide sufficient stirring or agitation at low flow rates to equalize temperature throughout the balloon through improved fluid delivery means.

In some embodiments, a channel may be provided to allow passive perfusion of blood through the balloon. In some embodiments, the passive blood perfusion carries heat away from the balloon. In some embodiments, flow may be motivated by mechanical, hydraulic, pneumatic or other means. Various embodiments of flow motivating means comprise: fluidic components, reeds, flappers, non-linear hydraulic mechanical elements, bistable elements, microfluidic actuators, cylinders, membranes and/or cantilevers.

In some embodiments, the jet is configured to entrain additional flow within the heat transfer chamber. In some embodiments, a shroud is provided to guide chamber fluid past the jet orifice. In other embodiments, the jet is in the form of an ejector or eductor. Ejectors and eductors are known in process industries and steam locomotives as a means of utilizing a high velocity, low flow rate jet to entrain a larger volume of fluid at a moderate velocity or flow rate.

FIGS. 33A-33D illustrate an embodiment of a fluid jet system 3300 of a balloon ablation catheter. The illustrated embodiment includes an enlarged diameter shroud, cowling or body to more efficiently provide circulation within the balloon chamber by entraining fluid. Elements of an ejector may include: 1) a small diameter jet outlet 3301; 2) openings 3302 to guide ambient flow past the jet; and 3) a tapered, converging/diverging or venturi shaped outlet 3303 to reduce flow detachment and increase efficiency. In various embodiments, the fluid jet system 3300 includes an extension member 3304. The fluid guiding body may be supported by one or more thin struts or web projections 3305 that support a central element in an annular configuration (e.g., similar to an extrusion die spider). Various embodiments may include one, some or all of these elements. Any of the structural and functional features of the fluid jet system of FIGS. 33A-33D may be incorporated into the other balloon catheters or ablation devices described herein.

FIGS. 34A and 34B show an embodiment of a balloon ablation catheter having a whistle-like apparatus for entraining fluid and promoting circulation. Fluid delivered through a lumen 3400 in a shaft 3401 forms a jet through a nozzle 3402. An opening 3403 provides access for surrounding fluid to be entrained. The opening 3403 may have a flared lip 3404. The nozzle or orifice 3402 may be formed by obstruction means 3405. Additional lumens 3406 may be provided as desired and/or required. In some embodiments, the balloon ablation catheter includes a guidewire lumen 3407 for over-the-wire delivery. A distal guidewire lumen 3408 portion may be an integral or separate component. Any of the structural and functional features of the ablation catheter of FIGS. 34A and 34B (e.g., whistle-like apparatus) may be incorporated into the other balloon catheters or ablation devices described herein.

Figure 35A:
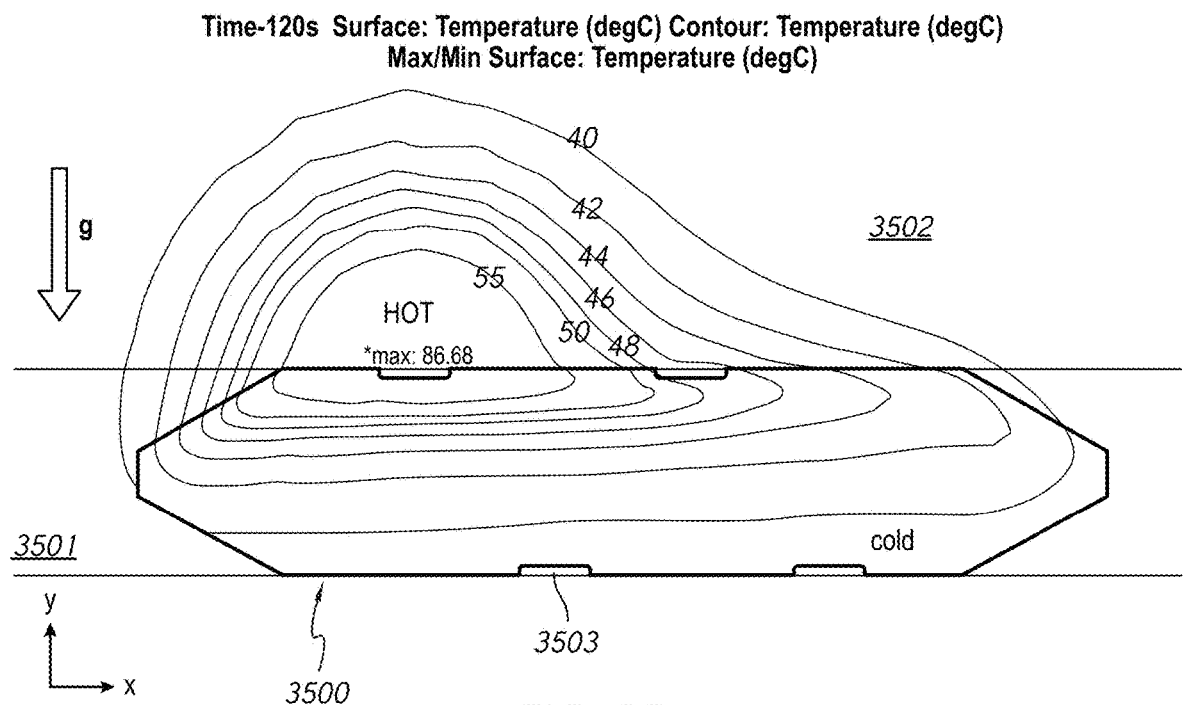
FIG. 35A provides simulation results illustrating a temperature distribution surrounding an ablation balloon subject to free convection.
Figure 35B:
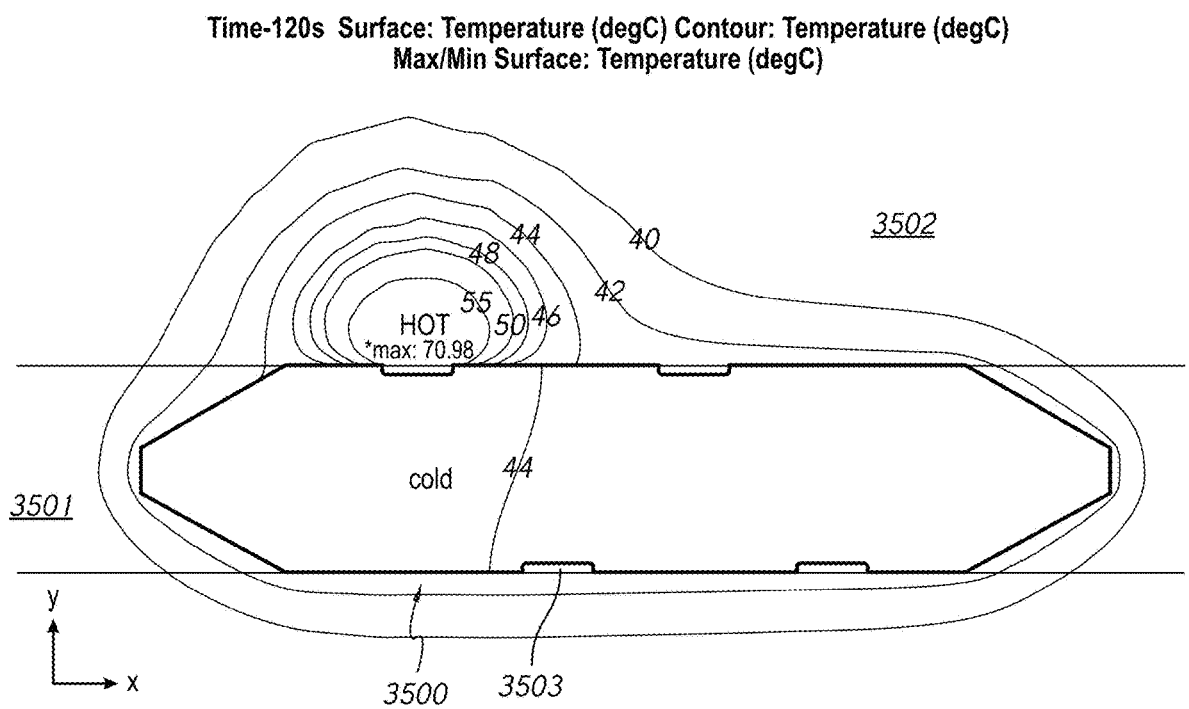
FIG. 35B provides simulation results illustrating a temperature distribution surrounding an ablation balloon having sufficient internal convection to achieve substantially uniform temperature within the balloon.

FIGS. 35A and 35B illustrate simulations of a temperature distribution surrounding an example of an obstructive ablation catheter 3500. In some embodiments, blood flow 3501 is obstructed. Tissue 3502 is heated by electrodes 3503. Heat is transferred from hot tissue back into a balloon 3500. Heat is also transferred from the balloon 3500 into the cooler regions of the surrounding tissue 3502. In some embodiments, increased heat transfer is obtained by increasing the length of the balloon 3500 beyond the ablation region. For example, the length of the balloon may be configured to extend beyond the ablation region (proximally, distally or split between both) by 5%-100% (e.g., 5%-20%, 20%-50%, 50%-100%, 50%-80%, 75%-100%, overlapping ranges thereof or greater than 100%), or by 1 cm-5 cm proximally, distally or split between both. In some embodiments, the shaft or various lumens or chambers therein provide heat transfer between the catheter and the surrounding blood/tissue, thereby acting as remote heat transfer component(s).

In some embodiments, the balloon 3500 may have multiple electrodes or other ablation elements mounted to its outer surface, as shown, for example, in FIGS. 4 and 12A-12E. Simulations predict an equilibrium condition for single lesion activation. Heat transfer is limited by balloon surface area and tissue heat transfer properties. Multiple electrodes activated simultaneously or in rapid succession increases heat transfer into the balloon by increasing the hot surface area while decreasing the cold surface area available for heat transfer into tissue. Total energy scales approximately with the number of multiplexed electrodes. For example, if a single electrode delivers 180 joules of energy in 2 minutes, 4 electrodes would deliver 720 Joules. Using the assumptions outlined below and neglecting the initial enthalpy change of the balloon fluid, this would require 4*2.1 mL=8.4 mL of perfusion fluid.

In some embodiments, the additional heat transfer required by multiplexed electrodes may advantageously be provided (or offset) by one or more of the following:
  increasing balloon surface area
  providing remote compliance/heat transfer element
  infusing fluid at a low average flow rate to eliminate heat
  directing one or more jets directly toward a back surface of each electrode.

In some embodiments, the luminal temperature is limited to less than 50 degrees C. In other embodiments, the luminal temperature is limited to 45 degrees C. or 47 degrees C. In some embodiments, the luminal temperature is limited except for footprint proximate an ablation electrode. Other temperatures may be targeted or used as desired and/or required. The electrode cooling structures and techniques described herein (e.g., electrodes with substantially enclosed spaces or cavities for fluid or balloon cooling embodiments) may be incorporated or implemented in any of the catheters and systems described herein for cooling energy delivery elements during treatment.

Lesion Parameters and Spacing

In accordance with several embodiments, the common hepatic artery is a target of ablation using an RF electrode catheter. For some subjects, a length of the common hepatic artery may limit the number of possible ablation sites. In some embodiments, minimizing the size of the lesions created along the longitudinal length of the common hepatic artery increases the number of ablation sites available within the vessel. In order to decrease the width of the lesions parallel to the vessel longitudinal axis while maintaining sufficient depth of the lesions and maximizing a surface of the electrode exposed to blood flow or cooling fluid for cooling, the electrode(s) of the RF electrode catheter may be constructed to have a diameter that is greater than or equal to its length. For example, if the electrode is generally 6 French in diameter (0.080 inches), then the length of the electrode may be 0.080 inches or less.

In accordance with several embodiments, consistency in lesion size is desired without being dependent on variations in vessel size, which may vary for the same target vessel across different subjects. For example, the inner diameter of the common hepatic artery may vary from 3 mm to 7 mm. In addition, overlap in lesion formation may be undesirable. Overlap in lesion formation can be difficult to avoid or prevent if a target treatment length is sufficiently short (e.g., due to patient anatomy) and multiple spaced-apart lesions are required to be formed along the vessel length.

In accordance with several embodiments, lesions may be coordinated and positioned to provide continuous oblique circumferential lesions without creating a circumferential lesion at any one location or cross-sectional slice. In some embodiments, both the position and the extent of the lesions are controlled. The lesions may be placed 180 degrees apart and displaced axially along the vessel length. In some embodiments, the circumferential and axial extent of the lesion are controlled so that the margins of the lesions just intersect at a location 90 degrees on either side of the energy delivery element (e.g., electrode) positions. In some embodiments, a reference electrode may be positioned between the lesions to measure temperature or impedance to detect lesion intersection. In some embodiments, lesions are spaced between 1-50 mm apart (e.g., 1, 5, 10, 12, 15, 20, 25, 50 mm, and overlapping ranges thereof). Lesions may be overlapping or non-overlapping. In one embodiment, multiple foci or ablation sites, which may or may not overlap, are created to generate lines of thermal injury. The foci or sites can be spaced at 0.2 mm to 20 mm apart (e.g., 0.2 mm to 2 mm, 5 mm to 15 mm, 10 mm to 20 mm, 1 mm to 12 mm, or overlapping ranges thereof). In some embodiments, lesions are non-circumferential. In some embodiments, lesions are circumferential, including off-set circumferential, partially circumferential, and fully circumferential. In various embodiments, lesions may be spaced between 1 to 15 times the electrode diameter. For example, for electrodes having diameters of 1 or 2 mm, the electrodes may be spaced from 1 mm to 30 mm apart (e.g., 1 to 12 mm, 5 to 15 mm, 10 to 20 mm, and overlapping ranges thereof). Lesion spacing may be adjusted based on vessel diameter. The number of ablations (or number of ablation locations) may also vary based on vessel diameter or on a desired dose-response (e.g., full dose-response rate) for a particular lesion spacing.

Because catheter tip temperature and impedance alone may be poor indicators of tissue temperature or lesion size, tip temperature and impedance may both be measured during ablation in order to monitor lesion development and/or to confirm lesion formation, thereby providing confirmation of denervation of target nerves.

Initially, tip temperature increases and impedance decreases. Tissue conductivity increases with temperature up to a certain threshold (e.g., approximately 80 degrees Celsius). Above this threshold temperature, tissue may begin to contract and desiccate and impedance may start to increase instead of decrease. The decoupling of temperature and impedance may be used as an indication of lesion formation to confirm denervation. If impedance begins to increase without a corresponding decrease in tip temperature, this may be used as an end point or as confirmation of lesion formation. The time of decoupling of temperature and impedance may also be used as feedback to trigger other changes in an energy delivery protocol, such as decreasing power or increasing cooling.

Figure 36:
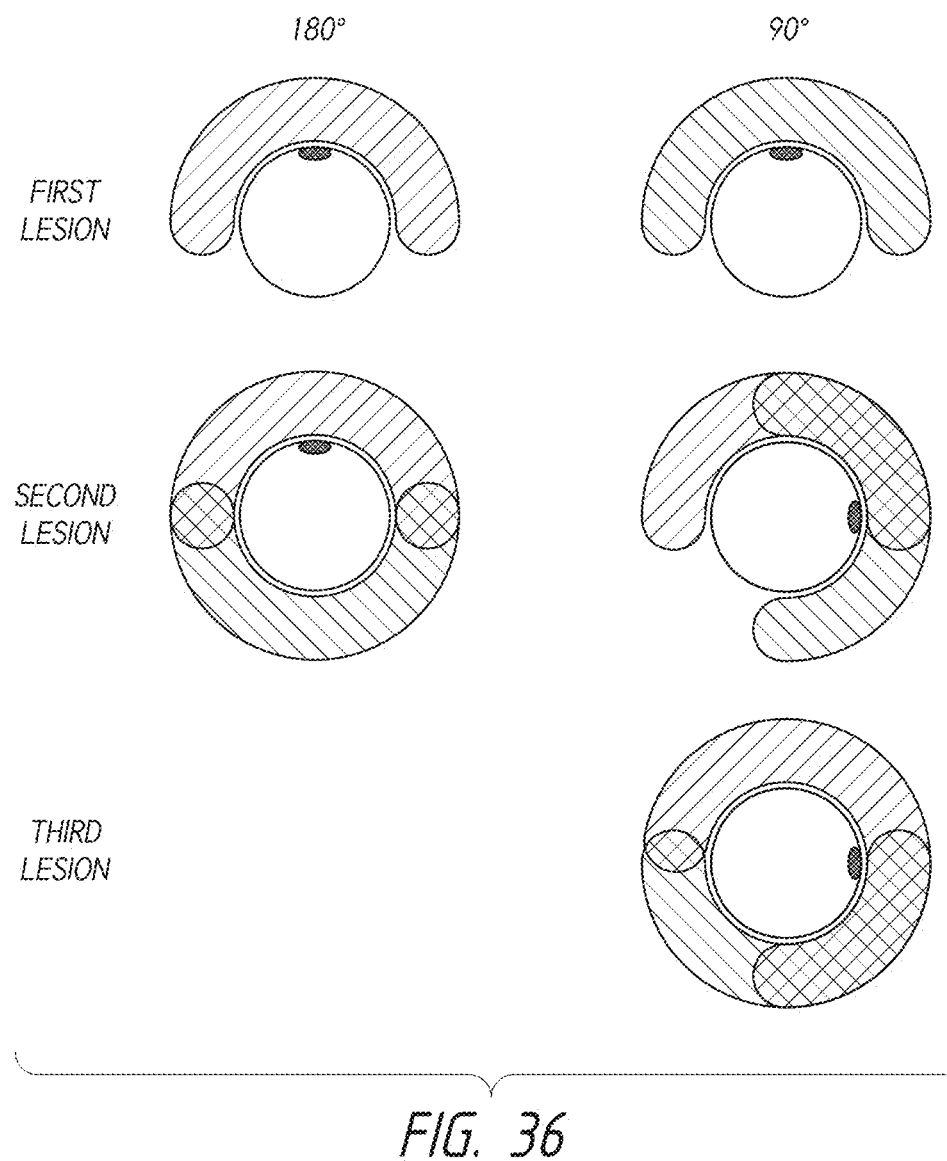
FIGS. 36, 37A and 37B illustrate various lesion zones or patterns.

In some embodiments, complete circumferential ablation of a vessel may be prevented or inhibited by spacing ablation sites radially at 90 degree intervals as opposed to at 180 degree intervals. FIG. 36 schematically illustrates ablation performed at 180 degree intervals and at 90 degree intervals. As shown, even if the 180 degree intervals are spaced apart axially along the length of the vessel, the "tails" of the ablation lesions could potentially overlap on both sides of the vessel (assuming that each ablation forms a lesion that extends around 180 degrees of the vessel circumference), thereby forming a complete circumferential lesion. When 90 degree intervals are used, there may potentially be overlap between adjacent lesions but the risk of complete vessel circumferentiality of the overall lesion composed of the multiple lesions is reduced. A single or multi-point RF ablation catheter may facilitate radial spacing of ablation sites by approximately 90 degrees and longitudinal spacing of at least one electrode length. In some embodiments, radial spacing of the ablation sites by 90 degrees causes less than complete circumferential ablation of the vessel (e.g., 75%-95%, 70%-90%, 65%-80%, 75%-90%, or overlapping ranges thereof). In some embodiments, treatment sites (e.g., ablation sites) may be spaced 120 degrees apart circumferentially (for example, if the energy delivery device includes three electrodes). In other embodiments, 180 degree spacing is alternatively used instead of 90 degree spacing or both 180 degree and 90 degree spacing are used.

In accordance with several embodiments, the systems and methods described herein advantageously increase the perivascular ablation size and nerve impact while decreasing vascular wall injury and adjacent structure involvement. For example, for RF electrode embodiments, the electrode shape and energy delivery parameters may be designed to maximize or increase the perivascular ablation area and nerve impact while minimizing vascular wall injury and adjacent structure involvement. In various embodiments, an energy delivery device consisting essentially of a single electrode is used. In other embodiments, an energy delivery device consisting essentially of two and only two electrodes is used. In some embodiments, an energy delivery device consisting essentially of four and only four electrodes is used. In other embodiments, an energy delivery device consisting essentially of three and only three electrodes is used. In yet other embodiments, an energy delivery device consisting essentially of five and only five electrodes is used.

Figure 37A:
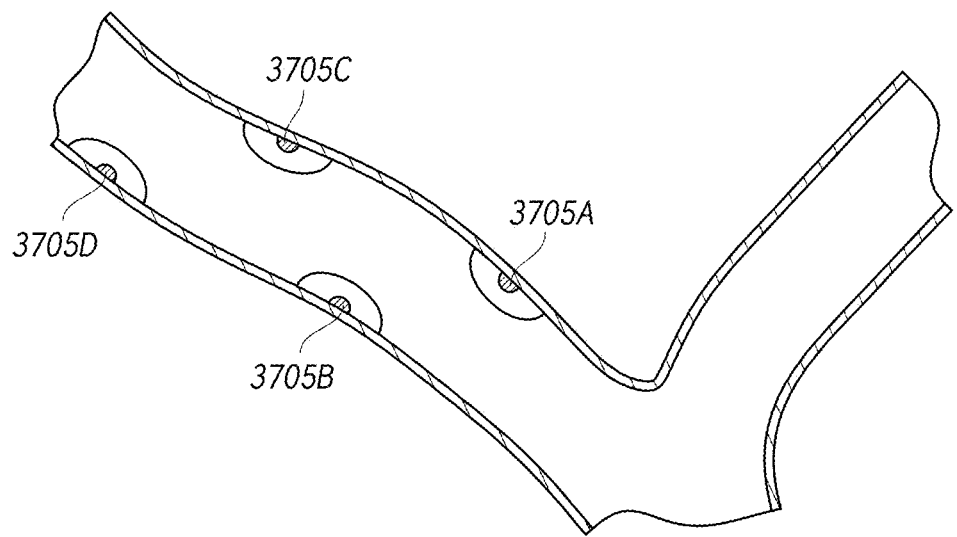
Figure 37B:
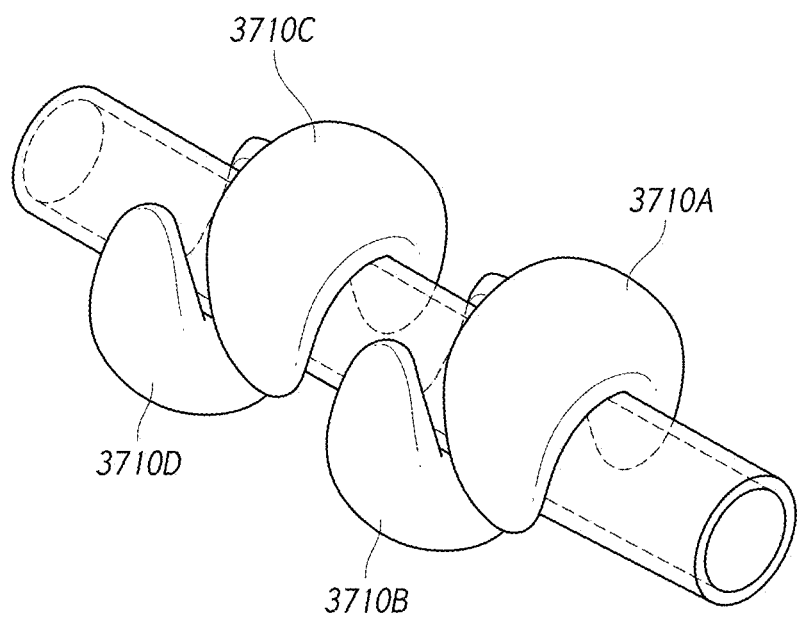

With reference to FIG. 37A and FIG. 37B, ablation patterns may advantageously increase the overall perivascular ablation volume while maintaining little to no thermal damage or endothelialization (e.g., less than 20% mean maximum circumference of vessel injury, no internal elastic lamina disruption, no arterial dissection, and/or no clinically significant neointimal formation, no long-term vascular stenosis, no circumferential vessel wall injury) to the portions of the vessel wall in contact with an ablation member (e.g., electrode, transducer). FIG. 37A illustrates one embodiment of an ablation pattern comprising four spaced-apart ablation locations 3705A-3705D. The ablation locations are spaced apart at an equal distance X and each ablation location is offset by 180 degrees from the next location. In some embodiments, the spacing between the locations is determined by a minimum threshold and the spacing does not necessarily have to be equal (just above the minimum threshold spacing). The minimum threshold spacing (between center points of lesion zones) may be between 2 and 8 mm (e.g., between 2 and 4 mm, between 3 and 6 mm, between 4 and 8 mm, between 3 and 7 mm, 2 mm, 3 mm, 4 mm, 5 mm, 6 mm, 7 mm, 8 mm, overlapping ranges thereof or any value of or within the ranges). In some embodiments, the minimum threshold spacing depends on anatomical limitations of target vessel length. For example, for the common hepatic artery, spacing is 4 mm or 6 mm in accordance with several embodiments. The spacing described with respect to FIG. 37A may be used for spacing of electrodes in any of the embodiments described herein. For devices having deployed configurations, the spacing may be the spacing when the devices are in the deployed configuration in contact with a vessel wall.

FIG. 37B illustrates a schematic representation of the lesion zones 3710A-D formed by ablation at the four locations shown in FIG. 37A. As shown, the combination of the spacing and 180-degree offset increases perivascular lesion blending to provide larger circumferential perivascular injury along the vessel length, thereby increasing the likelihood of efficacy, while avoiding circumferential vessel wall injury. Factors of electrode size, power, duration and level of contact may also contribute to efficacy. In accordance with several embodiments, the individual ablation point and subsequent lesion zone is influenced by the electrode size and shape, the energy algorithm applied by the ablation system, vessel diameter, vessel wall thickness, and blood flow rates. The spacing between the ablation points facilitates the blending or separation of the individual lesion zones in the vessel wall and the perivascular space. In accordance with several embodiments, increasing the space between ablation points reduces (e.g., minimizes) lesion zone blending while decreasing the space between ablation points increases (e.g., maximizes) lesion zone blending. When creating a lesion zone for disruption of nerves surrounding a vessel it is desirous to reduce (e.g., minimize) the lesion zone within the vessel wall and increase (e.g., maximize) the lesion zone in the perivascular space. Optimization of lesion zone blending increases the likelihood of a 360 degree (or near 360 degree) circumferential perivascular lesion zone while reducing the likelihood of circumferential vessel wall injury along the length of the treated vessel, thereby avoiding vascular stenosis. The frequency of 360 degree circumferential perivascular ablation zones along the length of the vessel can be increased while holding the vessel wall injury constant by reducing the distance between the ablation points from 8 mm or more (e.g., 8 mm, 9 mm, 10 mm, 11 mm, 12 mm) to 6 mm or less (e.g., 6 mm, 5 mm, 4 mm, 3 mm, 2 mm) within a vessel diameter range while holding the electrode diameter and length (e.g., electrode area of between 3 $mm^2$ and 16 $mm^2$ (e.g., between 3 $mm^2$ and 6 $mm^2$, between 4 $mm^2$ and 8 $mm^2$, between 4 $mm^2$ and 10 $mm^2$, between 6 $mm^2$ and 8 $mm^2$, between 8 $mm^2$ and 12 $mm^2$, between 10 $mm^2$ and 16 $mm^2$, 4 $mm^2$, 6 $mm^2$, 8 $mm^2$, 10 $mm^2$, overlapping ranges thereof or any value of or within the recited ranges) and energy algorithm constant (e.g., from 500 J/ablation point to 2000 J/ablation point, from 500 J/ablation point to 1000 J/ablation point, 1000 J/ablation point to 2000 J/ablation point, 500 J/ablation point, 1000 J/ablation point, 1200 J/ablation point, 1600 J/ablation point, 2000 J/ablation point). In accordance with several embodiments, the pattern (including point spacing, electrode size, energy algorithm, circumferential offset) is configured to produce ratios of circumferential perivascular injury to circumferential vessel wall injury of greater than or equal to 2:1 (e.g., 5:1, 4:1, 3:1, 2:1). In some embodiments, the pattern may also include level of contact (such as indentation depth or contact force). For example, indentation depth may range from 0-1 mm (e.g., 0.1 mm to 0.3 mm, 0.2 mm to 0.4 mm, 0.3 mm to 0.6 mm, 0.4 mm to 0.8 mm, 0.6 mm to 1 mm, overlapping ranges thereof or any value of or within the recited ranges). Contact force may range from 1 to 15 grams of force (gmf) (e.g., between 1 and 5 gmf, between 5 and 10 gmf, between 10 and 15 gmf, overlapping ranges thereof or any value of or within the recited ranges). In some embodiments, each ablation point is offset by 180 degrees. In other embodiments, the circumferential offset is between 90 and 180 degrees (e.g., between 90 and 130 degrees, between 100 and 140 degrees, between 110 and 160 degrees, between 130 and 180 degrees, overlapping ranges thereof or any value of or within the recited ranges).

One embodiment of a treatment configuration in a treatment vessel, such as the common hepatic artery, is to treat two or more zones (e.g., two, three, four, five, six, more than six zones by ablating at two or more locations (e.g., two, three, four, five, six, seven, eight, nine, ten, six to eight, four to eight, more than ten locations) that are longitudinally and/or rotationally spaced from each other. In some instances it may be advantageous to treat two or more zones wherein adjacent zones are both longitudinally and rotationally spaced from each other, such as shown in FIG. 37A. Such a series of treatment zones may be created with single electrode embodiments, by manipulations of the electrode both longitudinally and rotationally. In some cases it may be desirable to include two or more electrodes that tend to align along opposing quadrants (or sides) of the lumen of treatment vessel. This may be particularly beneficial if multiple non-overlapping treatment zones, such as described in FIG. 37A, are desired.

In accordance with several embodiments, the systems and methods described herein utilize a single electrode, two electrodes or four electrodes having a size and shape and energy delivery parameters that affect on average 5-30% (e.g., 5-10%, 10-15%, 15-20%, 20-25%, 25%-30% or overlapping ranges thereof) of the vessel wall circumference (e.g., common hepatic artery wall circumference) and between 40% and 80% (e.g., 40-60%, 45-55%, 50-60%, 60-85%, or overlapping ranges thereof) of perivascular circumference at depths of about 5 mm, thereby impacting a large number of nerves per ablation (by achieving larger ablation zones) while using fewer total ablations within the patient's artery to achieve a desired treatment effect. Because the length of the common hepatic artery is only 30 mm on average, for embodiments targeting the common hepatic artery the number of ablations that can be performed over the length of the common hepatic artery is constrained. Accordingly, it is advantageous to reduce the number of ablations and increase the effectiveness of the ablations when targeting this anatomy while still reducing or limiting damage to the vessel wall. In accordance with several embodiments, RF ablation catheters described herein maintain proper contact conditions to initiate or complete energy cycles required for successful ablations, thereby reducing the number of ablation cycles or placement locations despite the constrained vessel length. The number of ablation cycles or placement locations, the spacing of ablation locations, or other parameters may be selected or adjusted based on a desired dose-response rate for a particular vessel or particular treatment. For example, the number of ablation cycles or placement locations (and/or the spacing of the locations) can be selected to be a number (and/or spacing) that correlates with or results in a maximum or full dose-response rate. In some embodiments, a number of ablation cycles or placement locations (and/or the spacing of the locations) is selected to be a number (and/or spacing) that correlates with or results in a less than a maximum or full, but still effective, dose-response rate. The dose-response rate may be determined based on data obtained from prior ablations. In some embodiments, the dose-response rate is determined based on fasting glucose measurements, norepinephrine measurements (e.g., tissue norepinephrine level measurements, tissue impedance measurements, blood sugar levels, triglyceride levels, insulin levels, glucagon levels, lipid levels, gastrointestinal hormone levels, or combinations of two, three or more factors, parameters, measurements or characteristics). The various treatment (e.g., ablation) parameters may also be selected or adjusted based on dose-response rate for vessels other than the common hepatic artery. In some embodiments, increasing the number of ablations for a particular lesion spacing increases the dose-response rate.

FIGS. 38A and 38B illustrate an embodiment of a treatment catheter 3800 and positioning method that incorporates use of lesion spacing indicators, or markers 3802, to aid in the positioning of the treatment catheter 3800 when it is desired to position the treatment catheter 3800 at multiple locations to create multiple treatment zones, for example as shown in FIGS. 37A and 37B. The lesion spacing indicators and technique described could be incorporated into any embodiment of neuromodulation device (e.g., treatment catheter, ablation catheter or device) described herein, whereby the neuromodulation device (e.g., treatment catheter) would be repositioned to create multiple treatment zones 3804. The treatment catheter 3800 includes multiple electrodes 3805 (in this case, two electrodes) that, when in the deployed configuration, are longitudinally spaced by a separation distance of L, and contact the vessel on opposing sides of the vessel (e.g., offset by about 180 degrees). The treatment catheter 3800 may include two lesion spacing indicators 3802, and may be secured on the distal end portion of the treatment catheter 3800 distally of the electrodes 3805. The spacing of the lesion spacing indicators 3802 may be of a predetermined relationship to the longitudinal spacing (when deployed) of the electrodes 3805. In this case, the spacing of the lesion spacing indicators 3802 is twice the length L (or 2 L). As shown, the treatment catheter 3800 includes one electrode on a deflectable portion and one electrode on a non-deflectable portion; however, in other embodiments, both electrodes 3805 may be positioned along a deflectable portion or along a non-deflectable portion.

In use, the treatment catheter 3800 can be positioned within a desired treatment vessel with the aid of fluoroscopic angiographic imaging. Once positioned at a desired first location within the vessel (for example as shown in FIG. 38A), the electrodes 3805 are activated to create a first set of treatment zones 3804A, such as lesion zones, at contact locations of the electrodes 3805 with the vessel wall. The treatment catheter 3800 is re-positioned to a second location (in this case withdrawn) by positioning the distal lesion spacing indicator 3802B where the proximal lesion spacing indicator 3802A was previously. Once deployed, the electrodes 3805 are activated a second time to create a second set of treatment zones 3804B (as shown in FIG. 38B). In this manner, four relatively equally spaced treatment zones, on alternating opposing sides of the vessel are created.

When the treatment catheter 3800 is in the first position (e.g., the position shown in FIG. 38A), it may also be advantageous if a corresponding anatomic landmark is noted on the fluoroscopic or angiographic image (for example, a side branch adjacent the proximal marker 3802A). If a "roadmap" is created from this first angiographic image, the treatment catheter 3800 can be repositioned to the second location with only the use of fluoroscopic imaging "on top" of the roadmap, without the need of additional contrast delivery. The radiopaque markers 3802 can also be useful in the case of digital subtraction angiography. In this embodiment, a ghost image of the lesion spacing indicators 3802 can be created when the treatment catheter 3800 is in its first location. Repositioning to the second location can be accomplished without need of additional contrast delivery.

While two lesion spacing indicators, such as radiopaque marker bands, distal of the electrodes 3805 have been described, it is contemplated that the lesion spacing indicators could also be proximal of the electrodes, one of the electrodes 3805 could also be used as one of the lesion spacing indicators, as long as the electrode is fluoroscopically visible. Portions of the catheter shaft that incorporate radio dense materials could also be used. In some embodiments, one of the lesion spacing indicators is positioned distal of the electrodes 3805 and the other one of the lesion spacing indicators is positioned proximal of the electrodes 3805. In one embodiment, the lesion spacing indicators may be positioned within a balloon of the treatment catheter 3800, distal of the balloon, and/or proximal of the balloon.

In the above embodiment in which two electrodes when deployed are in a longitudinally spaced arrangement, but on opposing sides of the vessel, the lesion indicator spacing is advantageously twice the electrode spacing. However, in some embodiments in which the deployed electrodes may be longitudinally spaced, but on the same side of the vessel, the spacing between the lesion spacing indicators is advantageously equal to the spacing or half the spacing between the electrodes. The spacing between the electrodes may vary depending on vessel diameter. In other embodiments, the first two lesion zones 3804A are on the same side of the vessel and the second two lesion zones 3804B are on the opposite side of the vessel, with the treatment catheter 3800 being rotated to the opposite side of the vessel and positioned such that the distal electrode is positioned axially between the first two lesion zones 3804A, as may be determined by a spacing between and positioning of the lesion spacing indicators.

In accordance with several embodiments, controlled electrode deployment is desired to achieve consistent electrode positioning, contact force and orientation. Various means for controllably releasing and recovering multiple elastic or deformable electrode support members are described herein. In several embodiments, the means for controllable releasing and recovering electrodes functions even when an electrode is very close to (e.g., within 5 mm) a distal terminus of a guide catheter.

Energy Delivery Parameters

In some embodiments, an RF energy delivery system delivers RF energy waves of varying duration. In some embodiments, the RF energy delivery system varies the amplitude of the RF energy. In other embodiments, the RF energy delivery system delivers a plurality of RF wave pulses. For example, the RF energy delivery system may deliver a sequence of RF pulses. In some embodiments, the RF energy delivery system varies the frequency of RF energy. In other embodiments, the RF energy delivery system varies any one or more parameters of the RF energy, including, but not limited to, duration, amplitude, frequency, and total number of pulses or pulse widths. For example, the RF energy delivery system can deliver RF energy selected to most effectively modulate (e.g., ablate or otherwise disrupt) sympathetic nerve fibers in the hepatic plexus. In some embodiments, the frequency of the RF energy is maintained at a constant or substantially constant level.

In some embodiments, the frequency of the RF energy is between about 50 kHz and about 20 MHz, between about 100 kHz and about 2.5 MHz, between about 400 kHz and about 1 MHz, between about 50 kHz and about 5 MHz, between about 100 kHz and about 10 MHz, between about 500 kHz and about 15 MHz, less than 50 kHz, greater than 20 MHz, between about 3 kHz and about 300 GHz, or overlapping ranges thereof. Non-RF frequencies may also be used. For example, the frequency can range from about 100 Hz to about 3 kHz. In some embodiments, the amplitude of the voltage applied is between about 1 volt and 1000 volts, between about 5 volts and about 500 volts, between about 10 volts and about 200 volts, between about 20 volts and about 100 volts, between about 1 volt and about 10 volts, between about 5 volts and about 20 volts, between about 1 volt and about 50 volts, between about 15 volts and 25 volts, between about 20 volts and about 75 volts, between about 50 volts and about 100 volts, between about 100 volts and about 500 volts, between about 200 volts and about 750 volts, between about 500 volts and about 1000 volts, less than 1 volt, greater than 1000 volts, or overlapping ranges thereof.

In some embodiments, the current of the RF energy ranges from about 0.5 mA to about 500 mA, from about 1 mA to about 100 mA, from about 10 mA to about 50 mA, from about 50 mA to about 150 mA, from about 30 mA to about 400 mA, from about 100 mA to about 300 mA, from about 250 mA to about 400 mA, from about 300 to about 500 mA, or overlapping ranges thereof. The current density of the applied RF energy can have a current density between about 0.01 mA/cm$^2$ and about 100 mA/cm$^2$, between about 100 mA/cm$^2$ and about 10 A/cm$^2$, between about 0.1 mA/cm$^2$ and about 50 mA/cm$^2$, between about 0.2 mA/cm$^2$ and about 10 mA/cm$^2$, between about 0.3 mA/cm$^2$ and about 5 mA/cm$^2$, less than about 0.01 mA/cm$^2$, greater than about 100 mA/cm$^2$, or overlapping ranges thereof. In some embodiments, the power output of the RF generator ranges between about 0.1 mW and about 100 W, between about 1 mW and 100 mW, between about 1 W and 10 W, between about 1 W and 15 W, between 5 W and 20 W, between about 10 W and 50 W, between about 25 W and about 75 W, between about 50 W and about 90 W, between about 75 W and about 100 W, or overlapping ranges thereof. In some embodiments, the total RF energy dose delivered at the target location (e.g., at an inner vessel wall, to the media of the vessel, to the adventitia of the vessel, or to the target nerves within or adhered to the vessel wall) is between about 100 J and about 4000 J, between about 100 J and about 2000 J, between about 150 J and about 500 J, between about 300 J and about 800 J (including 500 J), between about 500 J and about 1000 J, between about 800 J and about 1200 J, between about 1000 J and about 1500 J, and overlapping ranges thereof. In some embodiments, the impedance ranges from about 100 ohms to about 1500 ohms, from about 10 ohms to about 600 ohms, from about 100 ohms to about 300 ohms, from about 50 ohms to about 200 ohms, from about 200 ohms to about 500 ohms, from about 300 ohms to about 600 ohms, and overlapping ranges thereof. In some embodiments, power is provided between 8 W and 14 W (e.g., 10 W, 12 W) for between 30 seconds and 3 minutes (e.g., 30 seconds, 1 minute, 90 seconds, 2 minutes, 150 seconds, 180 seconds) to provide a total energy delivery of between 240 J and 2520 J (e.g., 1200 J-10 W for 2 minutes, 1500 J-12 W for 2 minutes). Electrode(s) may be coupled (e.g., via wired or wireless connection) to an energy source (e.g., generator) even if the generator is not explicitly shown or described with each embodiment. The various treatment parameters listed herein (e.g., power, duration, energy, contact force/pressure, electrode size, pulsing, resistance, etc.) may be used for any of the embodiments of devices (e.g., catheters) or systems described herein.

In various embodiments, the generator comprises stored computer-readable instructions that, when executed, provide specific treatment (e.g., custom energy algorithm) to treat specific vessels selected by an operator. Accordingly, the generator facilitates delivery of RF energy having different treatment parameters using a single RF energy delivery device configured to provide similar or consistent performance across varying patient anatomy (e.g., one-size-fits-all). The generator may comprise safety controls tailored to environment: vessel size, flow, resistance, and/or other structures. The stored computer-readable instructions (e.g., software, algorithms) may be customized to deliver optimized lesion depth and/or may comprise pre-programmed operator-independent treatment algorithms. In some embodiments, a pre-programmed treatment course, which may include one or more parameters (such as power, treatment duration, number of target locations, spacing of target locations, energy, pulsed or non-pulsed, etc.) is provided. The pre-programmed treatment course may be based on vessel dimensions (e.g., diameter, segment length, wall thickness, age of patient, weight of patient, etc.). In one embodiment, a preconfigured or predetermined course of neuromodulation (e.g., ablation) may be performed (e.g., automatically or manually) to modulate (e.g., ablate) one or more nerves. The predetermined treatment course or profile may comprise a full or partial route of treatment or treatment points. The route may extend around a partial circumference of a blood vessel (e.g., 270 degrees, 220 degrees, 180 degrees, 90 degrees, or 60 degrees) or around the entire circumference.

For example, in some patients a target modulation (e.g., ablation) location (such as the common hepatic artery) may not be long enough to allow for complete modulation (e.g., ablation) of target nerves. In some embodiments, it may be desirable to treat multiple vessels adjacent to or that are portions of the hepatic artery vasculature (e.g., celiac, splenic, common hepatic, proper hepatic arteries) using a single energy delivery device. In some embodiments, an operator may select a vessel to be treated and the generator may automatically adjust the energy delivery parameters (e.g., select a pre-determined energy algorithm) based on the selected vessel. For example, different vessels may have different flow characteristics and different diameters. Accordingly, different energy profiles (e.g., varying power and/or time) may be associated with the different vessels to achieve a desired overall energy output. In ablation embodiments, the different energy profiles provide the same volume and/or circumferential arc of lesion for the various different vessels. The delivery of energy may be controlled manually or automatically according to a preconfigured energy profile determined by a controller, processor or other computing device (e.g., based on execution of instructions stored in memory) within the generator. For example, if the nominal vessel diameter (e.g., common hepatic artery) is greater than an adjacent vessel diameter, the power level and time can be adjusted lower as there will be a greater area of contact between the vessel wall and electrode surface. In some embodiments, the allowable temperature target or limit may be adjusted higher to compensate for a lower capacity of the blood flow to remove heat from the electrode. If the adjacent artery is larger, then power may be increased to modulate (e.g., ablation) a larger area in a single cycle. In some embodiments, a tendency towards more modulation (e.g., ablation) sites in the larger adjacent vessel may be employed.

In some embodiments, the energy output from the RF energy source (e.g., generator) may be modulated using constant temperature mode. Constant temperature mode turns the energy source on when a lower temperature threshold is reached and turns the energy source off when an upper temperature threshold is reached (similar to a thermostat). In some embodiments, an ablation catheter system using constant temperature mode requires feedback, which, in one embodiment, is provided by a temperature sensor. In some embodiments, the ablation catheter system comprises a temperature sensor that communicates with energy source (e.g., RF generator). In some of these embodiments, the energy source begins to deliver energy (e.g., turn on) when the temperature sensor registers that the temperature has dropped below a certain lower threshold level, and the energy source terminates energy delivery (e.g., turns off) when the temperature sensor registers that the temperature has exceeded a predetermined upper threshold level.

In some embodiments, the energy output from an energy delivery system may be modulated using a parameter other than temperature, such as tissue impedance. Tissue impedance may increase as tissue temperature increases. Impedance mode may be configured to turn the energy source on when a lower impedance threshold is reached and turn the energy source off when an upper impedance threshold is reached (in the same fashion as the constant temperature mode responds to increases and decreases in temperature). An energy delivery system using constant impedance mode may include some form of feedback mechanism, which, in one embodiment, is provided by an impedance sensor. In some embodiments, impedance is calculated by measuring voltage and current and dividing voltage by the current.

In some embodiments, a catheter-based energy delivery system comprises a first catheter with a first electrode and a second catheter with a second electrode. The first catheter is inserted within a target vessel (e.g., the common hepatic artery) and used to deliver energy to modulate nerves within the target vessel. The second catheter may be inserted within an adjacent vessel and the impedance can be measured between the two electrodes. For example, if the first catheter is inserted within the hepatic arteries, the second catheter can be inserted within the bile duct or the portal vein. In some embodiments, a second electrode is placed on the skin of the subject and the impedance is measured between the second electrode and an electrode of the catheter-based energy delivery system. In some embodiments, the second electrode may be positioned in other locations that are configured to provide a substantially accurate measurement of the impedance of the target tissues.

In some embodiments, the impedance measurement is communicated to the energy source (e.g., pulse generator). In some embodiments, the energy source begins to generate a pulse (i.e., turns on) when the impedance registers that the impedance has dropped below a certain lower threshold level, and the energy source terminates the pulse (i.e., turns off) when the impedance registers that the impedance has exceeded a predetermined upper threshold level.

In some embodiments, the energy output of the energy delivery system is modulated by time. In such embodiments, the energy source of the energy delivery system delivers energy for a predetermined amount of time and then terminates energy delivery for a predetermined amount of time. The cycle may repeat for a desired overall duration of treatment. In some embodiments, the predetermined amount of time for which energy is delivered and the predetermined amount of time for which energy delivery is terminated are empirically optimized lengths of time. In accordance with several embodiments, controlling energy delivery according to impedance and reducing energy delivery when impedance approaches a threshold level (or alternatively, modulating energy in time irrespective of impedance levels) advantageously provides for thermal energy to be focused at locations peripheral to the vessel lumen. For example, when the energy pulse is terminated, the vessel lumen may cool rapidly due to convective heat loss to blood, thereby protecting the endothelial cells from thermal damage. In some embodiments, the heat in the peripheral tissues (e.g., where the targeted nerves are located) dissipates more slowly via thermal conduction. In some embodiments, successive pulses tend to cause preferential heating of the peripheral (e.g., nerve) tissue. In accordance with several embodiments, when the impedance of tissue rises due to vaporization, electrical conductivity drops precipitously, thereby effectively preventing or inhibiting further delivery of energy to target tissues. In some embodiments, by terminating energy pulses before tissue impedance rises to this level (e.g., by impedance monitoring or time modulation), this deleterious effect may be avoided. In accordance with several embodiments, char formation is a consequence of tissue vaporization and carbonization, resulting from rapid increases in impedance, electrical arcing, and thrombus formation. By preventing or inhibiting impedance rises, charring of tissue may be avoided.

In some embodiments, total energy delivery is monitored by calculating the time integral of power output (which may be previously correlated to ablation characteristics) to track the progress of the therapy. In some embodiments, the relationship between temperature, time, and electrical field is monitored to obtain an estimate of the temperature field within the tissue surrounding the ablation electrode using the Arrhenius relationship. In some embodiments, a known thermal input is provided to the ablation electrode, on demand, in order to provide known initial conditions for assessing the surrounding tissue response. In some embodiments, a portion of the ablation region is temporarily cooled, and the resultant temperature is decreased. For example, for an endovascular ablation that has been in progress for a period of time, it may be expected that there is some elevated temperature distribution within the tissue. If a clinician wants to assess the progress of the therapy at a given time (e.g., $t_0$), the energy delivery can be interrupted, and cooled saline or gas can be rapidly circulated through the electrode to achieve a predetermined electrode temperature within a short period of time (e.g., about 1 second). In some embodiments, the resulting temperature rise (e.g., over about 5 seconds) measured at the electrode surface is then a representation of the total energy of the surrounding tissue. This process can be repeated through the procedure to track progress.

In some embodiments, a parameter, such as temperature, infrared radiation, or microwave radiation can be monitored to assess the magnitude of energy delivered to tissue, and thus estimate the degree of neuromodulation induced. Both the magnitude of thermal radiation (temperature), infrared radiation, and/or microwave radiation may be indicative of the amount of energy contained within a bodily tissue. In some embodiments, the magnitude is expected to decrease following the completion of the ablation as the tissue cools back towards body temperature, and the rate of this decrease, measured at a specific point (e.g., at the vessel lumen surface) can be used to assess the size of the ablation (e.g., slower decreases may correspond to larger ablation sizes). Any of the embodiments described herein may be used individually or in combination to indicate the actual size of the tissue lesion zone.

Electrode tip temperature control is often used as a control variable and treatment progress indicator for ablation procedures, particularly endovascular and/or cardiac ablation procedures. One potential problem with this approach is that although the goal is to treat tissue at a certain depth into the tissue, the temperature sensing element (thermocouple or thermistor) is generally only able to measure the surface temperature of the cardiac or vascular tissue. Furthermore, due to temperature gradients within the electrode itself, the temperature sensing element tends to measure the bulk temperature of the electrode, rather than precisely measure the surface temperature, which is often strongly influenced by the degree of convective blood flow about the electrode, which is typically about 37° C.

In some embodiments, a power-controlled ablation algorithm may be employed instead of a temperature-controlled algorithm because the temperature at the electrode(s) is not always a good indicator of the maximum temperature reached within the tissue. Since the electrode(s) is in contact with the blood, its temperature is not expected to rise significantly beyond 37° C., and may be considerably lower than the temperature within the tissues. Electrode temperature can be used to detect complications during RF ablation treatments of the hepatic artery. For example, if the electrode temperature rises too much (for example, above 80° C.), this may be a sign that something unexpected has happened (for instance, a hole has been formed in the arterial wall and the electrode is inserted directly in the tissue, or alternatively, thrombus formation). In several embodiments, electrode temperature monitoring provides an additional layer of control redundancy to ensure procedure safety, but it may not be used as a primary feedback variable to control RF energy.

During application of RF energy, the change in impedance as the tissue temperature increases should be close (e.g., within a 30% tolerance range) to the impedance-temperature curve, where an increase in tissue temperature should correspond to a slight decrease in impedance. If the impedance decreases too much (e.g., >30% from the curve), the electrode may not be in contact with the arterial wall and instead may be in substantial direct communication with the blood, which has a significantly lower resistivity. In this situation, the catheter is repositioned to ensure good contact with the arterial wall.

If the impedance remains higher than expected, the tissue may need to be heated further by increasing the RF power level. Alternatively, if the impedance is much higher than expected (e.g., higher than about 200-300Ω), this is likely to indicate formation of thrombus. In such case, the ablations are immediately aborted, as tissue thrombus causes the ablation to become unpredictable and unsafe.

Figure 39:
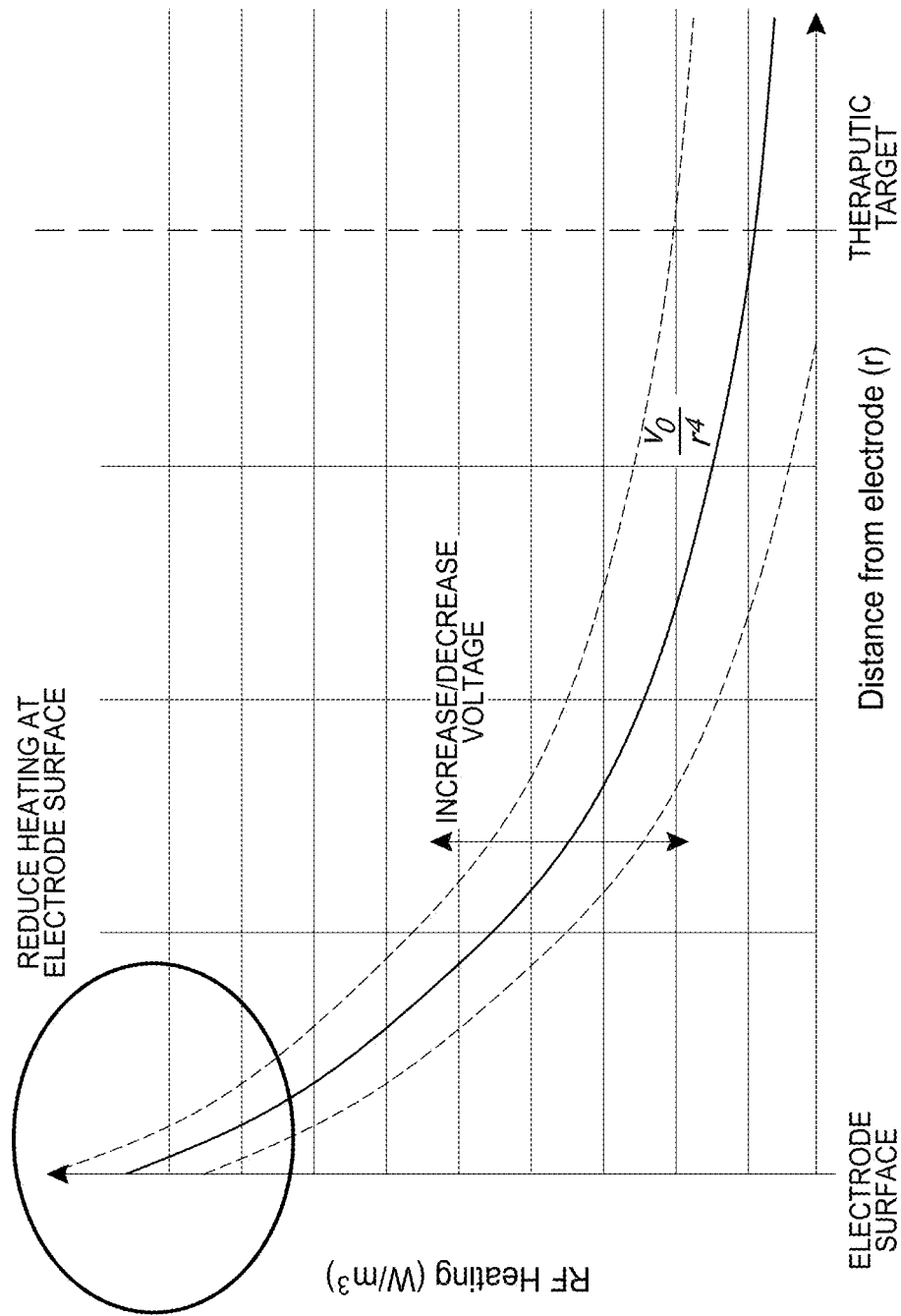
FIG. 39 illustrates a graph of RF heating versus distance from the electrode.

In accordance with several embodiments, electrode and vessel wall temperature are carefully monitored and controlled during vessel ablation. Depth of ablation may be monitored. In several embodiments, temperatures at the arterial wall are limited or reduced to avoid vessel spasm, thrombus formation, and stenosis. The ability to affect the convective cooling of the electrode and contacted tissue can be particularly advantageous in various embodiments. Electrode temperature can affect the depth of the lesion. In some embodiments, a main mechanism affecting electrode cooling is convective cooling from blood flow past the electrode and contacted vessel wall. Ablation of the renal artery has a flow rate of 550 mL/min. Flow through the common hepatic artery is ~100-200 mL/min (e.g., 150 mL/min), which is much slower than typical flow rates in renal arteries (~550 mL/min), where ablations have been performed with minimal or no electrode cooling. Because of the low and/or variable flow rate within the hepatic arteries, methods and systems aimed at increasing electrode cooling are provided herein. FIG. 39 illustrates an example of challenges of endovascular ablation given the reduced flow rates in the common hepatic artery. FIG. 39 illustrates a plot of the reduction in RF heating as the distance from the electrode surface increases. In some embodiments, reduced heating at the electrode surface requires a reduction in overall power, which can result in reduced heating at the therapeutic target (e.g., hepatic nerves, renal nerves or other peripheral nerves).

The RF energy can be pulsed or continuous. The voltage, current density, frequencies, treatment duration, power, and/or other treatment parameters can vary depending on whether continuous or pulsed signals are used. For example, the voltage or current amplitudes may be significantly increased for pulsed RF energy. The duty cycle for the pulsed signals can range from about 0.0001% to about 100%, from about 0.001% to about 100%, from about 0.01% to about 100%, from about 0.1% to about 100%, from about 1% to about 10%, from about 5% to about 15%, from about 10% to about 50%, from about 20% to about 60% from about 25% to about 75%, from about 50% to about 80%, from about 75% to about 100%, or overlapping ranges thereof. The pulse durations or widths of the pulses can vary. For example, in some embodiments, the pulse durations can range from about 10 microseconds to about 1 millisecond; however, pulse durations less than 10 microseconds or greater than 1 millisecond can be used as desired and/or required. In accordance with some embodiments, the use of pulsed energy may facilitate reduced temperatures, reduced treatment times, reduced cooling requirements, and/or increased power levels without risk of increasing temperature or causing endothelial damage due to heating. In some embodiments involving use of a catheter having a balloon, the balloon can be selectively deflated and inflated to increase lumen wall cooling and enhance the cooling function that pulsed energy provides.

The treatment time durations can range from 1 second to 1 hour, from 5 seconds to 30 minutes, from 10 seconds to 10 minutes, from 30 seconds to 30 minutes, from 1 minute to 20 minutes, from 1 minute to 3 minutes, from 2 to four minutes, from 5 minutes to 10 minutes, from 10 minutes to 40 minutes, from 30 seconds to 90 seconds, from 5 seconds to 50 seconds, from 60 seconds to 120 seconds, overlapping ranges thereof, less than 1 second, greater than 1 hour, about 120 seconds, or overlapping ranges thereof. The duration may vary depending on various treatment parameters (e.g., amplitude, current density, proximity, continuous or pulsed, type of nerve, size of nerve). In some embodiments, the RF or other electrical energy is controlled such that delivery of the energy heats the target nerves or surrounding tissue in the range of about 50 to about 90 degrees Celsius (e.g., 60 to 75 degrees, 50 to 80 degrees, 70 to 90 degrees, 60 to 90 degrees or overlapping ranges thereof). In some embodiments, the temperature can be less than 50 or greater than 90 degrees Celsius. The electrode tip energy may range from 37 to 100 degrees Celsius. In some embodiments, RF ablation thermal lesion sizes range from about 0 to about 3 cm (e.g., between 1 and 5 mm, between 2 and 4 mm, between 5 and 10 mm, between 15 and 20 mm, between 20 and 30 mm, overlapping ranges thereof, about 2 mm, about 3 mm) or within one to ten (e.g., one to three, two to four, three to five, four to eight, five to ten) media thickness differences from a vessel lumen (for example, research has shown that nerves surrounding the common hepatic artery and other branches of the hepatic artery are generally within this range). In several embodiments, the media thickness of the vessel (e.g., hepatic artery) ranges from about 0.1 cm to about 0.25 cm.

In some anatomies, at least a substantial portion of nerve fibers of the hepatic artery branches are localized within 0.5 mm to 1 mm from the lumen wall such that modulation (e.g., denervation) using an endovascular approach is effective with reduced power or energy dose requirements.

In some embodiments, an RF ablation catheter is used to perform RF ablation of sympathetic nerve fibers in the hepatic plexus at one or more locations. For example, the RF ablation catheter may perform ablation in a circumferential or radial pattern to ablate sympathetic nerve fibers in the hepatic plexus at one or more locations (e.g., one, two, three, four, five, six, seven, eight, nine, ten, six to eight, four to eight, more than ten locations). Cadaver studies have shown that the hepatic nerves are generally focused in the region defined by the midpoint between the origin of the common hepatic artery and the origin of the gastroduodenal artery, as the nerves tend to approach the arterial lumen along non-branching regions of the artery, and diverge from the arterial lumen in regions of branching. The cadaver studies have also shown that the hepatic nerves predominantly reside within an annulus defined by the lumen of the artery and a concentric ring spaced approximately 4 mm from the arterial lumen. In some embodiments, the number of nerves and the proximity to the arterial lumen of the nerves increases towards the common hepatic artery midpoint. In some embodiments, the sympathetic nerve fibers are advantageously modulated (e.g., ablated) at the midpoint between the origin of the common hepatic artery and the origin of the gastroduodenal artery. In some embodiments, the sympathetic nerve fibers are modulated (e.g., ablated) up to a depth of 4-6 mm, 3-5 mm, 3-6 mm, 2-7 mm) from the lumen of the hepatic artery. In other embodiments, the sympathetic nerve fibers in the hepatic plexus are ablated at one or more points by performing RF ablation at a plurality of points that are linearly spaced along a vessel length. For example, RF ablation may be performed at one or more points linearly spaced along a length of the proper hepatic artery to ablate sympathetic nerve fibers in the hepatic plexus. In some embodiments, RF ablation is performed at one or more locations in any pattern to cause ablation of sympathetic nerve fibers in the hepatic plexus as desired and/or required (e.g., a spiral pattern or a series of linear patterns that may or may not intersect). The ablation patterns can comprise continuous patterns or intermittent patterns. In accordance with various embodiments, the RF ablation does not cause any lasting damage to the vascular wall because heat at the wall is dissipated by flowing blood, by cooling provided external to the body, or by increased cooling provided by adjacent organs and tissue structures (e.g., portal vein cooling and/or infusion), thereby creating a gradient with increasing temperature across the intimal and medial layers to the adventitia where the nerves travel. The adventitia is the external layer of the arterial wall, with the media being the middle layer and the intima being the inner layer. The intima comprises a layer of endothelial cells supported by a layer of connective tissue. The media is the thickest of the three vessel layers and comprises smooth muscle and elastic tissue. The adventitia comprises fibrous connective tissue.

Catheter-Based Vascular Access Systems

The catheter embodiments described herein may be used in conjunction with an over-the-wire, rapid exchange or steerable catheter approach. In some embodiments, a handle or manifold (not shown) is located proximally on the shaft that enables conductive wire connections to the energy source (e.g., RF generator), attachment to a balloon inflation device, and/or access to a guide wire lumen and/or a mechanism to deflect the distal steerable segment.

In a rapid exchange embodiment, a guide wire port may be located 10 to 20 cm proximal of the distal tip. In one embodiment, the guide wire port is constructed to maintain a flexibility transition that is kink resistant while efficiently transferring push force to the distal assembly. Proximal to the guide wire port, the shaft maybe be constructed of a hypotube that is sheathed in polymer and includes an inflation lumen and protects the conductive wires.

In some embodiments, the catheters described herein (e.g., of the neuromodulation catheter system) have a diameter in the range of about 2-8 Fr, about 3-7 Fr, about 4-6 Fr (including about 5 Fr), and overlapping ranges thereof. The catheter (e.g., tube, probe or shaft) may have a varying diameter along its length such that the distal portion of the catheter is small enough to fit into progressively smaller vessels as the catheter is advanced within vasculature. In one embodiment, the catheter has an outside diameter sized to fit within the common hepatic artery (which may be as small as about 1 mm in lumenal diameter) or the proper hepatic artery. In some embodiments, the catheter is at least about 150 cm long, at least about 140 cm long, at least about 130 cm long, at least about 120 cm long, at least about 110 cm long, at least about 100 cm long, at least about 75 cm long, or at least about 90 cm long. In some embodiments, the flexibility of the catheter is sufficient to navigate tortuous hepatic arterial anatomy having bend radii of about 10 mm, about 9 mm, about 8 mm, about 7 mm, about 6 mm, about 5 mm, about 4 mm, about 3 mm, about 2 mm, about 1 mm, or about 0.5 mm.

In accordance with several embodiments, devices of the catheter-based systems described herein have actuatable, expandable, steerable, pre-curved, deflectable and/or flexible distal tip components or distal segments. The deflectability or flexibility may advantageously bias an energy applicator against the arterial wall to ensure effective and/or safe delivery of therapy, permit accurate positioning of the energy applicator, maintain contact of an energy delivery element against a vascular wall, maintain sufficient contact force or pressure with a vascular wall, and/or help navigate the catheter (e.g., neuromodulation catheter) to the target anatomy. In some embodiments, devices (e.g., catheters) with steerable, curvable or articulatable distal portions provide the ability to cause articulation, bending, or other deployment of the distal tip (which may contain an ablation element or energy delivery element) even when a substantial portion of the catheter (e.g., neuromodulation catheter) remains within a guide catheter or guide extension catheter. In some embodiments, the neuromodulation catheters provide the ability to be delivered over a guidewire, as placing guide catheters may be unwieldy and time-consuming to navigate. In some embodiments, the neuromodulation catheters are inserted within the vasculature through guide sheaths or guide extension catheters. In some embodiments, guidewires are not used.

Figure 40:
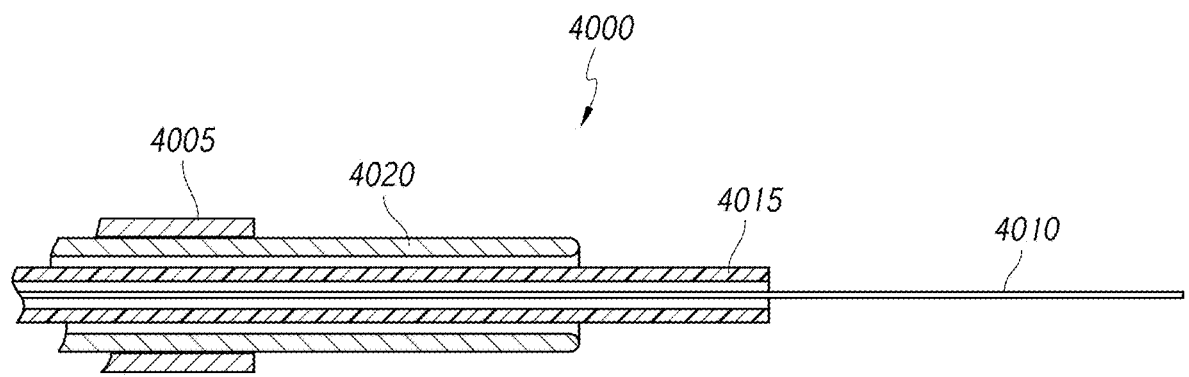
FIG. 40 illustrates an embodiment of a "telescoping" system for facilitating delivery of a low-profile neuromodulation catheter to a hepatic artery branch.

In accordance with several embodiments, catheter-based systems may comprise a guide catheter, a guide extension catheter or support catheter (e.g., a Guidezilla™ catheter or GuideLiner™ catheter), a microcatheter, and/or a guidewire, in addition to a neuromodulation catheter. FIG. 40 illustrates an embodiment of a "telescoping" system 4000 for facilitating delivery of a low-profile neuromodulation catheter to a hepatic artery branch. The "telescoping" system 4000 comprises a guide catheter 4005. In one embodiment, the guide catheter 4005 is a 7 Fr guide catheter that is configured to engage with the inner wall of the celiac artery to provide a stable anchoring and/or reference point. The system 4000 further comprises a guidewire 4010 (e.g., 0.014" guidewire) that may be configured to be delivered through a lumen of the guide catheter 4005 and advanced to a position beyond a target neuromodulation location within a hepatic artery or other vessel or organ. The system 4000 also comprises a microcatheter 4015 (e.g., 4 Fr or less) and a guide extension catheter 4020 (e.g., a 6 Fr guide extension catheter). The guide extension catheter 4020 may be configured to fit and be movable within a lumen of the guide catheter 4005 to provide support at a lower profile (e.g., outer diameter) than the guide catheter 4005. The microcatheter 4015 may be configured to fit and be movable within a lumen of the guide extension catheter 4020 and extend beyond a distal end of the guide extension catheter 4020. The microcatheter 4015 may facilitate tracking and advancement of the guide extension catheter 4020 over the guidewire 4010. In some embodiments, the microcatheter 4015 comprises a rapid exchange microcatheter. The guidewire 4010 may provide a "rail" to aid catheter tracking and lessen the risk of vessel damage when advancing a neuromodulation device.

In some embodiments, the guide catheter 4005 and/or the guide extension catheter 4020 comprises an expandable portion that is configured to be advanced to a desired location and then expanded before or during advancement of a neuromodulation device through the guide extension catheter 4020 or the guide catheter 4005. The expandable portion may enable transitory, or temporary, expansion of vessel inner diameters. In one embodiment, the expandable portion may be formed of multiple layers that slide over each other. In one embodiment, the expandable portion may be formed of a cylinder with interrupted longitudinal cuts and encapsulated by an elastic layer that keeps the cuts compressed in an unexpanded state. The expandable portion may provide stabilization or anchoring. Stabilization mechanisms (in addition to or instead of the expandable portion) may be provided at various locations along a length of the guide catheter 4005 and/or the guide extension catheter 4020 (e.g., balloons, ribbons, wires). In some embodiments, portions of the guide catheter 4005 or guide extension catheter 4020 may be stiffened after introduction of the neuromodulation device to provide stability and maintenance of positioning during neuromodulation procedures. In some embodiments, the "telescoping" system 4000 does not comprise a guidewire, as the guide extension catheter 4020 may obviate the need for a guide wire.

In some embodiments, the system 4000 may include a flexible introducer that provides a tapered transition between the guidewire 4010 and the guide catheter 4005 or guide extension catheter 4020, thereby facilitating access to the tortuous hepatic artery vasculature. The flexible introducer may replace the microcatheter 4015 and/or guide extension catheter 4020. In some embodiments, the flexible introducer comprises elastic or shape-memory materials such as nitinol or low durometer Pebax®. The flexible introducer may have a coil cut pattern or a torque converter or flexure cut pattern or a metallic coil may be encapsulated within the flexible introducer. Portions of the guide catheter 4005, guide extension catheter 4020 and/or microcatheter 4015 may be deflectable and/or steerable. The mechanisms for deflection and/or steering may comprise any of the deflection or steering mechanisms described herein (e.g., tension wire, hydraulics, magnetism, and/or the like). In some embodiments, portions of the guide catheter 4005, guide extension catheter 4020 and/or microcatheter 4015 are plastically deformable and/or shape set to provide deformability within vasculature, thereby functioning as accessory devices configured to fit unique and patient-specific anatomy.

Figure 41:
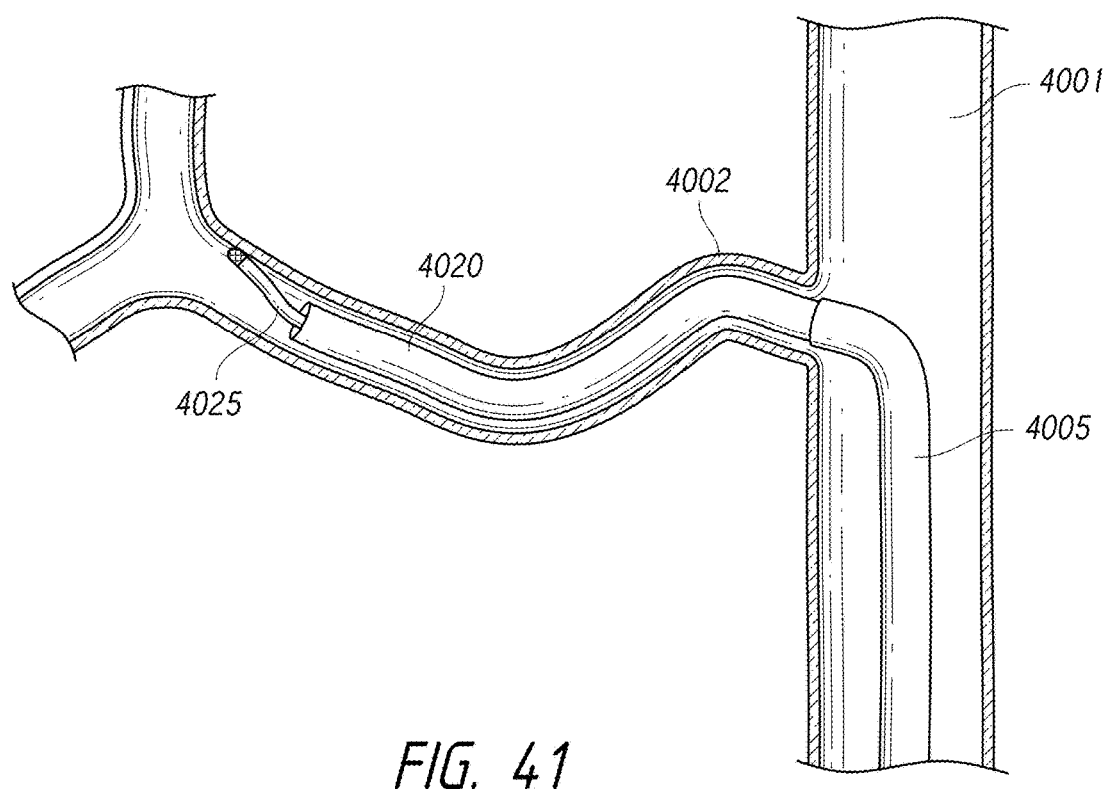
FIG. 41 illustrates an embodiment of use of the system of FIG. 39 to access a target neuromodulation location within a hepatic artery.

FIG. 41 illustrates an embodiment of use of the system of FIG. 40 to access a target neuromodulation location within a hepatic artery. The guide catheter 4005 is advanced to a position within an abdominal aorta 4001 or at an origin of the celiac artery 4002 off the abdominal aorta 4001. In some embodiments, the guidewire 4010 and microcatheter 4015 are then advanced to a position at or adjacent the target neuromodulation location and the guide extension catheter 4020 is advanced over the microcatheter 4015 to the target neuromodulation location. The guide extension catheter 4020 may be advanced over either the guidewire 4010 alone or over the microcatheter 4015 (which in turn is advanced over the guidewire 4010). FIG. 41 illustrates the system 4000 after the guidewire 4010 and/or microcatheter 4015 have been removed. FIG. 41 also illustrates an embodiment of a neuromodulation device 4025 advanced to the target neuromodulation location within the hepatic artery through the guide extension catheter 4020. In some embodiments, a guidewire 4010 or microcatheter 4015 may not be used and the guide extension catheter 4020 may be advanced beyond the target neuromodulation location and the neuromodulation device 4025 advanced to the target neuromodulation location and then the guide extension catheter 4020 is withdrawn to unsheathe the neuromodulation device 4025. In accordance with several embodiments, the guide extension catheter 4020 may facilitate torqueing of the neuromodulation device 4025 so as to allow for rotation of the neuromodulation device 4025 to multiple or all quadrants of the hepatic artery or other target vessel. In some embodiments, the guide extension catheter 4020 is removed following the initial "deployment" of the neuromodulation device 4025. Fluid (e.g., cooling fluid, contrast or selective dye) may be infused through the guide catheter 4005 or guide extension catheter 4020 during neuromodulation (e.g., ablation).

In some embodiments, the guide extension catheter 4020, or other access device within which the neuromodulation device 4025 is advanced, is configured to maintain a tight clearance between the inner diameter of the guide extension catheter 4020 or other access device and the outer diameter of the neuromodulation device 4025. For example, the inner diameter may have a low friction surface or coating and/or structures (e.g., raised ribs of a compliant material such as silicone) that reduce the number of contact points and provide an inward radial force against the outer surface of the neuromodulation device that run along the length of the guide extension catheter 4020 or other access device and are coated with a low-friction coating, such as a hydrophilic coating. The enhanced support along the flexible length of the neuromodulation device may allow the neuromodulation device to be more accurately flexed and may support increased torque efficiency.

Movement of the guide catheter 4005 or guide extension catheter 4020 may disturb the position of the neuromodulation device. For example, movement of the guide catheter 4005 or guide extension catheter 4020 may cause an electrode of an RF energy delivery device delivered through a lumen of the guide catheter 4005 or guide extension catheter 4020 to move due to friction between the devices. Accordingly, in some embodiments, anchoring the catheter 4005 or guide extension catheter 4020 may advantageously minimize or reduce movement artifacts.

Figure 42B:
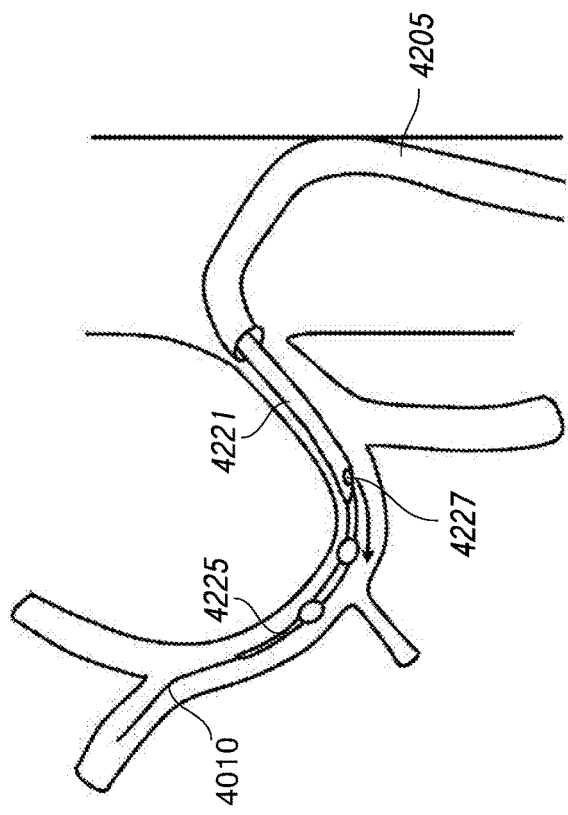
FIGS. 42A and 42B illustrate embodiments of a vascular access system comprising a guide sheath or captive sleeve.
Figure 42A:
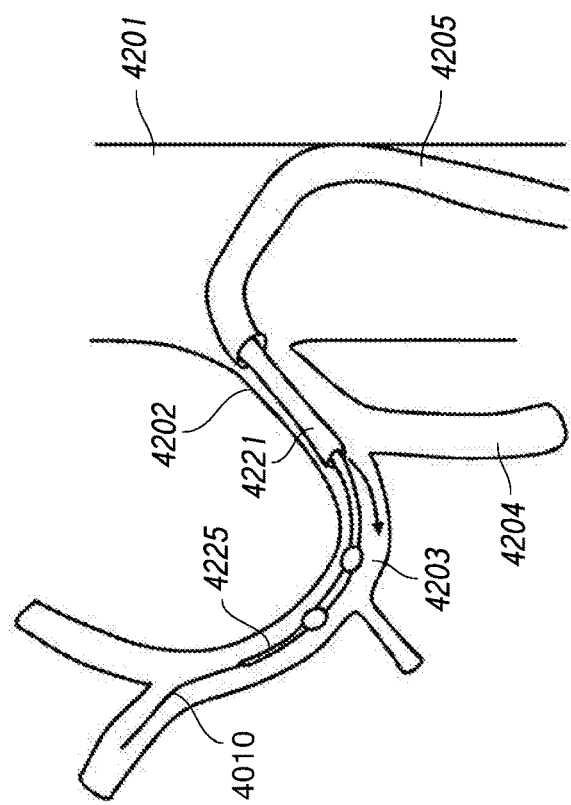

FIGS. 42A and 42B illustrate embodiments of a catheter-based vascular access system comprising a guide sheath or captive support sleeve 4221 to provide additional support to the shaft of a neuromodulation device 4225 (e.g., electrode treatment catheter). Similar to the systems described above in connection with FIGS. 40 and 41, the system comprises a guide catheter 4205 adapted to be advanced through the abdominal aorta 4201 to a location where the celiac artery 4202 branches off from the abdominal aorta 9501 (e.g., an ostium of the celiac artery). The guide sheath or captive support sleeve 4221 extends out of an open distal end of the guide catheter 4205. In the illustrated embodiment, the captive support sleeve 4221 has a length that corresponds to the length of the celiac artery 4202 from the abdominal aorta 4201 to the junction of the common hepatic artery 4203 and the splenic artery 4204. FIG. 42A illustrates a neuromodulation device 4225 comprising an over-the-wire RF energy delivery catheter having two spaced-apart electrodes positioned along a shaft of the catheter. The two spaced-apart electrodes are positioned such that at least one of the electrodes is in contact with an inner wall of the common hepatic artery 4203 for ablation. The electrodes may both be positioned in contact with the inner wall. The electrodes may comprise monopolar electrodes or a pair of bipolar electrodes.

In accordance with several embodiments, the neuromodulation device 4225 is positioned with the aid of angiographic and fluoroscopic visualization. Contrast media may be provided through the lumen of the guide catheter 4205. Alternatively, contrast media may be delivered through the guide sheath or captive support sleeve 4221, through which the neuromodulation device 4225 extends. If the guide sheath 4221 is positioned near the ostium of the common hepatic artery 4203, visualization may be enhanced as the majority of contrast would flow through the common hepatic artery instead of the splenic artery 4204. The guide sheath or captive support sleeve 4221 may also provide enhanced support to the proximal portion of the neuromodulation device 4225. Alternatively or additionally, the neuromodulation device 4225 can include an additional lumen for contrast delivery, whereby the contrast can exit at an outlet 4227 positioned distally of a major side vessel, such as the splenic artery 4204. FIG. 42B illustrates an embodiment of a neuromodulation device incorporating a contrast lumen. The outlet may be located along a portion of the captive support sleeve 4221 or at a location of the neuromodulation device 4225 distal of the captive support sleeve 4221). Although illustrated and described herein with respect to positioning within a common hepatic artery, the neuromodulation device 4225 could alternatively be positioned in other vessel segments, and catheter delivery could be performed by placement of a guide catheter at the ostium of any appropriate vessel.

Figure 43A:
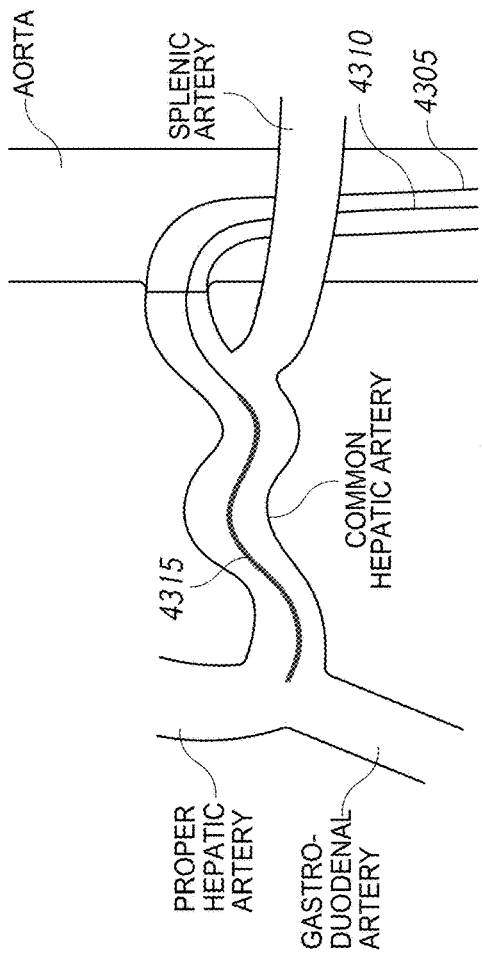
FIGS. 43A and 43B illustrate an embodiment of a neuromodulation balloon catheter configured to provide catheter stabilization within tortuous vasculature or within vasculature subject to movement during respiration.
Figure 43B:
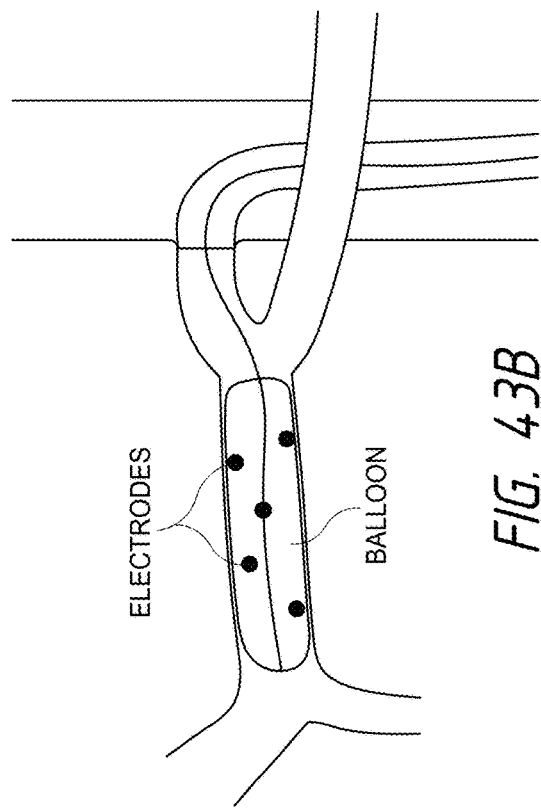

FIGS. 43A and 43B illustrate an embodiment of a catheter system configured to provide improved wall contact and catheter stabilization within tortuous vasculature (e.g., tortuous vasculature of the common hepatic artery). The catheter system comprises a guide catheter 4305 and an expandable element catheter 4310 (e.g., balloon catheter). In the illustrated embodiment, the expandable element catheter 4310 comprises a balloon catheter having a balloon positioned at a distal end of the balloon catheter. The balloon catheter may be inserted within the common hepatic artery in a deflated state (as shown in FIG. 43A) and then inflated to an expanded state (as shown in FIG. 43B). In some embodiments, expansion of the expandable element 4315 (e.g., inflation of a balloon) straightens out a tortuous vessel (e.g., hepatic artery portion) to facilitate wall contact of one or more electrodes or other treatment members (e.g., transducers, microwave emitters) disposed in or on the expandable element. If multiple electrodes or other treatment members are used, the multiple members may be spaced at various positions along the length and/or circumference of the expandable element, thereby facilitating treatment at multiple locations (simultaneously or separately). The expanded state may also result in improved catheter stabilization, thereby improving efficiency of the treatment procedure and reducing treatment times.

The expandable element may be self-expandable, mechanically expandable, or pneumatically expandable (e.g., inflatable). In one embodiment, the expandable element comprises shape memory material (e.g., a self-expandable stent-like element). In one embodiment, the catheter system comprises a passive segmented catheter (e.g., shape-lock assembly of one or more nested links) that guides the catheter into and through a tortuous vessel in a flexible state and then transitions to a rigid, shape-locked state. In one embodiment, the catheter enters the tortuous vessel in a curved state and then straightens out the vessel to cause the vessel to form a substantially straight cylindrical shape.

Respiration can cause movement of vessels being targeted for nerve modulation. For example, respiration can cause movement by as much as 2-5 cm in the area of the common hepatic artery, which may result in undesirable motion of a neuromodulation catheter or a treatment element (e.g., electrode, transducer or emitter) disposed thereon. The motion caused by respiration may adversely affect continuous and sufficient wall contact of a treatment element (e.g., electrode or transducer) against a vessel wall, and in several embodiments described herein, the adverse effect is reduced or removed.

In various embodiments, undesired motion of neuromodulation catheters (e.g., ablation catheters) can be reduced by substantially reducing the friction between the neuromodulation catheter and the guide catheter within which the neuromodulation catheter is inserted. The reduction of friction can be achieved, for example, by means of a hydrophobic (e.g., fluorine-based) lubricant or coating. In some embodiments, the force and/or displacement translation from the proximal end of the catheter (e.g., in contact with an introducer sheath) and the distal end of the catheter (e.g., electrode) can be reduced to address the motion of the catheter. In some embodiments, the friction near the catheter's distal end (e.g., electrode) and the target tissue can be increased to address the motion of the catheter.

Contact Assessment

In some embodiments, feedback and/or evaluative measures are provided for assessing the quality and/or magnitude of wall contact. For example, fluoroscopic imaging (e.g., angiography) can be used to assess the magnitude of lumen indentation caused by the contact of an electrode against a vessel (e.g., arterial) wall. The indentation size may be directly correlated to the contact force. Additionally, because there is a significant difference between blood and arterial resistivity and permittivity, the electrode impedance can be used as an indicator of contact force, with increased impedance generally correlated with improved contact. Prior to initiating an ablation, a test current can be applied by a generator to measure the impedance of the tissue immediately surrounding the electrode. Complex impedance can be obtained based on electromagnetic property measurements obtained using a single main electrode (monopolar), a split electrode (bipolar), one or more coils (e.g., loops or solenoids), one or more giant magneto resistance devices or other sensors positioned on the neuromodulation device or on separate adjunctive sensors. The complex impedance can be determined based on current, voltage, resistance and/or power measurements available from the generator. The contact sensing methods may use existing frequency content of an energy delivery signal (e.g., ablation signal) provided by the generator. The treatment electrode(s) may be used to perform contact sensing or adjunctive sensors or electrodes may be used. In some embodiments, the frequency used for contact sensing may range from 500 kHz to 10 MHz, which may be within or above the treatment frequency range. In other embodiments, the frequency used for contact sensing may range from 500 kHz to 100 MHz In one embodiment, the sensing frequency is different from the ablation frequency. In some embodiments, loss tangent, magnetic permeability, action potentials and/or components of complex impedance (e.g., resistance and reactance or magnitude and phase angle) are calculated and used to determine contact level. Contact sensing may also be determined based on thermal response using one or more temperature sensors positioned along the neuromodulation device or on stand-alone device(s). For example, an impulse or step response can be measured to facilitate contact assessment. In some embodiments, affirmative contact is not required because contact is guaranteed by a particular design of an intravascular neuromodulation device.

In various embodiments, two electrode elements are provided in close proximity to each other, separated by an adhesive or insulation layer. The at least two electrode elements may be connected in parallel for therapeutic power delivery in a unipolar mode, where the current return path is provided either by a ground pad, indifferent electrode or other return electrode remote from the treatment site. The at least two electrode elements can be excited in a differential or bipolar mode to provide sensing information related to the composition of tissue proximate the electrode elements. In some embodiments, the sensing information (signal) is used to assess the degree of contact between the electrode assembly and the vessel wall. In other embodiments, the sensing signal is used to assess the change in temperature of the tissue proximate the electrode assembly. In still other embodiments, the sensing signal is used to assess the distance between the electrode assembly and a tissue or structure.

In some embodiments, at least two electrode elements are created by splitting a larger electrode into sections of conductive material separated by thermally and/or electrically insulating material. In one embodiment, the larger electrode is substantially cylindrical. In another embodiment, the electrode is substantially spherical. In yet another embodiment, the electrode is comprised of separate cylindrical or spherical elements positioned adjacent to each other. In one embodiment, a first electrode element is positioned between a second and third electrode element. The second and third electrode elements may be connected in parallel. In various embodiments, the electrode elements are distributed coaxially along a shaft of a catheter. In some embodiments, the electrode elements are distributed longitudinally or circumferentially on a shaft of a catheter. In some embodiments, a first electrode element may be substantially contained within a second electrode element.

Figure 44C:
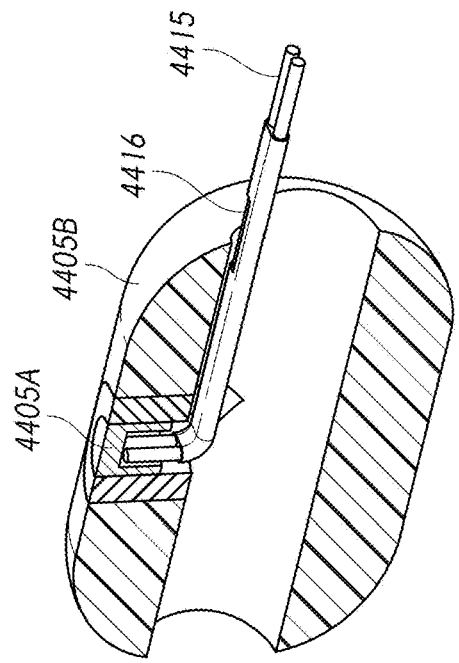
FIGS. 44A-44D illustrate embodiments of split electrode assemblies for tissue contact sensing.
Figure 44D:
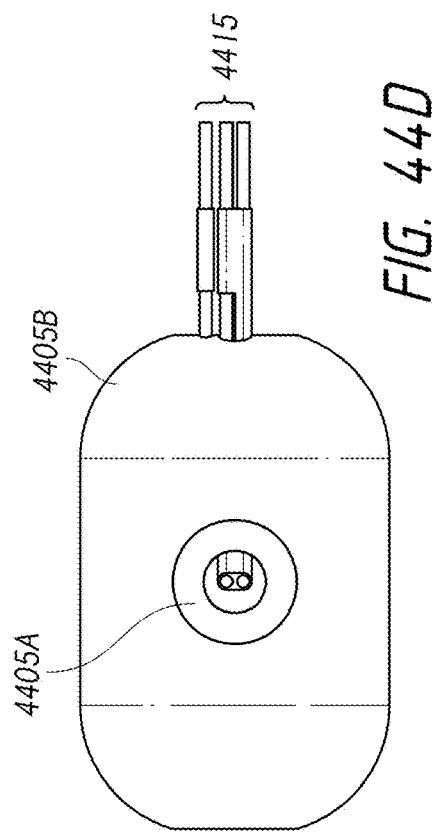
Figure 44A:
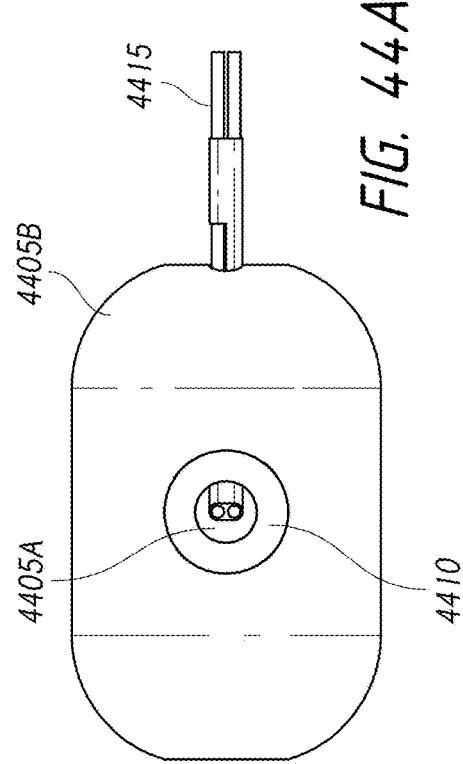
Figure 44B:
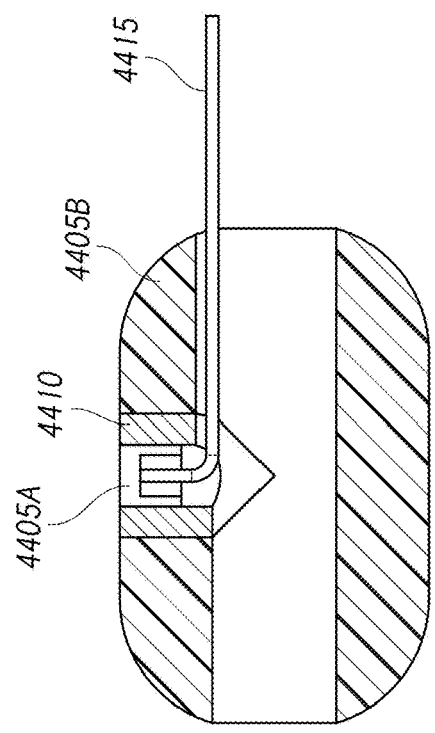

FIGS. 44A-44D illustrate embodiments of an electrode configuration or assembly adapted to provide power delivery for treatment (e.g., ablation or other neuromodulation) and tissue contact sensing comprising two coaxial electrodes. In the illustrated embodiment, a first electrode element 4405A is substantially contained within a second electrode element 4405B in a concentric manner. FIG. 44A is a top view, FIG. 44B is a cross-sectional side view and FIG. 44C is a cross-sectional isometric view of one embodiment of an electrode assembly configured for providing power delivery and tissue contact sensing. FIG. 44D is a top view of a second embodiment of an electrode assembly configured for providing power delivery and tissue contact sensing. In the illustrated embodiments, a first electrode element 4405A forms a circular aperture in a wall of a second electrode element 4405B such that the first electrode element is concentrically positioned within the second electrode element. In some embodiments, at least one of the electrode elements 4405 is configured to be placed near or in contact with the area or region where the electrode assembly contacts the vessel wall. The first electrode element 4405A may be substantially circular or spherical, polygonal, disk shaped or other regular geometric form. The electrode elements 4405 are separated by an electrically and/or thermally insulating material 4410. In some embodiments, the electrically and/or thermally insulating material 4410 may be formed from adhesives, polymers or ceramics selected from a group including, without limitation, delrin, epoxy, nylon, polyurethane, alumina, aluminum oxide, macor, polyethylene, cyano acrylate, acetal, PTFE, PFA, FEP and PEEK. In some embodiments, the shaft provides electrical and/or thermal isolation.

FIGS. 44A-44C illustrate two connecting wires 4415 connecting to the electrode elements 4405. FIG. 44C illustrates that the covering of one of the connecting wires 4415 (e.g., a copper wire) may include a slot 4416 such that a connection may be formed with the first electrode element 4405A and the second electrode element 4405B using a single connecting wire. In some embodiments, ablation current and sensing current can be apportioned among the electrode elements by providing separate connecting wires 4415 for each element, as shown for example in the embodiment illustrated in FIG. 44D. Filtering, modulation and multiplexing methods can be used to distribute power to the various connecting wires 4415. In one embodiment, the connecting wires 4415 in electrical contact with an electrode element form a thermocouple or other temperature measuring apparatus. In another embodiment, the connecting wire(s) 4415 to an electrode element is a single conductor. A non-limiting example of such connecting wire arrangement is to provide a thermocouple lead (e.g., 40 gauge T-type thermocouple lead) to the smaller of the electrode elements 4405A near the vessel wall contact area of the electrode assembly and a single power lead (e.g., 40 Gauge copper wire) to the surrounding electrode element 4405B. In some embodiments, ablative power (e.g., 5 W-20 W, 5 W-15 W, 8 W-12 W, 10 W-20 W) at a frequency between 400 kHz-650 kHz (e.g., 400 kHz, 450 kHz, 500 KHz, 550 kHz, 600 kHz, 650 kHz) may be delivered to the larger or both of the electrode elements in a unipolar mode (e.g., common mode signals delivered to both electrode elements with return signals going to a ground pad or indifferent electrode), while sensing signals (e.g., 1-20 mA (such as 10 mA) of current at 1 MHz to 100 MHz (e.g., 1 MHz to 10 MHz, 5 MHz to 15 MHz, 10 MHz, 15 MHz to 50 MHz, 30 MHz to 60 MHz, 50 MHZ to 100 MHz) may be delivered between the two electrode elements in a bipolar mode. Other power levels, current levels or frequencies may be used as desired and/or required. In accordance with several embodiments, the frequencies for sensing are outside the range of the frequencies used for ablative power. The complex impedance, phase, loss tangent, reactance and resistance of the sensing current can be analyzed at high sensitivity for the adjacent tissue. Sensing current may be provided at multiple frequencies and impedance can be compared or combined into a composite parameter describing the tissue contact. Sensing current may be analyzed in the time domain or the frequency domain. The sensing waveform may be swept, narrow band broad band, pulsed, square wave, chirp, frequency modulated, multitonal, or other suitable waveforms. A sensing system may comprise an external driver and generator to separate the frequencies of the sensing signals between the two electrodes. The sensing system may comprise common mode choke(s), high pass, low pass and/or band pass filters or other filtering circuitry. The sensing system may comprise a processing device adapted to determine whether a sufficient amount of contact exists or to determine a quantitative level of tissue contact based on tissue contact measurements received from the electrode assembly. The processing device may generate an output indicative of contact or the level of tissue contact for display or other output to a user. The tissue contact measurements may comprise bipolar contact impedance measurements or temperature measurements. The contact sensing features and embodiments described in connection with FIGS. 44A-44D may be incorporated into any of the neuromodulation devices (e.g., treatment catheters, ablation catheters or other devices) described herein.

In some embodiments, a temperature sensing device may be provided within a first electrode element in a manner to provide high thermal response and high sensitivity to the surrounding tissue. Temperature sensors may be comprised of thermocouples, resistance temperature detectors (RTDs), thermistors, fluoroptic temperature sensors, Fabry-Perot temperature sensors or other suitable sensors. In one embodiment, power delivered in a unipolar mode through at least one electrode element causes modest, benign, local heating of the tissue proximate the temperature sensor. The rate or magnitude of temperature change as measured by the sensor reflects the degree of contact with tissue or blood. Small contact area and low thermal mass and insulation from non-sensing surfaces increase responsiveness and sensitivity. In one non limiting example, a 40 Gauge type T thermocouple lead is connected to the smaller of the electrode elements 4405A near the vessel wall contact area of the electrode and a single 40 Gauge copper wire is connected to the surrounding electrode element 4405B. Other types or sizes of temperature-measurement devices or wires may be used as desired and/or required. In one embodiment, 1 W of power is delivered in a unipolar or bipolar mode through the electrode elements. The magnitude or rate of temperature rise or decay is taken as an indication of vessel wall contact. Other power levels may be used as desired and/or required Patient Selection and Physiologic Monitoring In accordance with several embodiments, the above physiology involving the liver and pancreas can be exploited by stimulation testing to enable confirmation of neural disruption, and potentially prediction of response in patients. Regardless of the disease and organ, some patients are more likely to benefit from denervation therapies and have significant contributions to their disease from sympathetic tone elevations. In accordance with several embodiments, likely responders are advantageously identified prior to treatment. In accordance with several embodiments, methods to confirm denervation and/or predict response include stimulating nerves surrounding hepatic arteries (e.g., common hepatic artery) or non-hepatic sympathetic targets (e.g., renal artery) and measuring physiologic responses such as blood glucose, blood insulin or blood pressure. Stimulation, in one embodiment, comprises delivering signals adapted to result in nerve blocking.

In some embodiments, stimulation (e.g., application or transmission of a stimulation signal or blocking signal) of the common hepatic artery (e.g., nerves within or surrounding the common hepatic artery) or other anatomical targets is performed using an endovascular electrode or various extravascular or extracorporeal techniques with a patient in a laboratory setting. The stimulation may be controlled so as to elicit or induce a transient glucose and/or insulin response to facilitate measurements. The stimulation may be performed prior to a denervation treatment and patients with larger rises in glucose levels could be selected as likely responders to therapy and those with lower rises in glucose levels could be excluded as likely non-responders to therapy. In some embodiments, methods may involve selection of patients with poor beta cell function and/or high fasting glucose levels for denervation therapy according to the parameters disclosed herein because these patients may respond to a greater degree than other patients. In some embodiments, patients may be selected for treatment based on determined threshold baseline levels of beta cell function markers (such as baseline insulin, C-peptide, OGTT insulin, or HOMA-B). Transient and stimulation-induced decreases in beta cell function marker levels (e.g., decreased peak or area or an OGTT insulin curve or decreased HOMA-B) may indicate a degree of beta cell function suppression by sympathetic neural inputs, which could advantageously be used as a predictor of patients likely to respond to hepatic denervation therapy in accordance with several embodiments. For example, patient selection may be limited to patients with low baseline insulin levels (e.g., less than 25 micro-international-units per milliliter, less than 24 micro-international-units per milliliter, less than 23 micro-international-units per milliliter, less than 22 micro-international-units per milliliter, less than 21 micro-international-units per milliliter, less than 20 micro-international-units per milliliter, less than 19 micro-international-units per milliliter, less than 18 micro-international-units per milliliter, less than 17 micro-international-units per milliliter, less than 16 micro-international-units per milliliter, less than 15 micro-international-units per milliliter) or low C-peptide levels (e.g., less than 1500 picomoles per liter, less than 1400 picomoles per liter, less than 1300 picomoles per liter, less than 1200 picomoles per liter, less than 1100 picomoles per liter, less than less than 1000 picomoles per liter). In some embodiments, patient selection may be based on changes in insulin or C-peptide levels during oral glucose tolerance test (OGTT) screening. For example, patients with less than a predetermined threshold of change during OGTT testing (e.g., less than a two times increase, less than a 1.5 times increase, less than a 2.5 times increase, less than a three times increase) may be selected for treatment.

In some embodiments, the stimulation of the common hepatic artery (e.g., nerves within or surrounding the common hepatic artery) or other anatomical targets is also performed after a denervation (e.g., ablation) procedure and the post-procedure levels are compared to the pre-procedure levels in the same patient or in a reference data set of untreated patients. Reductions in the rise in glucose levels or levels of other physiological parameters after stimulation may be correlated with the degree and success of denervation. Similar stimulation induced measurements of beta cell function markers may be performed after the denervation procedure as an indicator of denervation success and extent, for example evidenced by an increase in insulin level.

Stimulation (e.g., application or transmission of a stimulation signal or blocking signal) of non-hepatic artery sympathetic targets and measurement of non-metabolic physiologic markers may also be performed to predict likely patient response and/or to confirm successful denervation. For example, the renal artery could be stimulated and a blood pressure or heart rate rise elicited as an indicator of sympathetic tone-mediated disease could be measured. By inference, if the patient had sympathetic-mediated cardiovascular response, they may also benefit from denervation therapy for metabolic diseases. Similarly, if the stimulation-related blood pressure or heart rate response decreased from pre-procedure levels, this could indicate a successful denervation. In some embodiments, the carotid body is stimulated and blood pressure, heart rate, respiratory rate, or blood gasses (e.g., partial pressure of oxygen (PO2) or partial pressure of carbon dioxide (PCO2)) responses are measured pre and/or post procedure to determine likely patient response or to confirm successful denervation.

Various systems and methods are provided herein to provide the ability to detect (acutely and/or chronically) whether nerves have been ablated or denervated and the neural connections to the end-organ (e.g., liver, pancreas, duodenum, etc.) thus disrupted. In accordance with several embodiments, it may be desirable to detect in real-time the actual energy being delivered. Since nerves carry electrical signals, and denervated or ablated nerves can no longer carry these signals, it may be possible to measure conduction along the length of the nerve fibers. In some embodiments, a binary signal (e.g., on/off) or a quantitative signal correlating with degree of nerve disruption could be determined. In some embodiments, expected physiological responses (e.g., glucose changes, insulin or glucagon changes, GI motility, etc.) to stimulation of the target nerves (e.g., nerves surrounding the hepatic arteries) may be monitored directly after a denervation or nerve ablation procedure to determine whether or not the expected physiological responses occur, thereby leading to the possibility of a real-time intra-procedural diagnostic. In some embodiments, real-time feedback during the ablation procedure may facilitate delivery of only enough energy (or formation of only enough lesions) as needed for successful denervation, thereby opening up a wider population to the procedure due to anatomic constraints (e.g., vessel length, tortuosity, etc.) that may limit the number of possible ablations and/or reducing the likelihood of any safety effects (e.g., vascular or adjacent structure injury) due to excessive energy delivery.

In accordance with several embodiments, the catheter used for energy delivery (e.g., ablation) comprises sensing electrodes proximal and/or distal to the site of ablation. The sensing electrodes may be configured to be placed in contact with a vessel wall in order to detect conduction in the targeted nerve fibers (e.g., nerve fibers in the adventitia surrounding a common hepatic artery). Any of the structures and features described herein for facilitating contact of electrodes with vessel walls may be used. For example, a balloon ablation catheter may comprise ablation electrodes in the middle of the balloon and sensing electrodes on the same balloon proximal and distal of the ablation electrodes. In some embodiments, the same electrodes are configured to provide ablation and sensing functions. In some embodiments, a balloon ablation catheter may comprise multiple balloons, with sensing balloons (e.g., balloons with sensing electrodes) on either side of an ablation balloon (or balloon with ablation electrodes).

Similar technologies could be employed on a separate catheter from the ablation catheter, and a diagnostic procedure could be performed with the separate sensing catheter immediately after or within a certain time (e.g., 5 minutes, 10 minutes, 15 minutes, 20 minutes, 30 minutes, 45 minutes, 60 minutes) following the ablation or on some other diagnostic or treatment session in the future. In some embodiments, non-catheter-based diagnostic systems and methods are used. For example, the proximal and distal sensing electrodes may be positioned on cuffs, needles, patches, and/or the like. Access could be percutaneous, placed on the skin outside of the body, placed in adjacent structures (e.g., portal vein, bile duct, inferior vena cava), or placed in organ tissue (e.g., liver tissue) itself. In accordance with several embodiments, the methods advantageously involve monitoring at the physiology that is being targeted (e.g., neural electrical conduction), which provides the most direct measurement conceivable.

In the absence of nerve identification under direct observation, nerves can be identified based on their physiologic function. In some embodiments, mapping and subsequent modulation is performed using glucose and norepinephrine ("NE") levels. In some embodiments, glucose and NE levels respond with fast time constants. Accordingly, a clinician may stimulate specific areas (e.g., in different directions or circumferential clock positions or longitudinal positions) in a target artery or other vessel, monitor the physiologic response, and then modulate (e.g., ablate) only in the locations that exhibited the undesired physiologic response. Sympathetic nerves tend to run towards the anterior portion of the hepatic artery, while the parasympathetic nerves tend to run towards the posterior portion of the hepatic artery. Therefore, one may choose a location not only anterior, but also (using the aforementioned glucose and NE level measurements) a specific location in the anterior region that demonstrated the strongest physiologic response to stimulation (e.g., increase in glucose levels due to sympathetic stimulation). In some embodiments, stimulation with 0.1 s-on, 4.9 s-off, 14 Hz, 0.3 ms, 4 mA pulsed RF energy is a sympathetic activator and stimulation with 2 s-on, 3 s-off, 40 Hz, 0.3 ms, 4 mA pulsed RF energy is a parasympathetic activator. However, other parameters of RF energy or other energy types may be used.

In some embodiments, using electrical and/or positional selectivity, a clinician could apply a stimulation pulse or signal and monitor a physiologic response. Stimulation, in one embodiment, comprises delivering signals adapted to result in nerve blocking. Some physiologic responses that may indicate efficacy of treatment include, but are not limited to, the following: blood glucose levels, blood and/or tissue NE levels, vascular muscle tone, blood insulin levels, blood glucagon levels, blood C peptide levels, blood pressure (systolic, diastolic, average), and heart rate. In some cases, blood glucose and tissue NE levels may be the most accurate and readily measured parameters. The physiologic responses may be monitored or assessed by arterial or venous blood draws, nerve conduction studies, oral or rectal temperature readings, or percutaneous or surgical biopsy. In some embodiments, transjugular liver biopsies are taken after each incremental ablation to measure the resultant reduction in tissue NE levels and treatment may be titrated or adjusted based on the measured levels. For example, in order to measure tissue NE levels in the liver, a biopsy catheter may be inserted by a TIPS approach or other jugular access to capture a sample of liver parenchyma. In some embodiments, the vein wall of the portal vein may safely be violated to obtain the biopsy, as the vein is surrounded by the liver parenchyma, thereby preventing or inhibiting blood loss.

In various embodiments, a signal or response detected by a circuit comprised of sensing electrodes or other diagnostic members on both sides of the ablation or denervation site could be (1) impedance (e.g., a change in dynamic resistance or conductance of the circuit created) and/or (2) action potentials (e.g., the circuit could be probed with a brief voltage impulse and then electrical response monitored, since nerve fibers conduct physiologically using such action potentials). In some embodiments, physiologic responses are monitored, leading to several possibilities depending on the organ and physiology interrogated. Examples of physiologic responses include the following: (1) Liver/glucose: since stimulation of the hepatic sympathetic nerves increases net hepatic glucose production and thus systemic glucose levels, a lesser increase in blood glucose levels may be observed after denervation or ablation; (2) pancreas/insulin-glucagon: since stimulation of the pancreatic sympathetic nerves could increase insulin secretion and decrease glucagon secretion, both of these hormone levels could be measured pre and post denervation; and (3) duodenum-stomach/motility: since stimulation of the gastrointestinal (GI) sympathetics may lead to decreased motility, direct observation of motility or via a number of motility tests could be measured pre and post denervation or ablation. The systems and methods described above may be universally applicable to intravascular denervation regardless of the end organ (e.g., may apply to any organ innervated by nerves around an artery). The measurements (whether electrical or physiologic or other type) may be conducted serially during an ablation procedure, or chronically (e.g., at some period of time after the procedure), to assess success of denervation.

In embodiments involving liver, or hepatic, denervation, confirmation of denervation may be assessed by tissue norepinephrine levels. For example, the tissue norepinephrine levels may be reduced by more than 90%. In some embodiments involving hepatic denervation by ablating the common hepatic artery or other adjacent vessels, there may be a corresponding "dose-response" in the pancreas and duodenum. In other words, in some embodiments, the pancreas and/or duodenum may be sufficiently denervated (e.g., >90%) in addition to the liver being denervated, by ablating the common hepatic artery and/or surrounding vessels as described herein. Accordingly, physiologic assessments (e.g., established clinical tests or measurements) of the pancreas or duodenum that suggest impact of denervation may be used to confirm success of liver denervation. In some embodiments, ablations could be continued until an intended or expected clinical change is detected.

Clinical measurements for measuring pancreatic response affected by denervation may include oral glucose challenges and subsequent insulin response. Denervation of the pancreas in theory should lead to greater insulin secretion, and evidence of this has been observed in dog and clinical studies. Thus, multiple oral glucose challenges could be given, and blood insulin or C-peptide levels measured, and if the insulin or C-peptide levels increased, denervation success could be inferred. Clinical measurements for measuring pancreatic response may also include spot insulin or C-peptide measurements without glucose challenge. In some embodiments, glucagon measurements, which is a hormone secreted from the pancreas that may be affected by denervation) may be taken to confirm denervation of the liver.

Clinical measurements for measuring duodenal response may include GI motility testing, since with sympathetic denervation of the duodenum, there may be increased duodenal motility and decreased transit time. Several clinically validated tests exist to measure motility changes, including nuclear medicine tests looking at transit of radioactive food ingested, and C-acetate breath testing. In some embodiments, an endoscopy could be performed and the duodenum visualized directly to look at signs of motility changes.

In some embodiments, system-wide responses (due to possibility that afferent neural connections could be disrupted by ablating the common hepatic artery) may be measured to facilitate confirmation of liver denervation upon ablation of the common hepatic artery. Sympathetic outflow to other organs may be reduced via a reflex path from the liver to the brain to other organs. Parameters that could be affected and measured include, but are not limited to, blood pressure, heart rate and muscle sympathetic nerve activity (MSNA).

Sympathetic Tone Measurement

The rate at which sympathetic neurons fire under normal conditions is called the sympathetic tone. Likewise, the rate at which parasympathetic neurons fire under normal conditions is called the parasympathetic tone. Changes in the firing of the neurons, for example due to ablation or stimulation of one or more neurons, can result in changes to the tone. Tone can be measured, detected, or monitored before, during, and/or after treatment to provide information about the procedure. For example, a monitored change in sympathetic tone or physiological responses (e.g., as a way to measure tone) during or after a procedure can provide real-time verification about the efficacy of a sympathetic neuron denervation procedure. For another example, sympathetic tone can be measured before a procedure for patient screening, identifying regional locations for treatment, and the like. The measurement may be global or regional.

In some embodiments, tone can be measured using an intravascular device. For example, noradrenaline (NA) plasma concentration can be measured in an artery and/or a vein. Noradrenaline spillover can be measured throughout the vasculature, including as examples the heart (cardiac NA spillover), forearm (forearm NA spillover), kidney (renal NA spillover), liver (hepatic NA spillover), skeletal muscle vasculature, and the like. For another example, microneurography, for example, measuring MSNA, can be used to measure activity in superficial nerves. Other blood components can also be measured, for example but not limited to norepinephrine (NE). Certain blood components may be measured for the total body and/or proximate to a known or believed origination location. For example, NE may be measured proximate to a specific organ such as the lungs, which are believed to originate about 40% of NE. A measurement may be characterized by the value at a substantially steady-state condition, for example a change less than about 25%, less than about 10%, less than about 5%, etc. over a certain amount of time such as about 30 minutes, about 15 minutes, about 5 minutes, etc. Measurement in body lumens other than blood vessels is also possible. For example, urinary cathecholamines can be indicative of sympathetic tone. Body lumens in which measurement may occur include, for example, arteries, veins, chambers, arterioles, venules, ducts or tracts (e.g., urinary, gastrointestinal), pockets, tubules, and the like.

In an embodiment, a catheter is placed in a body lumen and navigated proximate to an organ. A probe may be deployed into the wall of the lumen, for example at a certain depth and/or angle. The position of the probe may be stabilized, for example by an anchor, barb, balloon, expandable cage or portion thereof, combinations thereof, and the like. The probe may receive electrophysiological signals that can be recorded, for example to generate a metric characteristic of sympathetic tone. Background signals or noise may be removed, for example, by deploying a probe to measure electrophysiological signals away from the organ. The probe may measure one or more of: blood or other fluid analyte level, blood or other fluid flow, blood or other fluid flow differential, blood oxygen saturation, blood perfusion, blood pressure, central sympathetic drive, an electroacoustic event, an electromyographic signal, evoked potential, a local field potential, a mechanomyographic signal, MSNA, nerve traffic, remote stimulation of nervous activity, temperature, tissue tone, vasodilation, vessel wall stiffness, water concentration, combinations thereof, and the like. A plurality of probes may be used to measure multiple signals or other properties, the same signal at different places in the body, and combinations thereof.

In an embodiment, a first catheter is placed in an artery proximate to an organ such as a liver and a second catheter is placed in a vein proximate to the organ. The first catheter comprises a first sensor configured to detect a blood component (e.g., NA, NE, and/or the like). The second catheter comprises a second sensor configured to detect the same blood component (e.g., NA, NE, and/or the like). At least one of the first catheter and the second catheter comprises a flowmeter configured to measure blood flowrate. Blood component spillover (e.g., in ng/min), which may be indicative of sympathetic tone, can be measured by multiplying a flowrate (e.g., in mL/min) by the difference in the concentration (e.g., in ng/mL) of the blood component in the artery and in the vein. In some embodiments, the first catheter and the second catheter may be placed in the same vessel, for example upstream and downstream of the organ.

In some embodiments, tone can be measured using a noninvasive device or a device external to the body. A non-invasive tool may be easier and/or more accurate than existing microneurographs such as for MSNA or an intravascular device. A change in sympathetic tone may be characterized by a change in resting heart rate, as acute modifications in sympathetic tone are paralleled by consensual heart rate changes. Heart rate may be measured using a blood pressure cuff, optical monitor, EKG, smart phone, smart watch, etc.

Spectral analysis of heart rate variability (HRV) can be used to assess changes in sympathetic tone. For example, an EKG can be used to measure spectral power or intensity at various frequencies. An HRV spectrum can be aggregated into three main frequency bands: a high frequency band (about 0.15 Hz to about 0.4 Hz), corresponding to a parasympathetic component, a low frequency band (about 0.04 Hz to about 0.15 Hz), corresponding to both sympathetic and parasympathetic components, and a very low frequency band (about 0.0033 Hz to about 0.04 Hz), which may reflect the influence of several physiological mechanisms including vasomotor tone. The resulting spectral power or intensity can be plotted against frequency. Peaks at certain frequencies can be indicative of sympathetic nerve activity such that changes to peaks can indicate changes in sympathetic nerve activity. In addition or alternatively, changes to the total spectral power, measured as the area under the spectral plot or a portion thereof (e.g., high frequency only, low frequency only, high frequency and low frequency only, etc.), can be indicative of sympathetic nerve activity such that changes to total spectral power can indicate changes in sympathetic nerve activity.

Measurement values of sympathetic tone, for example a static number obtained in a screening phase, may be indicative of a suitable subject for denervation or stimulation. Changes in measurement values of sympathetic tone, for example up or down depending on the measurement type and procedure, may be indicative of success of a procedure that should result in a change to sympathetic tone such as denervation or stimulation. If the expected result was not achieved, the procedure may be repeated or modified for example adjusting position, power, energy type, etc.

Mapping

In some embodiments, the sympathetic and parasympathetic nerves are mapped prior to modulation. In some embodiments, a sensor catheter is inserted within the lumen of the vessel near a target modulation area. The sensor catheter may comprise one sensor member or a plurality of sensors distributed along the length of the catheter body. After the sensor catheter is in place, either the sympathetic nerves or the parasympathetic nerves may be stimulated. In some embodiments, the sensor catheter is configured to detect electrical activity. In some embodiments, when the sympathetic nerves are artificially stimulated and parasympathetic nerves are left static, the sensor catheter detects increased electrical activity and the data obtained from the sensor catheter is used to map the sympathetic nervous geometry. In some embodiments, when the parasympathetic nerves are artificially stimulated and sympathetic nerves are left static, the sensor catheter detects increased electrical activity and the data obtained from the sensor catheter is used to map the parasympathetic nervous geometry. In some embodiments, mapping the nervous geometry using nervous stimulation and the sensor catheter advantageously facilitates improved or more informed selection of the target area to modulate, leaving select nerves viable while selectively ablating and disrupting others. As an example of one embodiment, to selectively ablate sympathetic nerves, the sympathetic nerves may be artificially stimulated while a sensor catheter, already inserted, detects and maps areas of increased electrical activity. To disrupt the sympathetic nerves, only the areas registering increased electrical activity may need to be ablated.

In one embodiment, a method of targeting sympathetic nerve fibers involves the use of electrophysiology mapping tools. While applying central or peripheral nervous signals intended to increase sympathetic activity (e.g., by administering noradrenaline or electrical stimulation), a sensing catheter may be used to map the geometry of the target vessel (e.g., hepatic artery) and highlight areas of increased electrical activity. An ablation catheter may then be introduced and activated to ablate the mapped areas of increased electrical activity, as the areas of increased electrical activity are likely to be innervated predominantly by sympathetic nerve fibers. In some embodiments, nerve injury monitoring (NIM) methods and devices are used to provide feedback regarding device proximity to sympathetic nerves located perivascularly. In one embodiment, a NIM electrode is connected laparascopically or thoracoscopically to sympathetic ganglia.

Additional Considerations

In some embodiments, any combination of drug delivery, chemoablation, and/or cryoablation is used for neuromodulation of any of the nerves described herein, and may be used in combination with an energy modality. In several embodiments, cooling systems are provided in conjunction with energy delivery to, for example, protect tissue adjacent the nerve fibers.

In addition to being delivered intravascularly through an artery, the neuromodulation systems described herein (e.g., ablation catheter systems and other access/delivery systems) can be delivered intravascularly through the venous system. For example, an ablation catheter system may be delivered through the portal vein. In other embodiments, an ablation catheter system is delivered intravascularly through the inferior vena cava. Any other intravascular delivery method or approach may be used to deliver neuromodulation systems, e.g., for modulation of sympathetic nerve fibers in the hepatic plexus.

In some embodiments, the neuromodulation systems (e.g., catheter and other access/delivery systems) are delivered transluminally to modulate nerve fibers. For example, catheter systems may be delivered transluminally through the stomach. In other embodiments, the catheter systems are delivered transluminally through the duodenum, or transluminally through the biliary tree via endoscopic retrograde cholangiopancreatography (ERCP). Any other transluminal or laparoscopic delivery method may be used to deliver the catheter systems according to embodiments described herein.

In some embodiments, the catheter systems are delivered percutaneously to the biliary tree to ablate sympathetic nerve fibers in the hepatic plexus. Any other minimally invasive delivery method may be used to deliver neuromodulation systems for modulation or disruption of sympathetic nerve fibers in the hepatic plexus as desired and/or required.

In some embodiments, an open surgical procedure is used to modulate sympathetic nerve fibers in the hepatic plexus. Any open surgical procedure may be used to access the hepatic plexus. In conjunction with an open surgical procedure, any of the modalities described herein for neuromodulation may be used. For example, RF ablation, ultrasound ablation, HIFU ablation, ablation via drug delivery, chemoablation, cryoablation, ionizing energy delivery (such as X-ray, proton beam, gamma rays, electron beams, and alpha rays) or any combination thereof may be used with an open surgical procedure. In one embodiment, nerve fibers (e.g., in or around the hepatic plexus) are surgically cut in conjunction with an open surgical procedure in order to disrupt sympathetic signaling, e.g., in the hepatic plexus.

In some embodiments, a non-invasive procedure or approach is used to ablate sympathetic nerve fibers in the hepatic plexus and/or other nerve fibers. In some embodiments, any of the modalities described herein, including, but not limited, to ultrasonic energy, HIFU energy, electrical energy, magnetic energy, light/radiation energy or any other modality that can effect non-invasive ablation of nerve fibers, are used in conjunction with a non-invasive (e.g., transcutaneous) procedure to ablate sympathetic nerve fibers in the hepatic plexus and/or other nerve fibers.

While the devices, systems and methods described herein have primarily addressed the treatment of diabetes (e.g., diabetes mellitus), other conditions, diseases, disorders, or syndromes can be treated using the devices, systems and methods described herein, including but not limited to ventricular tachycardia, atrial fibrillation or atrial flutter, inflammatory diseases, endocrine diseases, hepatitis, pancreatitis, gastric ulcers, gastric motility disorders, irritable bowel syndrome, autoimmune disorders (such as Crohn's disease), obesity, Tay-Sachs disease, Wilson's disease, NASH, NAFLD, leukodystrophy, polycystic ovary syndrome, gestational diabetes, diabetes insipidus, thyroid disease, and other metabolic disorders, diseases, or conditions.

In some embodiments, the system comprises one or more of the following: means for tissue modulation (e.g., an ablation or other type of modulation catheter or delivery device), means for energy delivery (e.g., generator or other energy generation module), means for deploying energy delivery members or other treatment elements (e.g., pull wire, preformed shape memory material, retractable sheaths, expansion members), means for cooling electrodes, means for monitoring physiologic responses, means for measuring tissue contact, means for identifying adjacent dense structures, means for mapping nerves, means for imaging, etc.

In some embodiments, the system comprises various features that are present as single features (as opposed to multiple features). For example, in one embodiment, the system includes a single ablation catheter with a single energy delivery member (e.g., radiofrequency electrode). A single thermocouple (or other means for measuring temperature) may also be included. Multiple features or components are provided in alternate embodiments.

The various illustrative logical blocks, modules, and circuits described in connection with the embodiments disclosed herein (e.g., generators) can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. The modules described herein may comprise structural hardware elements and/or non-structural software elements stored in memory (for example, algorithms or machine-readable instructions executable by processing or computing devices). Memory or computer-readable storage media can include RAM memory, flash memory, ROM memory, EPROM memory, EEPROM memory, registers, a hard disk, a removable disk, a CD-ROM, or any other form of computer-readable storage medium known in the art. Any methods described herein may be embodied in, and partially or fully automated via, software code modules stored in a memory and executed by one or more processors or other computing devices. The methods may be executed on the computing devices in response to execution of software instructions or other executable machine-readable code read from a tangible computer readable medium. A tangible computer readable medium is a data storage device that can store data that is readable by a computer system. Examples of computer readable mediums include read-only memory (for example, EEPROM), random-access memory, other volatile or non-volatile memory devices, CD-ROMs, magnetic tape, flash drives, and optical data storage devices. A storage medium may advantageously be coupled to a processor such that the processor can read information from, and write information to, the storage medium. In the alternative, the storage medium can be integral to the processor.

For example, hardware for performing selected tasks according to embodiments of the invention could be implemented as a chip or a circuit. As software, selected tasks according to embodiments of the invention could be implemented as an algorithm or a plurality of machine-readable instructions being executed by a computer using any suitable operating system. In one embodiment, a network (wired or wireless) connection is provided. A display and/or a user input device (such as a keyboard, mouse, touchscreen, user-actuatable inputs, trackpad) may optionally be provided.

Although certain embodiments and examples have been described herein, aspects of the methods and devices shown and described in the present disclosure may be differently combined and/or modified to form still further embodiments. Additionally, the methods described herein may be practiced using any device suitable for performing the recited steps. Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure (including the figures) herein of any particular feature, aspect, method, property, characteristic, quality, attribute, element, or the like in connection with various embodiments can be used in all other embodiments set forth herein. For example, features described in one figure may be used in conjunction with embodiments illustrated in other figures. Embodiments embodied or carried out in a manner may achieve one advantage or group of advantages as taught herein without necessarily achieving other advantages. The section headings used herein are merely provided to enhance readability and are not intended to limit the scope of the embodiments disclosed in a particular section to the features or elements disclosed in that section. The same numbers may be used as call-outs for similar components or features in different figures. Use of the same number does not necessarily mean that the different embodiments necessarily include all of the features of that same numbered component described in connection with other figures.

While embodiments are susceptible to various modifications, and alternative forms, specific examples thereof have been shown in the drawings and are herein described in detail. It should be understood, however, that the embodiments are not to be limited to the particular forms or methods disclosed, but to the contrary, the embodiments are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "delivering a neuromodulation catheter within a hepatic artery" include "instructing the delivery of a neuromodulation catheter within a hepatic artery."

Various embodiments of the invention have been presented in a range format. It should be understood that the description in range format is merely for convenience and brevity and should not be construed as an inflexible limitation on the scope of the invention. The ranges disclosed herein encompass any and all overlap, sub-ranges, and combinations thereof, as well as individual numerical values within that range. For example, description of a range such as from about 5 to about 30 minutes should be considered to have specifically disclosed subranges such as from 5 to 10 degrees, from 10 to 20 minutes, from 5 to 25 minutes, from 15 to 30 minutes etc., as well as individual numbers within that range, for example, 5, 10, 15, 20, 25, 12, 15.5 and any whole and partial increments therebetween. Language such as "up to," "at least," "greater than," "less than," "between," and the like includes the number recited. Numbers preceded by a term such as "about" or "approximately" include the recited numbers (for example, "about 3 mm" includes "3 mm"). The terms "approximately", "about", and "substantially" as used herein represent an amount close to the stated amount that still performs a desired function or achieves a desired result.

What is claimed:

1. An intraluminal ablation catheter comprising:
a proximal manifold;
an elongate shaft comprising at least one lumen, wherein the elongate shaft comprises a central longitudinal axis extending along its length;
a first balloon coupled to a distal end portion of the elongate shaft,
wherein the first balloon is adapted to transition between a folded configuration and an expanded, unfolded configuration,
wherein the first balloon comprises four electrodes,
wherein a first electrode and a second electrode of the four electrodes are located in a first circumferential cross-sectional plane along the first balloon and are located in opposite quadrants from each other around the circumference of the first balloon when the first balloon is in the expanded, unfolded configuration,
wherein a third electrode and a fourth electrode of the four electrodes are located within a second circumferential cross-sectional plane along the first balloon and are located in opposite quadrants from each other around the circumference of the first balloon when the first balloon is in the expanded, unfolded configuration, wherein the second circumferential cross-sectional plane is axially offset from the first circumferential cross-sectional plane;
a second balloon located within the first balloon, wherein the second balloon comprises at least one orifice positioned adjacent each of the four electrodes, the at least one orifice being adapted to direct at least one fluid jet toward a respective one of the four electrodes, wherein the at least one lumen comprises at least one fluid delivery lumen in fluid communication with an interior of the second balloon and adapted to deliver coolant within the second balloon.

2. The ablation catheter of claim 1, wherein the third electrode and the fourth electrode are in different quadrants than the first electrode and the second electrode.

3. The ablation catheter of claim 1, wherein the third electrode and the fourth electrode are in quadrants that are circumferentially offset by 90 degrees from the quadrants in which the first electrode and the second electrode are located.

4. The ablation catheter of claim 1, wherein the first electrode and the second electrode are located 180 degrees apart circumferentially from each other about the central longitudinal axis of the elongate shaft.

5. The ablation catheter of claim 4, wherein the third electrode and the fourth electrode are located 180 degrees apart circumferentially from each other about the central longitudinal axis of the elongate shaft.

6. The ablation catheter of claim 5, wherein the third and fourth electrodes are each circumferentially offset from the first and second electrodes by 90 degrees.

7. The ablation catheter of claim 1, wherein the at least one lumen further comprises a first central guidewire lumen adapted to track a guidewire.

8. The ablation catheter of claim 1, further comprising a nozzle or eductor positioned adjacent the at least one orifice, and wherein the nozzle or eductor is configured to direct the fluid jets toward the respective one of the four electrodes.

9. The ablation catheter of claim 1, wherein each of the four electrodes is directly mounted on an outer surface of the balloon.

10. The ablation catheter of claim 1, further comprising two spaced-apart lesion spacing indicators positioned along the elongate shaft to facilitate controlled spacing of lesion zones.

11. The ablation catheter of claim 1, further comprising a distal tracking segment coupled to a distal end of the balloon, wherein the distal tracking segment is adapted to vary a flexibility of the catheter from distal to proximal.

12. An intraluminal ablation catheter comprising:
a proximal manifold;
an elongate shaft comprising a plurality of lumens, wherein the plurality of lumens comprises a guidewire lumen and a fluid infusion lumen;
an inner inflatable member surrounding at least one of the plurality of lumens and being coupled to the at least one of the plurality of lumens,
wherein the fluid infusion lumen is configured to infuse cooling fluid into the inner inflatable member;
an outer inflatable member surrounding the inner inflatable member and being coupled to the elongate shaft, wherein the outer inflatable member comprises a plurality of electrodes;
a plurality of electrical conductors extending from a port of the proximal manifold to each of the plurality of electrodes;
wherein the inner inflatable member comprises a plurality of outlet orifices configured to direct jets of the cooling fluid from the inner inflatable member toward a bottom surface of each of the plurality of electrodes of the outer inflatable member so as to cool the plurality of electrodes.

13. The catheter of claim 12,
wherein each electrode of the plurality of electrodes has a surface area between 8 $mm^2$ and 16 $mm^2$;
wherein each of the outlet orifices has a diameter of between 0.05 mm and 0.25 mm,
wherein an annular gap between the inner inflatable member and the outer inflatable member ranges between 0.05 mm and 1.5 mm,
wherein a length of the outer inflatable member is between 10 mm and 30 mm, and
wherein a flow rate of the cooling fluid per electrode ranges from 0.1 to 1.0 mL/second.

14. The catheter of claim 12, wherein a width of each of the plurality of electrodes is configured such that the each of the plurality of electrodes lies on an outer surface of a fold when the outer inflatable member is in a non-expanded, folded configuration.

15. The catheter of claim 12, further comprising a moveable outer sheath coupled along a length of the elongate shaft and moveable with respect to the elongate shaft, wherein translational movement of the moveable outer sheath adjusts a push force on a distal end portion of the catheter or adjusts a flexibility of the elongate shaft.

16. The catheter of claim 12, wherein the ablation catheter is sized and adapted such that a distal end of the elongate shaft can be advanced to a location within a hepatic artery.

17. The catheter of claim 12, wherein the inner inflatable member is a first balloon, and wherein the outer inflatable member is a second balloon.

18. The catheter of claim 12, wherein the plurality of electrodes comprises four electrodes, wherein a first electrode and a second electrode of the four electrodes are located within a first circumferential cross-section along the outer inflatable member at a first axial distance from a distal end of the outer inflatable member and are located in opposite quadrants from each other about a central longitudinal axis of the elongate shaft when the outer inflatable member is in an expanded configuration, and wherein a third electrode and a fourth electrode of the four electrodes are located within a second circumferential cross-section along the outer inflatable member at a second axial distance from the distal end of the outer inflatable member and are located in opposite quadrants from each other about the central longitudinal axis of the elongate shaft when the outer inflatable member is in the expanded configuration, wherein the second axial distance is different from the first axial distance.

19. An intraluminal ablation catheter comprising:
   a proximal manifold;
   an elongate shaft coupled to the proximal manifold, the elongate shaft comprising multiple lumens extending therethrough,
   wherein a first lumen of the multiple lumens comprises a fluid infusion lumen, and
   wherein the elongate shaft comprises a central longitudinal axis extending along its length,
   an inner expandable member coupled to at least one of the multiple lumens,
   wherein the fluid infusion lumen is configured to infuse cooling fluid into the inner expandable member;
   an outer expandable member surrounding the inner expandable member and being coupled to a distal end portion of the elongate shaft,
   wherein the outer expandable member comprises a plurality of electrodes, and
   wherein the inner expandable member comprises a plurality of outlet orifices configured to direct jets of the cooling fluid from the inner expandable member toward a bottom surface of each of the plurality of electrodes of the outer expandable member so as to cool the plurality of electrodes.

20. The ablation catheter of claim 19:
   wherein the inner expandable member and the outer expandable member are configured to be expanded by the cooling fluid,
   wherein each electrode of the plurality of electrodes has a surface area between 8 $mm^2$ and 16 $mm^2$;
   wherein a second lumen of the multiple lumens comprises a guidewire lumen configured to facilitate advancement of the intraluminal ablation catheter over a guidewire,
   wherein each of the outlet orifices has a diameter of between 0.05 mm and 0.25 mm,
   wherein an annular gap between the inner inflatable member and the outer inflatable member ranges between 0.05 mm and 1.5 mm,
   wherein a length of the outer inflatable member is between 10 mm and 30 mm, and
   wherein a flow rate of the cooling fluid per electrode ranges from 0.1 to 1.0 mL/second.

* * * * *

UNITED STATES PATENT AND TRADEMARK OFFICE
CERTIFICATE OF CORRECTION

PATENT NO. : 10,524,859 B2
APPLICATION NO. : 15/614460
DATED : January 7, 2020
INVENTOR(S) : Anthony Ciro Vrba et al.

It is certified that error appears in the above-identified patent and that said Letters Patent is hereby corrected as shown below:

On the Title Page

On Page 4, Column 1, Item (56), Line 13, under U.S. Patent Documents, delete "Coe" and insert --Coe et al.--.

On Page 11, Column 1, Item (56), Line 5, under Other publications, delete "Metabolismin" and insert --Metabolism in--.

In the Specification

In Column 2, Line 42, delete "(efferently" and insert --(afferently--.

In Column 2, Line 47, delete "(efferently" and insert --(afferently--.

In Column 3, Lines 43-44, delete "vena caves," and insert --vena cavas,--.

In Column 27, Line 11, delete "FIGS. 130-1" and insert --FIGS. 13C-1--.

In Column 66, Line 5, delete "FIGS. 13C-2" and insert --FIG. 13C-2--.

In Column 66, Line 6, delete "FIGS." and insert --FIG.--.

In Column 68, Line 60, delete "FIGS." and insert --FIG.--.

In Column 69, Line 1, delete "FIGS. 160-1" and insert --FIG. 16C-1--.

In Column 69, Line 6, delete "FIGS." and insert --FIG.--.

In Column 69, Line 19, delete "FIGS." and insert --FIG.--.

Signed and Sealed this
Eighth Day of September, 2020

Andrei Iancu
*Director of the United States Patent and Trademark Office*

CERTIFICATE OF CORRECTION (continued)
U.S. Pat. No. 10,524,859 B2

In Column 69, Line 22, delete "FIGS." and insert --FIG.--.

In Column 69, Line 27, delete "FIGS." and insert --FIG.--.

In Column 69, Line 30, delete "FIGS." and insert --FIG.--.

In Column 75, Line 34, delete "20A-200" and insert --20A-20C--.

In Column 77, Line 63, delete "26908" and insert --23908--.

In Column 81, Line 64, delete "2700400" and insert --2700--.